United States Patent
Lehmann-Lintz et al.

(10) Patent No.: US 8,648,068 B2
(45) Date of Patent: *Feb. 11, 2014

(54) HETEROCYCLOALKYL-CONTAINING THIENOPYRIMIDINES FOR PHARMACEUTICAL COMPOSITIONS

(75) Inventors: Thorsten Lehmann-Lintz, Ochsenhausen (DE); Joerg Kley, Mittelbiberach (DE); Norbert Redemann, Biberach (DE); Achim Sauer, Ravensburg-Torkenweiler (DE); Leo Thomas, Biberach (DE); Dieter Wiedenmayer, Biberach (DE); Matthias Austen, Goettingen (DE); John Danilewicz, Canterbury (GB); Martin Schneider, Goettingen (DE); Kay Schreiter, Goettingen (DE); Phillip Black, Saffron Walden (GB); Wesley Blackaby, Saffron Walden (GB); Ian Linney, Saffron Walden (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 263 days.

This patent is subject to a terminal disclaimer.

(21) Appl. No.: 13/034,913

(22) Filed: Feb. 25, 2011

(65) Prior Publication Data
US 2011/0212102 A1    Sep. 1, 2011

(30) Foreign Application Priority Data

Feb. 26, 2010 (EP) .................................... 10154925

(51) Int. Cl.
| C07D 495/04 | (2006.01) |
| A61K 31/519 | (2006.01) |
| A61K 31/5355 | (2006.01) |
| A61P 35/00 | (2006.01) |
| A61P 25/28 | (2006.01) |
| A61P 3/10 | (2006.01) |

(52) U.S. Cl.
USPC ...... 514/217.06; 540/600; 544/278; 544/122; 514/260.1; 514/234.2

(58) Field of Classification Search
USPC ....................................... 544/278; 514/260.1
See application file for complete search history.

(56) References Cited

U.S. PATENT DOCUMENTS

| 5,686,457 | A | 11/1997 | Traxler et al. |
| 6,096,749 | A | 8/2000 | Traxler et al. |
| 6,395,733 | B1 | 5/2002 | Arnold et al. |
| 6,784,174 | B1 | 8/2004 | Cumming |
| 8,071,607 | B2 | 12/2011 | Coulter et al. |
| 2001/0027197 | A1 | 10/2001 | Bridges et al. |
| 2003/0162795 | A1 | 8/2003 | Munchhof et al. |
| 2006/0020042 | A1 | 1/2006 | McDonald et al. |
| 2007/0099877 | A1 | 5/2007 | Cai et al. |
| 2009/0163520 | A1 | 6/2009 | Coulter et al. |
| 2010/0015708 | A1 | 1/2010 | Quay et al. |
| 2010/0056548 | A1 | 3/2010 | Aicher et al. |
| 2010/0143341 | A1 | 6/2010 | Taylor et al. |
| 2010/0247517 | A1 | 9/2010 | Austen et al. |
| 2011/0021203 | A1 | 1/2011 | Yamada et al. |
| 2011/0212102 | A1 | 9/2011 | Lehmann-Lintz et al. |
| 2011/0217311 | A1 | 9/2011 | Lehmann-Lintz et al. |
| 2012/0128686 | A1 | 5/2012 | Austen et al. |
| 2013/0056914 | A1 | 3/2013 | Frankowski et al. |

FOREIGN PATENT DOCUMENTS

| CA | 2038521 A1 | 9/1991 |
| CH | 408945 A | 3/1966 |
| DD | 248593 A1 | 8/1987 |
| DE | 3036390 A1 | 5/1982 |
| EP | 0447891 A1 | 9/1991 |
| EP | 0452002 A2 | 10/1991 |
| EP | 0682027 A1 | 11/1995 |
| EP | 0729758 A2 | 9/1996 |
| EP | 1724268 A1 | 11/2006 |
| JP | 2005503345 A | 2/2005 |
| WO | 9413677 A1 | 6/1994 |
| WO | 9713771 A1 | 4/1997 |
| WO | 9924440 A1 | 5/1999 |
| WO | 0056738 A1 | 9/2000 |
| WO | 0075145 A1 | 12/2000 |

(Continued)

OTHER PUBLICATIONS

Banker, Gilbert S., et al; Modern Pharmaceutics (1996) 3rd Ed. Marcel Dekker, Inc. New York, p. 596.

(Continued)

*Primary Examiner* — Susanna Moore
(74) *Attorney, Agent, or Firm* — Michael P. Morris; Edward S. Lazer

(57) ABSTRACT

The present invention relates to novel pharmaceutical compositions comprising thienopyrimidine compounds. Moreover, the present invention relates to the use of the thienopyrimidine compounds of the invention for the production of pharmaceutical compositions for the prophylaxis and/or treatment of diseases which can be influenced by the inhibition of the kinase activity of Mnk1 and/or Mnk2 (Mnk2a or Mnk2b) and/or variants thereof.

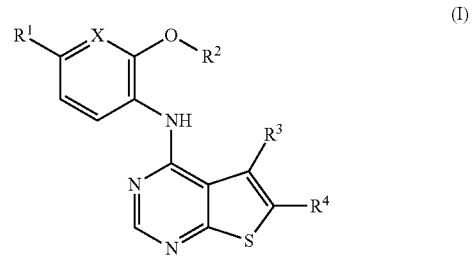

14 Claims, No Drawings

(56) References Cited

FOREIGN PATENT DOCUMENTS

| | | | |
|---|---|---|---|
| WO | 02088138 A1 | 11/2002 |
| WO | 03037362 A2 | 5/2003 |
| WO | 2004037159 A2 | 5/2004 |
| WO | 2004106340 A2 | 12/2004 |
| WO | 2004113347 A1 | 12/2004 |
| WO | 200510008 A1 | 2/2005 |
| WO | 2005042537 A1 | 5/2005 |
| WO | 2005080377 A1 | 9/2005 |
| WO | 2005117890 A2 | 12/2005 |
| WO | 2006014325 A2 | 2/2006 |
| WO | 2006066937 A2 | 6/2006 |
| WO | 2006094791 A1 | 9/2006 |
| WO | 2006124874 A2 | 11/2006 |
| WO | 2006136402 A1 | 12/2006 |
| WO | 2007056214 A2 | 5/2007 |
| WO | 2007056215 A2 | 5/2007 |
| WO | 2007059905 A2 | 5/2007 |
| WO | 2007081517 A2 | 7/2007 |
| WO | 2007084815 A2 | 7/2007 |
| WO | 2007115822 A1 | 10/2007 |
| WO | 2007147874 A1 | 12/2007 |
| WO | 2008006547 A2 | 1/2008 |
| WO | 2008041053 A2 | 4/2008 |
| WO | 2009065596 A2 | 5/2009 |
| WO | 2010023181 A1 | 3/2010 |
| WO | 2011104334 A1 | 9/2011 |
| WO | 2011104337 A1 | 9/2011 |
| WO | 2011104338 A1 | 9/2011 |
| WO | 2011104340 A1 | 9/2011 |

OTHER PUBLICATIONS

Baumgartner, A., et al; Uber Thieno-Verbindungen: 14. Mitteilung: Darstellung 4-Anninosubstituierter Thieno[2.3-d]pyrimidyn-6-carbosa bsauurederivate; Institut fur Pharnazeutischer, (1993).

Cheng, C.C., et al; Potential Purine Antagonists. VI. Synthesis of 1-Alkyl- and 1-Aryl-4-substituted Pyrazolo[3,4-d]pyrimidines1,2; Journal of Organic Chemistry, American Chemical Society (1956) vol. 21 pp. 1240-1256.

Dörwald, Florencio Zaragoza, et al; Side Reactions in Organic Synthesis: A Guide to Successful Synthesys Design; (2005) Wiley; VCH, Weinheim p. IX of preface.

http://www.medterms.com/script/main/art.asp?articlekey=12063, last accessed on Aug. 24, 2010.

International Search Report for PCT/EP2006/005980 mailed Nov. 16, 2006.

International Search Report for PCT/EP2007/003186 mailed Jun. 8, 2007.

International Search Report for PCT/EP2007/006109 mailed Dec. 20, 2007.

International Search Report for PCT/EP2009/060876 mailed Nov. 10, 2009.

International Search Report for PCT/EP2011/052810 mailed May 16, 2011.

International Search Report for PCT/EP2011/052811/mailed May 18, 2011.

International Search Report for PCT/EP2011/052813 mailed May 30, 2011.

International Search Reportfor PCT/EP2008/009880 mailed Jun. 25, 2009.

Jorgensen, Anker, et al; Phosphorus Pentoxide in Organic Synthesis. XX [1]. Synthesis of N-Aryl-7H-pyrrolo [2,3-d]pyrimidin-4-amines; Journal of Heterocyclic Chemistry (1985) pp. 859-863.

Mogensen, Jorgen, et al; Phosphorus Pentoxide in Organic Synthesis: XXXIV*. Synthesis of 3-Arylthieno[2,3-d]pyrimidin-4(3H)-imines and their Rearrangement to N-arylthieno[2,3-d]pyrimidin-4-amines; Chemica Scripta (1988) vol. 28 pp. 195-200.

Munchhof, Michael J., et al; Design and SAR of Thienopyrimidine and Thienopyridine Inhibitors of VEGFR-2 Kinase Activity; Bioorganic & Medicinal Chemistry Letters (2004) vol. 14 pp. 21-24.

Peat, Andrew, J., et al; Novel Pyrazolopyrimidine Derivates as GSK-3 Inhibitors; Bioorganic & Medicinal Chemistry Letters (2004) vol. 14 pp. 2121-2125.

Showalter, H. D. Hollis, et al; Tyrosine Kinase Inhibitors. 16. 6,5,6-Tricyclic Benzothieno[3-,2-d]pyrimidines and Pyrimido[5,4-b]- and -[4,5-b]indoles as Potent Inhibitors of the Epidermal Growth Factor Receptor Tyrosine Kinase; Journal of Medicinal Chemistry (1999) vol. 42 pp. 5464-5474.

Sobolov, Susan B., et al; Selective N-Alkylation of Pyrrolopyrimidines and Indoles by "Transfer of Activation"; Tetrahedron Letters (1998) vol. 39 pp. 5685-5688.

Traxler, Peter, et al; Use of a Pharmacophore Model for the Design of EGF-R Tyrosine Kinase Inhibitors: 4-(Phenylamino)pyrazolo[3,4-d]pyrimidines; Journal of Medicinal Chemistry (1997) vol. 40, No. 22 pp. 3601-3616.

Traxler, Peter, M., et al; 4-(Phenylamino)pyrrolopyrimidines: Potent and Selective, ATP Site Directed Inhibitors of the EGF-Receptor Protein Tyrosine Kinase; Journal of Medicinal Chemistry (1996) vol. 39 pp. 2285-2292.

West, R. A., et al; 2-Alkyl(aryl)-and2,7-Dimethyl-4-substituted Aminopyrrolo [2,3-d]pyrimidines; Journal of Organic Chemistry (1961) vol. 26 pp. 3809-3812.

Wolff, Manfred, E.; Principles and Practice; Burger's Medicinal Chemistry and Drug Discovery (1995) 5ed, vol. 1 pp. 975-977.

Young, Rodney, C., et al; Purine Derivates as Competitive Inhibitors of Human Erythrocyte Membrane Phosphatidylinositol 4-Kinase; Journal of Medicinal Chemistry (1990) vol. 33 pp. 2073-2080.

SEQUENCE LISTING

```
<160> NUMBER OF SEQ ID NOS: 7

<210> SEQ ID NO 1
<211> LENGTH: 29
<212> TYPE: DNA
<213> ORGANISM: Homo sapiens

<400> SEQUENCE: 1
tttaggatcc gtatcttctc aaaagttgg                                    29

<210> SEQ ID NO 2
<211> LENGTH: 28
<212> TYPE: DNA
<213> ORGANISM: Homo sapiens

<400> SEQUENCE: 2
ctgggtcgac tcagagtgct gtgggcgg                                     28

<210> SEQ ID NO 3
<211> LENGTH: 28
<212> TYPE: DNA
<213> ORGANISM: Homo sapiens

<400> SEQUENCE: 3
acagggatcc gtgcagaaga aaccagcc                                     28

<210> SEQ ID NO 4
<211> LENGTH: 29
<212> TYPE: DNA
<213> ORGANISM: Homo sapiens

<400> SEQUENCE: 4
gatggtcgac tcaggcgtgg tctcccacc                                    29

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Thr Ala Thr Lys Ser Gly Ser Thr Thr Lys Asn Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated-Ser

<400> SEQUENCE: 6

Thr Ala Thr Lys Ser Gly Ser Thr Thr Lys Asn Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phosphorylated-Ser
<220> FEATURE:
<223> OTHER INFORMATION: C-term CONH2

<400> SEQUENCE: 7

Cys Thr Ala Thr Lys Ser Gly Ser Thr Thr Lys Asn Arg
1               5                   10
```

HETEROCYCLOALKYL-CONTAINING THIENOPYRIMIDINES FOR PHARMACEUTICAL COMPOSITIONS

SEQUENCE LISTING

The instant application contains a Sequence Listing which has been submitted in ASCII format via EFS-Web and is hereby incorporated by reference in its entirety. Said ASCII copy, created on Apr. 29, 2011, is named 012598.txt and is 2,079 bytes in size.

The present invention relates to thienopyrimidine compounds and to novel pharmaceutical compositions comprising thienopyrimidine compounds.

Moreover, the present invention relates to the use of the thienopyrimidine compounds of the invention for the production of pharmaceutical compositions for the prophylaxis and/or treatment of diseases which can be influenced by the inhibition of the kinase activity of Mnk1 (Mnk1a or MnK1b) and/or Mnk2 (Mnk2a or Mnk2b) or further variants thereof. Particularly, the present invention relates to the use of the thienopyrimidine compounds of the invention for the production of pharmaceutical compositions for the prophylaxis and/or therapy of metabolic diseases, such as diabetes, hyperlipidemia and obesity, hematopoietic disorders, neurodegenerative diseases, kidney damage, inflammatory disorders, and cancer and their consecutive complications and disorders associated therewith.

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease. Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin.

Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMoL), multiple myeloma, polycythemia vera, lymphoma, acute lymphocytic leukemia (ALL), chronic lymphocytic leukemia (CCL), Wilm's tumor, or Ewing's Sarcoma.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, endometrial cancer, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, skin cancer, osteosarcoma, rhabdomyosarcoma, bladder cancer, metastatic cancer, cachexia, or pain.

Certain anti-cancer drugs such as cisplatin are linked to serious side effects such as nephrotoxicity or ototoxicity, which can be dose limiting. Activation of Mnks has been linked to these side effects. In a further embodiment of the present invention, the compounds and compositions of the present invention are useful for the treatment and/or prophylaxis of ear or kidney damage, in particular for the prevention or treatment of ear and kidney drug induced damage Furthermore, the present invention relates to the use of thienopyrimidine compounds for the production of pharmaceutical compositions for the prophylaxis and/or therapy of cytokine related diseases.

Such diseases are i.a. inflammatory diseases, autoimmune diseases, destructive bone disorders, proliferative disorders, infectious diseases, neurodegenerative diseases, allergies, or other conditions associated with proinflammatory cytokines.

Allergic and inflammatory diseases such as acute or chronic inflammation, chronic inflammatory arthritis, rheumatoid arthritis, psoriasis, COPD, inflammatory bowel disease, asthma and septic shock and their consecutive complications and disorders associated therewith.

Inflammatory diseases like rheumatoid arthritis, inflammatory lung diseases like COPD, inflammatory bowel disease and psoriasis afflict one in three people in the course of their lives. Not only do those diseases impose immense health care costs, but also they are often crippling and debilitating.

Although inflammation is the unifying pathogenic process of these inflammatory diseases below, the current treatment approach is complex and is generally specific for any one disease. Many of the current therapies available today only treat the symptoms of the disease and not the underlying cause of inflammation.

The compositions of the present invention are useful for the treatment and/or prophylaxis of inflammatory diseases and consecutive complications and disorders. such as chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Moreover, cytokines are also believed to be implicated in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis.

Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke.

Excessive cytokine production has, moreover, been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis. The treatment and/or prophylaxis of these diseases are also contemplated by the present invention Additionally, the inventive compositions may be used to treat inflammation associated with autoimmune diseases including, but not limited to, systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

In a further embodiment the compositions of the present invention may be used for the treatment and prevention of infectious diseases such as sepsis, septic shock, Shigellosis, and *Helicobacter pylori* and viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS or malignancy, malaria, mycobacterial infection and meningitis. These also include viral infections, by influenza virus, varicella-zoster virus (VZV), Epstein-Barr virus, human herpesvirus-6 (HHV-6), human herpesvirus-7 (HHV-7), human herpesvirus-8 (HHV-8), Poxvirus, Vacciniavirus, Monkeypoxvirus, pseudorabies and rhinotracheitis.

The compositions of the present invention may also be used topically in the treatment or prophylaxis of topical disease states mediated by or exacerbated by excessive cytokine production, such as inflamed joints, eczema, psoriasis and other inflammatory skin conditions such as sunburn; inflammatory eye conditions including conjunctivitis; pyresis, pain and other conditions associated with inflammation.

Periodontal disease has also been implemented in cytokine production, both topically and systemically. Hence, use of compositions of the present invention to control the inflammation associated with cytokine production in such peroral diseases such as gingivitis and periodontitis is another aspect of the present invention.

Finally, the compositions of the present invention may also be used to treat or prevent neurodegenerative disease selected from Alzheimer's disease, Parkinson's disease, amyotrophic lateral sclerosis, Huntington's disease, frontotemporal lobar dementia, spinocerebellar ataxia, dementia with Lewy bodies, cerebral ischemia or neurodegenerative disease caused by traumatic injury, glutamate neurotoxicity or hypoxia.

In a preferred embodiment the compositions of the present invention may be used to treat or prevent a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Protein kinases are important enzymes involved in the regulation of many cellular functions. The LK6-serine/threonine-kinase gene of Drosophila melanogaster was described as a short-lived kinase which can associate with microtubules (J. Cell Sci. 1997, 110(2): 209-219). Genetic analysis in the development of the compound eye of Drosophila suggested a role in the modulation of the RAS signal pathway (Genetics 2000 156(3): 1219-1230). The closest human homologues of Drosophila LK6-kinase are the MAP-kinase interacting kinase 2 (Mnk2, e.g. the variants Mnk2a and Mnk2b) and MAP-kinase interacting kinase 1 (Mnk1) and variants thereof. These kinases are mostly localized in the cytoplasm. Mnks are phosphorylated by the p42 MAP kinases Erk1 and Erk2 and the p38-MAP kinases. This phosphorylation is triggered in a response to growth factors, phorbol esters and oncogenes such as Ras and Mos, and by stress signaling molecules and cytokines. The phosphorylation of Mnk proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the Mnk1 and Mnk2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by Mnk proteins. Most publications describe a positive stimulatory effect on the cap-dependent protein translation upon activation of MAP kinase-interacting kinases. Thus, the activation of Mnk proteins can lead to an indirect stimulation or regulation of the protein translation, e.g. by the effect on the cytosolic phospholipase 2 alpha (BBA 1488:124-138, 2000).

WO 03/037362 discloses a link between human Mnk genes, particularly the variants of the human Mnk2 genes, and diseases which are associated with the regulation of body weight or thermogenesis. It is postulated that human Mnk genes, particularly the Mnk2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, such as e.g. diabetes mellitus and cancer. WO 03/03762 moreover discloses the use of nucleic acid sequences of the MAP kinase-interacting kinase (Mnk) gene family and amino acid sequences encoding these and the use of these sequences or of effectors of Mnk nucleic acids or polypeptides, particularly Mnk inhibitors and activators in the diagnosis, prophylaxis or therapy of diseases associated with the regulation of body weight or thermogenesis.

WO 02/103361 describes the use of kinases 2a and 2b (Mnk2a and Mnk2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of Mnk2a or Mnk2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human Mnk2 protein.

First evidence for a role of Mnks in inflammation was provided by studies demonstrating activation of Mnk1 by proinflammatory stimuli. The cytokines TNFα and IL-1β trigger the activation of Mnk1 in vitro (Fukunaga and Hunter, EMBO J 16(8): 1921-1933, 1997) and induce the phosphorylation of the Mnk-specific substrate eIF4E in vivo (Ueda et al., Mol Cell Biol 24(15): 6539-6549, 2004). In addition, administration of lipopolysaccharide (LPS), a potent stimulant of the inflammatory response, induces activation of Mnk1 and Mnk2 in mice, concomitant with a phosphorylation of their substrate eIF4E (Ueda et al., Mol Cell Biol 24(15): 6539-6549, 2004).

Furthermore, Mnk1 has been shown to be involved in regulating the production of proinflammatory cytokines. Mnk1 enhances expression of the chemokine RANTES (Nikolcheva et al., J Clin Invest 110, 119-126, 2002). RANTES is a potent chemotractant of monocytes, eosinophils, basophiles and, natural killer cells. It activates and induces proliferation of T lymphocytes, mediates degranulation of basophils and induces the respiratory burst in eosinophils (Conti and DiGioacchino, Allergy Asthma Proc 22(3):133-7, 2001)

WO 2005/00385 and Buxade et al., Immunity 23: 177-189, August 2005 both disclose a link between Mnks and the control of TNFα biosynthesis. The proposed mechanism is mediated by a regulatory AU-rich element (ARE) in the TNFα mRNA. Buxade et al. demonstrate proteins binding and controlling ARE function to be phosphorylated by Mnk1 and Mnk2. Specifically Mnk-mediated phosphorylation of the ARE-binding protein hnRNP A1 has been suggested to enhance translation of the TNFα mRNA.

TNFα is not the only cytokine regulated by an ARE. Functional AREs are also found in the transcripts of several interleukins, interferones and chemokines (Khabar, J Interf Cytokine Res 25: 1-10, 2005). The Mnk-mediated phosphorylation of ARE-binding proteins has thus the potential to control biosynthesis of cytokines in addition to that of TNFα.

Current evidence demonstrates Mnks as down stream targets of inflammatory signalling as well as mediators of the inflammatory response. Their involvement in the production of TNFα, RANTES, and potentially additional cytokines suggests inhibition of Mnks as strategy for anti-inflammatory therapeutic intervention.

Mnk1 and Mnk2 (including all splice forms) phosphorylate the translation factor eIF4E on Serine 209. Mnk1/2 double knockout mice completely lack phosphorylation on Serine 209, indicating that Mnk kinase are the only kinases able to phosphorylate this site in vivo (Ueda et al., Mol Cell Biol. 2004; 24(15):6539-49). eIF4E is overexpressed in a wide range of human malignancies, and high eIF4E expression is frequently associated with more aggressive disease and poor prognosis. Furthermore, eIF4E can act as an oncogene when assayed in standard assays for oncogenic activity (e.g. Ruggero et al., Nat Med. 2004 May; 10(5):484-6). eIF4E excerts its oncogenic activity by stimulating the translation of oncogenes such as c-myc and cyclinD1 (Culjkovic et al., J Cell Biol. 2006; 175(3):415-26), by increasing the expression of pro-survival factors such as MCP-1 (Wendel et al., Genes Dev. 2007; 21(24):3232-7) and by positively regulating pathways of drug resistance (Wendel et al., Nature 2004; 428 (6980):332-7; Graff et el., Cancer Res. 2008; 68(3):631-4; De Benedetti and Graff, Oncogene 2004; 23(18):3189-99; Barnhart and Simon, J Clin Invest. 2007; 117(9):2385-8). Suppression of eIF4E expression by antisense oligonucleotides has shown promise in preclinical experiments with human tumor cells (Graff et al., J Clin Invest. 2007; 117(9):2638-48). It has been shown that phosphorylation on Ser209 is strictly required for the oncogenic activity of eIF4E in vitro and in vivo (Topisirovic et al., Cancer Res. 2004; 64(23):8639-42; Wendel et al., Genes Dev. 2007; 21(24):3232-7). Thus, inhibition of Mnk1 and Mnk2 is expected to have beneficial effects in human malignancies.

Inhibitors of Mnk (referred to as CGP57380 and CGP052088) have been described (cf. Mol. Cell Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of Mnk1. CGP57380 is a low molecular weight selective, non-cytotoxic inhibitor of Mnk2 (Mnk2a or Mnk2b) or of Mnk1: The addition of CGP57380 to cell culture cells, transfected with Mnk2 (Mnk2a or Mnk2b) or Mnk1 showed a strong reduction of phosphorylated eIF4E.

Further inhibitors of Mnk have been described. See for example Applicants patent applications WO 06/066937, describing pyrazolopyrimidine compounds, WO 06/136402 describing certain thienopyrimidine compounds, WO 07/115,822 describing further thienopyrimidine compounds with modified core ring, and WO 08/006,547 describing pyrrolopyrimidines as inhibitors of Mnk kinases.

The problem underlying the present invention is to provide potent and selective Mnk1 and/or Mnk2 inhibitors which may effectively and safely be used for the treatment of metabolic diseases, inflammatory diseases, cancer, neurodegenerative diseases and their consecutive complication and disorders.

It has now been surprisingly found that certain thienopyrimidine compounds are potent inhibitors of the kinase enzymes Mnk1 and/or Mnk2 and/or variants thereof and as such may be useful in the prophylaxis and/or therapy of diseases which can be influenced by the inhibition of the kinase activity of Mnk1 and/or Mnk2 (Mnk2a or Mnk2b) and/or variants thereof.

In contrast to the thienopyrimidine compounds known in the art, for example, the compounds disclosed in the Applicants patent applications WO 06/136402 and WO 2007/115822, the thienopyrimidine compounds of the present invention provide several advantages, namely, enhanced solubility, the possibility to form stable salts, improved metabolic stability, enhanced or retained activity in biochemical or cellular Mnk activity assays and enhanced or retained selectivity against other kinases.

The thienopyrimidine compounds disclosed in WO 06/136402 and WO 07/115,822 exhibit high activity in Mnk enzyme assays and extremely high selectivity, however they show a very low solubility and are in most cases metabolic unstable resulting in undesired pharmacokinetic properties.

It has been surprisingly found that by the introduction of a polar group at the $R^4$-position in the compounds of general formula (I) below leads to surprising substantial metabolic stabilization, rendering the thienopyrimidines of the present invention useful for in vivo pharmacological applications.

Moreover, compounds described in this application also show improved solubility, have strong inhibitory potency in biochemical and cellular assays and are highly selective, resulting in overall greatly improved pharmacological properties.

If not specified otherwise, any alkyl moiety mentioned in this application may be straight-chained or branched.

Thienopyrimidine compounds of the present invention are compounds of the general formula (I):

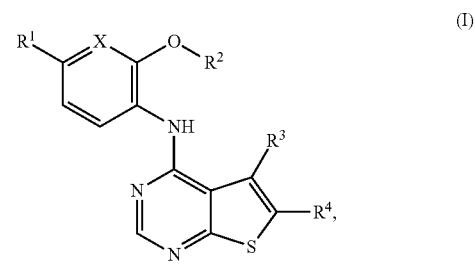

wherein
X is CH or N,
$R^1$ is H, halogen, CN, $CH_3$ or $CF_3$,
$R^2$ is a group selected from

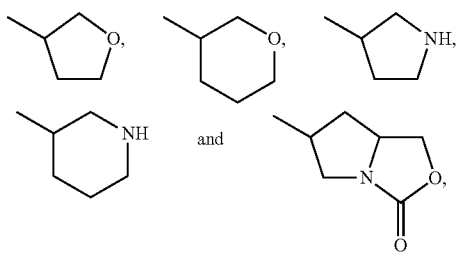

wherein the

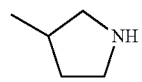

group may be substituted at the nitrogen atom by $-SO_2-(C_{1-3}$ alkyl), $-CO-(C_{1-3}$ alkyl), $-CO-(CH_2)_n-O-$ ($C_{1-3}$ alkyl), —CO—$(CH_2)_n$—$N(C_{1-3}$ alkyl$)_2$, $C_{1-4}$ alkyl, —$(CH_2)_n$—$CF_3$, —$(CH_2)_n$—$CHF_2$, —$(CH_2)_n$—OH, —$(CH_2)_n$—O—($C_{1-3}$ alkyl), —$(CH_2)_n$—CN,

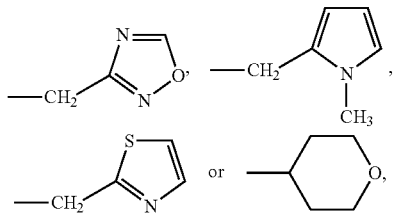

and wherein it may be substituted on a carbon atom by a —$CH_2OH$ group,
wherein n is 1 or 2,
and wherein the

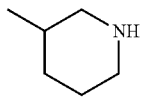

group may be substituted at the nitrogen atom by linear or branched $C_{1-4}$ alkyl, —$(CH_2)_n$—$CF_3$, —$(CH_2)_n$—$CHF_2$, —$(CH_2)_n$—OH, —$(CH_2)_n$—O—($C_{1-3}$ alkyl), —$(CH_2)_n$—CN, —$(CH_2)_n$—CO—$N(C_{1-3}$ alkyl$)_2$, —$SO_2$—($C_{1-3}$ alkyl), —CO—($C_{1-3}$ alkyl), —$CO_2$($C_{1-4}$ alkyl), —$CO_2$—$(CH_2)_n$—$CF_3$, —$CO_2$—$(CH_2)_n$—O—($C_{1-3}$ alkyl), —$CO_2$—$(CH_2)_n$—CO—$N(C_{1-3}$ alkyl$)_2$,

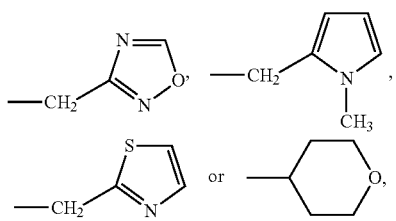

wherein n is 1 or 2,
$R^3$ is a $C_{1-2}$ alkyl group, and
$R^4$ is —COOH, —$CO_2$—($C_{1-3}$ alkyl), —$CO_2$—$(CH_2)_n$—$N(C_{1-3}$ alkyl$)_2$, —$CONH_2$, —CO—$NHR^5$, —CO—NH—$(CH_2)_p$—$R^6$, —CO—NH—$(CH_2)_m$—$R^7$, —CO—N$(CH_3)$—$(CH_2)_m$—$R^7$, CO—$N(CH_3)$—$(CH_2)$-cyclohexyl,

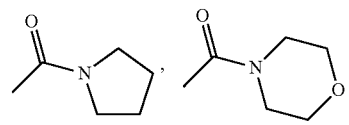

$R^5$ is —CN, —OH, linear or branched $C_{1-6}$ alkyl, —$O(C_{1-3}$ alkyl), $C_{3-6}$ cycloalkyl, —$SO_2$—($C_{1-3}$ alkyl); pyrazolyl optionally substituted by methyl; or piperidinyl optionally substituted by methyl,
wherein the $C_{3-6}$ cycloalkyl group may be substituted by —$NH_2$, —OH or —$OCH_3$,
$R^6$ is —$C(CH_3)_2Cl$; —$C(CH_3)_2OH$; —$CHC_{3-6}$ cycloalkyl, which is optionally substituted by OH; imidazolyl, which is optionally substituted by methyl; pyrrolidinyl, which is optionally substituted by $C_{1-3}$ alkyl or by an oxo group; tetrahydrofuranyl; tetrahydropyranyl; phenyl, which is optionally substituted by one or two —F, —Cl, —CN, —OH, $C_{1-3}$ alkyl or —O($C_{1-3}$ alkyl); naphthyl; pyridinyl; furanyl; thiophenyl; oxazolyl; thiazolyl; pyrazolyl; morpholinyl, which is optionally substituted by methyl; benzothiophenyl; —CO-phenyl; or —$SO_2$—N($C_{1-3}$ alkyl$)_2$, and $R^7$ is F, —OH, —$OCF_3$, —O—($C_{1-3}$ alkyl), —O-phenyl, —O—$(CH_2)_m$—OH, —$N(C_{1-3}$ alkyl$)_2$, —NH-phenyl, piperidinyl, pyrrolidinyl, azetedinyl or aziridinyl, and wherein the hydrogen atom in the NH groups may be replaced be $C_{1-3}$ alkyl, wherein p is 1, 2 or 3, and m is 2 or 3, or a tautomer, enantionmer, diastereomer or salt thereof.

Preferred compounds of formula (I) are those, wherein
X, $R^1$, $R^2$ and $R^4$ are as defined above and
$R^3$ is methyl,
or a tautomer or salt thereof.

A preferred subgroup concerns those compounds of formula (I), wherein
$R^2$ to $R^4$ are as defined above,
X is CH and
$R^1$ is F, Cl, CN, $CH_3$ or $CF_3$,
or a tautomer or salt thereof.

Another subgroup concerns those compounds of formula (I), wherein
$R^2$ to $R^4$ are as defined above,
X is N and
$R^1$ is H,
or a tautomer or salt thereof.

More preferred compounds of formula (I) are those, wherein
X, $R^1$, $R^3$ and $R^4$ are as defined above and
$R^2$ is

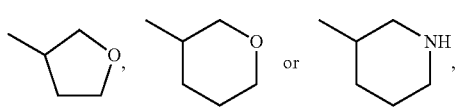

wherein the

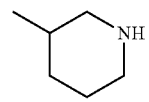

group may be substituted at the nitrogen atom by linear or branched $C_{1-4}$ alkyl, —$(CH_2)_n$—$CF_3$, —$(CH_2)_n$—$CHF_2$, —$(CH_2)_n$—OH, —$(CH_2)_n$—O—($C_{1-3}$ alkyl), —$(CH_2)_n$—CN, —$(CH_2)_n$—CO—$N(C_{1-3}$ alkyl$)_2$ or —$SO_2$—($C_{1-3}$ alkyl),
wherein n is 1 or 2,
or a tautomer or salt thereof.

A preferred subgroup of the more preferred compounds concerns those compounds of formula (I), wherein X, R$^1$, R$^3$ and R$^4$ are as defined above and R$^2$ is

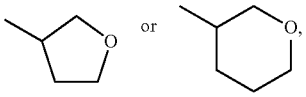

or a tautomer or salt thereof.

A second preferred subgroup of the more preferred compounds concerns those compounds of formula (I), wherein X, R$^1$, R$^3$ and R$^4$ are as defined above, and R$^2$ is

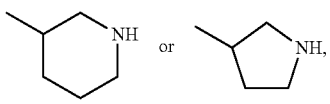

wherein the

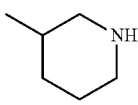

group may be substituted at the nitrogen atom by linear or branched C$_{1-4}$ alkyl, —(CH$_2$)$_n$—CF$_3$, —(CH$_2$)$_n$—CHF$_2$, —(CH$_2$)$_n$—OH, —(CH$_2$)$_n$—O—(C$_{1-3}$ alkyl), —(CH$_2$)$_n$—CN, —(CH$_2$)$_n$—CO—N(C$_{1-3}$ alkyl)$_2$ or —SO$_2$—(C$_{1-3}$ alkyl),
wherein n is 1 or 2,
and wherein the

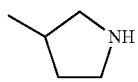

group may be substituted at the nitrogen atom by —SO$_2$—(C$_{1-3}$ alkyl), C$_{1-4}$ alkyl, —(CH$_2$)$_n$—CF$_3$, —(CH$_2$)$_n$—CHF$_2$, —(CH$_2$)$_n$—OH, —(CH$_2$)$_n$—O—(C$_{1-3}$ alkyl), —(CH$_2$)$_n$—CN,

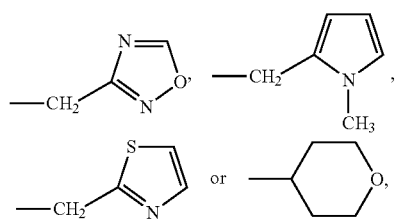

or a tautomer or salt thereof.

Even more preferred are those compound of formula (I), wherein
X, R$^1$, R$^2$ and R$^3$ are as defined above and
R$^4$ is —CONH$_2$, —CO—NHR$^5$, —CO—NH—(CH$_2$)$_p$—R$^6$, —CO—NH—(CH$_2$)$_n$—R$^7$,
R$^5$ is —CN, —OH, linear or branched C$_{1-6}$ alkyl, —O(C$_{1-3}$ alkyl), C$_{3-6}$ cycloalkyl, —SO$_2$—(C$_{1-3}$ alkyl); pyrazolyl optionally substituted by methyl; or piperidinyl optionally substituted by methyl,
wherein the C$_{3-6}$ cycloalkyl group may be substituted by —NH$_2$, —OH or OMe;
R$^6$ is —C(CH$_3$)$_2$Cl; —C(CH$_3$)$_2$OH; —CHC$_{3-6}$ cycloalkyl, which is optionally substituted by OH; imidazolyl, which is optionally substituted by methyl; pyrrolidinyl, which is optionally substituted by C$_{1-3}$ alkyl or by an oxo group; tetrahydrofuranyl; tetrahydropyranyl; phenyl, which is optionally substituted by one or two —F, —Cl, —CN, —OH, C$_{1-3}$ alkyl or —O(C$_{1-3}$ alkyl); naphthyl; pyridinyl; furanyl; thiophenyl; oxazolyl; thiazolyl; pyrazolyl; morpholinyl, which is optionally substituted by methyl; benzothiophenyl; —CO-phenyl; or —SO$_2$—N(C$_{1-3}$ alkyl)$_2$, and
R$^7$ is F, —OH, —OCF$_3$, —O—(C$_{1-3}$ alkyl), —O-phenyl, —O—(CH$_2$)$_m$—OH, —N(C$_{1-3}$ alkyl)$_2$, —NH-phenyl, pyrrolidinyl, azetedinyl or aziridinyl,
and wherein the hydrogen atom in the NH groups may be replaced be C$_{1-3}$ alkyl,
wherein p is 1, 2 or 3, and
m is 2 or 3,
or a tautomer, enantionmer, diastereomer or salt thereof,
particularly those compounds of formula (I), wherein
X, R$^1$, R$^2$ and R$^3$ are as defined above and
R$^4$ is —CO—NH$_2$, —CO—NHR$^5$, —CO—NH—(CH$_2$)$_p$—R$^6$, —CO—NH—(CH$_2$)$_m$—R$^7$,
R$^5$ is —CN, linear or branched C$_{1-6}$ alkyl, —O(C$_{1-3}$ alkyl), C$_{3-6}$ cycloalkyl, piperidinyl optionally substituted by methyl,
wherein the C$_{3-6}$ cycloalkyl group may be substituted by —NH$_2$, —OH or OMe;
R$^6$ is imidazolyl, which is optionally substituted by methyl; pyrrolidinyl, which is optionally substituted by C$_{1-3}$ alkyl or by an oxo group; tetrahydrofuranyl; tetrahydropyranyl; pyridinyl; oxazolyl; thiazolyl; pyrazolyl; morpholinyl, which is optionally substituted by methyl and
R$^7$ is F, —OH, —OCF$_3$, —O—(C$_{1-3}$ alkyl), —O-phenyl, —O—(CH$_2$)$_m$—OH, —N(C$_{1-3}$ alkyl)$_2$, piperidinyl, pyrrolidinyl, azetedinyl or aziridinyl,
and wherein the hydrogen atom in the NH groups may be replaced be C$_{1-3}$ alkyl,
wherein p is 1, 2 or 3, and
m is 2 or 3,
or a tautomer, enantionmer, diastereomer or salt thereof.

Even more preferred R$^4$ residues are:
carboxy, C$_{1-3}$ alkoxy-carbonyl, aminocarbonyl or N—(C$_{1-3}$ alkyl)-aminocarbonyl group,
wherein the methyl moiety of the above-mentioned N-(methyl)-aminocarbonyl group may optionally be substituted with a piperidinyl, N-methyl-piperidinyl or morpholinyl group, each bound via a carbon atom, and wherein the ethyl resp. propyl moiety of the above-mentioned N—(C$_{2-3}$ alkyl)-aminocarbonyl group may optionally be terminally substituted with hydroxy, methoxy, amino, N-methyl-amino, N,N-dimethyl-amino, morpholino, imidazolyl, 4-methyl-piperazinyl, 1-methyl-pyrrolidinyl, piperidinyl, pyrrolidinyl or 4-hydroxy-piperidino group.

Most preferred residues for R$^4$ are:
aminocarbonyl or N—(C$_{1-3}$ alkyl)-aminocarbonyl group,
wherein the methyl moiety of the above-mentioned N-(methyl)-aminocarbonyl group may optionally be substituted with a piperidinyl, N-methyl-piperidinyl or morpholinyl group, each bound via a carbon atom, and wherein the ethyl resp. propyl moiety of the above-mentioned N—(C$_{2-3}$ alkyl)-aminocarbonyl group may optionally be terminally substituted with hydroxy, methoxy, amino, N-methyl-amino, N,N-dimethyl-amino, morpholino, imidazolyl, 4-methyl-piperazinyl, 1-methyl-pyrrolidinyl, piperidinyl, pyrrolidinyl or 4-hydroxy-piperidino group.

Particularly preferred compounds of formula (I) are:

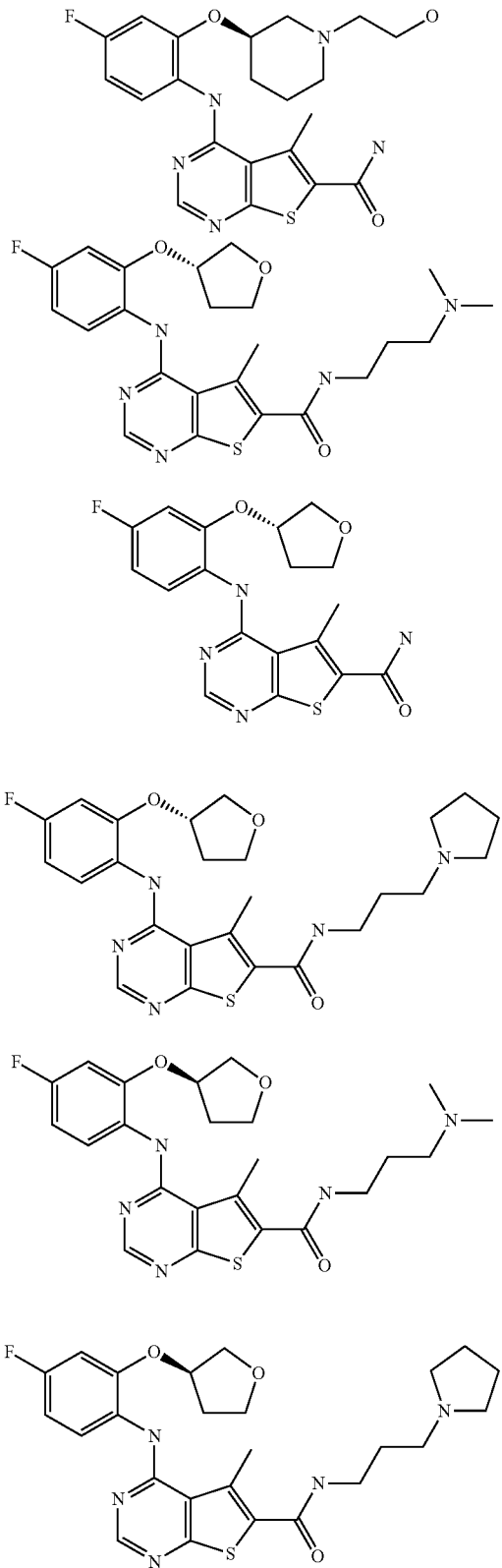

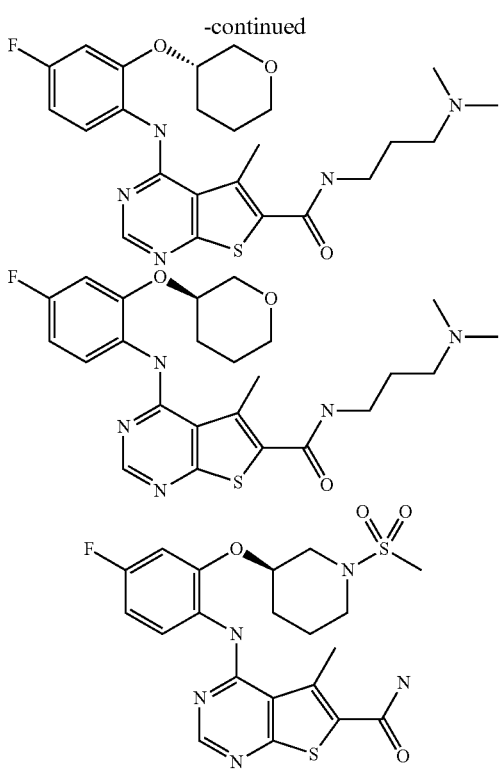

Typical methods of preparing the compounds of the invention are described below in the experimental section.

The potent inhibitory effect of the compounds of the invention may be determined by in vitro enzyme assays as described in the Examples in more detail.

The compounds of the present invention can be synthesized according to the following synthesis schemes:

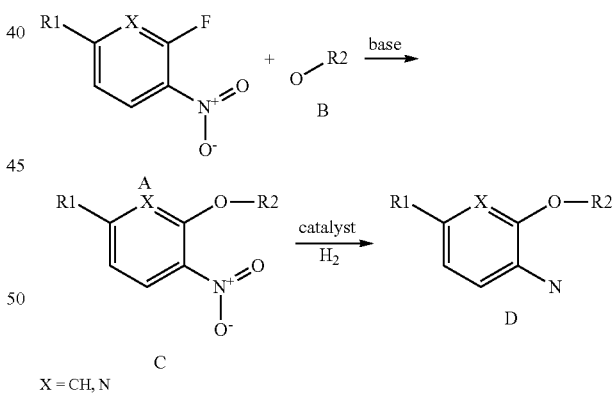

X = CH, N

Compounds of the general formula C can be synthesized by reaction of a compound A with the deprotonated alcohol B in appropriate solvents such as THF or DMF at a temperature between 0° C. and 150° C. The deprotonated form of B can be obtained by deprotonation with a base such as sodium hydride or lithium hexamethyldisilazane at a preferred temperature of 0° C. Hydrogenation of compound C in order to obtain a compound of the general formula D can be achieved by reacting C in the presence of hydrogen and a catalyst such as palladium or Raney nickel. The hydrogen can be introduced as a gas or stem from a hydrogen source such as ammonium formate.

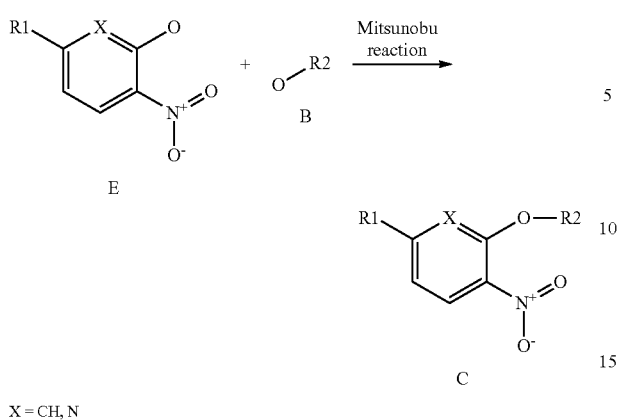

Compounds of the general formula C can be also obtained by Mitsunobu reaction of a compound with the general formula E with an alcohol B in the presence of triphenylphosphine and an dialkylazodicarboxylate such as diethylazodicarboxylate, diisopropylazodicarboxylate or di-tert.butylazodicarboxylate in a solvent such as THF at temperatures between −10° C. and 80° C., preferrably between 0° C. and 30° C.

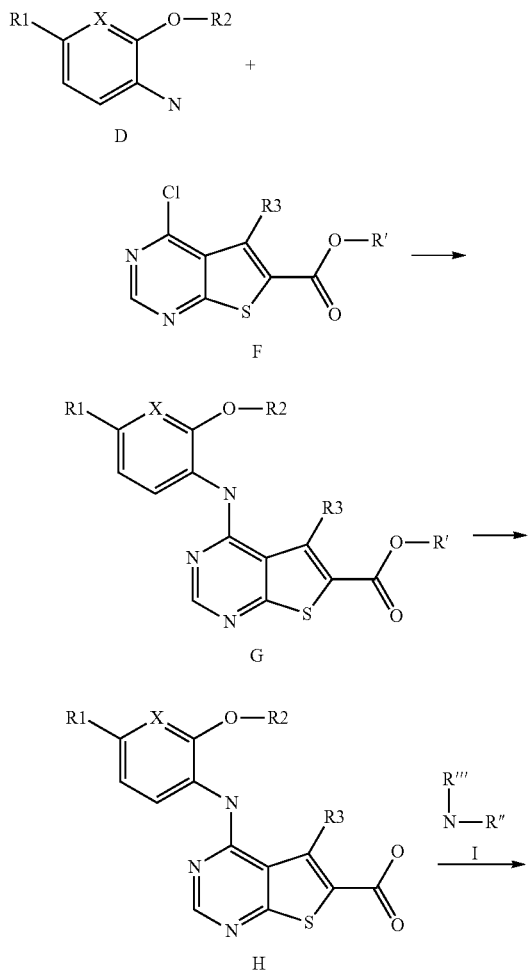

A compound of the formula G can be synthesized by reaction of compound D with F preferably in the presence of an acid such as p-toluene sulfonic acid or hydrochloric acid in solvents such as dioxan at temperatures between 10° C. and 150° C. Synthesis of a compound with the general formula H can be achieved by reaction of compound G with a base such as sodium hydroxide or lithium hydroxide in solvents such as methanol, ethanol, THF and water or mixtures thereof, preferably in ethanol/THF or THF/water at temperatures between 10° C. and 100° C. A compound of the general formula J can be obtained by reaction of compound H with amines of the general formula I using amide coupling procedures employing reagents such as TBTU, HATU or EDC/N-Hydroxysuccinimide in the presence or absence of bases such as diisopropylethylamine in solvents such as DMF or THF at temperatures between 0° C. and 120° C. preferably between 0° C. and 30° C.

Pharmaceutically acceptable salts of the compounds of the invention of formula (I) can be formed with numerous organic and inorganic acids and bases. Exemplary acid addition salts including acetate, adipate, alginate, ascorbate, aspartate, benzoate, benzenesulfonate, bisulfate, borate, butyrate, citrate, camphorate, camphersulfonate, cyclopentanepropionate, digluconate, dodecyl sulfate, ethane sulfonate, fumarate, glucoheptanoate, glycerophosphate, hemisulfate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulfate, 3-phenyl sulfonate, 3-phenylpropionate, phosphate, picrate, pivalate, propionate, salicylate, succinate, sulfate, sulfonate, tartrate, thiocyanate, toluene sulfonate such as tosylate, undecanoate, or the like.

Basic nitrogen-containing moieties can be quaternized with such agents as lower alkyl halides, such as methyl, ethyl, propyl, and butyl chloride, bromide and iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained.

Pharmaceutically acceptable basic addition salts include but are not limited to cations based on the alkaline and alkaline earth metals such as sodium, lithium, potassium, calcium, magnesium, aluminum salts and the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginine, lysine, or the like.

Compounds of the formula (I) can be present as tautomers. The present invention comprises all tautomeric forms. Furthermore, the present invention also comprises all stereoisomers of the compounds according to the invention, including its enantiomers and diastereomers. Individual stereoisomers of the compounds according to the invention can be substantially present pure of other isomers, in admixture thereof or as racemates or as selected stereoisomers.

As used herein the term "metabolite" refers to (i) a product of metabolism, including intermediate and products, (ii) any substance involved in metabolism (either as a product of metabolism or as necessary for metabolism), or (iii) any substance produced or used during metabolism. In particular it refers to the end product that remains after metabolism.

As used herein the term "prodrug" refers to (i) an inactive form of a drug that exerts its effects after metabolic processes within the body convert it to a usable or active form, or (ii) a substance that gives rise to a pharmacologically active metabolite, although not itself active (i.e. an inactive precursor).

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

As used herein the term "$C_{3-10}$ cycloalkyl" or "$C_{3-8}$ cycloalkyl" refers to mono- or polycyclic carbocyclic alkyl substituent or group having 3 to 10 or 3 to 8 ring atoms respectively, such as cyclopropyl, cyclobutyl, cyclopentyl, cyclohexyl, cycloheptyl, cyclobutenyl, cyclopentenyl, cyclopentadienyl, cyclohexenyl, cyclohexadienyl, cycloheptenyl, cycloheptadienyl, cycloheptatrienyl perhydrated naphthalene or indene, adamantyl or norbonanyl and the like.

The term "$C_{1-8}$ alkyl" as used herein alone or in combination with other terms such as in alkoxy refers to a $C_{1-8}$, preferably $C_{1-4}$ straight or branched alkyl/alkoxy group such as methyl, ethyl, propyl (iso-, n-), butyl (iso-, n-, sec-, tert-), pentyl, hexyl, methoxy, ethoxy, propoxy (iso-, n-), butoxy (iso-, n-, sec-, tert-), pentoxy, hexoxy; moreover, the term "$C_{1-8}$ alkyl" also includes an alkyl group which may contain oxygen in the chain and may be substituted with halogen to form an ether or halogenated ether group.

Any hydrogen atom, particularly in an alkyl, alkoxy or alkenyl group may be replaced by a fluorine atom.

The term "$C_{2-8}$ alkenyl" by itself or as part of another group refers to a straight or branched alkenyl group of 2 to 8 carbons, preferably 2 to 6 carbons, in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl.

The term "heterocyclyl" refers to monocyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperidinyl, pyridyl, pyrimidinyl, thiazolyl, indolyl, imidazolyl, oxadiazolyl, tetrazolyl, pyrazinyl, triazolyl, thiophenyl or furanyl.

The term "heteroaryl" refers to a mono- or bicyclic aromatic group with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl and benzimidazolyl.

In a further aspect the present invention provides pharmaceutical compositions comprising a thienopyrimidine compound of the present invention and optionally a pharmaceutically acceptable carrier.

The pharmaceutical composition according to the present invention may further comprise an additional therapeutic agent. Particularly preferred are compositions, wherein the additional therapeutic agent is selected from antidiabetics like insulin, long and short acting insulin analogues, sulfonylureas, biguanides, DPP-IV inhibitors, SGLT2 inhibitors, 11β-HSD inhibitors, glucokinase activators, AMPK activators, Glp-1 receptor agonists, GIP receptor agonists, DGAT inhibitors, PPARgamma agonists, PPARdelta agonists, and other antidiabetics derived from thiazolidinediones, lipid lowering agents such as statines, fibrates, ion exchange resins nicotinic acid derivatives, or HMG-CoA reductase inhibitors, cardiovascular therapeutics such as nitrates, antihypertensive such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites, or anti-obesity agents. Further preferred compositions are compositions wherein the additional therapeutic agent is selected from a histamine antagonist, a bradikinin antagonist, serotonin antagonist, leukotriene, an anti-asthmatic, an NSAID, an antipyretic, a corticosteroid, an antibiotic, an analgetic, a uricosuric agent, chemotherapeutic agent, an anti gout agent, a bronchodilator, a cyclooxygenase-2 inhibitor, a steroid, a 5-lipoxygenase inhibitor, an immunosuppressive agent, a leukotriene antagonist, a cytostatic agent, an antineoplastic agent, a mTor inhibitor, a Tyrosine kinase inhibitor, antibodies or fragments thereof against cytokines and soluble parts (fragments) of cytokine receptors.

More particularly preferred are compounds such as human NPH insulin, human lente or ultralente insulin, insulin Lispro, insulin Aspart, insulin Glulisine, insulin detemir or insulin Glargine, metformin, phenformin, acarbose, miglitol, voglibose, pioglitazone, rosiglizatone, rivoglitazone, aleglitazar, alogliptin, saxagliptin, sitagliptin, vildagliptin, exenatide, liraglutide, albiglutide, pramlintide, carbutamide, chlorpropamide, glibenclamide (glyburide), gliclazide, glimepiride, glipizide, gliquidone, tolazamide, tolbutamide, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, docetaxel, paclitaxel, carboplatin, cisplatin, oxaliplatin, BBR3464, satraplatin, busulfan, treosulfan, procarbazine, dacarbazine, temozolomide, chlorambucil, chlormethine, cyclophosphamide, ifosfamide, melphalan, bendamustine, uramustine, ThioTEPA, camptothecin, topotecan, irinotecan, rubitecan, etoposide, teniposide, cetuximab, panitumumab, trastuzumab, rituximab, tositumomab, alemtuzumab, bevacizumab, gemtuzumab, aminolevulinic acid, methyl aminolevulinate, porfimer sodium, verteporfin, axitinib, bosutinib, cediranib, dasatinib, erlotinib, gefitinib, imatinib, lapatinib, lestaurtinib, nilotinib, semaxanib, sorafenib, sunitinib, vandetanib, retinoids (alitretinoin, tretinoin), altretamine, amsacrine, anagrelide, arsenic trioxide, asparaginase (pegaspargase), bexarotene, bortezomib, denileukin diftitox, estramustine, ixabepilone, masoprocol, mitotane, testolactone, tipifarnib, abetimus, deforolimus, everolimus, gusperimus, pimecrolimus, sirolimus, tacrolimus, temsirolimus, antimetabolites such as cytarabin, fluorouracil, fluoroarabin, gemcitabin, tioguanin, capecitabin, combinations such as adriamycin/daunorubicin, cytosine arabinosid/cytarabine, 4-HC, or other phosphamides.

Other particularly preferred compounds are compounds such as clemastine, diphenhydramine, dimenhydrinate, promethazine, cetirizine, astemizole, levocabastine, loratidine, terfenadine, acetylsalicylic acid, sodoum salicylate, salsalate, diflunisal, salicylsalicylic acid, mesalazine, sulfasalazine, osalazine, acetaminophen, indomethacin, sulindac, etodolac, tolmetin, ketorolac, bethamethason, budesonide, chromoglycinic acid, dimeticone, simeticone, domperidone, metoclopramid, acemetacine, oxaceprol, ibuprofen, naproxen, ketoprofen, flubriprofen, fenoprofen, oxaprozin, mefenamic acid, meclofenamic acid, pheylbutazone, oxyphenbutazone, azapropazone, nimesulide, metamizole, leflunamide, eforicoxib, lonazolac, misoprostol, paracetamol, aceclofenac, valdecoxib, parecoxib, celecoxib, propyphenazon, codein, oxapozin, dapson, prednisone, prednisolon, triamcinolone, dexibuprofen, dexamethasone, flunisolide, albuterol, salmeterol, terbutalin, theophylline, caffeine, naproxen, glucosamine sulfate, etanercept, ketoprofen, adalimumab, hyaluronic acid, indometacine, proglumetacine dimaleate, hydroxychloroquine, chloroquine, infliximab, etofenamate, auranofin, gold, [$^{224}$Ra]radium chloride, tiaprofenic acid, dexketoprofen(trometamol), cloprednol, sodium aurothiomalate aurothioglucose, colchicine, allopurinol, probenecid, sulfinpyrazone, benzbromarone, carbamazepine, lornoxicam, fluorcortolon, diclofenac, efalizumab, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, or other phosphamides, penicillamine, a hyaluronic acid preparation, arteparon, glucosamine, MTX, soluble fragments of the TNF-receptor (such as etanercept (Enbrel)) and antibodies against TNF (such as infliximab (Remicade), natalizumab (Tysabri) and adalimumab (Humira)).

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds of the present invention may be administered orally, parenterally, such as bronchopulmonary, subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable excipients.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in Remington's Pharmaceutical Sciences, 15$^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or olageous solutions or emulsions for infusion, aqueous or olageous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

The amount of the compound of the present invention that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

In a further aspect of the invention the use of a thienopyrimidine compound of the present invention for the production of a pharmaceutical composition for inhibiting the activity of the kinase activity of Mnk1 or Mnk2 (Mnk2a, Mnk2b) or further variants thereof is provided, in particular for the prophylaxis or therapy of metabolic diseases, hematopoietic disorders, cancer and their consecutive complications and disorders. Whereby the prophylaxis and therapy of metabolic diseases of the carbohydrate and/or lipid metabolism is preferred.

Diseases of the invention that are influenced by the inhibition of the kinase activity of Mnk1 and/or Mnk2 (Mnk2a or Mnk2b) and/or further variants thereof include diseases related to the regulation of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/or sleep apnea and diseases related to reactive oxygen compounds (ROS defense) such as diabetes mellitus, neurodegenerative diseases and cancer.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus in a more preferred embodiment of this invention the use of a thienopyrimidine compound for the production of a pharmaceutical composition for the prophylaxis or therapy of metabolic diseases is provided.

In yet a further aspect of the invention the use of a thienopyrimidine compound of the invention for the production of a pharmaceutical composition for treating or preventing a cytokine mediated disorder such as an inflammatory disease is provided.

The pharmaceutical compositions of the invention are thus useful for the prophylaxis or therapy of inflammatory diseases, in particular chronic or acute inflammation, chronic inflammatory arthritis, rheumatoid arthritis, psoriatic arthritis, osteoarthritis, juvenile rheumatoid arthritis, gouty arthritis; psoriasis, erythrodermic psoriasis, pustular psoriasis, inflammatory bowel disease, Crohn's disease and related conditions, ulcerative colitis, colitis, diverticulitis, nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, chronic obstructive disease (COPD), inflammatory lung disease, allergic rhinitis, endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, dermatitis, endomyometritis, myometritis, metritis, cervicitis, endocervicitis, exocervicitis, parametritis, tuberculosis, vaginitis, vulvitis, silicosis, sarcoidosis, pneumoconiosis, inflammatory polyarthropathies, psoriatric arthropathies, intestinal fibrosis, bronchiectasis and enteropathic arthropathies.

As already stated above, the compositions of the present invention are particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Thus, in a more preferred embodiment of this invention the use of a thienopyrimidine compound for the production of a pharmaceutical composition for the prophylaxis or therapy of inflammatory diseases selected from chronic or acute inflammation, chronic inflammatory arthritis, rheumatoid arthritis, psoriasis, COPD, inflammatory bowel disease, septic shock Crohn's disease, ulcerative colitis, multiple sclerosis and asthma is provided.

In yet a further aspect of the invention the use of a thienopyrimidine compound of the invention for the production of a pharmaceutical composition for treating or preventing cancer, viral diseases or neurodegenerative diseases is provided.

For the purpose of the present invention, a therapeutically effective dosage will generally be from about 1 to 2000 mg/day, preferably from about 10 to about 1000 mg/day, and most preferably from about 10 to about 500 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician.

EXAMPLE 2

Kinase Fluorescence Polarization Assays

Assay Principle:
Inhibitory potency of compounds against Mnk1, Mnk2a and other kinases was assessed with assays based on a format known to those skilled in the art as the indirect (competitive) fluorescence polarization. The assay detection system comprises a small fluorophore-labeled phospho-peptide (termed ligand) bound to a phospho-specific antibody. The product generated by the kinase reaction competes with the ligand for antibody binding. Based on the larger molecular volume of the bound ligand, which results in a lower rotation rate in solution, its emitted light has a higher degree of polarization than the one from the free ligand.

Description of the Specific Homogenous Kinase Assay

EXAMPLE 2A

Mnk1 and Mnk2a In Vitro Kinase Assay

As a source of enzyme, human Mnk1 and human Mnk2a were expressed as GST fusion proteins in *E. coli*, purified to >80% homogeneity by glutathione affinity chromatography and activated in vitro with pre-activated ERK2. In brief, the open reading frames of human Mnk1 and Mnk2a were amplified from cDNA using the forward/reverse primer pairs

```
SEQ ID NO: 1    5'TTTAGGATCCGTATCTTCTCAAAAGTTGG/

SEQ ID NO: 2    5' CTGGGTCGACTCAGAGTGCTGTGGGCGG
and

SEQ ID NO: 3    5'ACAGGGATCCGTGCAGAAGAAACCAGCC/

SEQ ID NO: 4    5'GATGGTCGACTCAGGCGTGGTCTCCCACC
```

(utilized restriction sites underlined), respectively, and cloned into the BamHI and SalI sites of the vector pGEX-4T1 (Amersham, Sweden, cat. no. 27-4580-01). These constructs allow prokaryotic expression of Mnk1 or Mnk2a as fusion protein with a N-terminal glutathione S-transferase (GST) tag, referred to as GST-Mnk1 or GST-Mnk2a. The following expression and purification procedure was identical for GST-Mnk1 and GST-Mnk2a, referring in general to GST-Mnk, when not distinguishing between the two isoforms. Expression of GST-Mnk was in *E. coli* BL21 (Merck Biosciences, Germany, cat. no. 69449). Cells were grown in LB-Bouillon (Merck, Germany, cat. no. 1.10285) supplemented with 100 µg/ml ampicillin (Sigma, Germany, cat. no. A9518) at 37° C. When the culture had reached a density corresponding to an $A_{600}$ of 0.8, an equal volume of ice cold LB/ampicillin was added, the culture transferred to 25° C. and induced for 4 h with 1 mM isopropyl thiogalactoside (IPTG, Roth, Germany, cat. no. 2316.4). Cells harvested by centrifugation were resuspended in 10 ml lysis buffer (50 mM tris(hydroxymethyl)aminomethane hydrochloride (Tris/HCl, Sigma, Germany, cat. no. T5941) pH 7.5, 300 mM sodium chloride (NaCl, Sigma, Germany, cat. no. S7653), 5% (w/v) glycerol (Sigma, Germany, cat. no. G5516), 3 mM DTT dithiotreitol (DTT, Sigma, Germany, cat. no. D9779)) per gram wet weight cell pellet. Lysates were prepared by disruption of cells with a sonifier and subsequent clearing by centrifugation at 38000 g for 45 min at 4° C.

The lysate was applied to a GSTPrep FF 16/10 column (Amersham, Sweden, cat. no. 17-5234-01) equilibrated with lysis buffer. Removal of unbound material was with 3 column volumes (CV) lysis buffer. Elution was with 2 CV of elution buffer (50 mM Tris/HCl pH 7.5, 300 mM NaCl, 5% (w/v) glycerol, 20 mM glutathione (Sigma, Germany, cat. no. G4251)). Peak fractions were pooled and the protein transferred into storage buffer (50 mM Tris/HCl pH 7.5, 200 mM NaCl, 0.1 mM ethylene glycol-bis(2-aminoethylether)-N,N,N',N'-tetraacetic acid (EGTA, Aldrich, Germany, cat. no. 23, 453-2), 1 mM DTT, 10% (w/v) glycerol, 0.5 M sucrose (Sigma, Germany, cat. no. $SO_{389}$) by gel filtration on a PD10 desalting column (Amersham, Sweden, cat. no. 17-0851-01). Aliquots were shock frozen in liquid nitrogen and stored at −80° C.

Activation of Mnk1 and Mnk2a was at a concentration of 2.5 µM of either purified GST-Mnk1 or GST-Mnk2a by incubation with 150 nM pre-activated NHis-ERK2 (see ERK2 assay for preparation) and 50 µM adenosine triphosphate (ATP, Sigma, cat. no. A2699) in a buffer comprising 20 mM N-(2-hydroxyethyl)piperazine-N'-(2-ethanesulfonic acid) (HEPES, Fluka, Germany, cat. no 54459)/potassium hydroxide (KOH, Roth, Germany, cat. no 6751.1) pH 7.4, 10 mM magnesium chloride ($MgCl_2$, Sigma, Germany, cat. no. M2670), 0.25 mM DTT, 0.05% (w/v) polyoxyethylene 20 stearylether (Brij 78, Sigma, Germany, cat. no. P4019) (HMDB buffer) for 45 min at 30° C. After the incubation, the preparation was aliquoted into single-use samples, shock frozen in liquid nitrogen, stored at −80° C. and utilized for Mnk1 or Mnk2a kinase assays as detailed below. The presence of activating kinase has been tested to not interfere with the Mnk activity assay.

SUBSTRATE: A carboxy-terminal amidated 12 mer peptide with the sequence SEQ ID NO: 5 TATKSGSTTKNR, derived from the amino acid sequence around serine 209 of the eukaryotic translation initiation factor 4E (eIF4E) has been synthesized and purified by high performance liquid chromatography (HPLC) to >95% (Thermo, Germany). The serine residue phosphorylated by Mnk kinases is underlined.

LIGAND: The peptide TATKSG-pS-TTKNR (SEQ ID NO: 6), containing an amidated carboxy-terminus and conjugated at the amino-terminus with the oxazine derived fluorophore depicted below was synthesized and used as ligand.

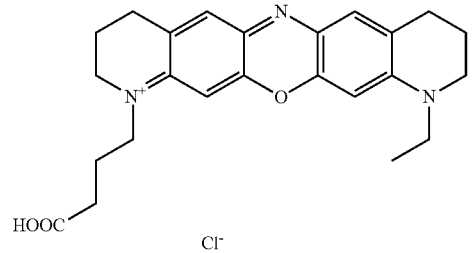 [SMILES: CCN1CCCc2cc3c(cc21)Oc1cc2c(cc1=N3)CCC[N+]=2CCCC(=O)O ; [Cl-]]

ANTIBODY: SPF New Zealand White. Rabbits have been immunized according to standard protocols with the peptide NH2-CTATKSG-pS-TTKNR—CONH2 (SEQ ID NO: 7), coupled to keyhole limpet hemocyanin (KLH). The immune globulin G (IgG) fraction was purified from serum of boosted animals by techniques known in the art. In brief, serum was subjected to protein A affinity chromatography. Eluted material was precipitated at 50% cold saturated ammonium sulfate, pellets dissolved and desalted. The resulting material was appropriate for use in below described assay without further antigen-specific purification.

ASSAY SETUP: Inhibition of kinase activity of Mnk1 and Mnk2a was assessed with the same assay system, using pre-activated GST-Mnk1 or GST-Mnk2a, respectively. The kinase reaction contains 30 µM substrate peptide, 20 µM ATP, 60 nM ligand and one of either 25 nM pre-activated Mnk1 or 2.5 nM pre-activated Mnk2a. The reaction buffer conditions are 16 mM HEPES/KOH pH 7.4, 8 mM $MgCl_2$, 0.4 mM DTT, 0.08% (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at 30° C. for 40 min. The kinase reaction is terminated by addition of 0.67 reaction volumes of 1 μM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylene-sorbitan monolaureate (Tween 20, Sigma, Germany, cat. no. P7949). After 1 h equilibration time at room temperature, samples are subjected to fluorescence polarization measurement. The fluorescence polarization readout was generated on an Analyst AD multimode reader (Molecular Devices, Sunnyvale, Calif., USA) equipped with a DLRP650 dichroic mirror (Omega Opticals, Brattleboro, Vt., USA, cat. no. XF2035), a 630AF50 band pass filter (Omega Opticals, Brattleboro, Vt., USA, cat. no. XF1069) on the excitation and a 695AF55 band pass filter on the emission side (Omega Opticals, Brattleboro, Vt., USA, cat. no. XF3076).

The activity of Mnk proteins can be assayed also by other in vitro kinase assay formats. For example, suitable kinase assays have been described in the literature in Knauf et al., Mol Cell Biol. 2001 August; 21(16):5500-11 or in Scheper et al., Mol Cell Biol. 2001 February; 21(3):743-54. In general, Mnk kinase assays can be performed such that a Mnk substrate such as a protein or a peptide, which may or may not include modifications as further described below, or others are phosphorylated by Mnk proteins having enzymatic activity in vitro. The activity of a candidate agent can then be determined via its ability to decrease the enzymatic activity of the Mnk protein.

The kinase activity may be detected by change of the chemical, physical or immunological properties of the substrate due to phosphorylation.

In one example, the kinase substrate may have features, designed or endogenous, to facilitate its binding or detection in order to generate a signal that is suitable for the analysis of the substrates phosphorylation status. These features may be, but are not limited to, a biotin molecule or derivative thereof, a glutathione-S-transferase moiety, a moiety of six or more consecutive histidine residues, an amino acid sequence or hapten to function as an epitope tag, a fluorochrome, an enzyme or enzyme fragment. The kinase substrate may be linked to these or other features with a molecular spacer arm to avoid steric hindrance.

In another example the kinase substrate may be labelled with a fluorophore. The binding of the reagent to the labelled substrate in solution may be followed by the technique of fluorescence polarization as it is described in the literature. In a variation of this example, a fluorescent tracer molecule may compete with the substrate for the analyte to detect kinase activity by a technique which is know to those skilled in the art as indirect fluorescence polarization.

In yet another example, radioactive gamma-ATP is used in the kinase reaction, and the effect of the test agent on the incorporation of radioactive phosphate in the test substrate is determined relative to control conditions.

It has been shown that the compounds of the invention exhibit $IC_{50}$ low values in in vitro biological screening assays as described in example 2a for inhibition of Mnk 1 and/or Mnk 2 kinase activity. The following table contains the test results for exemplary compounds.

| Example | MNK2 $IC_{50}$ [nM] |
|---|---|
| 1 | 490 |
| 2 | 470 |
| 3 | 120 |
| 4 | 110 |
| 5 | 110 |
| 6 | 120 |
| 7 | 4400 |
| 8 | 80 |
| 9 | 180 |
| 10 | 10 |
| 11 | 39 |
| 12 | 61 |
| 13 | 59 |
| 14 | 40 |
| 15 | 31 |
| 16 | 30 |
| 17 | 30 |
| 18 | 58 |
| 19 | 47 |
| 20 | 67 |
| 21 | 76 |
| 22 | 26 |
| 23 | 48 |
| 24 | 62 |
| 25 | 81 |
| 26 | 60 |
| 27 | 48 |
| 28 | 65 |
| 29 | 53 |
| 30 | 34 |
| 31 | 43 |
| 32 | 55 |
| 33 | 56 |
| 34 | 35 |
| 35 | 53 |
| 36 | 790 |
| 37 | 68 |
| 38 | 100 |
| 39 | 58 |
| 40 | 35 |
| 41 | 31 |
| 42 | 41 |
| 43 | 56 |
| 44 | 64 |
| 45 | 36 |
| 46 | 15 |
| 47 | 51 |
| 48 | 75 |
| 49 | 99 |
| 50 | 72 |
| 51 | 160 |
| 52 | 130 |
| 53 | 46 |
| 54 | 76 |
| 55 | 51 |
| 56 | 49 |
| 57 | 43 |
| 58 | 64 |
| 59 | 48 |
| 60 | 64 |
| 61 | 38 |
| 62 | 110 |
| 63 | 43 |
| 64 | 21 |
| 65 | 190 |
| 66 | 10 |
| 67 | 46 |
| 68 | 80 |
| 69 | 19 |
| 70 | — |
| 71 | 89 |
| 72 | 9 |
| 73 | 5 |
| 74 | 3 |
| 75 | 22 |
| 76 | 43 |
| 77 | 300 |
| 78 | 28 |
| 79 | 12 |
| 80 | 20 |

-continued

| Example | MNK2 IC$_{50}$ [nM] |
|---|---|
| 81 | 6 |
| 82 | 8 |
| 83 | 120 |
| 84 | 2 |
| 85 | 7 |
| 86 | 6 |
| 87 | 12 |
| 88 | 22 |
| 89 | 8 |
| 90 | 14 |
| 91 | 51 |
| 92 | 45 |
| 93 | 19 |
| 94 | 300 |
| 95 | 460 |
| 96 | 1100 |
| 97 | 58 |
| 98 | 94 |
| 99 | 6 |
| 100 | 5 |
| 101 | 11 |
| 102 | 32 |
| 103 | 26 |
| 104 | 12 |
| 105 | 20 |
| 106 | 25 |
| 107 | 26 |
| 108 | 26 |
| 109 | 9 |
| 110 | 21 |
| 111 | 22 |
| 112 | 21 |
| 113 | 420 |
| 114 | 550 |
| 115 | 100 |
| 116 | 22 |
| 117 | 22 |
| 118 | 29 |
| 119 | 26 |
| 120 | 22 |
| 121 | 33 |
| 122 | 48 |
| 123 | 38 |
| 124 | 31 |
| 125 | 25 |
| 126 | 26 |
| 127 | 17 |
| 128 | 41 |
| 129 | 32 |
| 130 | 36 |
| 131 | 35 |
| 132 | — |
| 133 | 12 |
| 134 | 16 |
| 135 | 43 |
| 136 | 71 |
| 137 | 84 |
| 138 | 70 |
| 139 | 35 |
| 140 | 92 |
| 141 | 53 |
| 142 | 38 |
| 143 | 41 |
| 144 | 47 |
| 145 | 42 |
| 146 | 70 |
| 147 | 15 |
| 148 | 68 |
| 149 | 37 |
| 150 | 70 |
| 151 | 57 |
| 152 | 40 |
| 153 | 113 |
| 154 | 215 |
| 155 | 38 |
| 156 | 50 |
| 157 | 65 |
| 158 | 42 |

-continued

| Example | MNK2 IC$_{50}$ [nM] |
|---|---|
| 159 | 44 |
| 160 | 59 |
| 161 | 56 |
| 162 | — |
| 163 | 60 |
| 164 | 27 |
| 165 | 39 |
| 166 | 37 |
| 167 | 43 |
| 168 | 23 |
| 169 | 38 |
| 170 | 125 |
| 171 | 41 |
| 172 | 43 |
| 173 | 39 |
| 174 | 60 |
| 175 | 50 |
| 176 | 105 |
| 177 | 67 |
| 178 | 047 |
| 179 | 166 |
| 180 | 33 |
| 181 | 21 |
| 182 | 30 |
| 183 | 51 |
| 184 | 22 |
| 185 | — |
| 186 | 30 |
| 187 | 27 |
| 188 | — |
| 189 | 25 |
| 190 | 66 |
| 191 | 47 |
| 192 | 42 |
| 193 | 33 |
| 194 | 63 |
| 195 | 67 |
| 196 | 34 |
| 197 | 28 |
| 198 | 29 |
| 199 | 30 |
| 200 | 69 |
| 201 | 31 |
| 202 | 70 |
| 203 | 51 |
| 204 | 66 |
| 205 | — |
| 206 | 43 |
| 207 | 41 |
| 208 | 59 |
| 209 | 69 |
| 210 | 60 |
| 211 | 29 |
| 212 | 31 |
| 213 | 21 |
| 214 | 76 |
| 215 | 30 |
| 216 | 54 |
| 217 | 49 |
| 218 | 33 |
| 219 | 33 |
| 220 | 42 |
| 221 | 38 |
| 222 | 51 |
| 223 | 2289 |
| 224 | 63 |
| 225 | 53 |
| 226 | 55 |
| 227 | 47 |
| 228 | 35 |
| 229 | 27 |
| 230 | 49 |
| 231 | 18 |
| 232 | 45 |
| 233 | 27 |
| 234 | 90 |
| 235 | 12 |
| 236 | 33 |

| Example | MNK2 IC$_{50}$ [nM] |
|---|---|
| 237 | 36 |
| 238 | 32 |
| 239 | 41 |
| 240 | 101 |
| 241 | 36 |
| 242 | 46 |
| 243 | 49 |
| 244 | 19 |
| 245 | 39 |
| 246 | 18 |
| 247 | 44 |
| 248 | 41 |
| 249 | 21 |
| 250 | — |
| 251 | 28 |
| 252 | 8417 |
| 253 | 34 |
| 254 | 42 |
| 255 | 22 |
| 256 | 37 |
| 257 | 40 |
| 258 | 20 |
| 259 | 38 |
| 260 | 39 |
| 261 | 46 |
| 262 | 53 |
| 263 | 115 |
| 264 | 23 |
| 265 | 34 |
| 266 | 25 |
| 267 | 36 |
| 268 | 100 |
| 269 | 34 |
| 270 | 298 |
| 271 | 40 |
| 272 | 40 |
| 273 | 49 |
| 274 | 19 |
| 275 | 38 |
| 276 | 53 |
| 277 | 59 |
| 278 | 79 |
| 279 | 77 |
| 280 | 40 |
| 281 | 42 |
| 282 | 53 |

HPLC Methods

Method A

Method Amsistandard:

ZQ 2000MS; Waters 2996 PDA (210-600 nm); Waters 2525 pump; Waters 515 make up pump; Waters 2767 injector/fraction collector, Waters columns and fluidics organizer (CFO)

mobile phases:

A: water with 0.20% trifluoroacetic acid

B: Methanol

| time in min | % A | % B | flow rate in ml/min |
|---|---|---|---|
| 0.00 | 72 | 18 | 55.00 |
| 2.00 | 72 | 18 | 55.00 |
| 2.50 | 62 | 38 | 55.00 |
| 9.50 | 18 | 72 | 55.00 |
| 10.00 | 0 | 100 | 55.00 |
| 12.00 | 0 | 100 | 55.00 |
| 12.50 | 0 | 100 | 0 |

Stationary phase:

X-terra MS C18; 30×100 mm*5 μm

Temperature 25° C.

Method B

Method Amslpolar1 Basic:

ZQ 2000MS; Waters 2996 PDA (210-600 nm); Waters 2525 pump; Waters 515 make up pump; Waters 2767 injector/fraction collector, Waters columns and fluidics organizer (CFO)

mobile phases:

A: water with 0.20% Triethylamine

B: Methanol

| time in min | % A | % B | flow rate in ml/min |
|---|---|---|---|
| 0.00 | 85 | 15 | 55.00 |
| 2.00 | 85 | 15 | 55.00 |
| 2.50 | 75 | 25 | 55.00 |
| 9.50 | 31 | 69 | 55.00 |
| 10.00 | 0 | 100 | 55.00 |
| 12.00 | 0 | 100 | 55.00 |
| 12.50 | 0 | 100 | 0 |

Stationary phase:

X-terra MS C18; 30×100 mm*5 μm

Temperature 25° C.

Method C

Method A_ALCMS2_10

Waters ZQ 2000; Waters 1515 Pumpe; Waters PDA 996 Detektor; Waters 2747 Injektor DAD 200-420 nm mobile phases:

A: water with 0.10% formic acid

B: acetonitrile with 0.10% formic acid

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

Stationary phase:

X-terra MS C18; 4.6×30 mm*2.5 μm

Method D

Method AC1

(A_ALCMS1_1 und A_ALCMS1_3/A_ALCMS2_1 und A_ALCMS2_3)

Waters ZQ 2000; Waters 1515 Pumpe; Waters PDA 996 Detektor; Waters 2747 Injektor DAD 210-420 nm mobile phases:

A: water with 0.10% formic acid

B: acetonitrile with 0.10% formic acid

| time in min | % A | % B | flow rate in ml/min |
|---|---|---|---|
| 0.00 | 95 | 5 | 1.00 |
| 0.10 | 95 | 5 | 1.00 |
| 3.10 | 2 | 98 | 1.00 |
| 4.50 | 2 | 98 | 1.00 |
| 5.00 | 95 | 5 | 1.00 |

Method E
Method A_ALCMS2_9
(pos/neg switch method)
Waters ZQ 2000; Waters 1515 Pumpe; Waters PDA 996 Detektor; Waters 2747 Injektor
DAD 200-420 nm
mobile phases:
A: water with 0.10% formic acid
B: acetonitrile with 0.10% formic acid

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

Stationary phase:
X-terra MS C18; 4.6×30 mm*2.5 µm
Method F
RP-HPLC MS analyses have been performed on a Waters ZQ2000 mass spectrometer,
HP1100 HPLC+DAD (Wavelength range (nm): 210 to 500) and 2700 AS
Mobile Phases:
A: Water with 0.1% TFA
B: MeOH

| Time in min | % A | % B | Flowrate in ml/min |
|---|---|---|---|
| 0.00 | 95 | 5 | 1.50 |
| 1.30 | 0 | 100 | 1.50 |
| 3.00 | 0 | 100 | 1.50 |
| 3.40 | 95 | 5 | 2.00 |

Stationary phase: Waters, Sunfire, C18, 3.5 µm, 4.6×50 mm.
Column temp: constant at 40° C.
Method G
Waters ZQ2000; Waters 1515 Pumpe, Waters PDA 996 Detektor, Waters 2747 Injektor
Mobile Phase: A water+0.1% formic acid
    B acetonitrile+0.1% formic acid
Gradient:

| time in min | % A | % B | Flow rate in mL/min |
|---|---|---|---|
| 0.00 | 95.0 | 5.0 | 1.00 |
| 0.10 | 95.0 | 5.0 | 1.00 |
| 3.10 | 2.00 | 98.00 | 1.00 |
| 4.50 | 2.00 | 98.00 | 1.00 |
| 5.00 | 95.0 | 5.0 | 1.00 |

Stationary phase: X-Terra™ MS C18 2.5 µm 4.6 mm×30 mm
Column temperature approximately 25° C.
Diode array detection wavelength: 210-420 nm
Mass: m/z 80 bis 800
Method H
RP-HPLC MS analyses have been performed on a Waters SQD mass spectrometer,
HP1100 HPLC+DAD (Wavelength range (nm): 210 to 500)
Mobile Phases:
A: Water with 0.032% NH4OH
B: MeOH
Gradient

| Flow | Flowrate in ml/min |
|---|---|
| 0.00: 95% A; | 1.0 |
| 2.00: 0% A; | 1.0 |
| 2.50: 0% A; | 1.0 |
| 2.60: 95% A | 1.0 |

Stationary phase: Waters, XBridge, C18, 1.7 µm; 2.1×50 mm.
Column temp: constant at 60° C.
Method I
RP-HPLC MS analyses have been performed on a Waters ZQ2000 mass spectrometer,
Mobile Phases:
A: water with 0.1% TFA
B: acetonitrile with 0.08% TFA
Gradient

| Time in min | % A | % B | Flowrate in ml/min |
|---|---|---|---|
| 0.00: 95% A; | | | 1.5 |
| 2.00: 0% A; | | | 1.5 |
| 2.50: 0% A; | | | 1.5 |
| 2.60: 95% A | | | 1.5 |

Stationary phase: Waters, Sunfire, C18, 3.5 µm, 4.6×50 mm.
Column temp: constant at 40° C.
Method J
RP-HPLC MS analyses have been performed on a Waters ZQ2000 mass spectrometer,
Mobile Phases:
A: water with 0.1% TFA
B: methanol
Gradient

| Time in min | % A | % B | Flowrate in ml/min |
|---|---|---|---|
| 0.00: 95% A; | | | 1.5 |
| 1.30: 0% A; | | | 1.5 |
| 2.50: 0% A; | | | 1.5 |
| 2.60: 95% A | | | 1.5 |

Stationary phase: Waters, Sunfire, C18, 3.5 µm, 4.6×50 mm.
Column temp: constant at 40° C.
Method K
RP-HPLC MS analyses have been performed on a Waters ZQ2000 mass spectrometer,
Mobile Phases:
A: water with 0.1% TFA
B: methanol
Gradient

| Time in min | % A | % B | Flowrate in ml/min |
|---|---|---|---|
| 0.00: 95% A; | | | 1.5 |
| 1.30: 0% A; | | | 1.5 |
| 3.00: 0% A; | | | 1.5 |
| 3.40: 95% A | | | 1.5 |

Stationary phase: Waters, Sunfire, C18, 3.5 μm, 4.6×50 mm.
Column temp: constant at 40° C.
Method L
RP-HPLC MS analyses have been performed on a Waters ZQ2000 mass spectrometer,
Mobile Phases:
A: water with 0.1% TFA
B: methanol
Gradient

| Time in min | % A | % B | Flowrate in ml/min |
|---|---|---|---|
| 0.00: 80% A; | | | 2 |
| 1.70: 0% A; | | | 2 |
| 2.50: 0% A; | | | 2 |
| 2.60: 95% A | | | 2 |

Stationary phase: Waters, Sunfire, C18, 3.5 μm, 4.6×50 mm.
Column temp: constant at 60° C.
Method M
RP-HPLC MS analyses have been performed on a Waters ZQ2000 mass spectrometer,
Mobile Phases:
A: water with 0.1% TFA
B: methanol
Gradient

| Time in min | % A | % B | Flowrate in ml/min |
|---|---|---|---|
| 0.00: 80% A; | | | 2 |
| 1.70: 0% A; | | | 2 |
| 2.50: 0% A; | | | 2 |
| 2.60: 80% A | | | 2 |

Stationary phase: Waters, Sunfire, C18, 3.5 μm, 4.6×50 mm.
Column temp: constant at 60° C.
Method X:
Column: Ascentis Express, C18, 2.1×50 mm, 2.7 μm
Solvents: A % H$_2$O containing 0.1% TFA; B % acetonitrile containing 0.1% TFA
Gradient:

| Time | A % | B % | Flow in ml/min |
|---|---|---|---|
| 0.00 | 95.0 | 5.0 | 1.050 |
| 1.00 | 5.0 | 95.0 | 1.050 |
| 1.25 | 5.0 | 95.0 | 1.050 |
| 1.30 | 95.0 | 5.0 | 1.050 |

Column Temperature (° C.) 65.0
Abbreviations:
HATU: (2-(7-aza-1H-benzotriazole-1-yl)-1,1,3,3-tetramethyluronium hexafluorophosphate)
TBTU: 2-(1H-Benzotriazol-1-yl)-1,1,3,3-tetramethyluroniumtetrafluorborat
THF: tetrahydrofuran
EtOH: ethanol
MeOH: methanol
DCM: methylene chloride
DMF: N,N-dimethylformamide
EtOAc: ethyl acetate
HCl: hydrochloric acid
t-BuOH: tert.butanol
DTAD: Di-ter-butyl azodicarboxylate
DEAD: diethyl azodicarboxylate
DIAD: diisopropyl azodicarboxylate
LiHMDS: lithium hexymethyldisilazane
DIPEA: diisopropylethyl amine
EDC: 1-ethyl-3-(3-dimethylaminopropyl)carbodiimid
CDI: Carbonyldiimidazol
TFA: trifluoro acetic acid
brine: saturated sodium chloride solution in water
rt: room temperature
min: minute
TLC: thin layer chromatographie Intermediates Intermediate I (S)-tert-butyl 3-(2-amino-5-fluorophenoxy)piperidine-1-carboxylate

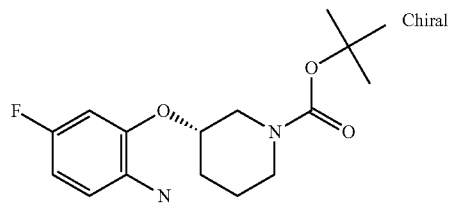 [SMILES: CC(C)(C)OC(=O)N1CCC[C@H](Oc2cc(F)ccc2N)C1]

I.1. (S)-tert-butyl 3-(5-fluoro-2-nitrophenoxy)piperidine-1-carboxylate

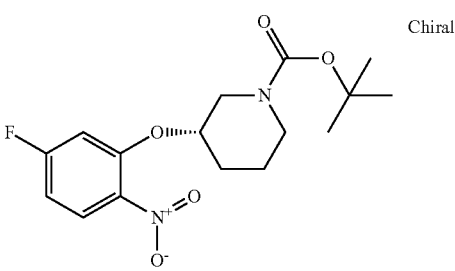 [SMILES: CC(C)(C)OC(=O)N1CCC[C@H](Oc2cc(F)ccc2[N+](=O)[O-])C1]

LiHMDS 1M solution in THF (6.4 ml) was added into a solution of (S)-1-Boc-3-hydroxypiperidine (1.3 g) in anhydrous THF (20.0 ml). The reaction was stirred at 0° C. for 0.5 h. Then 2,4-difluoro-1-nitro-benzene (703 μl) was added in a single portion. The reaction was allowed to warm to room temperature overnight when TLC indicated the consumption of the starting material. The reaction was quenched by addition of sat NH4Cl (5.0 ml) and diluted with EtOAc (100.0 ml). The organic layer was washed with sat. NH4Cl (50.0 ml) and the aqueous back extracted with EtOAc. The combined organic phases were washed with brine, dried, filtered and concentrated in vacuo. The residue was purified by chromatography to give the intended product.
Yield: 1.78 g I.2: (S)-tert-butyl 3-(2-amino-5-fluorophenoxy)piperidine-1-carboxylate

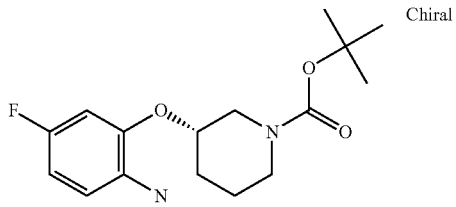 [SMILES: CC(C)(C)OC(=O)N1CCC[C@H](Oc2cc(F)ccc2N)C1]

To a solution of (S)-tert-butyl 3-(5-fluoro-2-nitrophenoxy)piperidine-1-carboxylate (6.41 g) in MeOH (70.0 ml) was added palladium on charcoal (600.0 mg), the mixture hydrogenated at room temperature and 50 psi. The catalyst was filtered off and the filtrate was concentrated under reduced pressure. The residue was purified by silica chromatography to give the desired product.

Yield: 1.45 g
ESI mass spectrum: m/z=311 (M+H)$^+$

Intermediate II (R)-tert-butyl 3-(2-amino-5-fluorophenoxy)piperidine-1-carboxylate

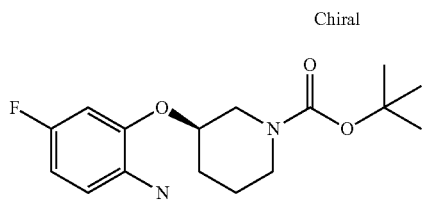 [SMILES: CC(C)(C)OC(=O)N1CCC[C@@H](Oc2cc(F)ccc2N)C1]

II.1. (R)-tert-butyl 3-(5-fluoro-2-nitrophenoxy)piperidine-1-carboxylate

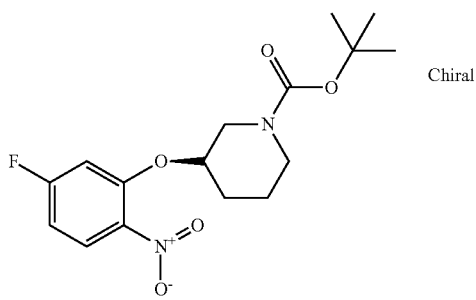

DTAD (1.140 g) was added into a solution of 5-fluoro-2-nitro-phenol (0.650 g), (S)-1-Boc-3-hydroxypiperine (1.0 g) and triphylphosphine (1.34 g) in anhydrous dichloromethane (10.0 ml) at 0° C. The reaction was allowed to warm to room temperature. The reaction mixture was concentrated in vacuo and the residue was purified by chromatography to give the desired product.

Yield: 1.25 g

II.2: (R)-tert-butyl 3-(2-amino-5-fluorophenoxy)piperidine-1-carboxylate

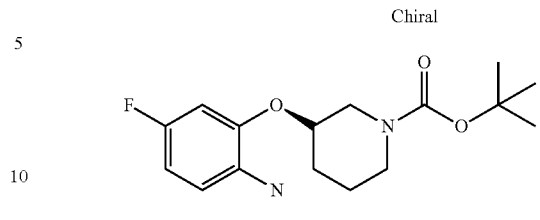

Amoniumformiate (1.0 g) was added into a suspension of (R)-tert-butyl 3-(5-fluoro-2-nitrophenoxy)piperidine-1-carboxylate and palladium on charcoal (125.0 mg) in anhydrous MeOH (10.0 ml) at room temperature. The reaction was stirred at room temperature overnight when LCMS analysis indicated consumption of the starting material. The solution was filtered through celite and washed with MeOH. The filtrate was concentrated in vacuo. The residue was triturated with diethylether to remove the ammoniumformiate residues. The solution was filtered and concentrated in vacuo. The residue was purified by chromatography.

Yield: 0.33 g

Intermediate III (2S,4S)-tert-butyl 4-(2-amino-5-fluorophenoxy)-2-(hydroxymethyl)pyrrolidine-1-carboxylate

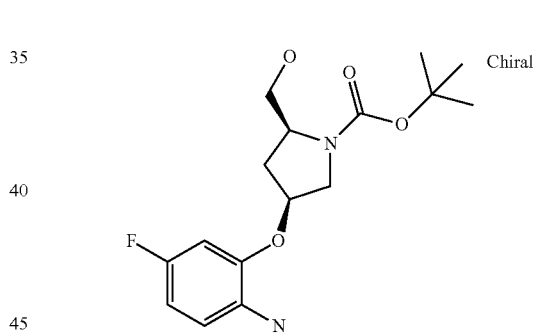

III.1 (2S,4S)-1-tert-butyl 2-methyl 4-(5-fluoro-2-nitrophenoxy)pyrrolidine-1,2-dicarboxylate

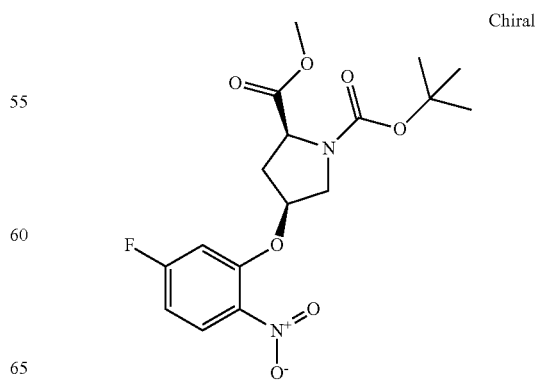

Diethylazodicarboxylate (1.76 ml) was added dropwise to a solution of N-Boc-trans-4-hydroxy-L-proline methyl ester (2.74 g), 5-fluoro-2-nitrophenol (1.47 g) and triphenylphosphine (2.93 g) in dichlormethane under cooling at 0° C. The coolant was removed after 20 min and the reaction mixture was stirred at room temperature over the weekend. The solvent was evaporated and the residue war purified by chromatography to give the desired product.

Yield: 1.25 g

III.2. (2S,4S)-1-tert-butyl 2-methyl 4-(2-amino-5-fluorophenoxy)pyrrolidine-1,2-dicarboxylate

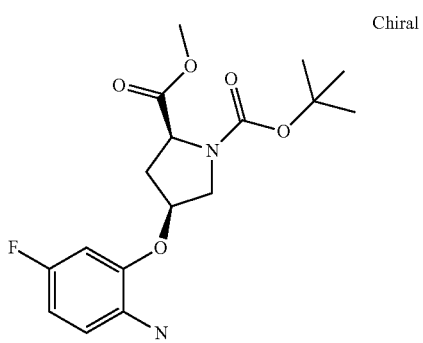 [SMILES: COC(=O)[C@@H]1C[C@H](Oc2cc(F)ccc2N)CN1C(=O)OC(C)(C)C]

Prepared analogously to example II.2 from (2S,4S)-1-tert-butyl 2-methyl 4-(5-fluoro-2-nitrophenoxy)pyrrolidine-1,2-dicarboxylate Yield: 2.52 g

III.3. (2S,4S)-tert-butyl 4-(2-amino-5-fluorophenoxy)-2-(hydroxymethyl)pyrrolidine-1-carboxylate

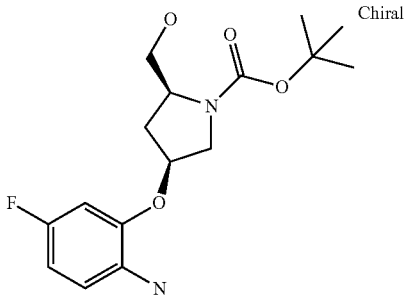 [SMILES: CC(C)(C)OC(=O)N1C[C@@H](Oc2cc(F)ccc2N)C[C@H]1CO]

Lithium aluminium hydride (540.0 mg) added to a cooled (0-4° C.) solution of (2S,4S)-1-tert butyl 2-methyl 4-(2-amino-5-fluorophenoxy)pyrrolidine-1,2-dicarboxylate (3.36 g) in THF (30.0 ml). The reaction mixture was stirred at this temperature for 4 h. After this time the mixture was quenched with water (0.54 ml), NaOH (2M; 0.54 ml) and water (3×0.54 ml). The mixture was stirred for 1.5 h, then diluted with EtOAc and MgSO4 was added. The suspension was filtered through celite and the filtrate evaporated. The residue was purified by chromatography.

Yield: 2.69 g

Intermediate IV (S)-tert-butyl 3-(2-amino-5-fluorophenoxy)pyrrolidine-1-carboxylate

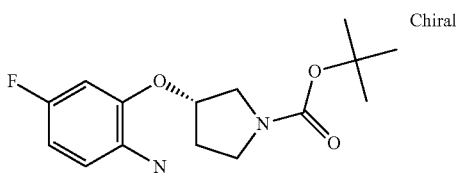 [SMILES: CC(C)(C)OC(=O)N1CC[C@H](Oc2cc(F)ccc2N)C1]

IV.1. (S)-tert-butyl 3-(5-fluoro-2-nitrophenoxy)pyrrolidine-1-carboxylate

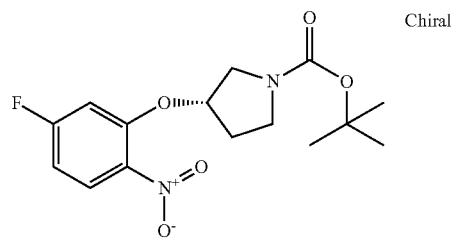 [SMILES: CC(C)(C)OC(=O)N1CC[C@H](Oc2cc(F)ccc2[N+](=O)[O-])C1]

Prepared analogously to example I.1 from (S)-(+)-N-Boc-3-hydroxypyrrolidine

Yield: 0.435 g

IV.2. (S)-tert-butyl 3-(2-amino-5-fluorophenoxy)pyrrolidine-1-carboxylate

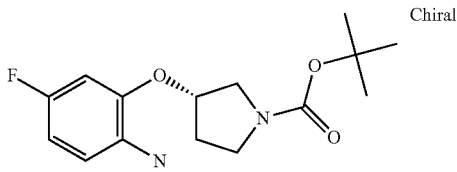 [SMILES: CC(C)(C)OC(=O)N1CC[C@H](Oc2cc(F)ccc2N)C1]

Amoniumformiate (0.41 g) was added into a suspension of (S)-tert-butyl 3-(5-fluoro-2-nitrophenoxy)pyrrolidine-1-carboxylate and palladium on charcoal (90.0 mg) in MeOH (5.0 ml) at room temperature. The mixture was heated at 35° C. for 30 mins. The suspension was filtered through a pad of celite and the filtercake was washed with dichloromethane. The filtrate was washed with water then passed through a hydrophobic frit and evaporated.

Yield: 0.37 g

Intermediate V

4-[2-((R)-1-tert-Butoxycarbonyl-pyrrolidin-3-yloxy)-4-fluoro-phenylamino]-5-methyl-thieno[2,3-d]pyrimidine-6-carboxylic acid methyl ester

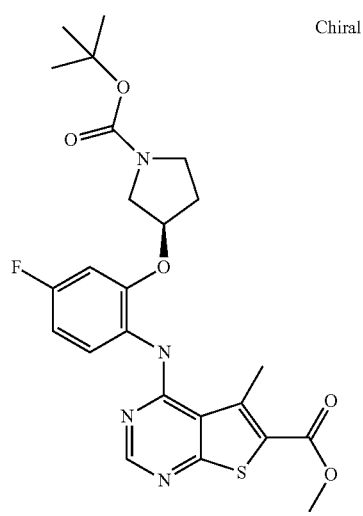 [SMILES: COC(=O)c1sc2ncnc(Nc3ccc(F)cc3O[C@@H]3CCN(C(=O)OC(C)(C)C)C3)c2c1C]

V.1. 4-(4-Fluoro-2-hydroxy-phenylamino)-5-methyl-thieno[2,3-d]pyrimidine-6-carboxylic acid methyl ester

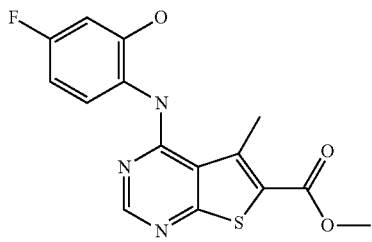 [SMILES: COC(=O)c1sc2ncnc(Nc3ccc(F)cc3O)c2c1C]

4-Chloro-5-methyl-thieno[2,3-d]pyrimidine-6-carboxylic acid methyl ester (2.43 g), 2-amino-5-fluorophenol (2.43 g) and p-toluenesulfonic acid (190.0 mg) were dissolved in dioxane (50.0 ml) and heated at 120° C. for 4 h under nitrogen. The reaction mixture was allowed to cool and treated with 3M NH$_4$OH. The resultant suspension was filtered, the solid was washed with ether and dried in vacuo at 60° C. over P$_2$O$_5$.

Yield: 2.97 g

V.2. 4-[2-((R)-1-tert-Butoxycarbonyl-pyrrolidin-3-yloxy)-4-fluoro-phenylamino]-5-methyl-thieno[2,3-d]pyrimidine-6-carboxylic acid methyl ester

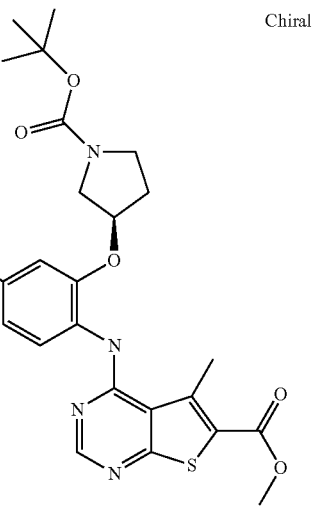

4-(4-Fluoro-2-hydroxy-phenylamino)-5-methyl-thieno[2,3-d]pyrimidine-6-carboxylic acid methyl ester carboxylate (445.0 mg), (S)-1 Boc-3-methansulfonyloxy-pyrrolidine (708.0 mg) and potassium carbonate (368.0 mg) were dissolved in DMF (7.0 ml). The reaction mixture was heated at 70° C. overnight and at 80° C. for further 4 h. EtOAc and H2O were added and the resultant suspension was filtered. The solid was washed with water and EtOAc and dried under vacuo over P$_2$O$_5$. The residue was dissolved in dichloromethane, passed through an hydrophobic frit and the solvent was evaporated. The residue triturated with diethylether.

Yield: 482.0 mg

Intermediate VI

(R)-4-fluoro-2-(tetrahydrofuran-3-yloxy)aniline

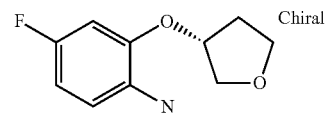 [SMILES: Nc1ccc(F)cc1O[C@@H]1CCOC1]

VI.1. (R)-3-(5-fluoro-2-nitrophenoxy)tetrahydrofuran

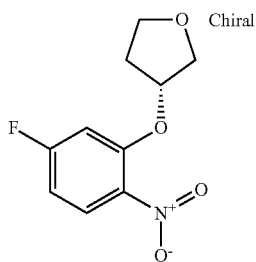 [SMILES: O=[N+]([O-])c1ccc(F)cc1O[C@@H]1CCOC1]

Prepared analogously to example III.1 from (S)-(+)-3-hydroxytetrahydrofuran and diisopropylazodicarboxylate
Yield: 1.8 g VI.2:
(R)-4-fluoro-2-(tetrahydrofuran-3-yloxy)aniline

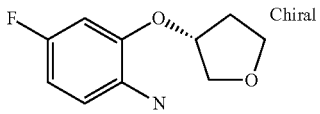

To a solution of (R)-3-(5-fluoro-2-nitrophenoxy)tetrahydrofuran (1.8 g) in MeOH (60.0 ml) was added Ra/Ni (200.0 mg), the mixture hydrogenated at room temperature. The catalyst was filtered off and the filtrate was concentrated.
Yield: 1.6 g
ESI mass spectrum: m/z=198 (M+H)$^+$ Intermediate VII (S)-tert-butyl 3-(2-amino-5-(trifluoromethyl)phenoxy)piperidine-1-carboxylate

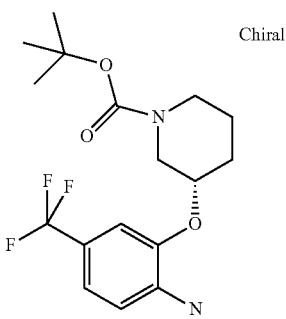 [SMILES: CC(C)(C)OC(=O)N1CCC[C@H](Oc2cc(C(F)(F)F)ccc2N)C1]

VII.1. (S)-tert-butyl 3-(2-nitro-5-(trifluoromethyl)phenoxy)piperidine-1-carbonylate

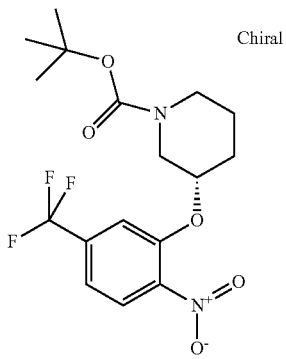 [SMILES: CC(C)(C)OC(=O)N1CCC[C@H](Oc2cc(C(F)(F)F)ccc2[N+](=O)[O-])C1]

LiHMDS 1M solution in THF was added to a ice-cooled solution of (S)-(+)-N-Boc-3-hydroxypiperidine in THF (4.0 ml). After 45 min 3-fluoro-4-nitrobenzoetrifluoride (418. 0 mg) in THF (2.0 ml) was added. The reaction mixture allowed to warm slowly to room temperature overnight. The mixture was diluted with dichloromethane and shaken with 10% aq. KHSO$_4$. The mixture was passed through a hydrophobic frit and the organic phase was evaporated. The residue was purified by chromatography.
Yield: 576.0 mg VII.2. (S)-tert-butyl 3-(2-amino-5-(trifluoromethyl)phenoxy)piperidine-1-carboxylate

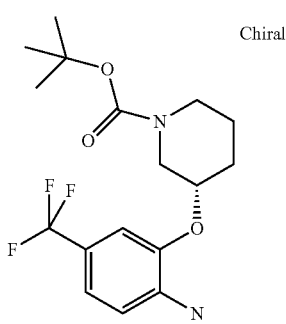 [SMILES: CC(C)(C)OC(=O)N1CCC[C@H](Oc2cc(C(F)(F)F)ccc2N)C1]

Prepared analogously to example IV.2 from (S)-tert-butyl 3-(2-nitro-5-(trifluoromethyl)phenoxy)piperidine-1-carboxylate
Yield: 494.0 mg Intermediate VIII (S)-1-(3-(2-amino-5-chlorophenoxy)piperidin-1-yl)-2,2,2-trifluoroethanone

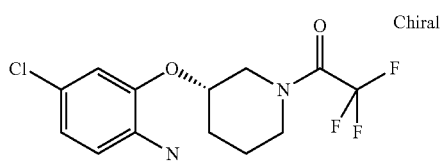 [SMILES: Nc1ccc(Cl)cc1O[C@H]1CCCN(C(=O)C(F)(F)F)C1]

VIII.1. (S)-tert-butyl 3-(5-chloro-2-nitrophenoxy)piperidine-1-carboxylate

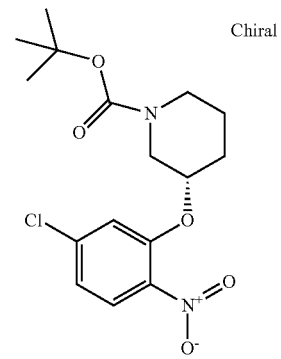 [SMILES: CC(C)(C)OC(=O)N1CCC[C@H](Oc2cc(Cl)ccc2[N+](=O)[O-])C1]

Prepared analogously to example VII.1 from (S)-(+)-N-Boc-3-hydroxypiperidine and 4-chloro-2-fluoronitrobenzene
Yield: 515.0 mg

VIII.2. (S)-1-(3-(5-chloro-2-nitrophenoxy)piperidin-1-yl)-2,2,2-trifluoroethanone

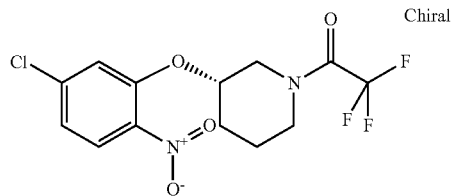 [SMILES: O=C(N1CCC[C@H](Oc2cc(Cl)ccc2[N+](=O)[O-])C1)C(F)(F)F]

HCl in dioxane (4M; 10.0 ml) was added to (S)-tert-butyl 3-(5-chloro-2-nitrophenoxy)piperidine-1-carboxylate (505.0 mg) and stirred for 1 h. The solvent was removed in vacuo and the residue was dissolved in MeOH. Triethylamine (395.0 µl) followed by ethyl trifluoroacetate (170.0 µl) were added to the reaction mixture and stirred at room temperature overnight. Further ethyl trifluoroacetate (170.0 µl) and triethylamine (198.0 µl) were added. The mixture was stirred for a further 2 h. After this time the solvent was evaporated. The resultant residue was redissolved in dichloromethane and washed with 10% aq. KHSO4. The organic layer was separated and passed through an hydrophobic frit. The solvent was evaporated.

Yield: 476.0 mg

VIII.3. (S)-1-(3-(2-amino-5-chlorophenoxy)piperidin-1-yl)-2,2,2-trifluoroethanone

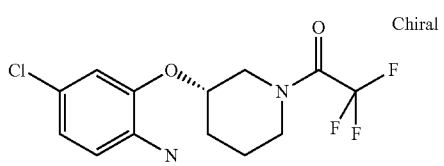 [SMILES: Nc1ccc(Cl)cc1O[C@H]1CCCN(C(=O)C(F)(F)F)C1]

(S)-1-(3-(5-chloro-2-nitrophenoxy)piperidin-1-yl)-2,2,2-trifluoroethanone (465.0 mg) and SnCl2*H2O (1.49 g) was dissolved in EtOAc (10.0 ml) and heated at reflux for 3.5 h. The reaction mixture was diluted with EtOAc an 10% aq. K2CO3. The mixture was separated and the organic layer washed with water and brine. The organic phase was dried and poured through an hydrophobic frit. The solvent was evaporated to give the intended product.

Yield: 346.0 mg

Intermediate IX (S)-1-(3-(2-amino-5-methylphenoxy)piperidin-1-yl)-2,2,2-trifluoroethanone

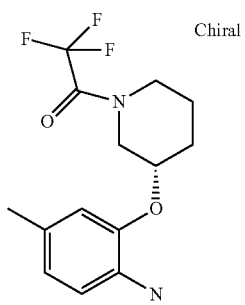 [SMILES: Cc1ccc(N)c(O[C@H]2CCCN(C(=O)C(F)(F)F)C2)c1]

IX.1. (S)-tert-butyl 3-(5-methyl-2-nitrophenoxy)piperidine-1-carboxylate

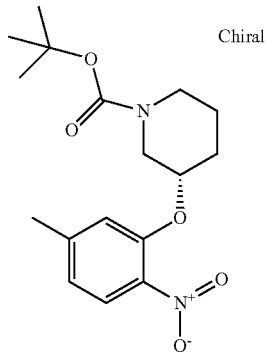 [SMILES: Cc1ccc([N+](=O)[O-])c(O[C@H]2CCCN(C(=O)OC(C)(C)C)C2)c1]

Prepared analogously to example VII.1 from (S)-(+)-N-Boc-3-hydroxypiperidine and 3-fluoro-4-nitrotoluene Yield: 302.0 mg

IX.2. (S)-2,2,2-trifluoro-1-(3-(5-methyl-2-nitrophenoxy)piperidin-1-yl)ethanone

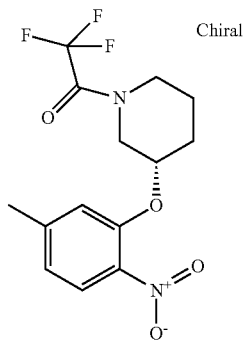 [SMILES: Cc1ccc([N+](=O)[O-])c(O[C@H]2CCCN(C(=O)C(F)(F)F)C2)c1]

Prepared analogously to example VIII. 2 from (S)-tert-butyl 3-(5-methyl-2 nitrophenoxy)piperidine-1-carboxylate.

Yield: 259.0 mg

IX.3. (S)-1-(3-(2-amino-5-methylphenoxy)piperidin-1-yl)-2,2,2-trifluoroethanone

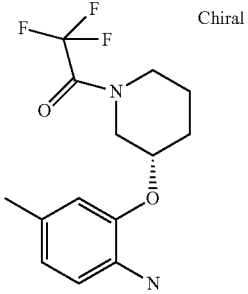 [SMILES: Cc1ccc(N)c(O[C@H]2CCCN(C(=O)C(F)(F)F)C2)c1]

Amoniumformiate (0.238 g) was added into a suspension of (S)-2,2,2-trifluoro-1-(3-(5-methyl-2-nitrophenoxy)piperidin-1-yl)ethanone and palladium on charcoal (50.0 mg) in MeOH (6.0 ml) at room temperature. The mixture was heated at reflux for 40 mins. The mixture was filtered through a pad of celite and the filtercake was washed with dichloromethane. The filtrate was washed with water and. The residue was purfied by chromatography.

Yield: 168.0 mg

Intermediate X (S)-tert-butyl 3-(3-aminopyridin-2-yloxy)piperidine-1-carboxylate

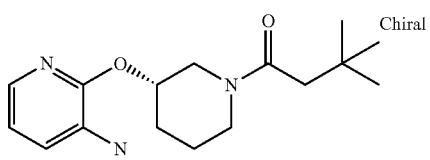 [SMILES: CC(C)(C)CC(=O)N1CCC[C@H](Oc2ncccc2N)C1]

X.1. (S)-tert-butyl 3-(3-nitropyridin-2-yloxy)piperidine-1-carboxylate

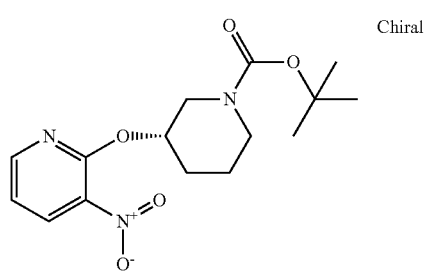 [SMILES: CC(C)(C)OC(=O)N1CCC[C@H](Oc2ncccc2[N+](=O)[O-])C1]

Prepared analogously to example VII.1 from (S)-1-Boc-3-Hydroxypiperidine and 2-Fluoro-3-nitro-pyridine Yield: 2.19 g X.2. (S)-tert-butyl 3-(3-aminopyridin-2-yloxy)piperidine-1-carboxylate

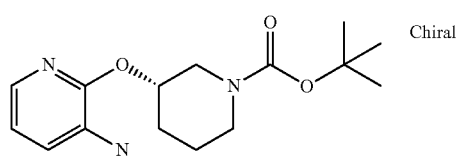 [SMILES: CC(C)(C)OC(=O)N1CCC[C@H](Oc2ncccc2N)C1]

Prepared analogously to example IX. 3 from, (S)-tert-butyl 3-(3-nitropyridin-2yloxy)piperidine-1-carboxylate Yield: 1.60 g

Intermediate XI (S)-4-amino-3-(1-(2,2,2-trifluoroacetyl)piperidin-3-yloxy)benzonitrilie

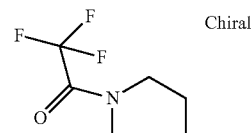

XI.1. (S)-tert-butyl 3-(5-cyano-2-nitrophenoxy)piperidine-1-carboxylate

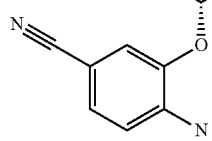

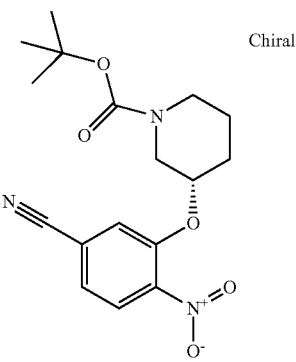 [SMILES: CC(C)(C)OC(=O)N1CCC[C@H](Oc2cc(C#N)ccc2[N+](=O)[O-])C1]

Prepared analogously to example VII.1 from (S)-1-Boc-3-hydroxypiperidine and 3-Fluoro-4-nitrobenzonitrlie Yield: 0.633 g XI.2. (S)-4-nitro-3-(1-(2,2,2-trifluoroacetyl)piperidinin-3-yloxy)benzonitrile

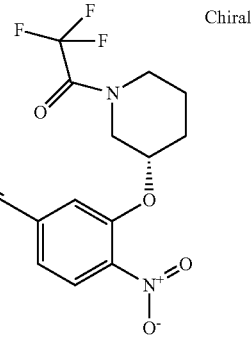

Prepared analogously to example VIII. 2 from (S)-tert-butyl 3-(5-cyano-2 nitrophenoxy)piperidine-1-carboxylate.

Yield: 541.0 mg

XI.3. (S)-4-amino-3-(1-(2,2,2-trifluoroacetyl)piperidin-3-yloxy)benzonitrilie

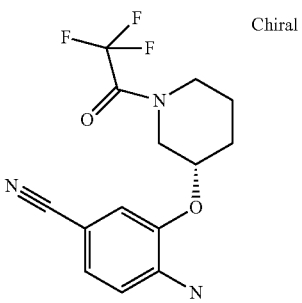 [SMILES: N#Cc1ccc(N)c(O[C@H]2CCCN(C(=O)C(F)(F)F)C2)c1]

Prepared analogously to example IX. 3 from (S)-4-nitro-3-(1-(2,2,2-trifluoroacetyl)piperidinin-3-yloxy)benzonitrile;
Yield: 99.0 mg Intermediate XII 4-[4-Fluoro-2-((S)-1-isopropoxycarbonyl-piperidin-3-yloxy)-phenylamino]-5-methyl-thieno[2,3-d]pyrimidine-6-carboxylic acid methyl ester

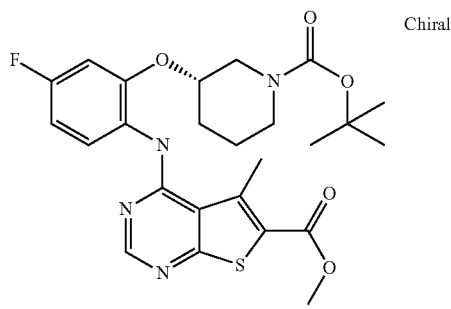 [SMILES: COC(=O)c1sc2ncnc(Nc3ccc(F)cc3O[C@H]3CCCN(C(=O)OC(C)(C)C)C3)c2c1C]

XII.1

This starting material was described in V.1

XII.2 (S)-methyl 4-(2-(1-(tert-butoxycarbonyl)piperidin-3-yloxy)-4-fluorophenylamino)-5-methylthieno[2,3-d]yrimidine-6-carboxylate

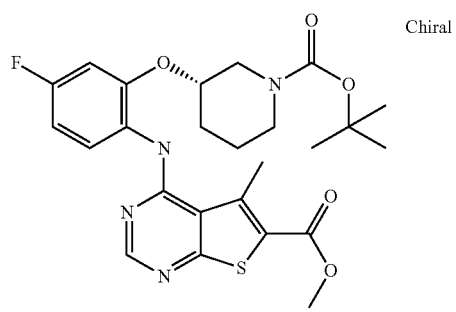 [SMILES: COC(=O)c1sc2ncnc(Nc3ccc(F)cc3O[C@H]3CCCN(C(=O)OC(C)(C)C)C3)c2c1C]

Prepared analogously to example V. 2 from methyl 4-(4-fluoro-2-hydroxyphenylamino)-5-methylthieno[2,3-d]pyrimidine-6-carboxylate and (R)-tert-butyl 3-(methylsulfonyloxy)piperidine-1-carboxylate.

Intermediate XIII (S)-4-fluoro-2-(tetrahydro-2H-pyran-3-yloxy)aniline

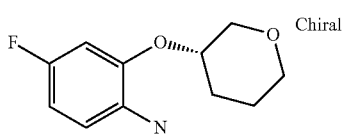 [SMILES: Nc1ccc(F)cc1O[C@H]1CCCOC1]

XIII.1. (S)-3-(5-fluoro-2-nitrodhenoxy)tetrahydro-2H-pyran

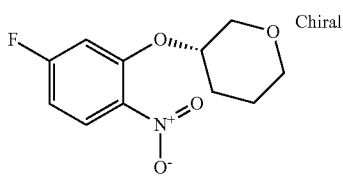 [SMILES: O=[N+]([O-])c1ccc(F)cc1O[C@H]1CCCOC1]

Prepared analogously to example II.1 from (R)-tetrahydro-2H-pyran-3-ol
Yield: 1.17 g XIII.2 (S)-4-fluoro-2-(tetrahydro-2H-pyran-3-yloxy)aniline

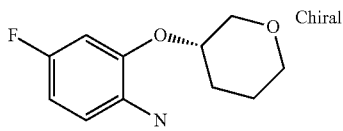 [SMILES: Nc1ccc(F)cc1O[C@H]1CCCOC1]

Prepared analogously to example IX.3 from (S)-3-(5-fluoro-2-nitrophenoxy)tetrahydro-2H-pyran
Yield: 0.26 g Intermediate XIV (R)-4-fluoro-2-(tetrahydro-2H-pyran-3-yloxy)aniline

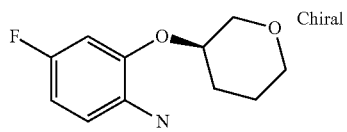

XIV.1. (R)-3-(5-fluoro-2-nitrophenoxy)tetrahydro-2H-pyran

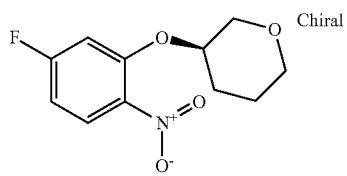 [SMILES: O=[N+]([O-])c1ccc(F)cc1O[C@@H]1CCCOC1]

Prepared analogously to example II.1 from (R)-Tetrahydro-2H-pyran-3-ol
Yield: 0.87 g XIV.2 (R)-4-fluoro-2-(tetrahydro-2H-pyran-3-yloxy)aniline

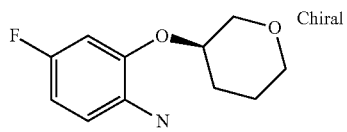 [SMILES: Nc1ccc(F)cc1O[C@@H]1CCCOC1]

Prepared analogously to example IX.3 from (R)-3-(5-fluoro-2-nitrophenoxy)tetrahydro-2H-pyran
Yield: 0.61 g Intermediate XV 4-[2-((R)-1-tert-Butoxycarbonyl-pyrrolidin-3-yloxy)-4-fluoro-phenylamino]-5-methyl-thieno[2,3-d]pyrimidine-6-carboxylic acid methyl ester

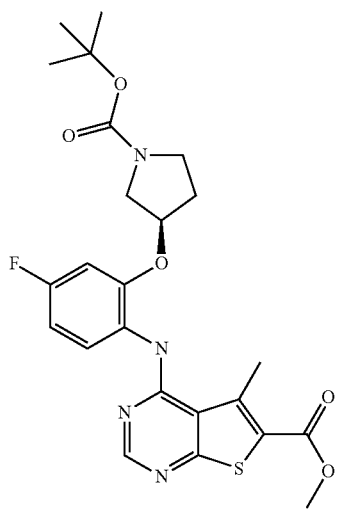

XV.1.

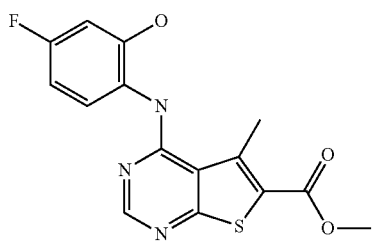 [SMILES: COC(=O)c1sc2ncnc(Nc3ccc(F)cc3O)c2c1C]

This starting material was described in V.1

XV.2 4-[2-(R)-1-tert-Butoxycarbonyl-pyrrolidin-3-yloxy)-4-fluoro-phenylamino]-5-methyl-thieno[2,3-d]pyrimidine-6-carboxylic acid methyl ester

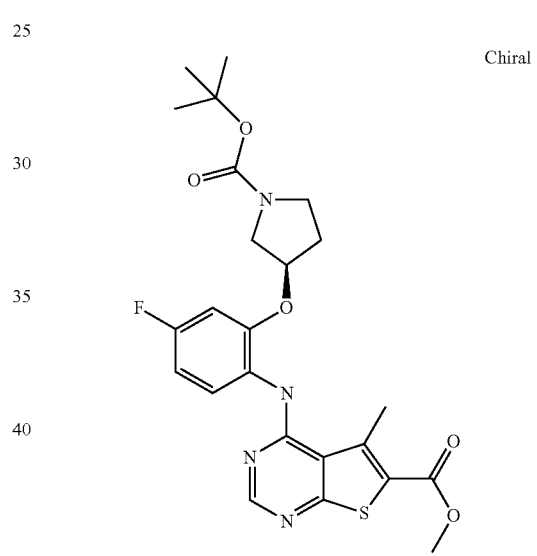

Mesylchloride (232.0 µl) was added to an ice-cooled solution of the (S)-1-N-Boc-3-hydroxypyrrolidine (374.0 mg) and triethylamine (556.0 µl) in dichloromethane (10.0 ml) The mixture was stirred at this temperature for 3 h. After this time the reaction mixture was diluted with dichloromethane, washed with 10% aq. KHSO4, 10% aq. K2CO3 and passed through a hydrophobic frit. The solvent was evaporated. The residue was combined with methyl 4-(4-fluoro-2-hydroxyphenylamino)-5-methylthieno[2,3-d]pyrimidine-6-carboxylate (333.3 mg) and potassium carbonate (276.0 mg) in DMF (7.0 ml) and heated at 80° C. overnight. EtOAc and water were added and the suspension was filtered. The filtrate was separated, the aqueous layer was discarded and the organic was washed with brine (2×). After drying the organic passed through a hydrophobic frit and the solvent was evaporated. The residue was triturated with MeOH and solids combined. The solids were washed with Et$_2$O and dried.

Yield: 311.0 mg

Intermediate XVI

4-[4-Fluoro-2-(1-methanesulfonyl-pyrrolidin-3-yloxy)-phenylamino]-5-methyl-thieno[2,3-d]pyrimidine-6-carboxylic acid methyl ester

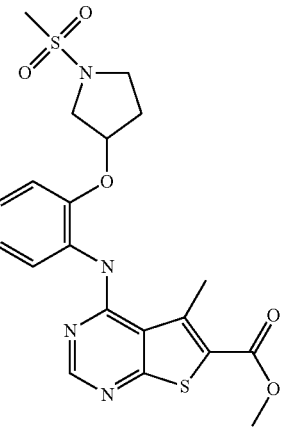

XVI.1 1-(Methylsulfonyl)pyrrolidin-3-yl methansulfonate

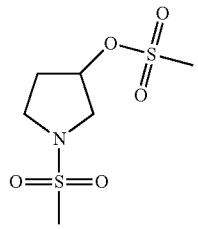

Methansulfonyl chloride (1.93 ml) added to an ice cooled solution of 3-pyrrolidinol (871.0 mg) and triethylamine (3.47 ml) in dichloromethane (30.0 ml). After 10 mins the coolant was removed and the mixture was stirred at room temperature for 2 h. The mixture was washed with 10% KHSO₄ and 10% aq. K₂CO₃. The organic layer was passed through a hydrophobic frit and the solvent was evaporated.
Yield: 1.18 g

XVI.2 4-[4-Fluoro-2-(1-methanesulfonyl-pyrrolidin-3-yloxy)-phenylamino]-5-methyl-thieno[2,3-d]pyrimidine-6-carboxylic acid methyl ester

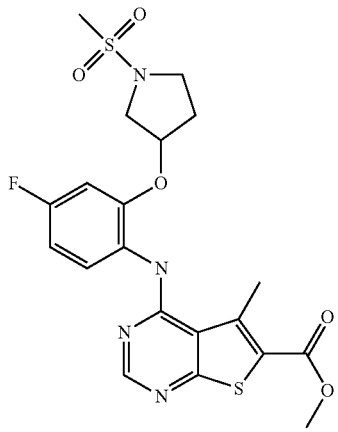 [SMILES: COC(=O)c1sc2ncnc(Nc3ccc(F)cc3OC3CCN(S(C)(=O)=O)C3)c2c1C]

Methyl 4-(4-fluoro-2-hydroxyphenylamino)-5-methylthieno[2,3-d]pyrimidine-6-carboxylate (described in V.1) (1.0 g), 1-(methylsulfonyl)pyrrolidin-3-yl methansulfonate and potassium carbonate (664.0 mg) were combined in DMF (15.0 ml) and heated at 60° C. overnight. The temperature was increased at 80° C. and heated for 6 h again. The reaction mixture was allowed to cool overnight. The mixture was portioned between EtOAc and water. The suspension was fitlered, solid washed with EtOAc and air-dried under vacuum.

Intermediate XVII

4-[2-((S)-1-tert-Butoxycarbonyl-pyrrolidin-3-yloxy)-4-fluoro-phenylamino]-5-methyl-thieno[2,3-d]pyrimidine-6-carboxylic acid methyl ester

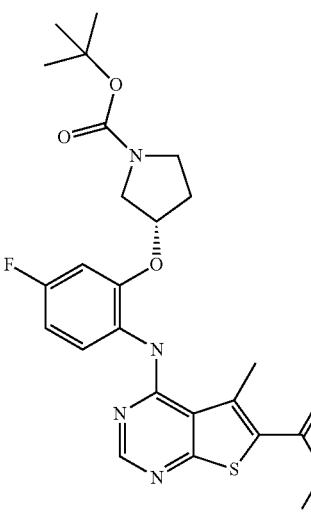

XVII.1 (R)-tert-butyl 3-(methylsulfonyloxy)pyrrolidine-1-carboxylate

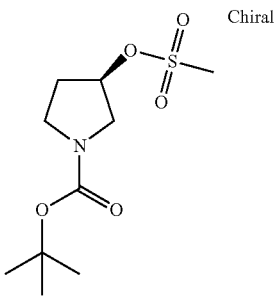 [SMILES: CC(C)(C)OC(=O)N1CC[C@@H](OS(C)(=O)=O)C1]

Prepared analogously to example XVI.1 from (R)-(−)-N-Boc-3-pyrrolidinol
Yield: 0.89 g

XVII.2 4-[2-((S)-1-tert-Butoxycarbonyl-pyrrolidin-3-yloxy)-4-fluoro-phenylamino]-5-methyl-thieno[2,3-d]pyrimidine-6-carboxylic acid methyl ester

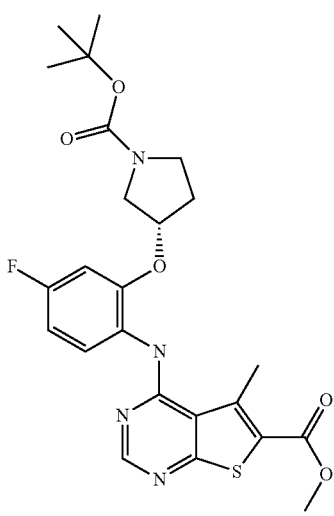

Chiral

Prepared analogously to example XVI.2 from (R)-tert-butyl 3-(methylsulfonyloxy)pyrrolidine-1-carboxylate
Yield: 0.61 g

Intermediate XVIII

4-[4-Fluoro-2-(pyrrolidin-3-yloxy)-phenylamino]-5-methyl-thieno[2,3-d]pyrimidine-6-carboxylic acid methyl ester

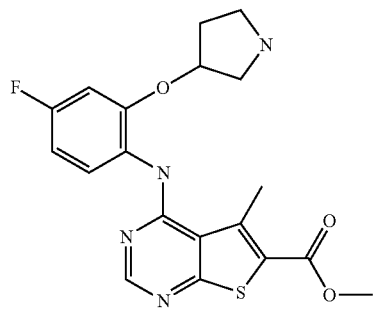 [SMILES: COC(=O)c1sc2ncnc(Nc3ccc(F)cc3OC3CCNC3)c2c1C]

XVIII.1 tert-butyl 3-(methylsulfonyloxy)pyrrolidine-1-carboxylate

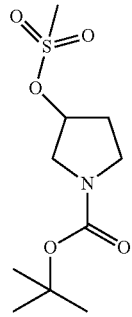 [SMILES: CC(C)(C)OC(=O)N1CCC(OS(C)(=O)=O)C1]

To a solution of 3-hydroxypyrrolidine HCl (5.0 g) in dry MeOH (40.0 ml) was added triethylamine (8.45 ml) and the solution was cooled to 0° C. in an ice bath. Di t-butyl dicarbonate (8.80 g) was added portionwise over a period of 30 min. The reaction was allowed to warm to room temperature and stirred for 5 h. The solvent was removed and the residue was dissolved in dichloromethane (50.0 ml) and washed with water. The organic phase was passed through a PTFE separation frit and the solvent was evaporated in vacuum.

The residue was used without further purification.

Dichloromethane (20.0 ml) was added to the residue and the solution was cooled to 0° C. in an ice bath. Triethylamine (8.4 ml) was than added followed by dropwise addition of methansulfonyl chloride (3.13 ml. The solution was allowed to warm to room temperature and was stirred for 18 h. The reaction was portioned between water and dichloromethane and the organic layer was separated, dried, filtered and evaporated.

Yield: 8.26 g

XVIII.2 4-[2-(1-tert-Butoxycarbonyl-pyrrolidin-3-yloxy)-4-fluoro-phenylamino]-5-methyl-thieno[2,3-d]pyrimidine-6-carboxylic acid methyl ester

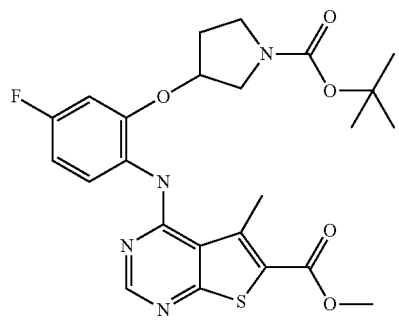 [SMILES: COC(=O)c1sc2ncnc(Nc3ccc(F)cc3OC3CCN(C(=O)OC(C)(C)C)C3)c2c1C]

Prepared analogously to example XVI.2 from tert-butyl 3-(methylsulfonyloxy)pyrrolidine-1-carboxylate
Yield: 1.25 g

XVIII.3 4-[4-Fluoro-2-(pyrrolidin-3-yloxy)-phenylamino]-5-methyl-thieno[2,3-d]pyrimidine-6-carboxylic acid methyl ester

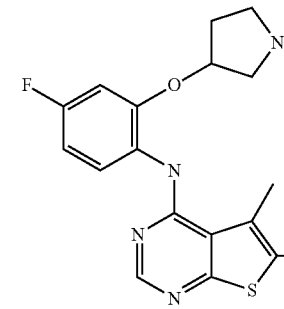

To a stirred suspension of 4-[2-(1-tert-Butoxycarbonyl-pyrrolidin-3-yloxy)-4-fluoro-phenylamino]-5-methyl-thieno[2,3-d]pyrimidine-6-carboxylic acid methyl ester (1.2 g) in MeOH (4.0 ml) was added HCl in dioxane (4N; 4.0 ml)

dropwise. The reaction mixture was stirred for 8 h. The solvent was removed under reduced pressure. The residue was purified by chromatography.

Intermediate XIX (S)-4-fluoro-2-(tetrahydrofuran-3-yloxy)aniline

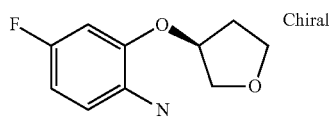 [SMILES: Nc1ccc(F)cc1O[C@H]1CCOC1]

XIX.1.
(S)-3-(5-fluoro-2-nitrophenoxy)tetrahydrofuran

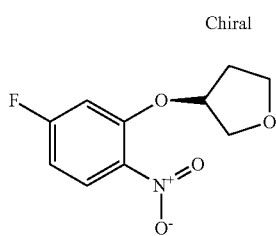

Prepared analogously to example I.1 from (S)-(+)-3-Hydroxytetrahydrofuran and 2,4-difluornitrobenzol
Yield: 1.265 g XIX.2:
(S)-4-fluoro-2-(tetrahydrofuran-3-yloxy)aniline

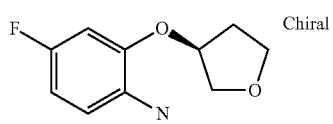 [SMILES: Nc1ccc(F)cc1O[C@H]1CCOC1]

Prepared analogously to II.2 from (S)-3-(5-fluoro-2-nitrophenoxy)tetrahydrofuran.
Yield: 1.01 g Intermediate XX 4-fluoro-2-(tetrahydro-2H-pyran-4-yloxy)aniline

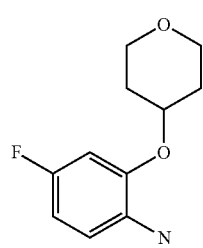 [SMILES: Nc1ccc(F)cc1OC1CCOCC1]

XX.1 4-(5-fluoro-2-nitrophenoxy)tetrahydro-2-H-pyran

5-Fluoro-2-nitrophenole (13 g) and tetrahydro-4H-pyran-4-ol (9.9 g) were dissolved in dichloromethane (50 ml). Triphenylphosphine (33 g) was added. The mixture was cooled with ice water and diisopropylazodicarboxylate (25.1 g) was added. The reaction was stirred at room temperature overnight. A further aliquot of triphenylphosphine (10.7 g) and diisopropylazodicarboxylate (8.3 g) were added and the reaction mixture was stirred at room temperature for 2 h again.

The reaction was purified by chromatography (Cyclohexane: EE 70/30→50/50). The desired fraktions were combined and evaporated. The crude product was purified by chromatography (Cyclohexane: EE 90/10→80/20). The product fractions was combined and evaporated.

The residue was crystallized from hot cyclohexane to give the desired product.
Yield: 8.42 g
ESI mass spectrum: m/z=259 (M+NH4)$^+$
Retention time HPLC: 2.09 (method F)

XX.2
4-fluoro-2-(tetrahydro-2H-pyran-4-yloxy)aniline

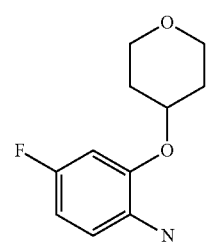 [SMILES: Nc1ccc(F)cc1OC1CCOCC1]

4-(5-Fluoro-2-nitrophenoxy)tetrahydro-2-H-pyran (8.4 g) was dissolved in ethylacetate (30 ml) and Pd/C (500 mg) was added. The reaction was hydrogenated at room temperature and 50 PSI. The mixture was concentrated in vacuo to give the intended product.
Yield: 7.17 g
ESI mass spectrum: m/z=212 (M+NH4)$^+$

Intermediate XXI

2-[(R)-(Tetrahydro-pyran-3-yl)oxy]-pyridin-3-ylamine

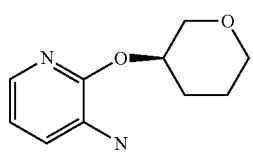 [SMILES: Nc1cccnc1O[C@@H]1CCCOC1]

XXI.1 3-Nitro-2-[(R)-(tetrahydro-pyran-3-yl)oxy]-pyridine

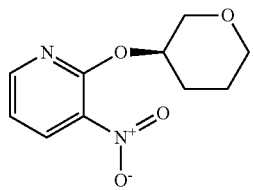 [SMILES: O=[N+]([O-])c1cccnc1O[C@@H]1CCCOC1]

Prepared analogously to I.1 from 2-fluor-3-nitropyridine and (R)-tetrahydro-pyran-3-ol.
Yield: 4.2 g (96%)
ESI mass spectrum: m/z=225 (M+H)$^+$ P XXI.2 2-[(R)-(Tetrahydro-pyran-3-yl)oxy]-pyridin-3-ylamine

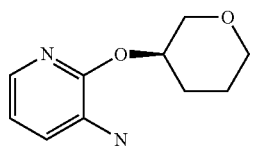 [SMILES: Nc1cccnc1O[C@@H]1CCCOC1]

Prepared analogously to VI.2 from 3-nitro-2-[(R)-(tetrahydro-pyran-3-yl)oxy]-pyridine
Yield: 3.5 g (96%)
ESI mass spectrum: m/z=195 (M+H)$^+$

Intermediate XXII

2-[(R)-(Tetrahydro-furan-3-yl)oxy]-pyridin-3-ylamine

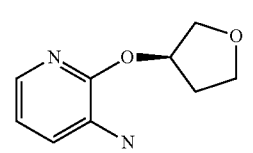 [SMILES: Nc1cccnc1O[C@@H]1CCOC1]

XXII.1 3-Nitro-2-[(R)-(tetrahydro-furan-3-yl)-oxy]-pyridine

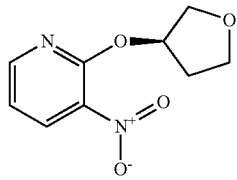 [SMILES: O=[N+]([O-])c1cccnc1O[C@@H]1CCOC1]

Prepared analogously to I.1 from 2-fluor-3-nitropyridine and (R)-tetrahydro-furan-3-ol.
Yield: 208 mg (99%)
ESI mass spectrum: m/z=211 (M+H)$^+$ XXII.2 2-[(R)-(Tetrahydro-furan-3-yl)oxy]-pyridin-3-ylamine

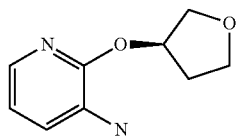 [SMILES: Nc1cccnc1O[C@@H]1CCOC1]

Prepared analogously to I.2 from 3-nitro-2-[(R)-(tetrahydro-furan-3-yl)oxy]-pyridine
Yield: 166 mg (93%)
ESI mass spectrum: m/z=181 (M+H)$^+$

Intermediate XXIII

2-[(S)-(Tetrahydro-furan-3-yl)oxy]-pyridin-3-ylamine

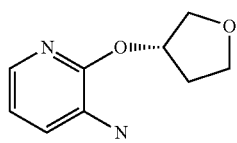 [SMILES: Nc1cccnc1O[C@H]1CCOC1]

XXIII.1 3-Nitro-2-[(S)-(tetrahydro-furan-3-yl)oxy]-pyridine

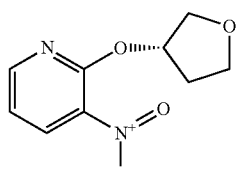

Prepared analogously to I.1 from 2-chlor-3-nitropyridine and (S)-tetrahydro-furan-3-ol.
Yield: 168 mg (80%)
ESI mass spectrum: m/z=211 (M+H)$^+$

XXIII.2 2-[(S)-(Tetrahydro-furan-3-yl)oxy]-pyridin-3-ylamine trifluoroacetate

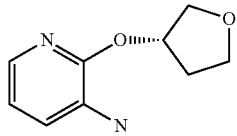 [SMILES: Nc1cccnc1O[C@H]1CCOC1]

Prepared analogously to I.2 from 3-nitro-2-[(S)-(tetrahydro-furan-3-yl)oxy]-pyridine
Yield: 77 mg (32%)
ESI mass spectrum: m/z=181 (M+H)$^+$

Intermediate XXIV 2-(Tetrahydro-pyran-4-yloxy)-pyridin-3-ylamine

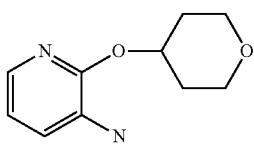 [SMILES: Nc1cccnc1OC1CCOCC1]

XXIV.1 3-Nitro-2-(tetrahydro-pyran-4-yloxy)-pyridine

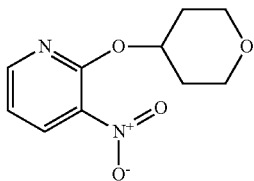 [SMILES: O=[N+]([O-])c1cccnc1OC1CCOCC1]

Prepared analogously to I.1 from 2-fluor-3-nitropyridine and tetrahydro-pyran-4-ol.
Yield: 2.33 g (54%)
ESI mass spectrum: m/z=247 (M+Na)$^+$

XXIV.2 2-(Tetrahydro-pyran-4-yloxy)-pyridin-3-ylamine

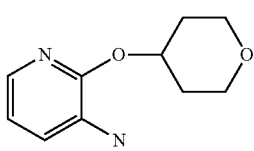 [SMILES: Nc1cccnc1OC1CCOCC1]

Prepared analogously to I.2 from 3-nitro-2-[(S)-(tetrahydro-furan-3-yl)oxy]-pyridine
Yield: 3.8 g (87%)
ESI mass spectrum: m/z=195 (M+H)$^+$

End Compounds

EXAMPLE 1

4-{4-Fluoro-2-[(S)-1-(2-methoxy-ethyl)-piperidin-3-yloxy]-phenylamino}-5-methyl-thieno[2,3-d]pyrimidine-6-carboxylic acid amide

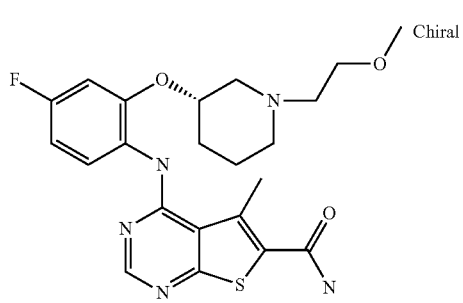 [SMILES: COCCN1CCC[C@H](Oc2cc(F)ccc2Nc2ncnc3sc(C(N)=O)c(C)c23)C1]

1.1 4-[2-((S)-1-tert-Butoxycarbonyl-piperidin-3-yloxy)-4-fluoro-phenylamino]-5-methyl-thieno[2,3-d]pyrimidine-6-carboxylic acid methyl ester

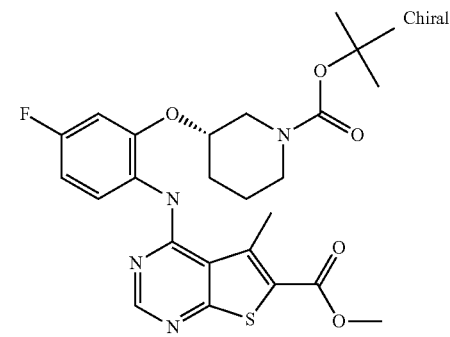 [SMILES: COC(=O)c1sc2ncnc(Nc3ccc(F)cc3O[C@H]3CCCN(C(=O)OC(C)(C)C)C3)c2c1C]

4-Chloro-5-methyl-thieno[2,3-d]pyrimidine-6-carboxylic acid methyl ester (1.17 g), (S)-tert-butyl 3-(2-amino-5-fluorophenoxy)piperidine-1-carboxylate (Intermediate 1.1 g) was dissolved in dioxane (10 ml) and p-toluenesulfonic acid (61 mg) was added. The reaction was heated at 70° C. for 1.5 h. The solution was poured into sat. NaHCO$_3$ (50 ml) and extracted with chloroform. The organic phases were passed through a phase separator and concentrated in vaco. The sample was purified by chromatography (silica gel; solvent: isohexan:EtOAc 3:1→2:1) to give the desired product.

Yield: 1.56 g

1.2 4-[2-((S)-1-tert-Butoxycarbonyl-piperidin-3-yloxy)-4-fluoro-phenylamino]-5-methyl-thieno[2,3-d]pyrimidine-6-carboxylic acid

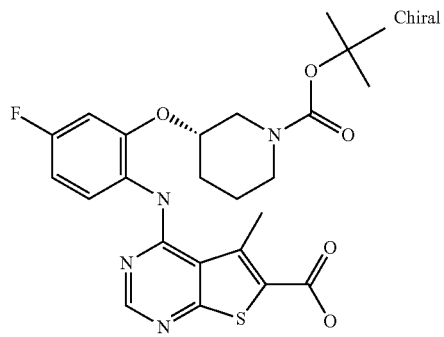 [SMILES: Cc1c(C(=O)O)sc2ncnc(Nc3ccc(F)cc3O[C@H]3CCCN(C(=O)OC(C)(C)C)C3)c12]

Lithium hydroxide (0.732 g) was added into a solution of 4-[2-((S)-1-tert-Butoxycarbonyl-piperidin-3-yloxy)-4-fluoro-phenylamino]-5-methyl-thieno[2,3-d]pyrimidine-6-carboxylic acid methyl ester_(1.5 g) in THF/water (2:1; 75 ml). The reaction was stirred at room temperature overnight. The reaction was cooled in an ice-bath and neutralised (~pH 6) with HCl (2M). The THF was removed in vacuo and the residue diluted with water and chloroform. The organic layer was separated and the aqueous extracted with chloroform. The combined organic phases were passed through a phase-separator and concentrated in vacuo. The crude product was recrystallised from hot acetonitrile.

Yield: 1.18 g

1.3 4-[4-Fluoro-2-((S)-piperidin-3-yloxy)-phenylamino]-5-methyl-thieno[2,3-d]pyrimidine-6-carboxylic acid

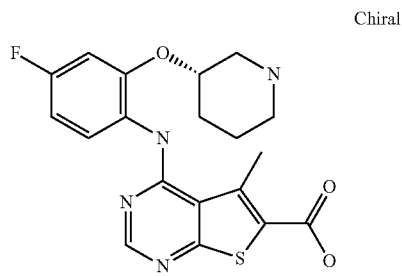 [SMILES: Cc1c(C(=O)O)sc2ncnc(Nc3ccc(F)cc3O[C@H]3CCCNC3)c12]

HCl in Methanol (4M; 0.250 ml) was added into a solution of 4-[2-((S)-1-tert-butoxycarbonyl-piperidin-3-yloxy)-4-fluoro-phenylamino]-5-methyl-thieno[2,3-d]pyrimidine-6-carboxylic acid (50 mg) in dioxane (2.5 ml) at room temperature. The reaction was stirred over the weekend. The reaction mixture was purified by chromatography. The product was triturated from hot MeOH to give the intended product.

Yield: 20 mg

ESI mass spectrum: m/z=403 (M+H)$^+$

Retention time HPLC: 1.18 (method X)

1.4 (S)-3-[2-(6-Carbamoyl-5-methyl-thieno[2,3-d]pyrimidin-4-ylamino)-5-fluoro-phenoxy]-piperidine-1-carboxylic acid tert-butyl ester

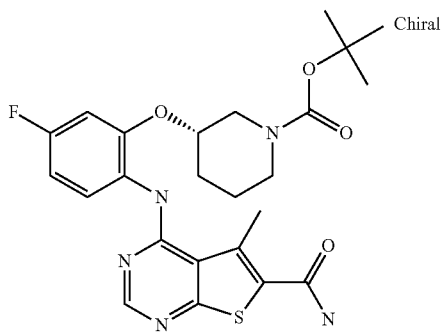 [SMILES: Cc1c(C(N)=O)sc2ncnc(Nc3ccc(F)cc3O[C@H]3CCCN(C(=O)OC(C)(C)C)C3)c12]

HATU (1.1 g) was added into a solution of 4-[4-fluoro-2-((S)-piperidin-3-yloxy)-phenylamino]-5-methyl-thieno[2,3-d]pyrimidine-6-carboxylic acid (1.2 g) and DIPEA (0.490 ml) in anhydrous DMF (10 ml) at 0° C. The reaction was stirred for 0.5 h when ammonia in methanol (7M; 3.4 ml) was added and the reaction was allowed to warm to room temperature overnight. The DMF was removed by co evaporation from toluene and the residue triturated from Methanol to give the desired product.

Yield: 1.03 g

1.5 4-[4-Fluoro-2-((S)-piperidin-3-yloxy)-phenylamino]-5-methyl-thieno[2,3-d]pyrimidine-6-carboxylic acid amide

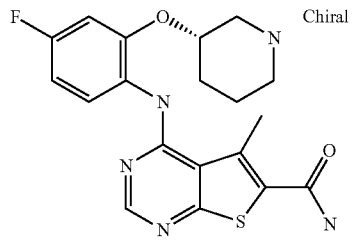 [SMILES: Cc1c(C(N)=O)sc2ncnc(Nc3ccc(F)cc3O[C@H]3CCCNC3)c12]

HCl in methanol (4M; 2.5 ml) was added into a suspension of (S)-3-[2-(6-carbamoyl-5-methyl-thieno[2,3-d]pyrimidin-4-ylamino)-5-fluoro-phenoxy]-piperidine-1-carboxylic acid tert-butyl ester (0.96 g) in methanol (10 ml). The reaction was stirred at room temperature for 3.5 h. The solvent was removed in vacuo and the residue co-evaporated with chloroform. The crude HCl salt was purified by chromatography.

Yield: 0.73 g

ESI mass spectrum: m/z=402 (M+H)$^+$

1.6 4-{4-Fluoro-2-[(S)-1-(2-methoxy-ethyl)-piperidin-3-yloxy]-phenylamino}-5-methyl-thieno[2,3-d]pyrimidine-6-carboxylic acid amide

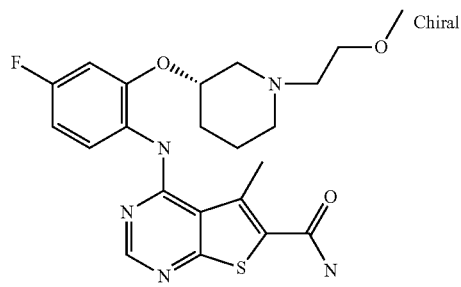 [SMILES: COCCN1CCC[C@H](Oc2cc(F)ccc2Nc2ncnc3sc(C(N)=O)c(C)c23)C1]

2-Bromoethyl methylether (21 μl) was added into a suspension of 4-[4-fluoro-2-((S)-piperidin-3-yloxy)-phenylamino]-5-methyl-thieno[2,3-d]pyrimidine-6-carboxylic acid amide (100 mg) and $K_2CO_3$ (63 mg) in anhydrous DMF (2 ml) at room temperature. The reaction was stirred for a weekend. A further aliquot of 2-bromoethyl methylether (5 μl) and $K_2CO_3$ (16 mg) were added and the reaction stirred overnight. The mixture was purified by chromatography.

Yield: 26 mg

ESI mass spectrum: m/z=460 $(M+H)^+$

Retention time HPLC: 1.15 (method X)

The following compounds were prepared analogously to 1.6 from: 4-[4-fluoro-2-((S)-piperidin-3-yloxy)-phenylamino]-5-methyl-thieno[2,3-d]pyrimidine-6-carboxylic acid amide and the corresponding halogenide (see in Table 1)

TABLE 1

| Example | Structure | Mass | Retention time | halogenide |
|---|---|---|---|---|
| 2 | 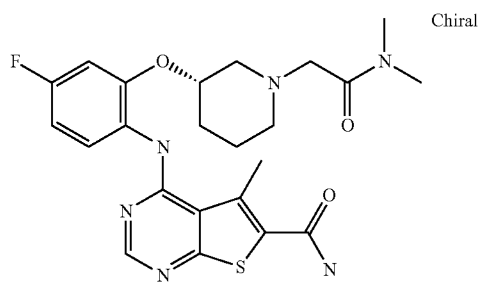 [SMILES: Cc1c(C(N)=O)sc2ncnc(Nc3ccc(F)cc3O[C@H]3CCCN(CC(=O)N(C)C)C3)c12] | 487 $(M + H)^+$ | 1.13 (method X) | |
| 3 | 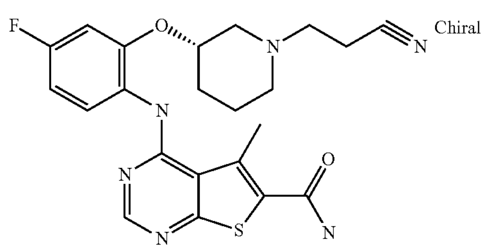 [SMILES: Cc1c(C(N)=O)sc2ncnc(Nc3ccc(F)cc3O[C@H]3CCCN(CCC#N)C3)c12] | 455 $(M + H)^+$ | 1.14 (method X) | |
| 4 | 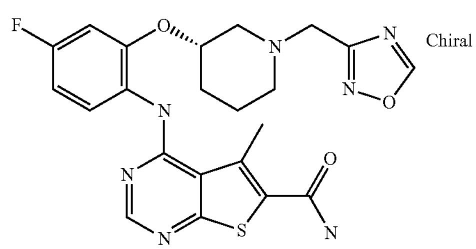 [SMILES: Cc1c(C(N)=O)sc2ncnc(Nc3ccc(F)cc3O[C@H]3CCCN(Cc4ncon4)C3)c12] | 484 $(M + H)^+$ | 1.14 (method X) | |
| 5 | 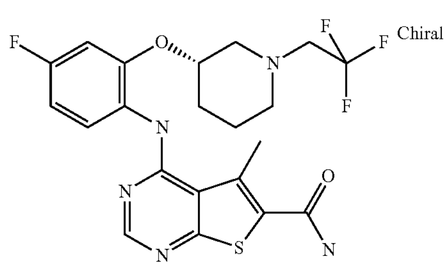 [SMILES: Cc1c(C(N)=O)sc2ncnc(Nc3ccc(F)cc3O[C@H]3CCCN(CC(F)(F)F)C3)c12] | 484 $(M + H)^+$ | 1.40 (method X) | |

Compound 6

(S)-4-(4-fluoro-2-(1-(2-hydroxyethyl)piperidin-3-yloxy)phenylamino)-5-methylthieno[2,3-d]pyrimidine-6-carboxamide

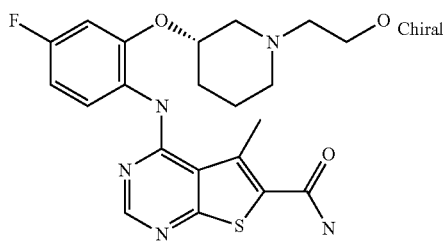 [SMILES: Cc1c(C(N)=O)sc2ncnc(Nc3ccc(F)cc3O[C@H]3CCCN(CCO)C3)c12]

4-[4-Fluoro-2-((S)-piperidin-3-yloxy)-phenylamino]-5-methyl-thieno[2,3-d]pyrimidine-6-carboxylic acid amide (50 mg) and (tert-butyldimethylsilyloxy)acetaldehyde (235 µl) were dissolved in dichloromethane:methanol (1:1; 2 ml). Into this solution was added acetic acid (11 µl) followed by sodium cyanoborohydride (91 mg). The reaction was stirred at room temperature over the weekend. The reaction mixture was directly purified by chromatography.

Yield: 10 mg

ESI mass spectrum: m/z=446 (M+H)$^+$

Retention time HPLC: 1.12 (method X)

The following compounds were prepared analogously to example 6 from 4-[4-fluoro-2-((S)-piperidin-3-yloxy)-phenylamino]-5-methyl-thieno[2,3-d]pyrimidine-6-carboxylic acid amide and the corresponding aldehydes (see in Table 2)

TABLE 2

| Example | Structure | Mass | Retention time | aldehyde |
|---|---|---|---|---|
| 7 | 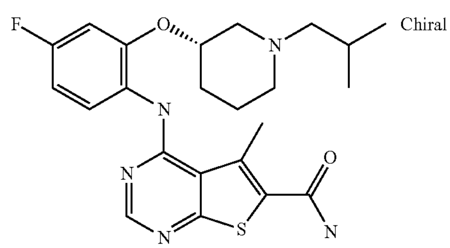 [SMILES: Cc1c(C(N)=O)sc2ncnc(Nc3ccc(F)cc3O[C@H]3CCCN(CC(C)C)C3)c12] | 458 (M + H)$^+$ | 1.17 (method X) | |
| 8 | 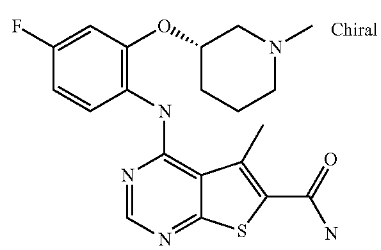 [SMILES: Cc1c(C(N)=O)sc2ncnc(Nc3ccc(F)cc3O[C@H]3CCCN(C)C3)c12] | 416 | 1.13 (method X) | |
| 9 | 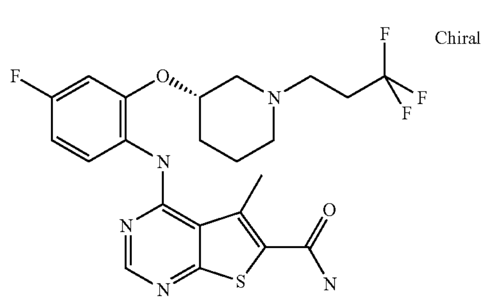 [SMILES: Cc1c(C(N)=O)sc2ncnc(Nc3ccc(F)cc3O[C@H]3CCCN(CCC(F)(F)F)C3)c12] | 498 | 1.18 (method X) | |

Compound 10

(S)-4-(4-fluoro-2-(1-(methylsulfonyl)piperidin-3-yloxy)phenylamino)-5-methylthieno[2,3-d]pyrimidine-6-carboxamide

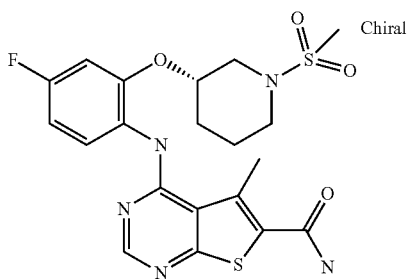 [SMILES: Cc1c(C(N)=O)sc2ncnc(Nc3ccc(F)cc3O[C@H]3CCCN(S(C)(=O)=O)C3)c12]

10.1 4-[4-Fluoro-2-((S)-piperidin-3-yloxy)-phenylamino]-5-methyl-thieno[2,3-d]pyrimidine-6-carboxylic acid methyl ester

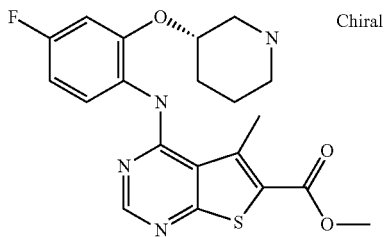 [SMILES: COC(=O)c1sc2ncnc(Nc3ccc(F)cc3O[C@H]3CCCNC3)c2c1C]

To a solution of 4-[2-((S)-1-tert-butoxycarbonyl-piperidin-3-yloxy)-4-fluoro-phenylamino]-5-methyl-thieno[2,3-d]pyrimidine-6-carboxylic acid methyl ester (300 mg) in methanol (3 ml) was added HCl in dioxan (4M; 3 ml) and the solution was stirred for 3 h. The solvent was removed and the residue was purified by chromatography.

Yield: 240 mg

10.2 4-[4-Fluoro-2-((S)-1-methanesulfonyl-piperidin-3-yloxy)-phenylamino]-5-methyl-thieno[2,3-d]pyrimidine-6-carboxylic acid methyl ester

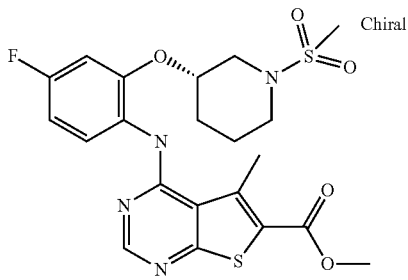 [SMILES: COC(=O)c1sc2ncnc(Nc3ccc(F)cc3O[C@H]3CCCN(S(C)(=O)=O)C3)c2c1C]

To a solution of 4-[4-fluoro-2-((S)-piperidin-3-yloxy)-phenylamino]-5-methyl-thieno[2,3-d]pyrimidine-6-carboxylic acid methyl ester (110 mg) in dichloromethane (3 ml) at 0° C. was added DIPEA (55 μl) followed by methanesulfonyl chloride (25 μl) and the reaction was allowed to warm to room temperature and stirred for 2 h.

Yield: 130 mg

10.3 4-[4-Fluoro-2-((S)-1-methanesulfonyl-piperidin-3-yloxy)-phenylamino]-5-methyl-thieno[2,3-d]pyrimidine-6-carboxylic acid

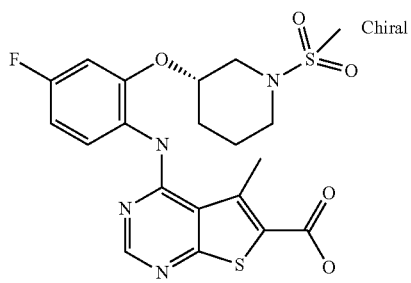 [SMILES: Cc1c(C(=O)O)sc2ncnc(Nc3ccc(F)cc3O[C@H]3CCCN(S(C)(=O)=O)C3)c12]

4-[4-Fluoro-2-((S)-1-methanesulfonyl-piperidin-3-yloxy)-phenylamino]-5-methyl-thieno[2,3-d]pyrimidine-6-carboxylic acid methyl ester (130 mg) was dissolved in THF (3 ml) and a solution of lithium hydroxide* H$_2$O (60 mg) in water (3 ml) was added. The mixture was stirred for 4 h. HCl (2M) was added to adjusted to pH 5 and the volatile solvent partially removed until crystallization occurred. The solid was collected by filtration. The filter cake was washed with water and was dried to give the desired product.

Yield: 125 mg

10.4 (S)-4-(4-fluoro-2-(1-(methylsulfonyl)piperidin-3-yloxy)phenylamino)-5-methylthieno[2,3-d]pyrimidine-6-carboxamide

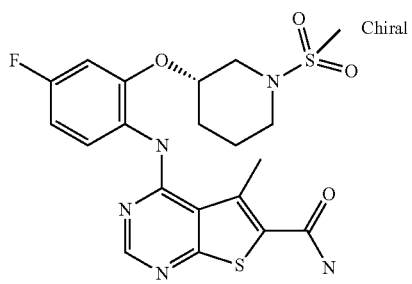

To a solution of 4-[4-Fluoro-2-((S)-1-methanesulfonyl-piperidin-3-yloxy)-phenylamino]-5-methyl-thieno[2,3-d]pyrimidine-6-carboxylic acid (120 mg) at 0° C. was added DIPEA (49 μl) followed by HATU (104 mg) and the solution was stirred for 30 min. A solution of ammonia in methanol (7M; 0.3 ml) was added and the solution allowed to warm to room temperature and stirred for 1 h. The solvent was evaporated and traces of DMF removed by co-evaporation with toluene. The residue was triturated with MeOH and the solid collected by filtration to give the desired product.

Yield: 45 mg

ESI mass spectrum: m/z=480 (M+H)$^+$

Retention time HPLC: 1.28 (method X)

Compound 11

4-[4-Fluoro-2-((S)-piperidin-3-yloxy)-phenylamino]-5-methyl-thieno[2,3-d]pyrimidine-6-carboxylic acid methylamide

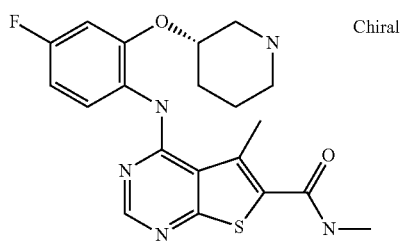 [SMILES: CNC(=O)c1sc2ncnc(Nc3ccc(F)cc3O[C@H]3CCCNC3)c2c1C]

11.1 4-[2-((S)-1-tert-Butoxycarbonyl-piperidin-3-yloxy)-4-fluoro-phenylamino]-5-methyl-thieno[2,3-d]pyrimidine-6-carboxylic acid 2,5-dioxo-pyrrolidin-1-yl ester

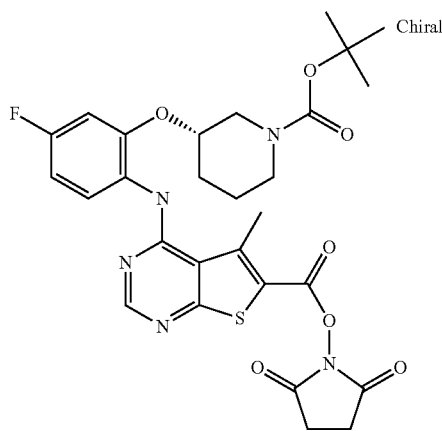 [SMILES: Cc1c(C(=O)ON2C(=O)CCC2=O)sc2ncnc(Nc3ccc(F)cc3O[C@H]3CCCN(C(=O)OC(C)(C)C)C3)c12]

EDC (290 mg) was added into a solution of 4-[2-((S)-1-tert-butoxycarbonyl-piperidin-3-yloxy)-4-fluoro-phenylamino]-5-methyl-thieno[2,3-d]pyrimidine-6-carboxylic acid (640 mg) and N-hydroxysuccinimide (218 mg) in anhydrous DMF (10 ml). The reaction was stirred at room temperature overnight. A further aliqout of EDC (58 mg) and N-hydroxysuccinimide (44 mg) were added and the reaction stirred for further 2 h. The DMF was removed in vacuo and the residue co-evaporated from toluene. The solid was portioned between EtOAc and water. The organic layer was separated and washed with brine. The combined organics were passed through a phase separator and concentrated in vacuo.

Yield: 710 mg

11.2 4-[4-Fluoro-2-((S)-piperidin-3-yloxy)-phenylamino]-5-methyl-thieno[2,3-d]pyrimidine-6-carboxylic acid methylamide

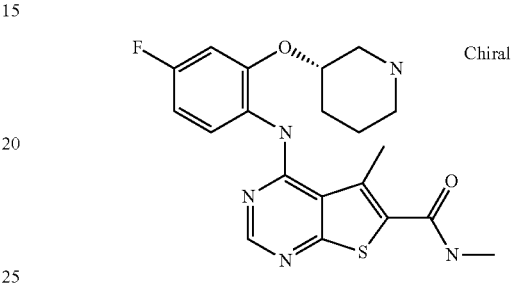

Methyl amine in THF (2M; 0.420 ml) was added into a solution of 4-[2-((S)-1-tert-butoxycarbonyl-piperidin-3-yloxy)-4-fluoro-phenylamino]-5-methyl-thieno[2,3-d]pyrimidine-6-carboxylic acid 2,5-dioxo-pyrrolidin-1-yl ester (100 mg) in anhydrous DMF (2 ml). The reaction was stirred at room temperature overnight. The DMF was removed and methanol (2 ml) was added to the residue.

HCl in Dioxan (4M; 0.5 ml) was added. The reaction mixture was stirred at room temperature overnight. The volatiles were removed in vacuo and the residue was purified by RP-chromatography to give the desired product.

Yield: 40 mg
ESI mass spectrum: m/z=416 (M+H)$^+$
Retention time HPLC: 1.15 (method X)

The following compounds were prepared analogously to 11.2 from compound 11.1 and the corresponding amine.

In case of structures where no chirality is indicated a mixture of 4-[2-((S)-1-tert-Butoxycarbonyl-piperidin-3-yloxy)-4-fluoro-phenylamino]-5-methyl-thieno[2,3-d]pyrimidine-6-carboxylic acid 2,5-dioxo-pyrrolidin-1-yl ester and 4-[2-((R)-1-tert-Butoxycarbonyl-piperidin-3-yloxy)-4-fluoro-phenylamino]-5-methyl-thieno[2,3-d]pyrimidine-6-carboxylic acid 2,5-dioxo-pyrrolidin-1-yl ester was used.

TABLE 3

| Example | Structure | | Mass | Retention time |
|---|---|---|---|---|
| 12 | 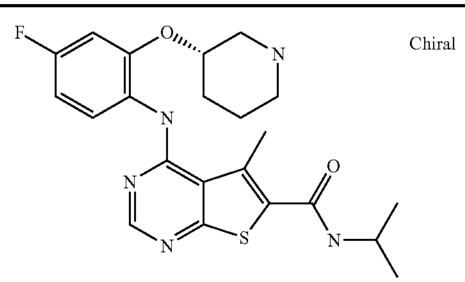 | Chiral | 444 (M + H)$^+$ | 1.20 (method X) |

TABLE 3-continued

| Example | Structure | Mass | Retention time |
|---|---|---|---|
| 13 | 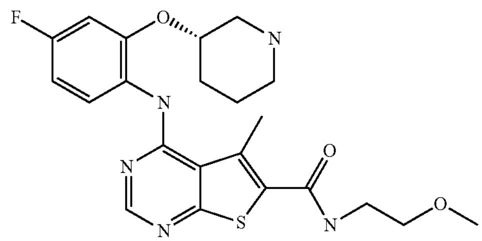 | Chiral 460 (M + H)+ | 1.17 (method X) |
| 14 | 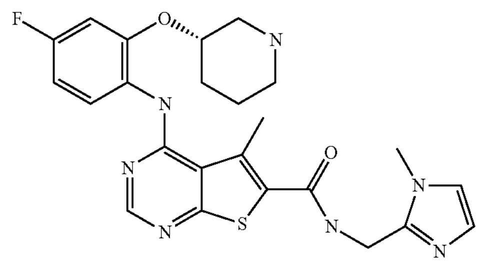 | Chiral 496 (M + H)+ | 1.11 (method X) |
| 15 | 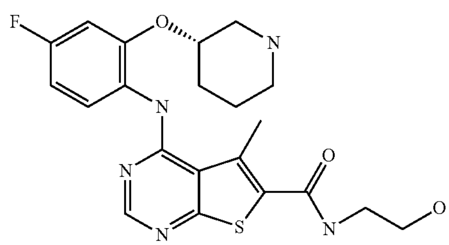 | Chiral 446 (M + H)+ | 1.12 (method X) |
| 16 | 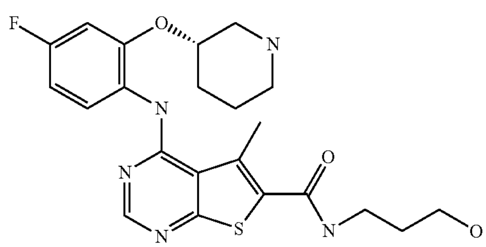 | Chiral 460 (M + H)+ | 1.13 (method X) |
| 17 | 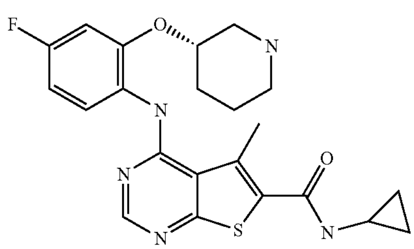 | Chiral 442 (M + H)+ | 1.18 (method X) |
| 18 | 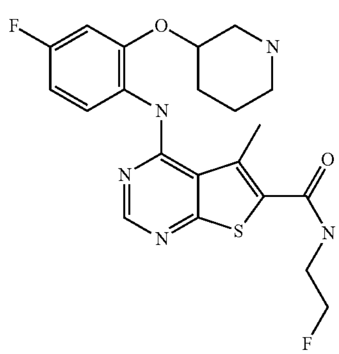 [SMILES: Cc1c(C(=O)NCCF)sc2ncnc(Nc3ccc(F)cc3OC3CCCNC3)c12] | 448 (M + H)+ | 1.17 (method X) |

TABLE 3-continued

| Example | Structure | Mass | Retention time |
|---|---|---|---|
| 19 | 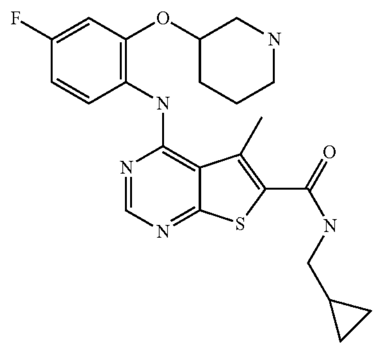 [SMILES: Cc1c(C(=O)NCC2CC2)sc2ncnc(Nc3ccc(F)cc3OC3CCCNC3)c12] | 456 (M + H)+ | 1.22 (method X) |
| 20 | 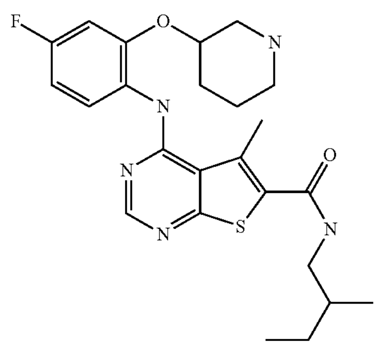 [SMILES: CCC(C)CNC(=O)c1sc2ncnc(Nc3ccc(F)cc3OC3CCCNC3)c2c1C] | 472 (M + H)+ | 1.28 (method X) |
| 21 | 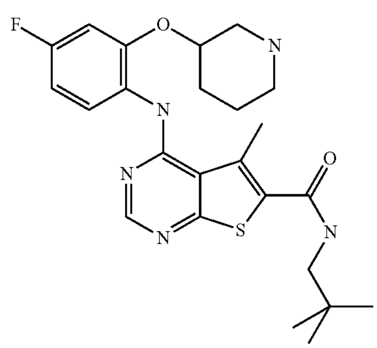 [SMILES: Cc1c(C(=O)NCC(C)(C)C)sc2ncnc(Nc3ccc(F)cc3OC3CCCNC3)c12] | 472 (M + H)+ | 1.27 (method X) |
| 22 | 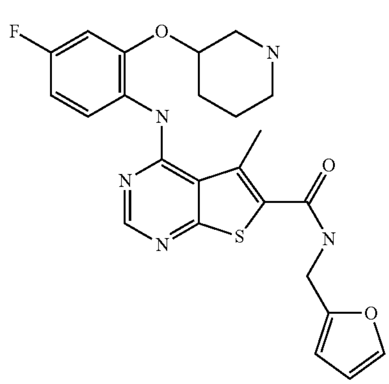 [SMILES: Cc1c(C(=O)NCc2ccco2)sc2ncnc(Nc3ccc(F)cc3OC3CCCNC3)c12] | 482 (M + H)+ | 1.23 (method X) |

TABLE 3-continued

| Example | Structure | Mass | Retention time |
|---|---|---|---|
| 23 | 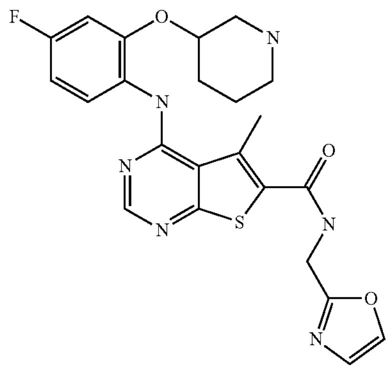 [SMILES: Cc1c(C(=O)NCc2ncco2)sc2ncnc(Nc3ccc(F)cc3OC3CCCNC3)c12] | 483 (M + H)+ | 1.17 (method X) |
| 24 | 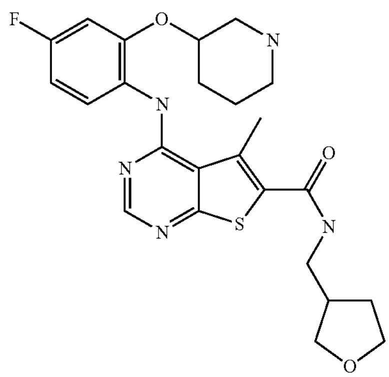 [SMILES: Cc1c(C(=O)NCC2CCOC2)sc2ncnc(Nc3ccc(F)cc3OC3CCCNC3)c12] | 486 (M + H)+ | 1.17 (method X) |
| 25 | 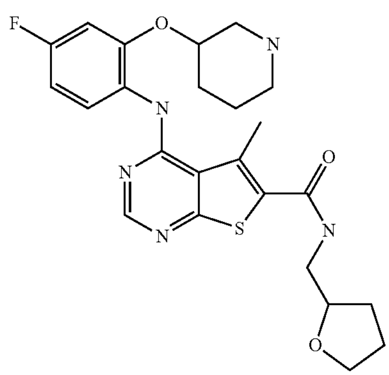 [SMILES: Cc1c(C(=O)NCC2CCCO2)sc2ncnc(Nc3ccc(F)cc3OC3CCCNC3)c12] | 486 (M + H)+ | 1.19 (method X) |
| 26 | 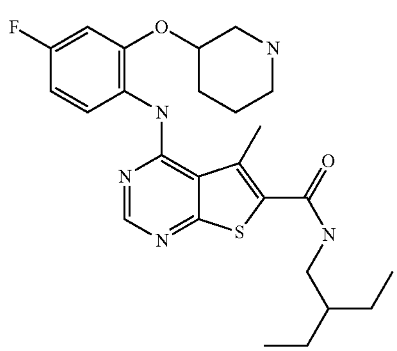 [SMILES: CCC(CC)CNC(=O)c1sc2ncnc(Nc3ccc(F)cc3OC3CCCNC3)c2c1C] | 486 (M + H)+ | 1.31 (method X) |

TABLE 3-continued
| Example | Structure | Mass | Retention time |
|---|---|---|---|
| 27 | 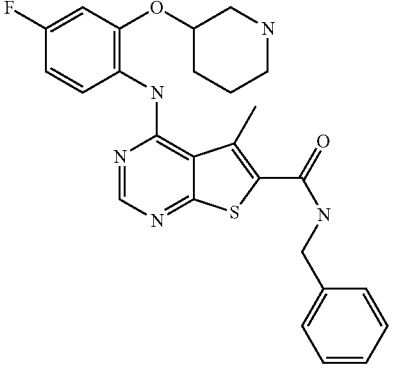 [SMILES: Cc1c(C(=O)NCc2ccccc2)sc2ncnc(Nc3ccc(F)cc3OC3CCCNC3)c12] | 492 (M + H)+ | 1.26 (method X) |
| 28 | 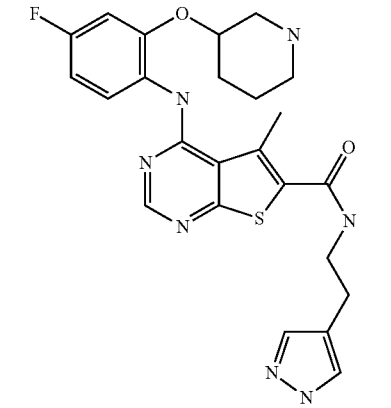 [SMILES: Cc1c(C(=O)NCCc2cn[nH]c2)sc2ncnc(Nc3ccc(F)cc3OC3CCCNC3)c12] | 496 (M + H)+ | 1.13 (method X) |
| 29 | 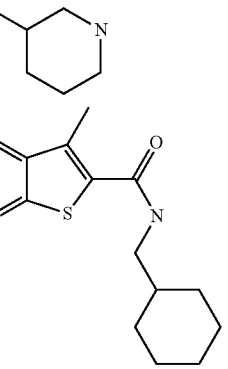 | 498 (M + H)+ | 1.32 (method X) |
| 30 | 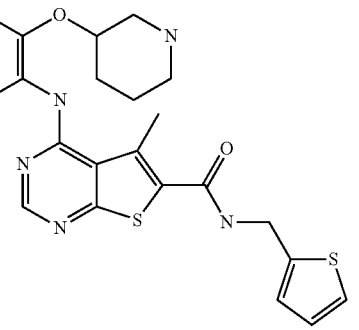 | 498 (M + H)+ | 1.25 (method X) |

TABLE 3-continued

| Example | Structure | Mass | Retention time |
|---|---|---|---|
| 31 | 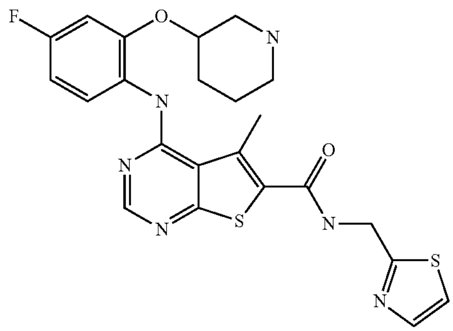 [SMILES: Cc1c(C(=O)NCc2nccs2)sc2ncnc(Nc3ccc(F)cc3OC3CCCNC3)c12] | 499 (M + H)+ | 1.19 (method X) |
| 32 | 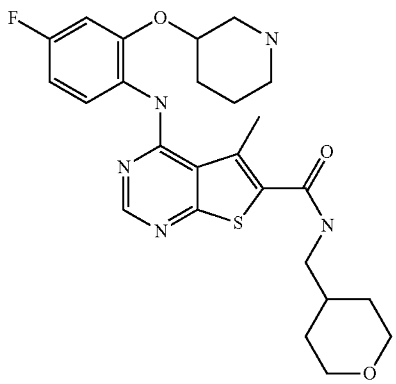 [SMILES: Cc1c(C(=O)NCC2CCOCC2)sc2ncnc(Nc3ccc(F)cc3OC3CCCNC3)c12] | 500 (M + H)+ | 1.19 (method X) |
| 33 | 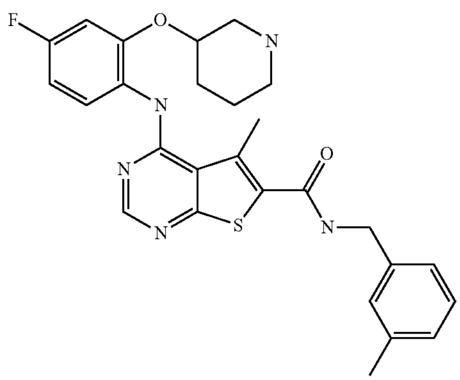 [SMILES: Cc1cccc(CNC(=O)c2sc3ncnc(Nc4ccc(F)cc4OC4CCCNC4)c3c2C)c1] | 506 (M + H)+ | 1.3 (method X) |
| 34 | 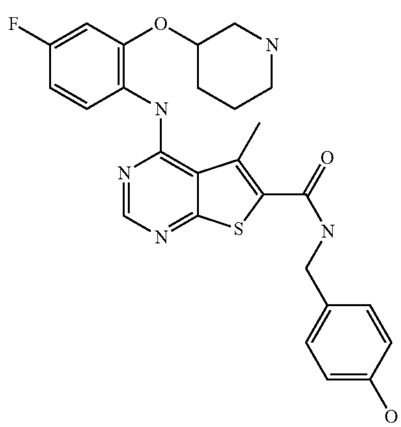 [SMILES: Cc1c(C(=O)NCc2ccc(O)cc2)sc2ncnc(Nc3ccc(F)cc3OC3CCCNC3)c12] | 508 (M + H)+ | 1.2 (method X) |

TABLE 3-continued
| Example | Structure | Mass | Retention time |
|---|---|---|---|
| 35 | 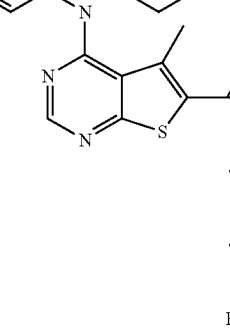 | 510 (M + H)+ | 1.27 (method X) |
| 36 | 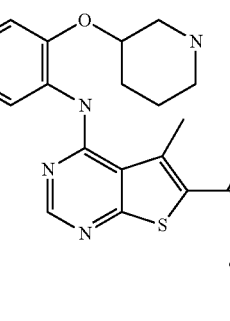 | 512 (M + H)+ | 1.35 (method X) |
| 37 | 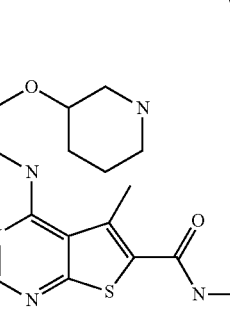 | 512 (M + H)+ | 1.27 (method X) |
| 38 | 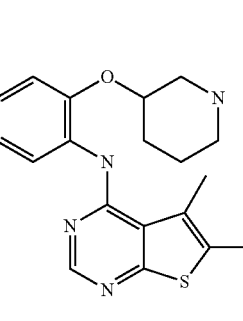 | 514 (M + H)+ | 1.26 (method X) |

TABLE 3-continued

| Example | Structure | Mass | Retention time |
|---|---|---|---|
| 39 | 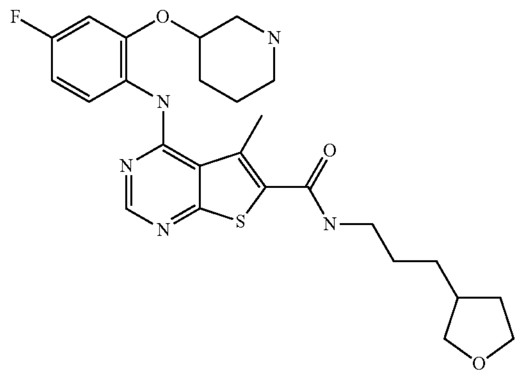 [SMILES: Cc1c(C(=O)NCCCC2CCOC2)sc2ncnc(Nc3ccc(F)cc3OC3CCCNC3)c12] | 514 (M + H)+ | 1.21 (method X) |
| 40 | 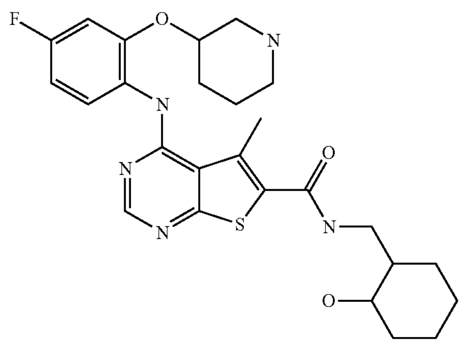 [SMILES: Cc1c(C(=O)NCC2CCCCC2O)sc2ncnc(Nc3ccc(F)cc3OC3CCCNC3)c12] | 514 (M + H)+ | 1.23 (method X) |
| 41 | 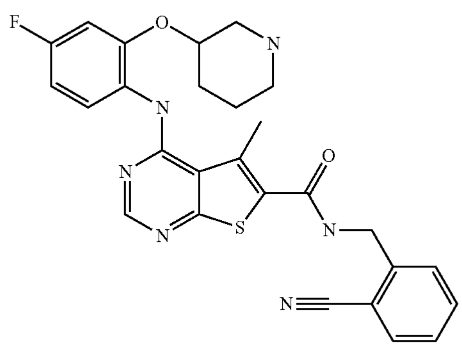 [SMILES: Cc1c(C(=O)NCc2ccccc2C#N)sc2ncnc(Nc3ccc(F)cc3OC3CCCNC3)c12] | 517 (M + H)+ | 1.25 (method X) |
| 42 | 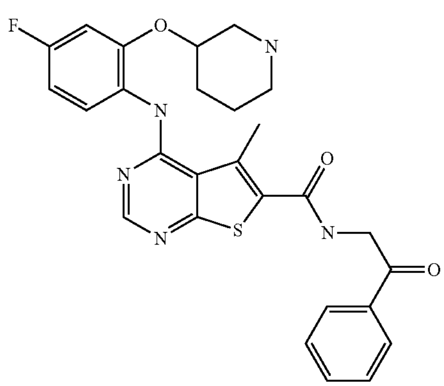 [SMILES: Cc1c(C(=O)NCC(=O)c2ccccc2)sc2ncnc(Nc3ccc(F)cc3OC3CCCNC3)c12] | 520 (M + H)+ | 1.26 (method X) |

TABLE 3-continued
| Example | Structure | Mass | Retention time |
|---|---|---|---|
| 43 | 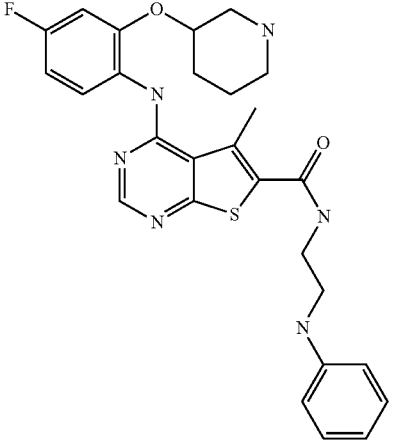 [SMILES: Cc1c(C(=O)NCCNc2ccccc2)sc2ncnc(Nc3ccc(F)cc3OC3CCCNC3)c12] | 521 (M + H)⁺ | 1.19 (method X) |
| 44 | 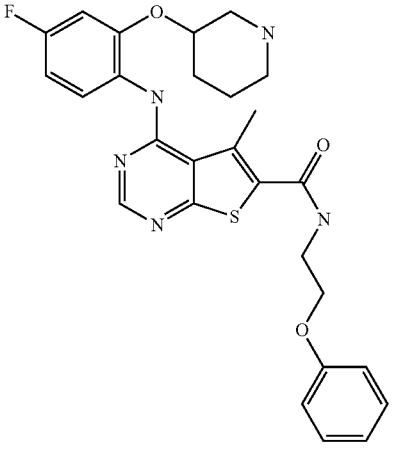 [SMILES: Cc1c(C(=O)NCCOc2ccccc2)sc2ncnc(Nc3ccc(F)cc3OC3CCCNC3)c12] | 522 (M + H)⁺ | 1.28 (method X) |
| 45 | 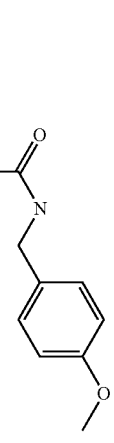 | 522 (M + H)⁺ | 1.26 (method X) |

TABLE 3-continued

| Example | Structure | Mass | Retention time |
|---|---|---|---|
| 46 | 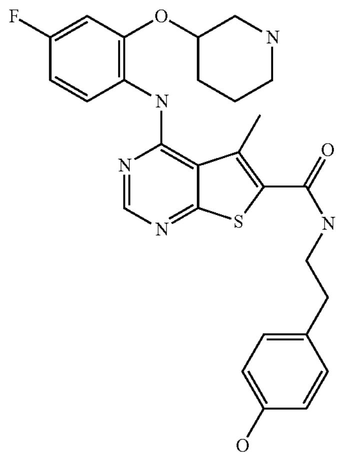 [SMILES: Cc1c(C(=O)NCCc2ccc(O)cc2)sc2ncnc(Nc3ccc(F)cc3OC3CCCNC3)c12] | 522 (M + H)+ | 1.21 (method X) |
| 47 | 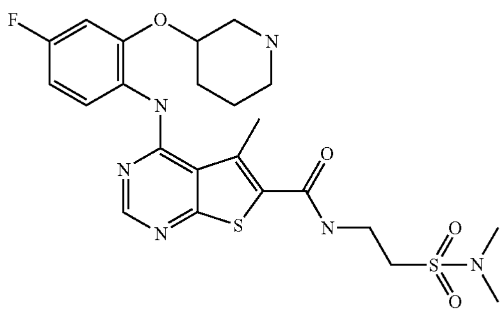 [SMILES: Cc1c(C(=O)NCCS(=O)(=O)N(C)C)sc2ncnc(Nc3ccc(F)cc3OC3CCCNC3)c12] | 537 (M + H)+ | 1.19 (method X) |
| 48 | 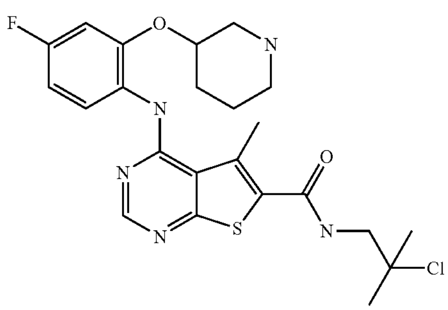 [SMILES: Cc1c(C(=O)NCC(C)(C)Cl)sc2ncnc(Nc3ccc(F)cc3OC3CCCNC3)c12] | 492 (M + H)+ | 1.26 (method X) |
| 49 | 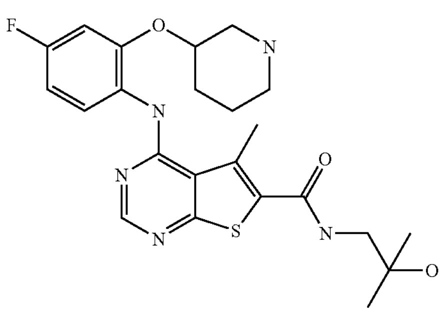 [SMILES: Cc1c(C(=O)NCC(C)(C)O)sc2ncnc(Nc3ccc(F)cc3OC3CCCNC3)c12] | 474 (M + H)+ | 1.15 (method X) |

TABLE 3-continued

| Example | Structure | | Mass | Retention time |
|---|---|---|---|---|
| 50 | 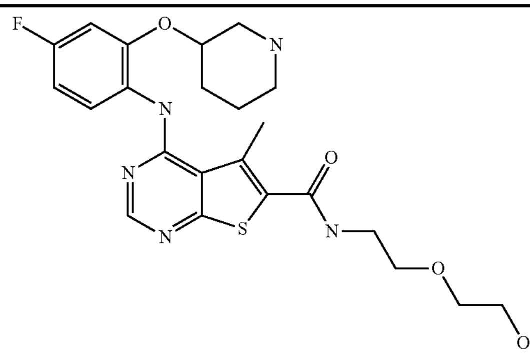 | | 490 (M + H)+ | 1.13 (method X) |
| 51 | 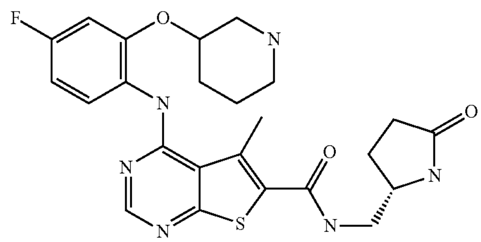 | Chiral | 499 (M + H)+ | 1.13 (method X) |
| 52 | 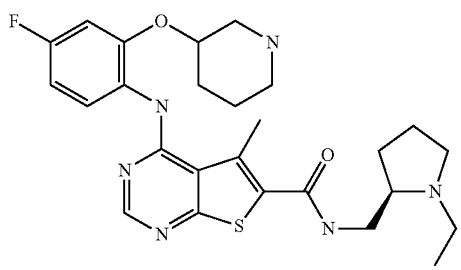 | Chiral | 513 (M + H)+ | 1.12 (method X) |
| 53 | 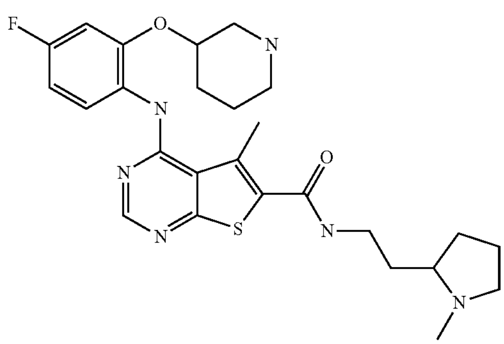 [SMILES: Cc1c(C(=O)NCCC2CCCN2C)sc2ncnc(Nc3ccc(F)cc3OC3CCCNC3)c12] | | 513 (M + H)+ | 1.11 (method X) |
| 54 | 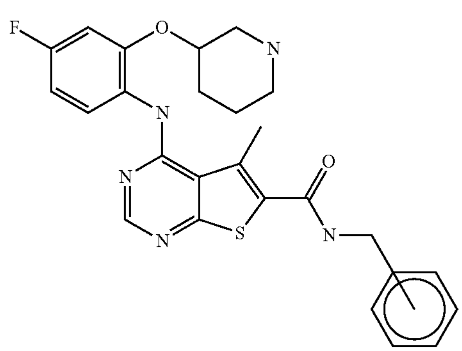 | | 514 (M + H)+ | 1.23 (method X) |

TABLE 3-continued

| Example | Structure | Mass | Retention time |
|---|---|---|---|
| 55 | 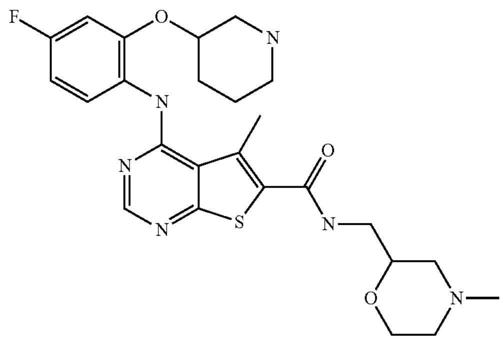 [SMILES: Cc1c(C(=O)NCC2CN(C)CCO2)sc2ncnc(Nc3ccc(F)cc3OC3CCCNC3)c12] | 515 (M + H)+ | 1.1 (method X) |
| 56 | 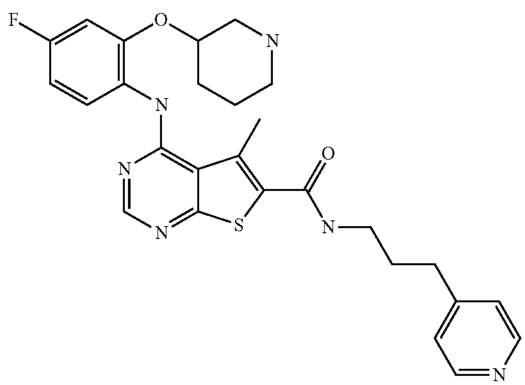 [SMILES: Cc1c(C(=O)NCCCc2ccncc2)sc2ncnc(Nc3ccc(F)cc3OC3CCCNC3)c12] | 521 (M + H)+ | 1.12 (method X) |
| 57 | 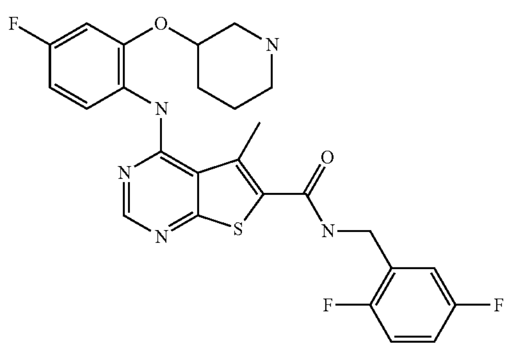 [SMILES: Cc1c(C(=O)NCc2cc(F)ccc2F)sc2ncnc(Nc3ccc(F)cc3OC3CCCNC3)c12] | 528 (M + H)+ | 1.28 (method X) |
| 58 | 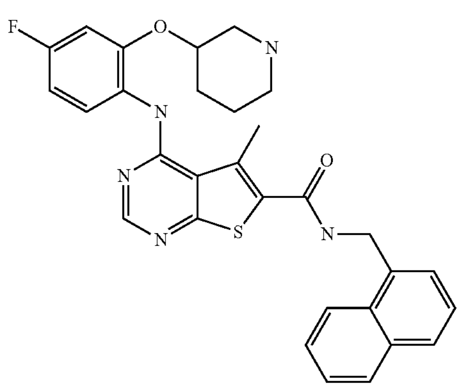 [SMILES: Cc1c(C(=O)NCc2cccc3ccccc23)sc2ncnc(Nc3ccc(F)cc3OC3CCCNC3)c12] | 542 (M + H)+ | 1.33 (method X) |

TABLE 3-continued

| Example | Structure | Mass | Retention time |
|---|---|---|---|
| 59 | 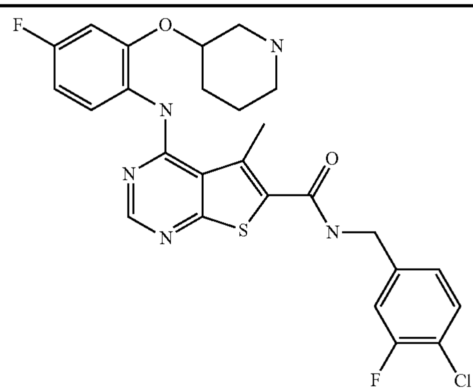 | 544 (M + H)+ | 1.32 (method X) |
| 60 | 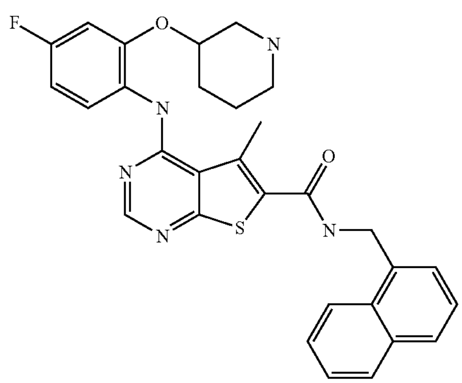 [SMILES: Cc1c(C(=O)NCc2cccc3ccccc23)sc2ncnc(Nc3ccc(F)cc3OC3CCCNC3)c12] | 542 (M + H)+ | 1.33 (method X) |
| 61 | 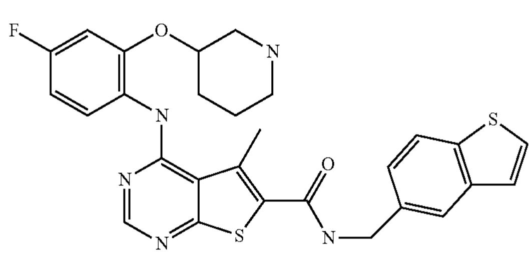 [SMILES: Cc1c(C(=O)NCc2ccc3sccc3c2)sc2ncnc(Nc3ccc(F)cc3OC3CCCNC3)c12] | 548 (M + H)+ | 1.31 (method X) |
| 62 | 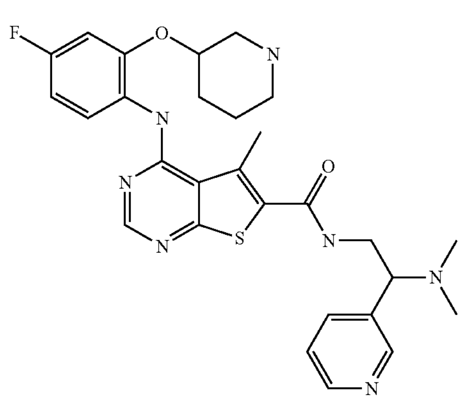 [SMILES: Cc1c(C(=O)NCC(c2cccnc2)N(C)C)sc2ncnc(Nc3ccc(F)cc3OC3CCCNC3)c12] | 550 (M + H)+ | 1.09 (method X) |

TABLE 3-continued

| Example | Structure | Mass | Retention time |
|---|---|---|---|
| 63 | 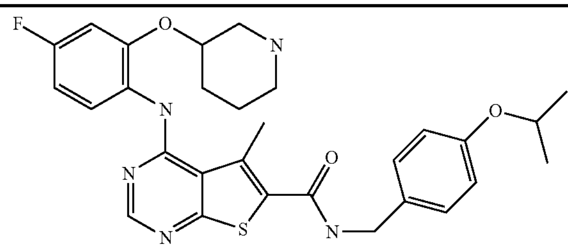 | 550 (M + H)+ | 1.32 (method X) |

Compound 64

4-[4-Fluoro-2-((S)-piperidin-3-yloxy)-phenylamino]-5-methyl-thieno[2,3-d]pyrimidine-6-carboxylic acid (1-methyl-1H-pyrazol-3-yl)-amide

64.1 (S)-3-{5-Fluoro-2-[5-methyl-6-(1-methyl-1H-pyrazol-3-ylcarbamoyl)-thieno[2,3-d]pyrimidin-4-ylamino]-phenoxy}-piperidine-1-carboxylic acid tert-butyl ester HATU was added into a solution of 4-[2-((S)-1-tert-Butoxycarbonyl-piperidin-3-yloxy)-4-fluoro-phenylamino]-5-methyl-thieno[2,3-d]pyrimidine-6-carboxylic acid (100 mg) and DIPEA in anhydrous DMF (2 ml) at 0° C. The reaction was stirred for 0.5 h when 1-methyl-1H-pyrazol-3-amine (100 µl) was added and the reaction allowed to warm to room temperature and stirred for 2 h. The DMF was removed by co-evaporation from toluene and the residue was purified by chromatography to give the intended product.

Yield: 120 mg

64.2 4-[4-Fluoro-2-((S)-piperidin-3-yloxy)-phenylamino]-5-methyl-thieno[2,3-d]pyrimidine-6-carboxylic acid (1-methyl-1H-pyrazol-3-yl)-amide Prepared analogously to example 1.3. from (S)-3-{5-fluoro-2-[5-methyl-6-(1-methyl-1H-pyrazol-3-ylcarbamoyl)-thieno[2,3-d]pyrimidin-4-ylamino]-phenoxy}-piperidine-1-carboxylic acid tert-butyl ester Yield: 80 mg ESI mass spectrum: m/z=482 (M+H)+

Retention time HPLC: 1.19 (method X)

Compound 65

5-Methyl-4-[2-((S)-piperidin-3-yloxy)-4-trifluoromethyl-phenylamino]-thieno[2,3-d]pyrimidine-6-carboxylic acid amide

65.1 4-[2-((S)-1-tert-Butoxycarbonyl-piperidin-3-yloxy)-4-trifluoromethyl-phenylamino]-5-methyl-thieno[2,3-d]pyrimidine-6-carboxylic acid methyl ester

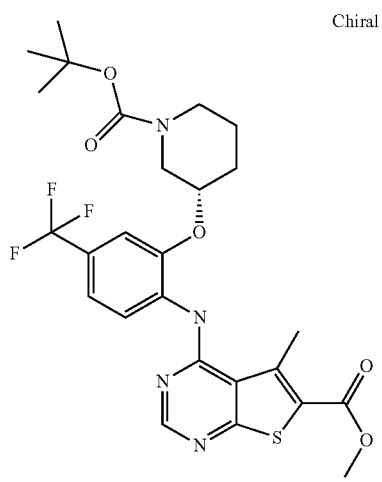 [SMILES: COC(=O)c1sc2ncnc(Nc3ccc(C(F)(F)F)cc3O[C@H]3CCCN(C(=O)OC(C)(C)C)C3)c2c1C]

4-Chloro-5-methyl-thieno[2,3-d]pyrimidine-6-carboxylic acid methyl ester (326 mg) and (S)-tert-butyl 3-(2-amino-5-(trifluoromethyl)phenoxy)piperidine-1-carboxylate (485 mg) was dissolved in dioxane (4 ml), p-toluenesulfonic acid (26 mg) was added. The reaction mixture was heated at 80° C. for about 5 h. The mixture was diluted with dichloromethane and 10% aq. K2CO3 solution. The organic layer was separated, passed through a hydrophobic frit and concentrated in vacuo. The residue was purified by column chromatography (silica gel; solvent:100% iso hexane→4:1 H:E).

Yield: 181 mg

65.2 4-[2-(S)-1-tert-Butoxycarbonyl-piperidin-3-yloxy)-4-trifluoromethyl-phenylamino]-5-methyl-thieno[2,3-d]pyrimidine-6-carboxylic acid

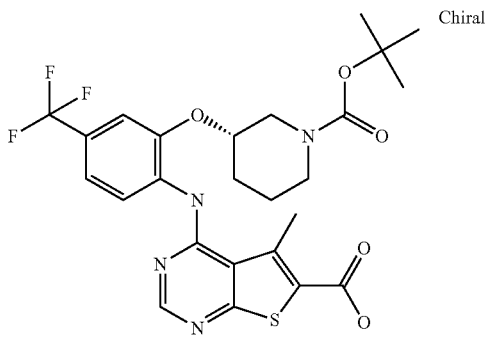 [SMILES: Cc1c(C(=O)O)sc2ncnc(Nc3ccc(C(F)(F)F)cc3O[C@H]3CCCN(C(=O)OC(C)(C)C)C3)c12]

4-[2-((S)-1-tert-butoxycarbonyl-piperidin-3-yloxy)-4-trifluoromethyl-phenylamino]-5-methyl-thieno[2,3-d]pyrimidine-6-carboxylic acid methyl ester (181 mg) was dissolved in THF (1 ml)/methanol (1 ml) and NaOH (2M; 0.8 ml) was added. The reaction was heated at reflux for 10 min. The organic solvent was evaporated and the residue treated with 10% aq. KHSO4. Water was added and the suspension was filtered. Solid was washed with water and the solid dried in vacuo over P2O5.

Yield: 200 mg

65.3 4-[2-((S)-1-tert-Butoxycarbonyl-piperidin-3-yloxy)-4-trifluoromethyl-phenylamino]-5-methyl-thieno[2,3-d]pyrimidine-6-carboxylic acid amide

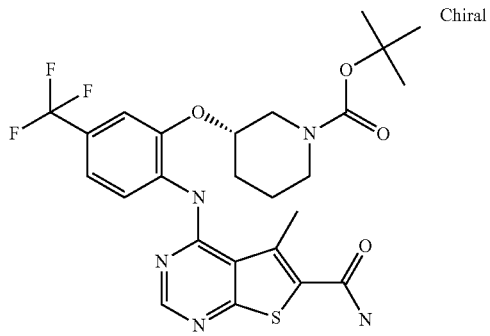 [SMILES: Cc1c(C(N)=O)sc2ncnc(Nc3ccc(C(F)(F)F)cc3O[C@H]3CCCN(C(=O)OC(C)(C)C)C3)c12]

EDC (74 mg) added to a mixture of the 4-[2-((S)-1-tert-butoxycarbonyl-piperidin-3-yloxy)-4-trifluoromethyl-phenylamino]-5-methyl-thieno[2,3-d]pyrimidine-6-carboxylic acid (177 mg) and N-hydroxysuccinimide (55 mg) in DMF (4 ml). The reaction mixture was stirred at room temperature overnight. The reaction was diluted with EtOAc and washed with water and brine. The organics were passed through a hydrophobic frit and the solvent was evaporated. The residue was dissolved in DMF (2 ml) and ammonia in methanol (2 ml) was added. The reaction was stirred for 1 h. Further ammonia in methanol (2 ml) was added and the reaction was stirred again. After 30 min the reaction was diluted with EtOAc and washed with water and brine.

Yield: 77 mg

65.4 (S)-5-methyl-4-(2-(piperidin-3-yloxy)-4-(trifluoromethyl)phenylamino)thieno[2,3-d]pyrimidine-6-carboxamide 4-[2-((S)-1-tert-butoxycarbonyl-piperidin-3-yloxy)-4-trifluoromethyl-phenylamino]-5-methyl-thieno[2,3-d]pyrimidine-6-carboxylic acid amide (77 mg) was dissolved in dichloromethane (1 ml) and HCl in dioxan (4M; 1.5 ml) was added. The reaction was stirred at room temperature for 1 h. The solvent was removed in vacuo and the residue was purfied by chromatography to give the inteded product.

Yield: 30.5 mg

ESI mass spectrum: m/z=452 (M+H)+

Retention time HPLC: 1.24 (method X)

Compound 66

4-[4-Chloro-2-((S)-piperidin-3-yloxy)-phenylamino]-5-methyl-thieno[2,3-d]pyrimidine-6-carboxylic acid amide

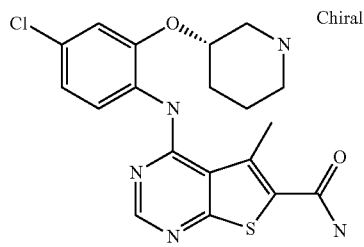 [SMILES: Cc1c(C(N)=O)sc2ncnc(Nc3ccc(Cl)cc3O[C@H]3CCCNC3)c12]

66.1 4-{4-Chloro-2-[(S)-1-(2,2,2-trifluoro-acetyl)-piperidin-3-yloxy]-phenylamino}-5-methyl-thieno[2,3-d]pyrimidine-6-carboxylic acid methyl ester

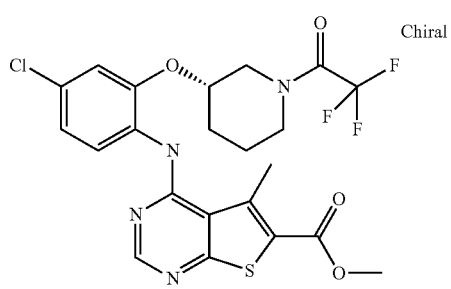 [SMILES: COC(=O)c1sc2ncnc(Nc3ccc(Cl)cc3O[C@H]3CCCN(C(=O)C(F)(F)F)C3)c2c1C]

Prepared analogously to example 65.1. from 4-chloro-5-methyl-thieno[2,3-d]pyrimidine-6-carboxylic acid methyl ester and (S)-1-(3-(2-amino-5-chlorophenoxy)piperidin-1-yl)-2,2,2-trifluoroethanone. The temperature was 110° C. for 2 h and no purification with chromatography was necessarily.

Yield: 420 mg

66.2 4-[4-Chloro-2-((S)-piperidin-3-yloxy)-phenylamino]-5-methyl-thieno[2,3-d]pyrimidine-6-carboxylic acid amide

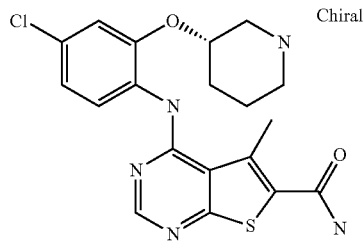 [SMILES: Cc1c(C(N)=O)sc2ncnc(Nc3ccc(Cl)cc3O[C@H]3CCCNC3)c12]

4-{4-Chloro-2-[(S)-1-(2,2,2-trifluoro-acetyl)-piperidin-3-yloxy]-phenylamino}-5-methyl-thieno[2,3-d]pyrimidine-6-carboxylic acid methyl ester (150 mg) and ammonia in methanol (7M; 5 ml) were combined and heated at 100° C. in sealed tube. The reaction heated under these conditions for 48 h. The residue was purified by chromatography tho give the inteded product.

Yield: 30 mg

ESI mass spectrum: m/z=418 (M+H)$^+$

Retention time HPLC: 1.18 (method X)

Compound 67

4-[4-Cyano-2-((S)-piperidin-3-yloxy)-phenylamino]-5-methyl-thieno[2,3-d]pyrimidine-6-carboxylic acid amide

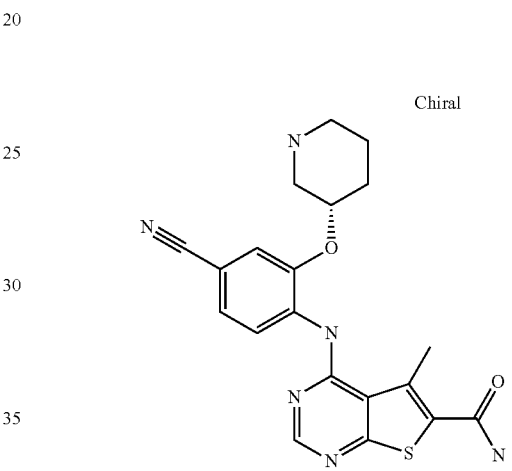

67.1 4-{4-Cyano-2-[(S)-1-(2,2,2-trifluoro-acetyl)-piperidin-3-yloxy]-phenylamino}-5-methyl-thieno[2,3-d]pyrimidine-6-carboxylic acid methyl ester

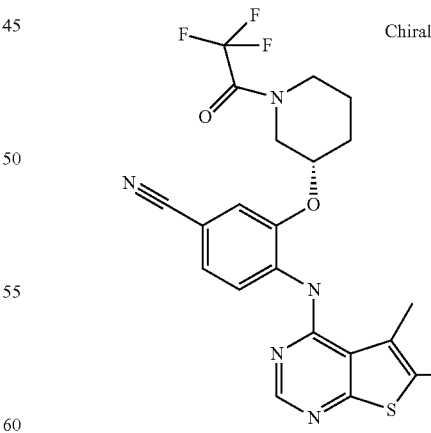

Prepared analogously to example 65.1. from 4-chloro-5-methyl-thieno[2,3-d]pyrimidine-6-carboxylic acid methyl ester and (S)-4-amino-3-(1-(2,2,2-trifluoroacetyl)piperidin-3-yloxy)benzonitrilie Yield: 72 mg

101

67.2 4-[4-Cyano-2-((S)-piperidin-3-yloxy)-phenylamino]-5-methyl-thieno[2,3-d]pyrimidine-6-carboxylic acid amide

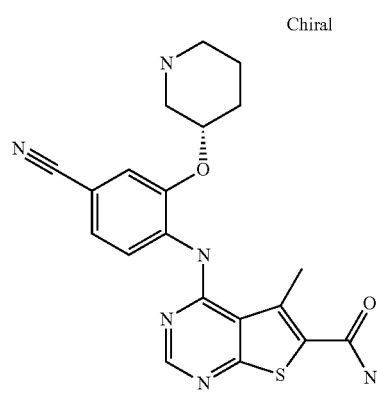 [SMILES: Cc1c(C(N)=O)sc2ncnc(Nc3ccc(C#N)cc3O[C@H]3CCCNC3)c12]

Prepared analogously to example 66.2. from 4-{4-cyano-2-[(S)-1-(2,2,2-trifluoro-acetyl)-piperidin-3-yloxy]-phenylamino}-5-methyl-thieno[2,3-d]pyrimidine-6-carboxylic acid methyl ester.

Yield: 20 mg

ESI mass spectrum: m/z=409 (M+H)$^+$

Retention time HPLC: 1.17 (method X)

Compound 68

4-[4-Methyl-2-((S)-piperidin-3-yloxy)-phenylamino]-5-methyl-thieno[2,3-d]pyrimidine-6-carboxylic acid amide

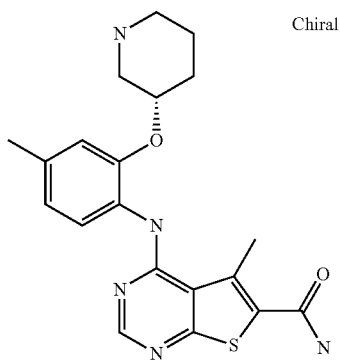 [SMILES: Cc1ccc(Nc2ncnc3sc(C(N)=O)c(C)c23)c(O[C@H]2CCCNC2)c1]

102

68.1 4-{4-Methyl-2-[(S)-1-(2,2,2-trifluoro-acetyl)-piperidin-3-yloxy]-phenylamino}-5-methyl-thieno[2,3-d]pyrimidine-6-carboxylic acid methyl ester

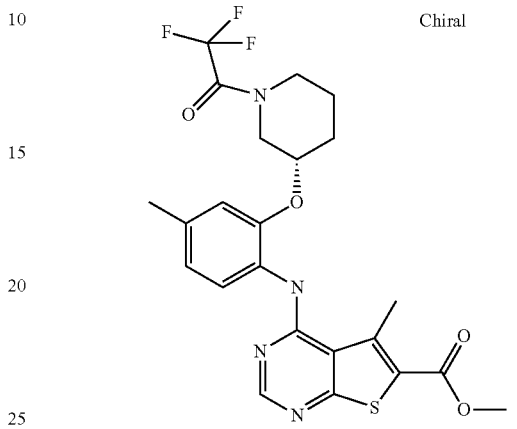

Prepared analogously to example 65.1. from 4-chloro-5-methyl-thieno[2,3-d]pyrimidine-6-carboxylic acid methyl ester and (S)-1-(3-(2-amino-5-methylphenoxy)piperidin-1-yl)-2,2,2-trifluoroethanone Yield: 196 mg 68.2 4-[4-Methyl-2-((S-piperidin-3-yloxy)-phenylamino]-5-methyl-thieno[2,3-d]pyrimidine-6-carboxylic acid amide

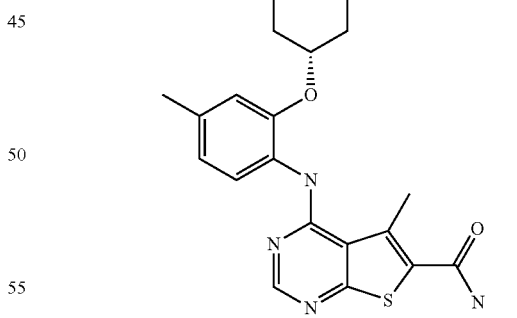

Prepared analogously to example 66.2. from 4-{4-methyl-2-[(S)-1-(2,2,2-trifluoro-acetyl)-piperidin-3-yloxy]-phenylamino}-5-methyl-thieno[2,3-d]pyrimidine-6-carboxylic acid methyl ester.

Yield: 55 mg

ESI mass spectrum: m/z=398 (M+H)$^+$

Retention time HPLC: 1.15

HPLC method: Method X

Compound 69

5-Methyl-4-[2-((S)-piperidin-3-yloxy)-pyridin-3-ylamino]thieno[2,3-d]pyrimidine-6-carboxylic acid amide

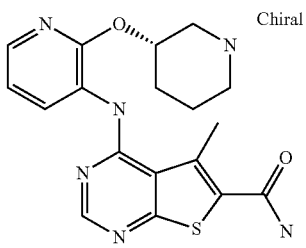 [SMILES: Cc1c(C(N)=O)sc2ncnc(Nc3cccnc3O[C@H]3CCCNC3)c12]

69.1 4-[2-((S)-1-tert-Butoxycarbonyl-piperidin-3-yloxy)-pyridin-3-ylamino]-5-methyl-thieno[2,3-d]pyrimidine-6-carboxylic acid methyl ester

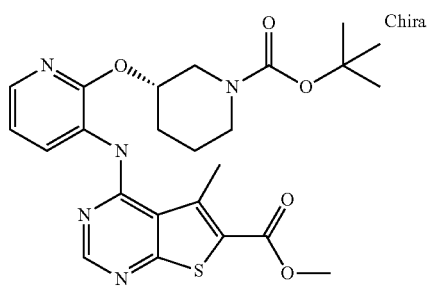

Prepared analogously to example 1.1. from 4-chloro-5-methyl-thieno[2,3-d]pyrimidine-6-carboxylic acid methyl ester and (S)-tert-butyl 3-(3-aminopyridin-2-yloxy)piperidine-1-carboxylate (Intermediate X)

Yield: 810 mg

69.2 4-[2-((S)-1-tert-Butoxycarbonyl-piperidin-3-yloxy)-pyridin-3-ylamino]-5-methyl-thieno[2,3-d] pyrimidine-6-carboxylic acid

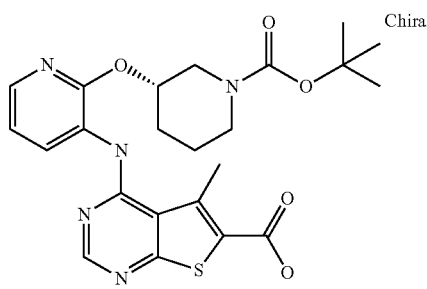

Prepared analogously to example 1.2. from 4-[2-((S)-1-tert-Butoxycarbonyl-piperidin-3-yloxy)-pyridin-3-ylamino]-5-methyl-thieno[2,3-d]pyrimidine-6-carboxylic acid methyl ester Yield: 915 mg

69.3 4-[2-((S)-1-tert-Butoxycarbonyl-piperidin-3-yloxy)-pyridin-3-ylamino]-5-methyl-thieno[2,3-d] pyrimidine-6-carboxylic acid amide

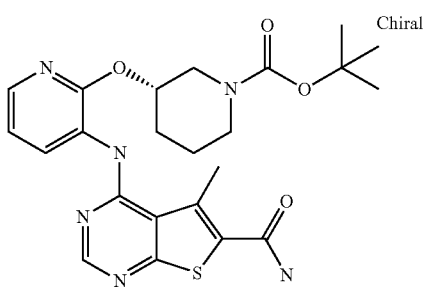 [SMILES: Cc1c(C(N)=O)sc2ncnc(Nc3cccnc3O[C@H]3CCCN(C(=O)OC(C)(C)C)C3)c12]

Prepared analogously to example 1.4. from 4-[2-((S)-1-tert-butoxycarbonyl-piperidin-3-yloxy)-pyridin-3-ylamino]-5-methyl-thieno[2,3-d]pyrimidine-6-carboxylic acid.

69.4 5-Methyl-4-[2-((S)-piperidin-3-yloxy)-pyridin-3-ylamino]-thieno[2,3-d]pyrimidine-6-carboxylic acid amide

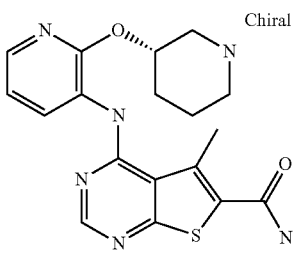 [SMILES: Cc1c(C(N)=O)sc2ncnc(Nc3cccnc3O[C@H]3CCCNC3)c12]

HCl in Dioxane (4M; 4 ml) was added into a solution of (S)-tert-butyl 3-(3-(6-carbamoyl-5-methylthieno[2,3-d]pyrimidin-4-ylamino)pyridin-2-yloxy)piperidine-1-carboxylate (250 mg) in Methanol (8 ml). The reaction was stirred at room temperature for 1.5 h. The solution was purified by chromatography.

Yield: 40 mg

ESI mass spectrum: m/z=385 (M+H)$^+$

Retention time HPLC: 1.12 (method X)

Compound 70

4-[2-((S)-1-tert-Butoxycarbonyl-piperidin-3-yloxy)-4-fluoro-phenylamino]-5-methyl-thieno[2,3-d]pyrimidine-6-carboxylic acid ethyl ester

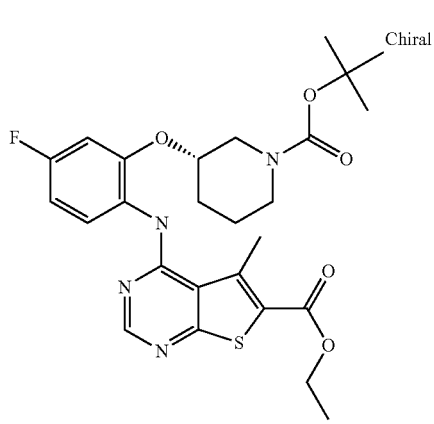 [SMILES: CCOC(=O)c1sc2ncnc(Nc3ccc(F)cc3O[C@H]3CCCN(C(=O)OC(C)(C)C)C3)c2c1C]

Prepared analogously to example 1.1. from 4-chloro-5-methyl-thieno[2,3-d]pyrimidine-6-carboxylic acid methyl ester and (S)-tert-butyl 3-(2-amino-5-fluorophenoxy)piperidine-1-carboxylate (Intermediate I).

Yield: 1.14 g
ESI mass spectrum: m/z=331 (M+H)$^+$
Retention time HPLC: 3.98 (method G)

Compound 71

4-[4-Fluoro-2-((R)-piperidin-3-yloxy)-phenylamino]-5-methyl-thieno[2,3-d]pyrimidine-6-carboxylic acid amide

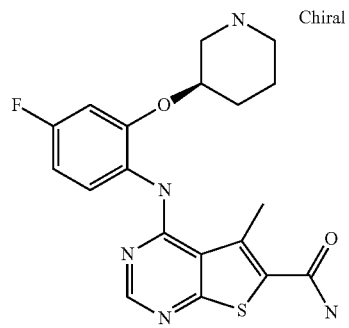 [SMILES: Cc1c(C(N)=O)sc2ncnc(Nc3ccc(F)cc3O[C@@H]3CCCNC3)c12]

71.1 4-[2-((R)-1-tert-Butoxycarbonyl-piperidin-3-yloxy)-4-fluoro-phenylamino]-5-methyl-thieno[2,3-d]pyrimidine-6-carboxylic acid methyl ester

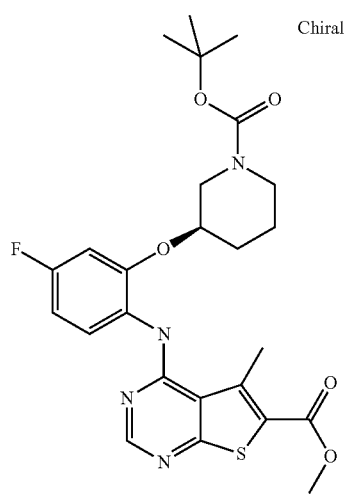 [SMILES: COC(=O)c1sc2ncnc(Nc3ccc(F)cc3O[C@@H]3CCCN(C(=O)OC(C)(C)C)C3)c2c1C]

Prepared analogously to example 65.1. from 4-chloro-5-methyl-thieno[2,3-d]pyrimidine-6-carboxylic acid methyl ester and (R)-tert-butyl 3-(2-amino-5-fluorophenoxy)piperidine-1-carboxylate (Intermediate II).

Yield: 1.65 g

71.2 4-[2-((R)-1-tert-Butoxycarbonyl-piperidin-3-yloxy)-4-fluoro-Phenylamino]-5-methyl-thieno[2,3-d]pyrimidine-6-carboxylic acid

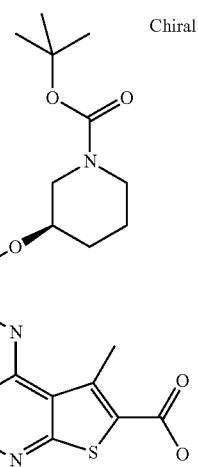

A mixture of 4-[2-((R)-1-tert-Butoxycarbonyl-piperidin-3-yloxy)-4-fluoro-phenylamino]-5-methyl-thieno[2,3-d]pyrimidine-6-carboxylic acid methyl ester (1.65 g) in MeOH/THF (1:1; 20 ml) was treated with NaOH (2M; 8 ml) and heated at reflux for 10 mins. Organic solvent was removed in vacuo. HCl (2M; 8 ml) was added to pH 1 and water was added. The suspension was filtered and washed with water. The solid was suspended in EtOH and evaporated. The residue was triturated with Acetonitrile to give the desired product.

Yield: 1.41 g 71.3 4-[2-((R)-1-tert-Butoxycarbonyl-piperidin-3-yloxy)-4-fluoro-phenylamino]-5-methyl-thieno[2,3-D]yrimidine-6-carboxylic acid amide

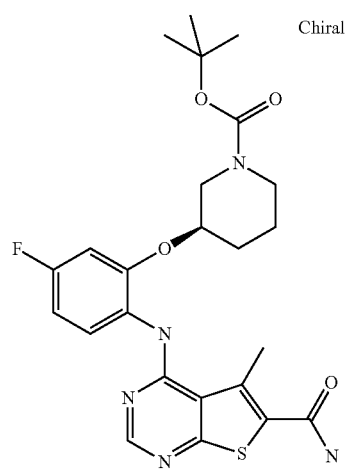 [SMILES: Cc1c(C(N)=O)sc2ncnc(Nc3ccc(F)cc3O[C@@H]3CCCN(C(=O)OC(C)(C)C)C3)c12]

Prepared analogously to example 65.3. from 4-[2-((R)-1-tert-Butoxycarbonyl-piperidin-3-yloxy)-4-fluoro-phenylamino]-5-methyl-thieno[2,3-d]pyrimidine-6-carboxylic acid.

Yield: 417 mg 71.4 4-[4-Fluoro-2-((R)-piperidin-3-yloxy)-phenylamino]-5-methyl-thieno[2,3-d]pyrimidine-6-carboxylic acid amide

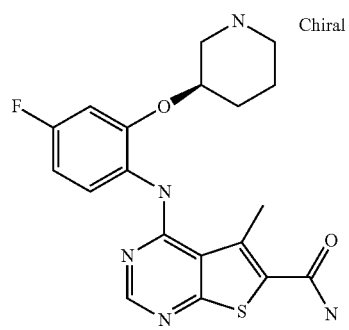 [SMILES: Cc1c(C(N)=O)sc2ncnc(Nc3ccc(F)cc3O[C@@H]3CCCNC3)c12]

Prepared analogously to example 68.4. from (R)-tert-butyl 3-(2-(6-carbamoyl-5-methylthieno[2,3-d]pyrimidin-4-ylamino)-5-fluorophenoxy)piperidine-1-carboxylate Yield: 222 mg ESI mass spectrum: m/z=402 (M+H)$^+$ Compound 72

4-[4-Fluoro-2-((R)-1-[1,2,4]oxadiazol-3-ylmethyl-piperidin-3-yloxy)-phenylamino]-5-methyl-thieno[2,3-d]pyrimidine-6-carboxylic acid amide

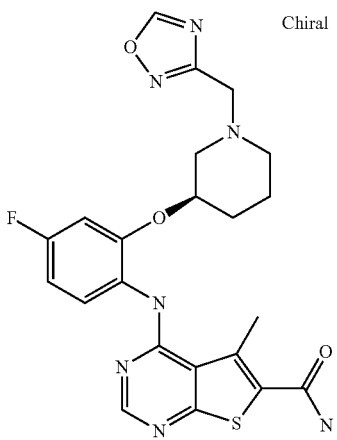 [SMILES: Cc1c(C(N)=O)sc2ncnc(Nc3ccc(F)cc3O[C@@H]3CCCN(Cc4ncon4)C3)c12]

Prepared analogously to example 1.6. from 4-[4-fluoro-2-((R)-piperidin-3-yloxy)-phenylamino]-5-methyl-thieno[2,3-d]pyrimidine-6-carboxylic acid amide.

Yield: 31.4 mg

ESI mass spectrum: m/z=484 (M+H)$^+$

Retention time HPLC: 1.14 (method X)

The following compound was prepared analogously to example 72 from 4-[4-fluoro-2-((R)-piperidin-3-yloxy)-phenylamino]-5-methyl-thieno[2,3-d]pyrimidine-6-carboxylic acid amide and trifluoro-methanesulfonic acid 2,2,2-trifluoro-ethyl ester.

TABLE 4

| Example | Structure | Mass | Retention time |
|---|---|---|---|
| 73 | Chiral | 484 (M + H)+ | 1.39 (method X) |

Compound 74

4-{2-[(R)-1-(2,2-Difluoro-ethyl)-piperidin-3-yloxy]-4-fluoro-phenylamino}-5-methyl-thieno[2,3-d]pyrimidine-6-carboxylic acid amide

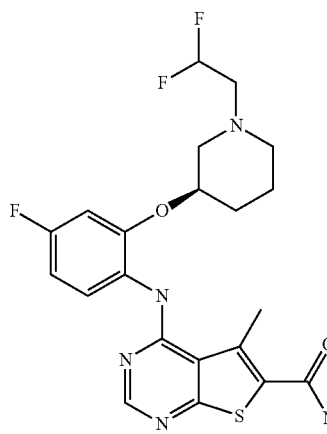

4-[4-Fluoro-2-((R)-piperidin-3-yloxy)-phenylamino]-5-methyl-thieno[2,3-d]pyrimidine-6-carboxylic acid amide (80 mg), 2,2-difluorobromoethane (58 mg) and triethylamine (56 μl) was dissolved in acetonitrile (1 ml). The reaction was heated under microwave radiation at 120° C. for 4 h. Further 2,2-difluorobromoethane (50 mg) was added and the reaction was heated again for 2 h. The mixture was diluted with dichloromethane, washed with water and passed through a hydrophobic frit. The organic phase was evaporated and the residue was purified by chromatography.

Yield: 57 mg
ESI mass spectrum: m/z=466 (M+H)+
Retention time HPLC: 1.15 (method X)

The following compound was prepared analogously to example 74 from 4-[4-fluoro-2-((R)-piperidin-3-yloxy)-phenylamino]-5-methyl-thieno[2,3-d]pyrimidine-6-carboxylic acid amide and 3-bromoethyl methyl ether

TABLE 5

| Example | Structure | Mass | Retention time |
|---|---|---|---|
| 75 | Chiral | 460 (M + H)+ | 1.15 (method X) |

Compound 76

4-[4-Fluoro-2-((R)-1-methyl-piperidin-3-yloxy)-phenylamino]-5-methyl-thieno[2,3-d]pyrimidine-6-carboxylic acid amide

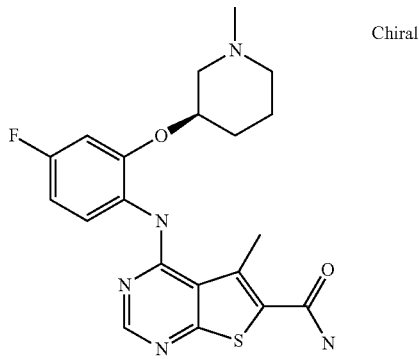 [SMILES: Cc1c(C(N)=O)sc2ncnc(Nc3ccc(F)cc3O[C@@H]3CCCN(C)C3)c12]

Prepared analogously to example 6.1 from (R)-4-(4-fluoro-2-(piperidin-3yloxy)phenylamino)-5-methylthieno[2,3-d]pyrimidine-6-carboxamide and formaldehyde.

Yield: 86 mg

ESI mass spectrum: m/z=416 (M+H)$^+$

Retention time HPLC: 1.12 (method X)

The following compounds were prepared analogously to 76.1 from 4-[4-fluoro-2-((R)-piperidin-3-yloxy)-phenylamino]-5-methyl-thieno[2,3-d]pyrimidine-6-carboxylic acid amide and the corresponding aldehydes or ketones.

TABLE 5

| Example | Structure | Mass | Retention time | aldehydes |
|---|---|---|---|---|
| 77 | 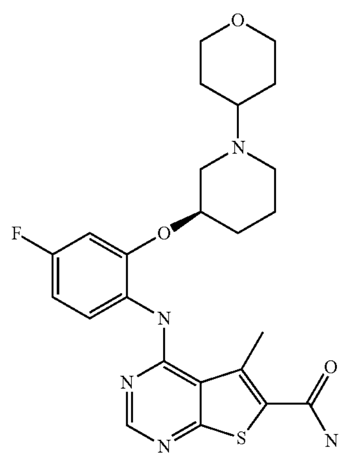 [SMILES: Cc1c(C(N)=O)sc2ncnc(Nc3ccc(F)cc3O[C@@H]3CCCN(C4CCOCC4)C3)c12] | 468 (M + H)$^+$ | 1.14 (method X) | |
| 78 | 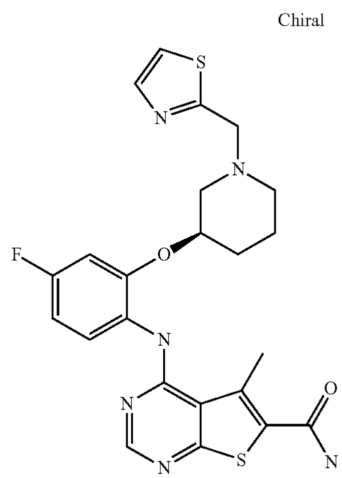 [SMILES: Cc1c(C(N)=O)sc2ncnc(Nc3ccc(F)cc3O[C@@H]3CCCN(Cc4nccs4)C3)c12] | 499 (M + H)$^+$ | 1.15 (method X) | |

TABLE 5-continued
| Example | Structure | Mass | Retention time | aldehydes |
|---------|-----------|------|----------------|-----------|
| 79 | 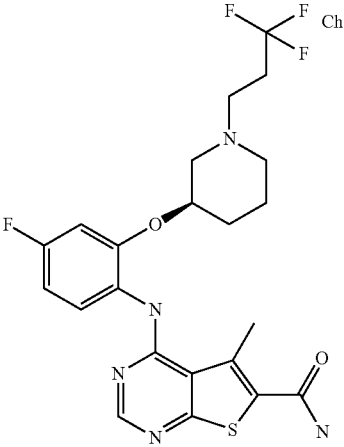 | 498 (M + H)+ | 1.18 (method X) | 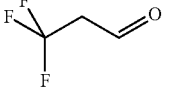 |
| 80 | 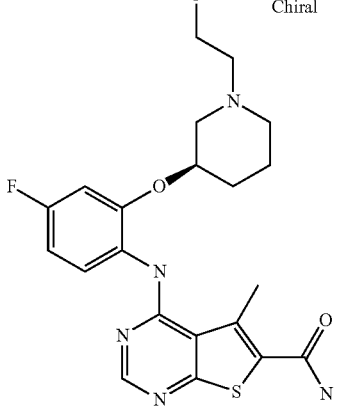 | 446 (M + H)+ | 1.12 (method X) | 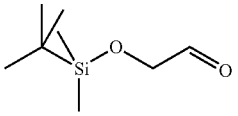 |
| 81 | 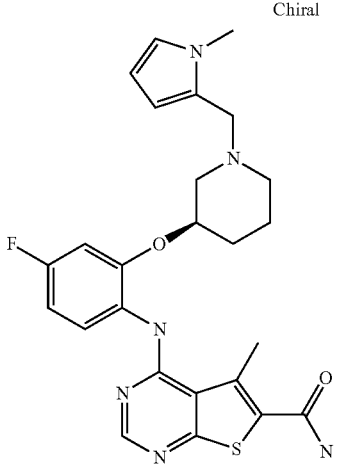 [SMILES: Cc1c(C(N)=O)sc2ncnc(Nc3ccc(F)cc3O[C@@H]3CCCN(Cc4cccn4C)C3)c12] | 495 (M + H)+ | 1.19 (method X) | 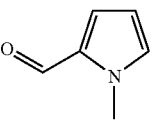 |

Compound 82

4-{2-[(R)-1-(2-Cyano-ethyl)-piperidin-3-yloxy]-4-fluoro-phenylamino}-5-methyl-thieno[2,3-d]pyrimidine-6-carboxylic acid amide

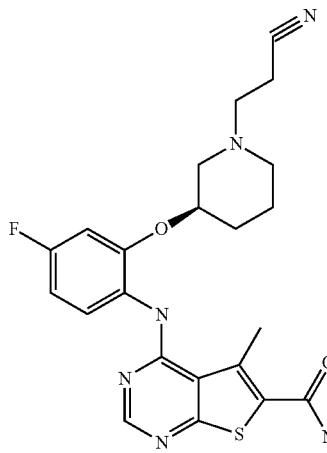

Acrylonitrile (20 μl) was added to a suspension of 4-[4-fluoro-2-((R)-piperidin-3-yloxy)-phenylamino]-5-methyl-thieno[2,3-d]pyrimidine-6-carboxylic acid amide (60 mg) and triethylamine (42 μl), in methanol (1 ml). After 1 h DMF (0.5 ml) was added. The reaction mixture was stirred at room temperature overnight. The reaction was diluted with EtOAc and washed with water and brine. The organic phase was passed through a hydrophobic frit and evaporated. The residue was triturated with diethylether.

Yield: 60 mg
ESI mass spectrum: m/z=455 (M+H)$^+$
Retention time HPLC: 1.14
HPLC method: Method X

Compound 83

(4-[2-((R)-1-Acetyl-piperidin-3-yloxy)-4-fluoro-phenylamino]-5-methyl-thieno[2,3-d]pyrimidine-6-carboxylic acid amide

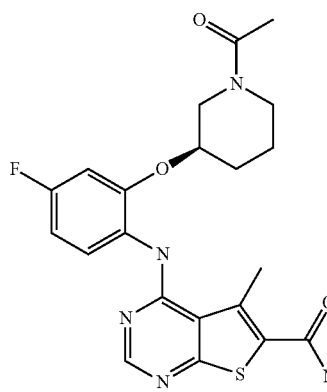

83.1 4-[4-Fluoro-2-((R)-piperidin-3-yloxy)-phenylamino]-5-methyl-thieno[2,3-d]pyrimidine-6-carboxylic acid methyl ester

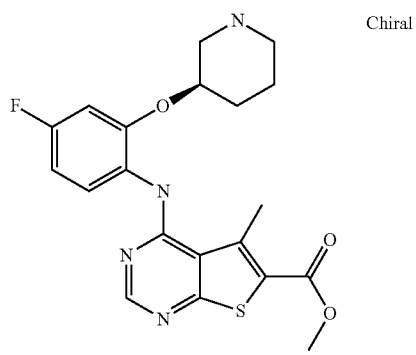 [SMILES: COC(=O)c1sc2ncnc(Nc3ccc(F)cc3O[C@@H]3CCCNC3)c2c1C]

Prepared analogously to example 1.5 from 4-[2-((R)-1-tert-butoxycarbonyl-piperidin-3-yloxy)-4-fluoro-phenylamino]-5-methyl-thieno[2,3-d]pyrimidine-6-carboxylic acid methyl ester.

Yield: 280 mg 83.2 (4-[2-((R)-1-Acetyl-piperidin-3-yloxy)-4-fluoro-phenylamino]-5-methyl-thieno[2,3-d]pyrimidine-6-carboxylic acid methylester

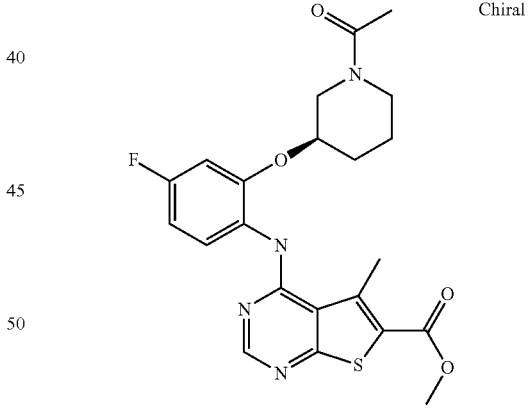

4-[4-Fluoro-2-((R)-piperidin-3-yloxy)-phenylamino]-5-methyl-thieno[2,3-d]pyrimidine-6-carboxylic acid methyl ester (128 mg) and DIPEA (64 μl) were cooled to 0° C. in anhydrous dichloromethane (2.5 ml). Into this solution was added acetyl chloride (35 μl) and the reaction was allowed to warm to room temperature overnight. The solution was diluted with dichloromethane and washed with KHSO$_4$ followed by 10% K$_2$CO$_3$. The organic layer was passed through a phase separator and concentrated in vacuo.

Yield: 160 mg

83.3 (4-[2-((R)-1-Acetyl-piperidin-3-yloxy)-4-fluoro-phenylamino]-5-methyl-thieno[2,3-d]pyrimidine-6-carboxylic acid

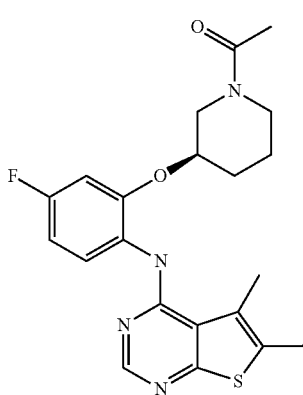

Prepared analogously to example 1.2 from (4-[2-((R)-1-acetyl-piperidin-3-yloxy)-4-fluoro-phenylamino]-5-methyl-thieno[2,3-d]pyrimidine-6-carboxylic acid methylester.

Yield: 130 mg

83.4 (4-[2-((R)-1-Acetyl-piperidin-3-yloxy)-4-fluoro-phenylamino]-5-methyl-thieno[2,3-d]pyrimidine-6-carboxylic acid amide

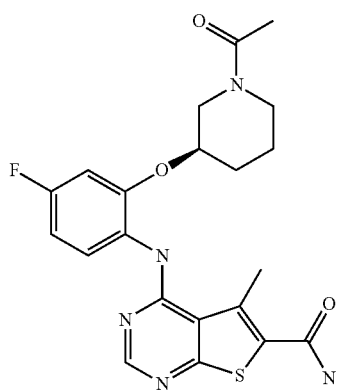

Prepared analogously to example 1.4 from (4-[2-((R)-1-Acetyl-piperidin-3-yloxy)-4-fluoro-phenylamino]-5-methyl-thieno[2,3-d]pyrimidine-6-carboxylic acid.

Yield: 60 mg

ESI mass spectrum: m/z=444 (M+H)$^+$

Retention time HPLC: 1.22 (method X)

Compound 84

4-[4-Fluoro-2-((R)-1-methanesulfonyl-piperidin-3-yloxy)-phenylamino]-5-methyl-thieno[2,3-d]pyrimidine-6-carboxylic acid amide

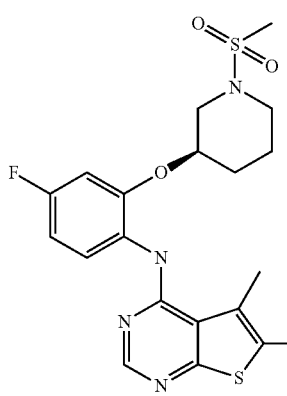

84.1 4-[4-Fluoro-2-((R)-1-methanesulfonyl-piperidin-3-yloxy)-phenylamino]-5-methyl-thieno[2,3-d]pyrimidine-6-carboxylic acid methyl ester

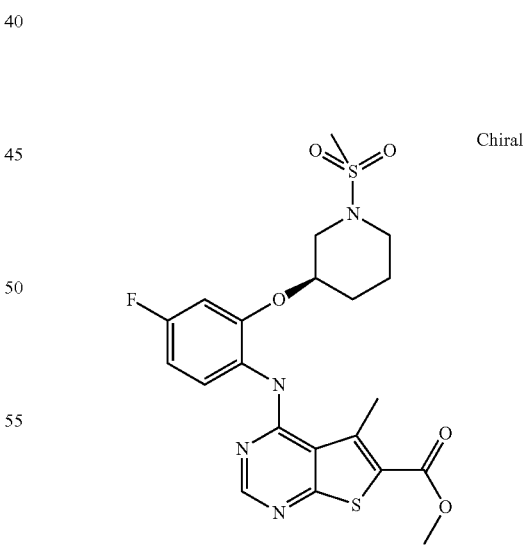

Prepared analogously to example 10.2 from 4-[4-Fluoro-2-((R)-piperidin-3-yloxy)-phenylamino]-5-methyl-thieno[2,3-d]pyrimidine-6-carboxylic acid methyl ester.

Yield: 180 mg

84.2 4-[4-Fluoro-2-((R)-1-methanesulfonyl-piperidin-3-yloxy)-phenylamino]-5-methyl-thieno[2,3-d]pyrimidine-6-carboxylic acid

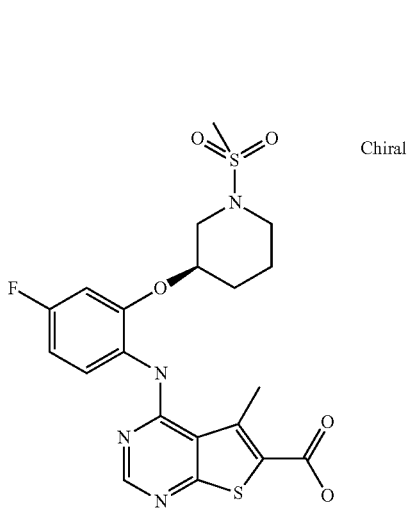 [SMILES: Cc1c(C(=O)O)sc2ncnc(Nc3ccc(F)cc3O[C@@H]3CCCN(S(C)(=O)=O)C3)c12]

Prepared analogously to example 10.3 from 4-[4-fluoro-2-((R)-1-methanesulfonyl-piperidin-3-yloxy)-phenylamino]-5-methyl-thieno[2,3-d]pyrimidine-6-carboxylic acid methyl ester Yield: 170 mg

84.3 4-[4-Fluoro-2-((R)-1-methanesulfonyl-piperidin-3-yloxy)-phenylamino]-5-methyl-thieno[2,3-d]pyrimidine-6-carboxylic acid amide

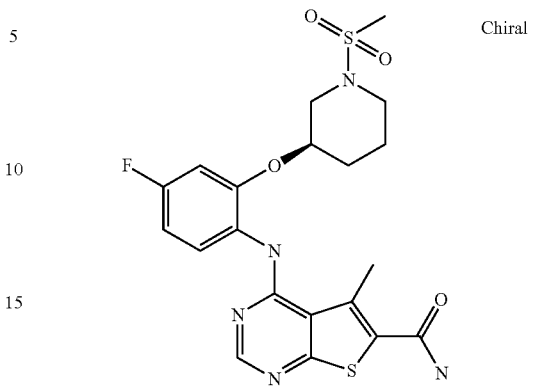

Prepared analogously to example 10.4 from 4-[4-fluoro-2-((R)-1-methanesulfonyl-piperidin-3-yloxy)-phenylamino]-5-methyl-thieno[2,3-d]pyrimidine-6-carboxylic acid and ammonia in methanol.

Yield: 100 mg
ESI mass spectrum: m/z=480 (M+H)$^+$
Retention time HPLC: 1.28 (method X)

The following compounds were prepared analogously to 84.3 from 4-[4-fluoro-2-((R)-1-methanesulfonyl-piperidin-3-yloxy)-phenylamino]-5-methyl-thieno[2,3-d]pyrimidine-6-carboxylic acid and the corresponding amines

TABLE 5

| Example | Structure | Mass | Retention time | amines |
|---|---|---|---|---|
| 85 | (structure) | 565 (M + H)$^+$ | 1.23 (method X) | (amine structure) |
| 86 | (structure) | 524 (M + H)$^+$ | 1.26 (method X) | (amine structure) |

Compound 87

4-{4-Fluoro-2-[(S)-(tetrahydro-pyran-3-yl)oxy]-phenylamino}-5-methyl-thieno[2,3-d]pyrimidine-6-carboxylic acid (3-dimethylamino-propyl)-amide

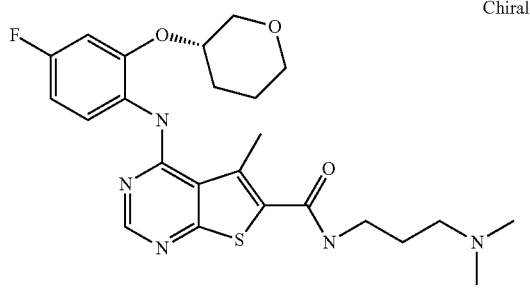 [SMILES: Cc1c(C(=O)NCCCN(C)C)sc2ncnc(Nc3ccc(F)cc3O[C@H]3CCCOC3)c12]

87.1 4-{4-Fluoro-2-[(S)-(tetrahydro-pyran-3-yl)oxy]-phenylamino}-5-methyl-thieno[2,3-d]pyrimidine-6-carboxylic acid methyl ester

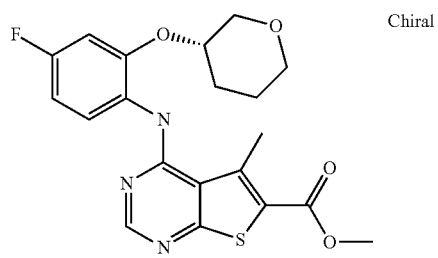 [SMILES: COC(=O)c1sc2ncnc(Nc3ccc(F)cc3O[C@H]3CCCOC3)c2c1C]

Prepared analogously to example 1.1 from 4-chloro-5-methyl-thieno[2,3-d]pyrimidine-6-carboxylic acid methyl ester and (S)-4-fluoro-2-(tetrahydro-2H-pyran-3yloxy)aniline (Intermediate XIII).

The reaction stirred at reflux and cooled to room temperature after 2 h. After cooling a precipitate was formed, which was filtrated.

Yield: 310 mg

87.2 4-{4-Fluoro-2-[(S)-(tetrahydro-pyran-3-yl)oxy]-phenylamino}-5-methyl-thieno[2,3-d]pyrimidine-6-carboxylic acid methyl ester

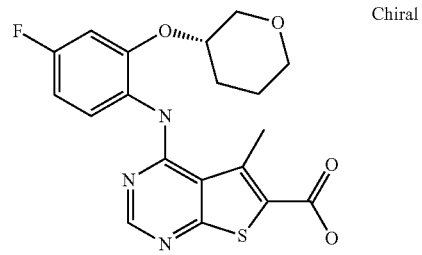 [SMILES: Cc1c(C(=O)O)sc2ncnc(Nc3ccc(F)cc3O[C@H]3CCCOC3)c12]

Prepared analogously to example 1.2 from 4-{4-fluoro-2-[(S)-(tetrahydro-pyran-3-yl)oxy]-phenylamino}-5-methyl-thieno[2,3-d]pyrimidine-6-carboxylic acid methyl ester Lithiumhydroxide was replaced by NaOH (2M).

Yield: 280 mg

87.3 4-{4-Fluoro-2-[(S)-(tetrahydro-pyran-3-yl)oxy]-phenylamino}-5-methyl-thieno[2,3-d]pyrimidine-6-carboxylic acid (3-dimethylamino-propyl)-amide

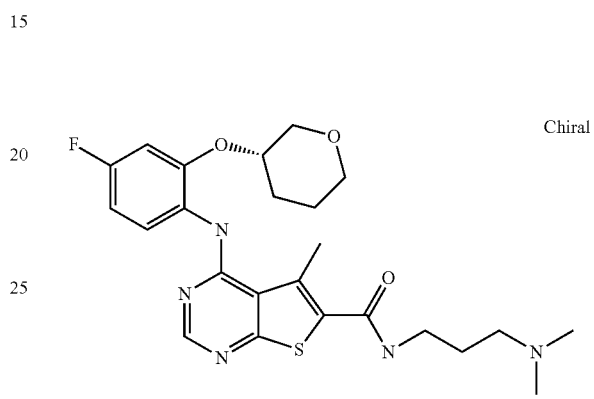

Prepared analogously to example 10.4 from 4-{4-fluoro-2-[(S)-(tetrahydro-pyran-3-yl)oxy]-phenylamino}-5-methyl-thieno[2,3-d]pyrimidine-6-carboxylic acid methyl ester and N,N-dimethyl-1,3-propanediamine.

Yield: 20 mg

ESI mass spectrum: m/z=488 (M+H)$^+$

Retention time HPLC: 1.25 (method X)

Compound 88

4-{4-Fluoro-2-[(R)-(tetrahydro-pyran-3-yl)oxy]-phenylamino}-5-methyl-thieno[2,3-d]pyrimidine-6-carboxylic acid (3-dimethylamino-propyl)-amide

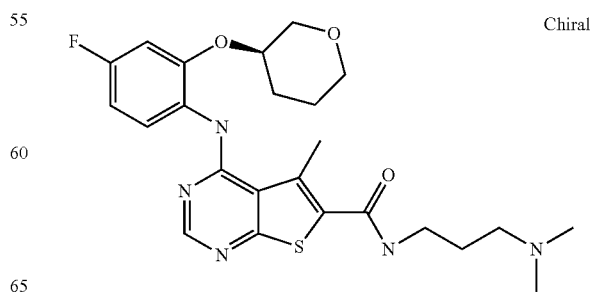

88.1 4-{4-Fluoro-2-[(R)-(tetrahydro-pyran-3-yl)oxy]-phenylamino}-5-methyl-thieno[2,3-d]pyrimidine-6-carboxylic acid methyl ester

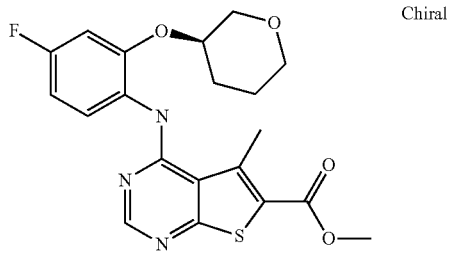 [SMILES: COC(=O)c1sc2ncnc(Nc3ccc(F)cc3O[C@@H]3CCCOC3)c2c1C]

Prepared analogously to example 87.1 from 4-chloro-5-methyl-thieno[2,3-d]pyrimidine-6-carboxylic acid methyl ester and (R)-4-fluoro-2-(tetrahydro-2H-pyran-3-yloxy) aniline (Intermediate XIV).

Yield: 910 mg 88.2 4-{4-Fluoro-2-[(R)-(tetrahydro-pyran-3-yl)oxy]-phenylamino}-5-methyl-thieno[2,3-d]pyrimidine-6-carboxylic acid

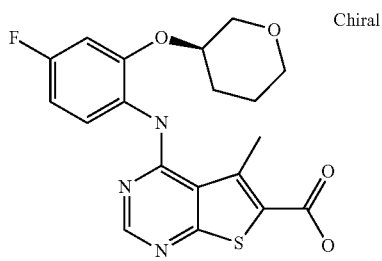 [SMILES: Cc1c(C(=O)O)sc2ncnc(Nc3ccc(F)cc3O[C@@H]3CCCOC3)c12]

Prepared analogously to example 87.2. from 4-{4-fluoro-2-[(R)-(tetrahydro-pyran-3-yl)oxy]-phenylamino}-5-methyl-thieno[2,3-d]pyrimidine-6-carboxylic acid methyl ester.

Yield: 450 mg 88.3 4-{4-Fluoro-2-[(R)-(tetrahydro-pyran-3-yl)oxy]-phenylamino}-5-methyl-thieno[2,3-d]pyrimidine-6-carboxylic acid (3-dimethylamino-propyl)-amide

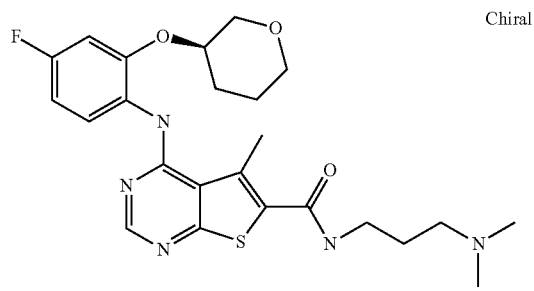 [SMILES: Cc1c(C(=O)NCCCN(C)C)sc2ncnc(Nc3ccc(F)cc3O[C@@H]3CCCOC3)c12]

Prepared analogously to example 10.4 from 4-{4-fluoro-2-[(R)-(tetrahydro-pyran-3-yl)oxy]-phenylamino}-5-methyl-thieno[2,3-d]pyrimidine-6-carboxylic acid and N,N-dimethyl-1,3-propanediamine.

Yield: 30 mg

ESI mass spectrum: m/z=488 (M+H)$^+$

Retention time HPLC: 1.25 (method X)

Compound 89

4-[4-Fluoro-2-(1-methanesulfonyl-pyrrolidin-3-yloxy)-phenylamino]-5-methyl-thieno[2,3-d]pyrimidine-6-carboxylic acid amide

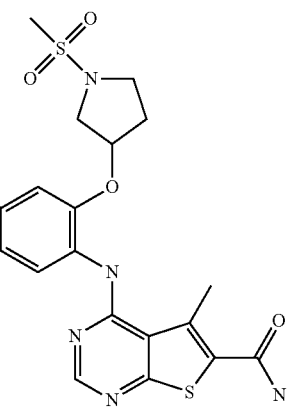

89.1 4-[4-Fluoro-2-(1-methanesulfonyl-pyrrolidin-3-yloxy)-phenylamino]-5-methyl-thieno[2,3-d]pyrimidine-6-carboxylic acid

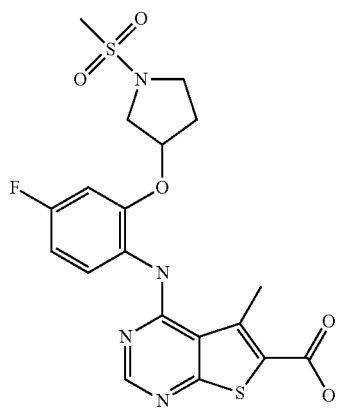 [SMILES: Cc1c(C(N)=O)sc2ncnc(Nc3ccc(F)cc3OC3CCN(S(C)(=O)=O)C3)c12]

NaOH (2M; 5.6 ml) was added to a mixture of Intermediate XVII (1 g) in EtOH/THF (1:1; 20 ml). The mixture was heated at reflux for 45 mins. The solvent was removed in vacuo. The residue treated with 10% aq. KHSO4 and the resultant suspension was filtered. The filter cake was washed with water and diethylether.

Yield: 30 mg

89.2 4-[4-Fluoro-2-(1-methanesulfonyl-pyrrolidin-3-yloxy)-phenylamino]-5-methyl-thieno[2,3-d]pyrimidine-6-carboxylic acid amide

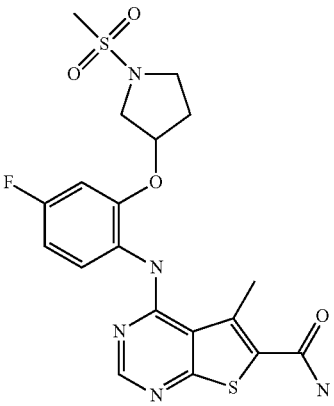 [SMILES: Cc1c(C(N)=O)sc2ncnc(Nc3ccc(F)cc3OC3CCN(S(C)(=O)=O)C3)c12]

Prepared analogously to example 10.4 from 4-[4-fluoro-2-(1-methanesulfonyl-pyrrolidin-3-yloxy)-phenylamino]-5-methyl-thieno[2,3-d]pyrimidine-6-carboxylic acid and ammonia in methanol.

Yield: 65 mg

ESI mass spectrum: m/z=466 (M+H)$^+$

Retention time HPLC: 1.25 (method X)

The following compounds were prepared analogously to 89.2 from 4-[4-fluoro-2-(1-methanesulfonyl-pyrrolidin-3-yloxy)-phenylamino]-5-methyl-thieno[2,3-d]pyrimidine-6-carboxylic acid and the corresponding amines

TABLE 6

| Example | Structure | Mass | Retention time | amines |
|---|---|---|---|---|
| 90 | 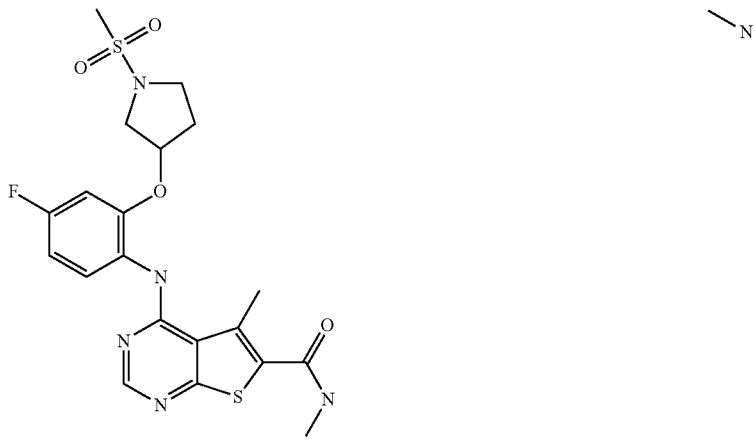 | 480 (M + H)$^+$ | 1.27 (method X) | |
| 91 | 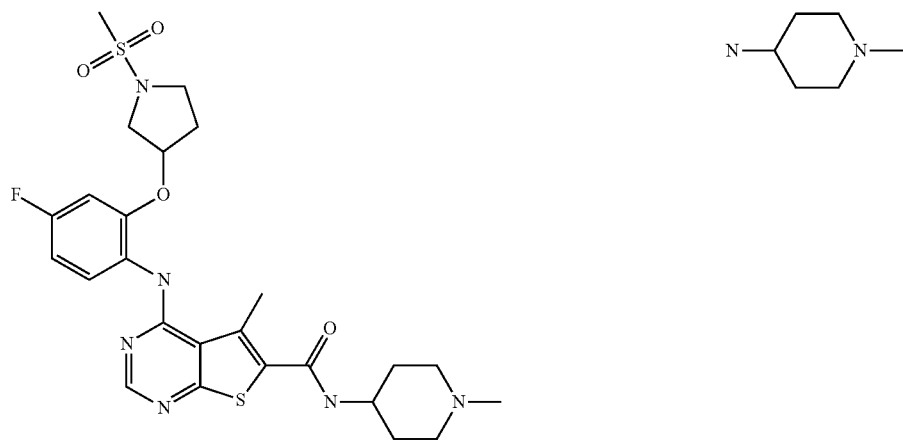 | 563 (M + H)$^+$ | 1.21 (method X) | |

TABLE 6-continued

| Example | Structure | Mass | Retention time | amines |
|---------|-----------|------|----------------|--------|
| 92 | 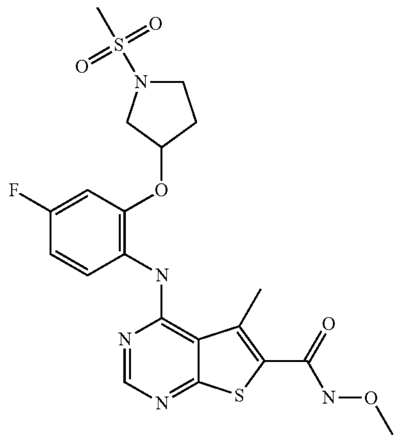 [SMILES: CONC(=O)c1sc2ncnc(Nc3ccc(F)cc3OC3CCN(S(C)(=O)=O)C3)c2c1C] | 496 (M + H)⁺ | 1.28 (method X) | N—O—CH₃ |
| 93 | 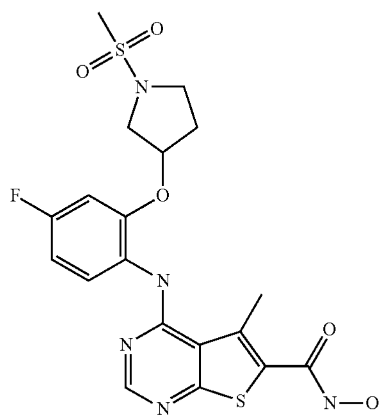 [SMILES: Cc1c(C(=O)NO)sc2ncnc(Nc3ccc(F)cc3OC3CCN(S(C)(=O)=O)C3)c12] | 482 (M + H)⁺ | 1.21 (method X) | N—O |

Compound 94

4-{4-Fluoro-2-[1-(2-methoxy-acetyl)-pyrrolidin-3-yloxy]-phenylamino}-5-methyl-thieno[2,3-d]pyrimidine-6-carboxylic acid amide 94.1 4-{4-Fluoro-2-[1-(2-methoxy-acetyl)-pyrrolidin-3-yloxy]-phenylamino}-5-methyl-thieno[2,3-d]pyrimidine-6-carboxylic acid methyl ester Methoxyacetyl chloride (27 µl) was added into a solution of XVIII (0.1 g) and DIPEA (52 µl) in anhydrous Dichloromethane (2 ml). The reaction was allowed to warm to room temperature overnight. The solution was diluted with Dichloromethane and the organic layer was shift with KHSO₄ and 10% K₂CO₃. The organic layer was passed through a phase separator and concentrated in vacuo to give the desired product.

Yield: 120 mg

94.2 4-{4-Fluoro-2-[1-(2-methoxy-acetyl)-pyrrolidin-3-yloxy]-phenylamino}-5-methyl-thieno[2,3-d]pyrimidine-6-carboxylic acid methyl ester

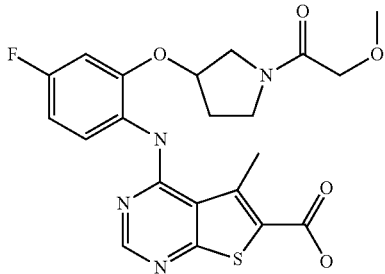

Prepared analogously to example 1.2 from 4-{4-fluoro-2-[1-(2-methoxy-acetyl)-pyrrolidin-3-yloxy]-phenylamino}-5-methyl-thieno[2,3-d]pyrimidine-6-carboxylic acid methyl ester
Yield: 100 mg

94.3 4-{4-Fluoro-2-[1-(2-methoxy-acetyl)-pyrrolidin-3-yloxy]-phenylamino}-5-methyl-thieno[2,3-d]pyrimidine-6-carboxylic acid amide

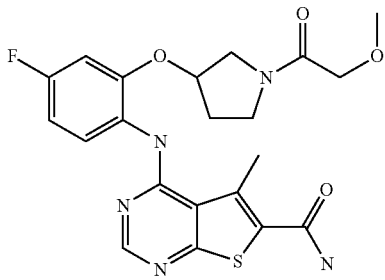 [SMILES: COCC(=O)N1CCC(Oc2cc(F)ccc2Nc2ncnc3sc(C(N)=O)c(C)c23)C1]

Prepared analogously to example 1.4 from 4-{4-fluoro-2-[1-(2-methoxy-acetyl)-pyrrolidin-3-yloxy]-phenylamino}-5-methyl-thieno[2,3-d]pyrimidine-6-carboxylic acid methyl ester and ammonia in methanol.
Yield: 90 mg
ESI mass spectrum: m/z=460 (M+H)$^+$
Retention time HPLC: 1.22 (method X)

Compound 95

4-{2-[1-(2-Dimethylamino-acetyl)-pyrrolidin-3-yloxy]-4-fluoro-phenylamino}-5-methyl-thieno[2,3-d]pyrimidine-6-carboxylic acid amide

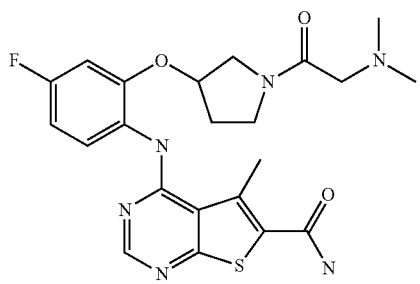 [SMILES: Cc1c(C(N)=O)sc2ncnc(Nc3ccc(F)cc3OC3CCN(C(=O)CN(C)C)C3)c12]

95.1 4-{2-[1-(2-Dimethylamino-acetyl)-pyrrolidin-3-yloxy]-4-fluoro-phenylamino}-5-methyl-thieno[2,3-d]pyrimidine-6-carboxylic acid methyl ester

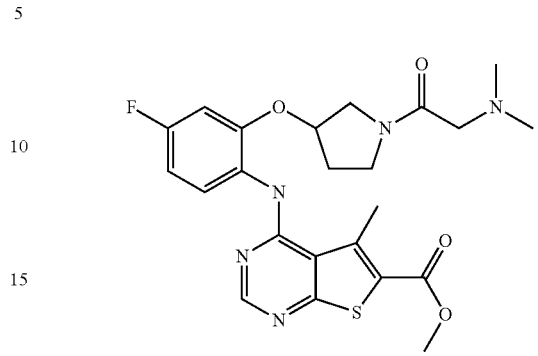

Prepared analogously to example 94.1 from Intermediate XVIII and dimethylaminoacetyl chloride hydrochloride.
Yield: 120 mg

95.2 4-{2-[1-(2-Dimethylamino-acetyl)-pyrrolidin-3-yloxy]-4-fluoro-phenylamino}-5-methyl-thieno[2,3-d]pyrimidine-6-carboxylic acid

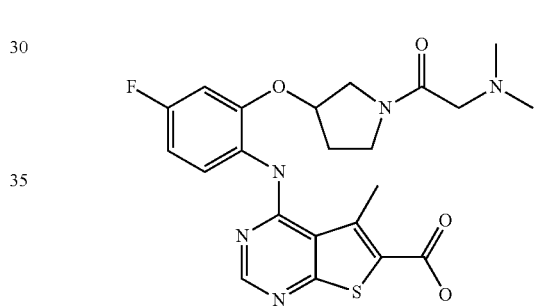

Prepared analogously to example 1.2 from 4-{2-[1-(2-dimethylamino-acetyl)-pyrrolidin-3-yloxy]-4-fluoro-phenylamino}-5-methyl-thieno[2,3-d]pyrimidine-6-carboxylic acid methyl ester
Yield: 98 mg

95.3 4-{2-[1-(2-Dimethylamino-acetyl)-pyrrolidin-3-yloxy]-4-fluoro-phenylamino}-5-methyl-thieno[2,3-d]pyrimidine-6-carboxylic acid amide

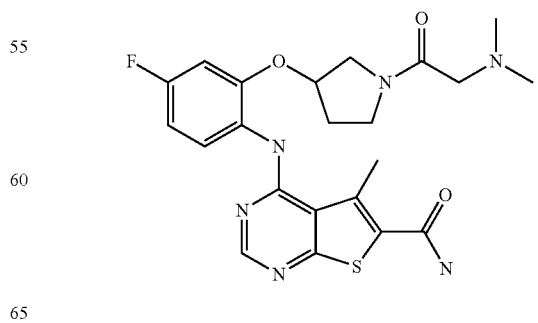

Prepared analogously to example 1.4 from 4-{2-[1-(2-Dimethylamino-acetyl)-pyrrolidin-3-yloxy]-4-fluoro-phenylamino}-5-methyl-thieno[2,3-d]pyrimidine-6-carboxylic acid and ammonia in methanol.

Yield: 36 mg

ESI mass spectrum: m/z=473 (M+H)⁺

Retention time HPLC: 1.16 (method X)

Compound 96

4-[2-((S)-1-Acetyl-pyrrolidin-3-yloxy)-4-fluoro-phenylamino]-5-methyl-thieno[2,3-d]pyrimidine-6-carboxylic acid amide

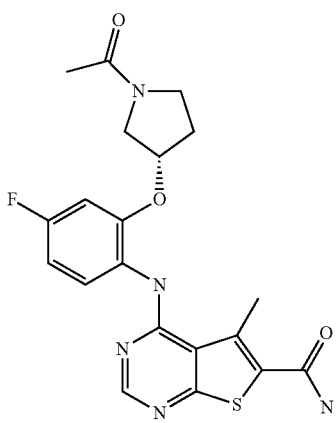

96.1 4-[2-((S)-1-tert-Butoxycarbonyl-pyrrolidin-3-yloxy)-4-fluoro-phenylamino]-5-methyl-thieno[2,3-d]pyrimidine-6-carboxylic acid,

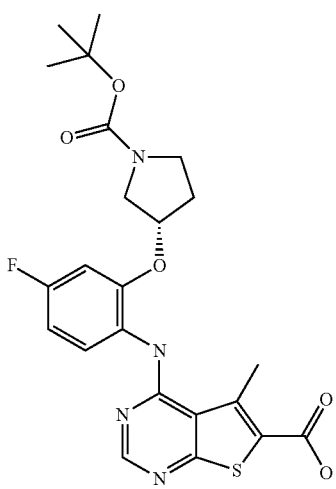

NaOH (2M; 3 ml) was added to a mixture of Intermediate XVII in THF. The mixture was heated at 50° C. for 1 h. 10% aq. KHSO₄ was added and the suspension was stirred for 1 h. The suspension was filtered and the filter cake was washed with water and diethlyether.

Yield: 543 mg 96.2 4-[2-((S-1-tert-Butoxycarbonyl-pyrrolidin-3-yloxy)-4-fluoro-phenylamino]-5-methyl-thieno[2,3-d]pyrimidine-6-carboxylic acid amide

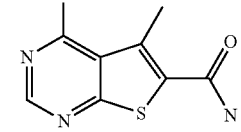

Prepared analogously to example 1.4 from 4-[2-((S)-1-tert-butoxycarbonyl-pyrrolidin-3-yloxy)-4-fluoro-phenylamino]-5-methyl-thieno[2,3-d]pyrimidine-6-carboxylic acid and ammonia in methanol.

Yield: 363 mg 96.3 4-[4-Fluoro-2-((S-pyrrolidin-3-yloxy)-phenylamino]-5-methyl-thieno[2,3-d]pyrimidine-6-carboxylic acid amide hydrochloride

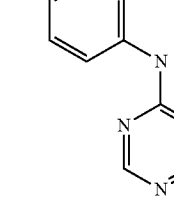

Prepared analogously to example 1.3 from 4-[2-((S)-1-tert-butoxycarbonyl-pyrrolidin-3-yloxy)-4-fluoro-phenylamino]-5-methyl-thieno[2,3-d]pyrimidine-6-carboxylic acid amide.

ESI mass spectrum: m/z=388 (M+H)⁺

Retention time HPLC: 1.12 (method X)

96.4 4-[2-((S)-1-Acetyl-pyrrolidin-3-yloxy)-4-fluoro-phenylamino]-5-methyl-thieno[2,3-d]pyrimidine-6-carboxylic acid amide

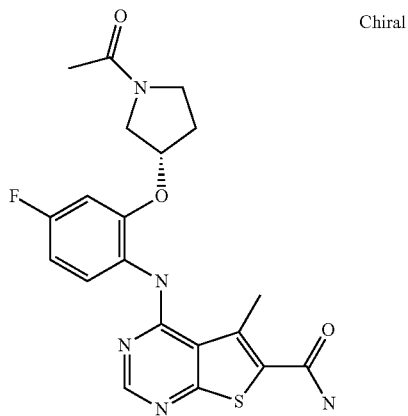 [SMILES: CC(=O)N1CC[C@H](Oc2cc(F)ccc2Nc2ncnc3sc(C(N)=O)c(C)c23)C1]

Acetic anydride (28 µl) was added to a suspension of 4-[4-fluoro-2-((S)-pyrrolidin-3-yloxy)-phenylamino]-5-methyl-thieno[2,3-d]pyrimidine-6-carboxylic acid amide hydrochloride (85 mg) and triethylamine (83 µl) in dichloromethane (2 ml) The reaction was stirred at room temperature overnight. The reaction was diluted with dichloromethane and 10% aq. KHSO$_4$ and the resultant suspension was filtered. The filter cake was washed with water and diethylether. The residue was taken up in methanol and heated to reflux. The reaction was allowed to cool and the solid was collected by filtration.

Yield: 64 mg

ESI mass spectrum: m/z=430 (M+H)$^+$

Retention time HPLC: 1.21 (method X)

The following compound was prepared analogously to 96.4 from 4-[4-fluoro-2-((S)-pyrrolidin-3-yloxy)-phenylamino]-5-methyl-thieno[2,3-d]pyrimidine-6-carboxylic acid amide hydrochloride and methansulfonyl chloride

TABLE 7

| Example | Structure | Mass | Retention time |
|---|---|---|---|
| 97 | ![structure] Chiral | 466 (M + H)$^+$ | 1.24 (method X) |

Compound 98

4-[2-((R)-1-Acetyl-pyrrolidin-3-yloxy)-4-fluoro-phenylamino]-5-methyl-thieno[2,3-d]pyrimidine-6-carboxylic acid amide

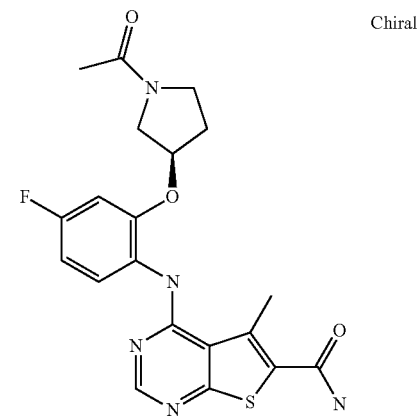 [SMILES: CC(=O)N1CC[C@@H](Oc2cc(F)ccc2Nc2ncnc3sc(C(N)=O)c(C)c23)C1]

98.1 4-[2-((S)-1-tert-Butoxycarbonyl-pyrrolidin-3-yloxy)-4-fluoro-phenylamino]-5-methyl-thieno[2,3-d]pyrimidine-6-carboxylic acid

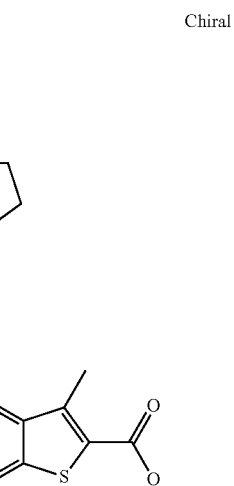

Prepared analogously to example 96.1 from Intermediate XV.

Yield: 393 mg

98.2 4-[2-((S)-1-tert-Butoxycarbonyl-pyrrolidin-3-yloxy)-4-fluoro-phenylamino]-5-methyl-thieno[2,3-d]pyrimidine-6-carboxylic acid amide

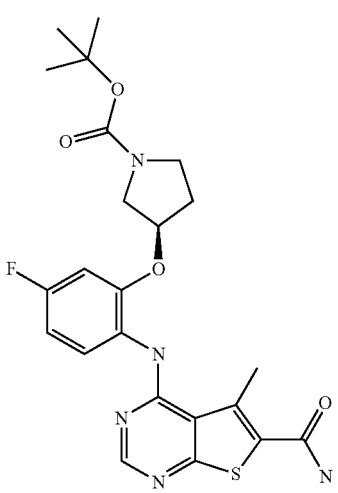

Prepared analogously to example 1.4 from 4-[2-((S)-1-tert-butoxycarbonyl-pyrrolidin-3-yloxy)-4-fluoro-phenylamino]-5-methyl-thieno[2,3-d]pyrimidine-6-carboxylic acid and ammonia in methanol.

Yield: 324 mg

98.3 4-[4-Fluoro-2-((R)-pyrrolidin-3-yloxy)-phenylamino]-5-methyl-thieno[2,3-d]pyrimidine-6-carboxylic acid amide hydrochloride

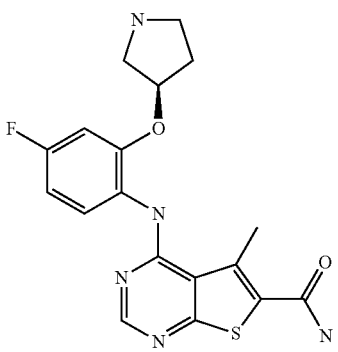

Prepared analogously to example 10.1 from 4-[2-((S)-1-tert-butoxycarbonyl-pyrrolidin-3-yloxy)-4-fluoro-phenylamino]-5-methyl-thieno[2,3-d]pyrimidine-6-carboxylic acid amide.

Yield: 184 mg

ESI mass spectrum: m/z=388 (M+H)$^+$

Retention time HPLC: 1.12 (method X)

98.4 4-[2-((R)-1-Acetyl-pyrrolidin-3-yloxy)-4-fluoro-phenylamino]-5-methyl-thieno[2,3-d]pyrimidine-6-carboxylic acid amide

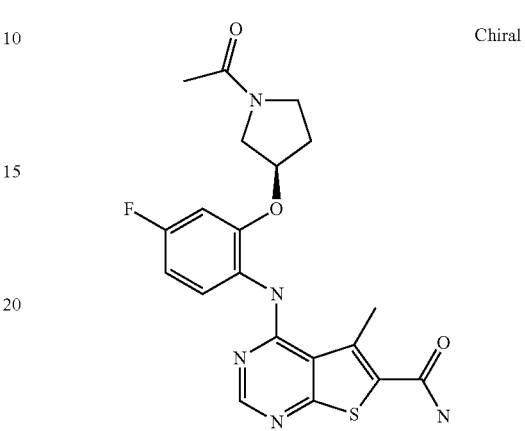

Prepared analogously to example 99.4 from 4-[4-fluoro-2-((R)-pyrrolidin-3-yloxy)-phenylamino]-5-methyl-thieno[2,3-d]pyrimidine-6-carboxylic acid amide hydrochloride and acetic anhydride.

Yield: 62 mg

ESI mass spectrum: m/z=430 (M+H)$^+$

Retention time HPLC: 1.21 (method X)

Compound 99

4-[4-Fluoro-2-((R)-1-methanesulfonyl-pyrrolidin-3-yloxy)-phenylamino]-5-methyl-thieno[2,3-d]pyrimidine-6-carboxylic acid amide

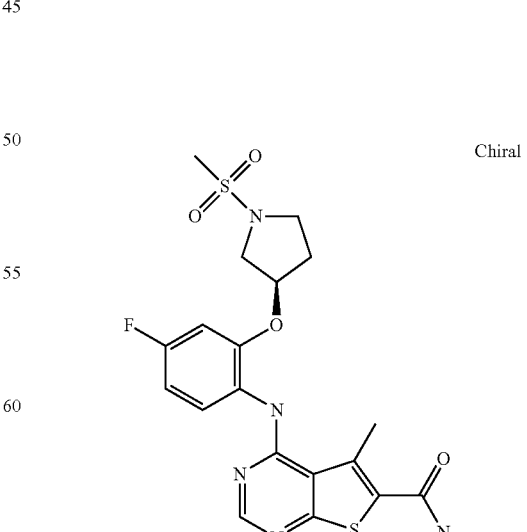

99.1 4-[4-Fluoro-2-((R)-pyrrolidin-3-yloxy)-phenylamino]-5-methyl-thieno[2,3-d]pyrimidine-6-carboxylic acid methyl ester

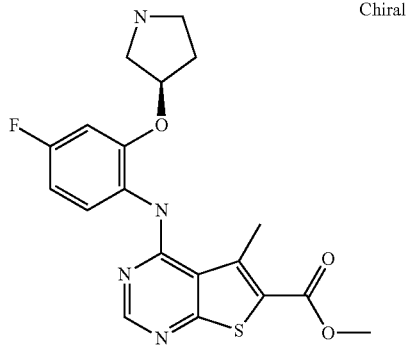 [SMILES: COC(=O)c1sc2ncnc(Nc3ccc(F)cc3O[C@@H]3CCNC3)c2c1C]

Prepared analogously to example 10.1 from 4-[2-((R)-1-tert-Butoxycarbonyl-pyrrolidin-3-yloxy)-4-fluoro-phenylamino]-5-methyl-thieno[2,3-d]pyrimidine-6-carboxylic acid methyl ester.

Yield: 418 mg

99.2 4-[4-Fluoro-2-((R)-1-methanesulfonyl-pyrrolidin-3-yloxy)-phenylamino]-5-methyl-thieno[2,3-d]pyrimidine-6-carboxylic acid methyl ester Prepared analogously to example 10.2 from 4-[4-Fluoro-2-((R)-pyrrolidin-3-yloxy)-phenylamino]-5-methyl-thieno[2,3-d]pyrimidine-6-carboxylic acid methyl ester and methansulfonyl chloride.

Yield: 128 mg

99.3 4-[4-Fluoro-2-((R)-1-methanesulfonyl-pyrrolidin-3-yloxy)-phenylamino]-5-methyl-thieno[2,3-d]pyrimidine-6-carboxylic acid

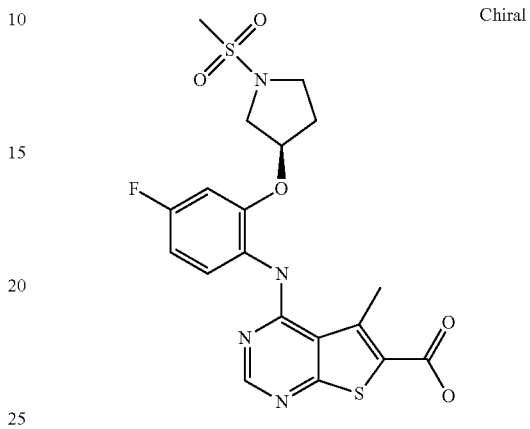

Prepared analogously to example 96.1 from 4-[4-fluoro-2-((R)-1-methanesulfonyl-pyrrolidin-3-yloxy)-phenylamino]-5-methyl-thieno[2,3-d]pyrimidine-6-carboxylic acid methyl ester Yield: 110 mg

99.4 4-[4-Fluoro-2-((R)-1-methanesulfonyl-pyrrolidin-3-yloxy)-phenylamino]-5-methyl-thieno[2,3-d]pyrimidine-6-carboxylic acid amide

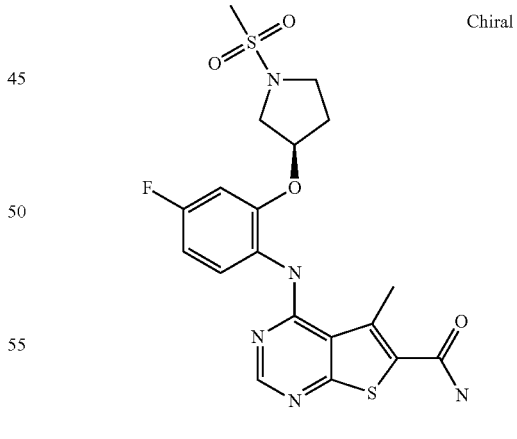

Prepared analogously to example 1.4 from 4-[4-fluoro-2-((R)-1-methanesulfonyl-pyrrolidin-3-yloxy)-phenylamino]-5-methyl-thieno[2,3-d]pyrimidine-6-carboxylic acid and Ammonia in Methanol.

Yield: 66 mg

ESI mass spectrum: m/z=466 (M+H)$^+$

Retention time HPLC: 1.24 (method X)

Compound 100

(R)—N-cyano-4-(4-fluoro-2-(tetrahydrofuran-3-yloxy)phenylamino)-5-methylthieno[2,3-d]pyrimidine-6-carboxamide

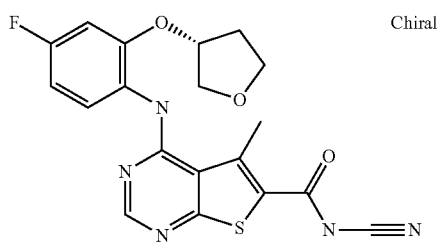 [SMILES: Cc1c(C(=O)NC#N)sc2ncnc(Nc3ccc(F)cc3O[C@@H]3CCOC3)c12 ; "Chiral"]

100.1 (R)-methyl 4-(4-fluoro-2-(tetrahydrofuran-3-yloxy)phenylamino)-5-methylthieno[2,3-d]pyrimidine-6-carboxylate

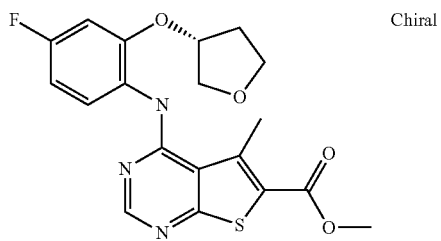 [SMILES: COC(=O)c1sc2ncnc(Nc3ccc(F)cc3O[C@@H]3CCOC3)c2c1C ; "Chiral"]

4-Chloro-5-methyl-thieno[2,3-d]pyrimidine-6-carboxylic acid methyl ester (100 mg) and (R)-4-fluoro-2-(tetrahydrofuran-3-yloxy)aniline (Intermediate VI) (81 mg) was dissolved in Dioxan (2 ml) and p-Toluenesulfonic acid (15 mg) was added. The reaction heated at 110° C. under microwave radiation. The resultant precipitate was filtered and dissolved in dichloromethane/Methanol. The solution was dried and concentrated to give the desired product.

Yield: 150 mg

ESI mass spectrum: m/z=404 (M+H)+

100.2 4-{4-Fluoro-2-[(R)-(tetrahydro-furan-3-yl)oxy]-phenylamino}-5-methyl-thieno[2,3-d]pyrimidine-6-carboxylic acid

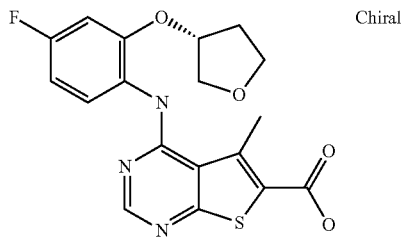 [SMILES: Cc1c(C(=O)O)sc2ncnc(Nc3ccc(F)cc3O[C@@H]3CCOC3)c12 ; "Chiral"]

4-{4-Fluoro-2-[(R)-(tetrahydro-furan-3-yl)oxy]-phenylamino}-5-methyl-thieno[2,3-d]pyrimidine-6-carboxylic acid ethyl ester (150 mg) was dissolved in methanol (5 ml) and NaOH (1M; 1.9 ml) was added. The reaction was stirred over the weekend. The organic solvent was evaporated and the residue was neutralised with HCl. The resultant precipitate was filtered and dried.

Yield: 130 mg

ESI mass spectrum: m/z=404 (M+H)+

100.3

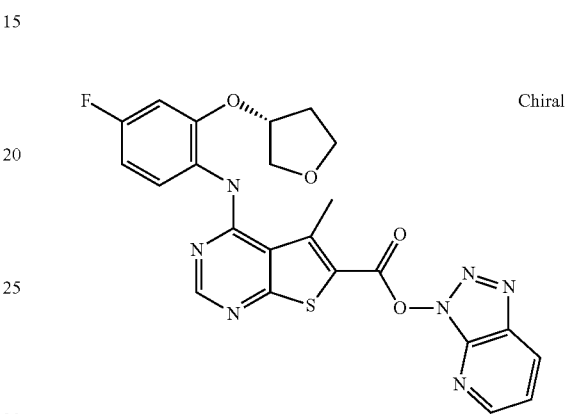

Prepared analogously to example 1.4 from 4-{4-Fluoro-2-[(R)-(tetrahydro-furan-3-yl)oxy]-phenylamino}-5-methyl-thieno[2,3-d]pyrimidine-6-carboxylic acid and HATU.

Yield: 85 mg

ESI mass spectrum: m/z=508 (M+H)+

100.4 (R)—N-cyano-4-(4-fluoro-2-(tetrahydrofuran-3-yloxy)phenylamino)-5-methylthieno[2,3-d]pyrimidine-6-carboxamide

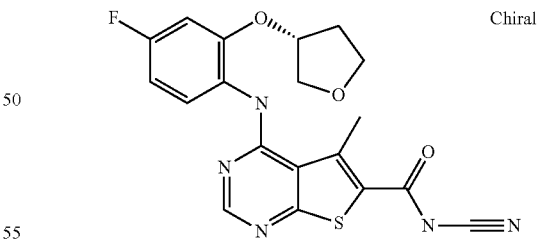

Cyanamide (6.7 mg) was dissolved in THF (2 ml) and LiHMDS (1M; 158 μl) was added, the reaction stirred for 10 mins. After this time compound 103.4_(80 mg) was added and the reaction stirred for 2-3 weeks. The solvent was removed in vacuo. The residue was purified by RP-chromatography (method B) to give the desired product.

Yield: 15 mg

ESI mass spectrum: m/z=414 (M+H)+

Retention time HPLC:: 1.28 (method E)

Compound 101

N-(4-{4-Fluoro-2-[(R)-(tetrahydro-furan-3-yl)oxy]-phenylamino}-5-methyl-thieno[2,3-d]pyrimidine-6-carbonyl)-methanesulfonamide

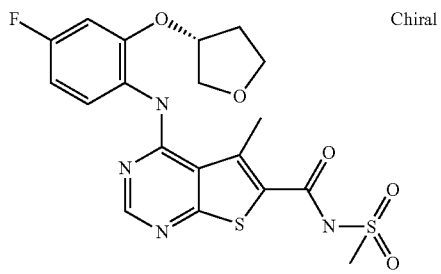 [SMILES: Cc1c(C(=O)NS(C)(=O)=O)sc2ncnc(Nc3ccc(F)cc3O[C@@H]3CCOC3)c12 ; "Chiral"]

4-{4-Fluoro-2-[(R)-(tetrahydro-furan-3-yl)oxy]-phenylamino}-5-methyl-thieno[2,3-d]pyrimidine-6-carboxylic acid (150 mg), 4-dimethylaminopyridine (61 mg) and 1-ethyl-3-(3-dimethylaminopropyl)carbodiimide hydrochloride (96 mg) was dissolved in dichloromethane. To this mixture methanesulfonamide (48 mg) was added and the reaction was stirred overnight. The reaction mixture was diluted with KHSO$_4$ The organic layer was separated, dried and concentrated. The residue was purified by silica chromatography (Dichloromethane/MeOH/NH3 10:1:0,1).

Yield: 40 mg

ESI mass spectrum: m/z=467(M+H)$^+$

Retention time HPLC:: 1.85 (method E)

Compound 102

4-{4-Fluoro-2-[(R)-(tetrahydro-furan-3-yl)oxy]-phenylamino}-5-methyl-thieno[2,3-d]pyrimidine-6-carboxylic acid methoxy-amide

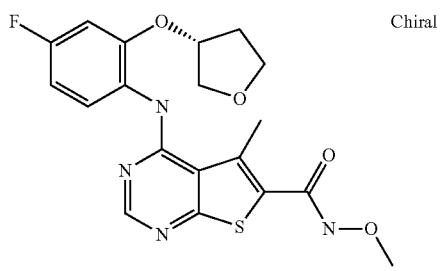 [SMILES: CONC(=O)c1sc2ncnc(Nc3ccc(F)cc3O[C@@H]3CCOC3)c2c1C ; "Chiral"]

4-{4-Fluoro-2-[(R)-(tetrahydro-furan-3-yl)oxy]-phenylamino}-5-methyl-thieno[2,3-d]pyrimidine-6-carboxylic acid (100 mg) was dissolved in DMF (3 ml) and triethylamine (79 μl) was added. To this mixture TBTU (90 mg) was added and the reaction was stirred for 10 mins. After this time methylhydroxylamine hydrochloride (27 mg) was added and the reaction was stirred at 40° C. overnight. The mixture was purified by RP-chromatography (method A).

Yield: 40 mg

ESI mass spectrum: m/z=419(M+H)$^+$

Retention time HPLC: 1.68 (method E)

Compound 103

4-{4-Fluoro-2-[(R)-(tetrahydro-furan-3-yl)oxy]-phenylamino}-5-methyl-thieno[2,3-d]pyrimidine-6-carboxylic acid (3-dimethylamino-propyl)-amide

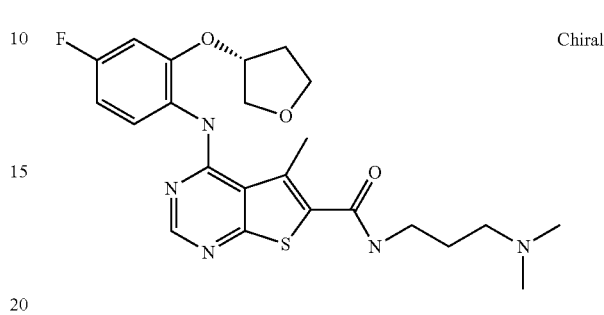

103.1

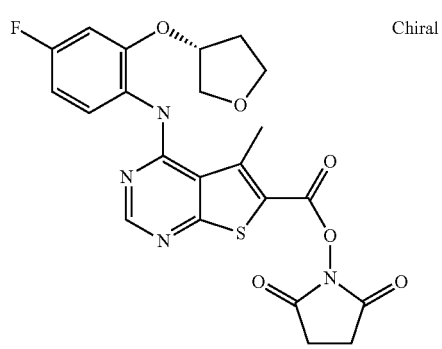 [SMILES: Cc1c(C(=O)ON2C(=O)CCC2=O)sc2ncnc(Nc3ccc(F)cc3O[C@@H]3CCOC3)c12 ; "Chiral"]

Prepared analogously to example 11.1 from 4-{4-Fluoro-2-[(R)-(tetrahydro-furan-3-yl)oxy]-phenylamino}-5-methyl-thieno[2,3-d]pyrimidine-6-carboxylic acid and N-Hydroxysuccinimde.

The product was used directly in the next step

103.2 4-{4-Fluoro-2-[(R)-(tetrahydro-furan-3-yl)oxy]-phenylamino}-5-methyl-thieno[2,3-d]pyrimidine-6-carboxylic acid (3-dimethylamino-propyl)-amide

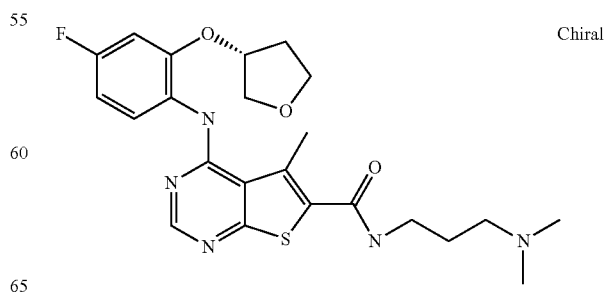

Compound 103.1 (130 mg) and N,N-dimethyl-1,3-propanediamine was dissolved in DMF (2 ml) and the reaction was stirred at room temperature overnight. The solvent was removed and the residue was purified by RP-chromatography.

Yield: 100 mg
ESI mass spectrum: m/z=474 (M+H)$^+$
Retention time HPLC: 1.22 (method X)
The following compounds were prepared analogously to 103.2:
from compound 103.1 and the corresponding amine.

TABLE 8

| Example | Structure | Mass | Retention time | amines |
|---|---|---|---|---|
| 104 | 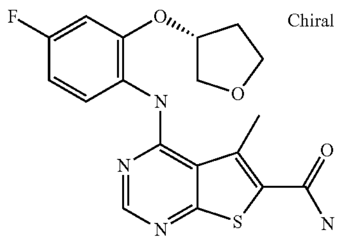 [SMILES: Cc1c(C(N)=O)sc2ncnc(Nc3ccc(F)cc3O[C@@H]3CCOC3)c12] | 389 (M + H)$^+$ | 1.28 (method X) | NH$_3$ |
| 105 | 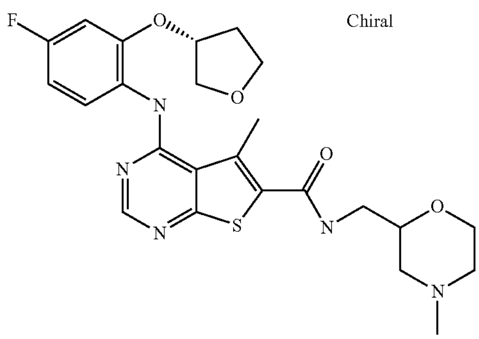 [SMILES: Cc1c(C(=O)NCC2CN(C)CCO2)sc2ncnc(Nc3ccc(F)cc3O[C@@H]3CCOC3)c12] | 502 (M + H)$^+$ | 1.22 (method X) | |
| 106 | 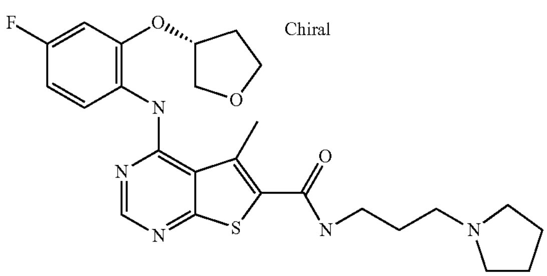 [SMILES: Cc1c(C(=O)NCCCN2CCCC2)sc2ncnc(Nc3ccc(F)cc3O[C@@H]3CCOC3)c12] | 500 (M + H)$^+$ | 1.24 (method X) | |
| 107 | 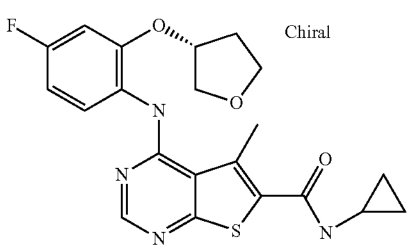 [SMILES: Cc1c(C(=O)NC2CC2)sc2ncnc(Nc3ccc(F)cc3O[C@@H]3CCOC3)c12] | 429 (M + H)$^+$ | 1.35 (method X) | |

145

Compound 108

4-{4-Fluoro-2-[(S)-(tetrahydro-furan-3-yl)oxy]-phenylamino}-5-methyl-thieno[2,3-d]pyrimidine-6-carboxylic acid (3-dimethylamino-propyl)-amide

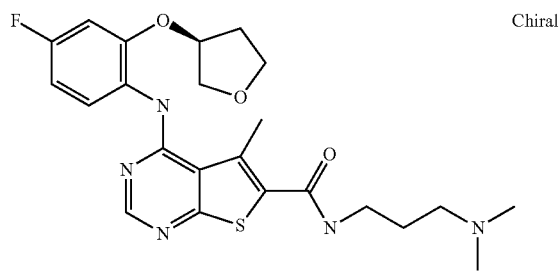 [SMILES: Cc1c(C(=O)NCCCN(C)C)sc2ncnc(Nc3ccc(F)cc3O[C@H]3CCOC3)c12 ; "Chiral"]

108.1 4-{4-Fluoro-2-[(S)-(tetrahydro-furan-3-yl)oxy]-phenylamino}-5-methyl-thieno[2,3-d]pyrimidine-6-carboxylic acid methyl ester

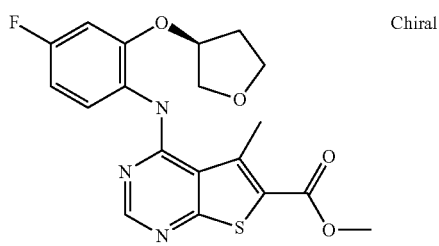 [SMILES: COC(=O)c1sc2ncnc(Nc3ccc(F)cc3O[C@H]3CCOC3)c2c1C ; "Chiral"]

Prepared analogously to example 100.1. from 4-chloro-5-methyl-thieno[2,3-d]pyrimidine-6-carboxylic acid methyl ester and (S)-4-fluoro-2-(tetrahydrofuran-3-yloxy)aniline (Intermediate XIX)

Yield: 780 mg 108.2 4-{4-Fluoro-2-[(S)-(tetrahydro-furan-3-yl)oxy]-phenylamino}-5-methyl-thieno[2,3-d]pyrimidine-6-carboxylic acid

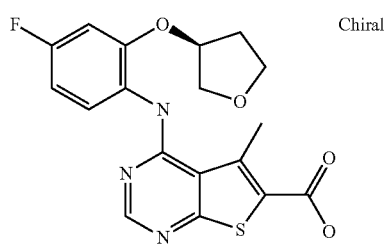 [SMILES: Cc1c(C(=O)O)sc2ncnc(Nc3ccc(F)cc3O[C@H]3CCOC3)c12 ; "Chiral"]

146

Prepared analogously to example 96.1. from 4-{4-fluoro-2-[(R)-(tetrahydro-furan-3-yl)oxy]-phenylamino}-5-methyl-thieno[2,3-d]pyrimidine-6-carboxylic acid methyl ester Yield: 650 mg 108.3

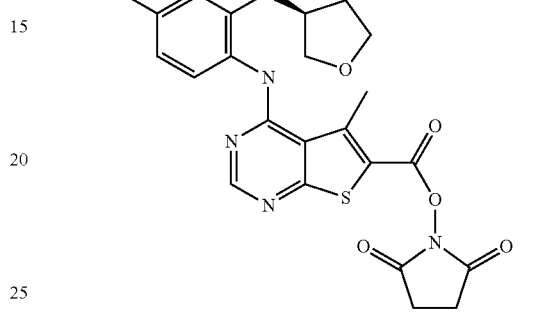

Prepared analogously to example 11.1. from 4-{4-fluoro-2-[(R)-(tetrahydro-furan-3-yl)oxy]-phenylamino}-5-methyl-thieno[2,3-d]pyrimidine-6-carboxylic acid and N-hydroxysuccinimde.

The product use directly in the next step 108.4 4-{4-Fluoro-2-[(S)-(tetrahydro-furan-3-yl)oxy]-phenylamino}-5-methyl-thieno[2,3-d]pyrimidine-6-carboxylic acid (3-dimethylamino-propyl)-amide

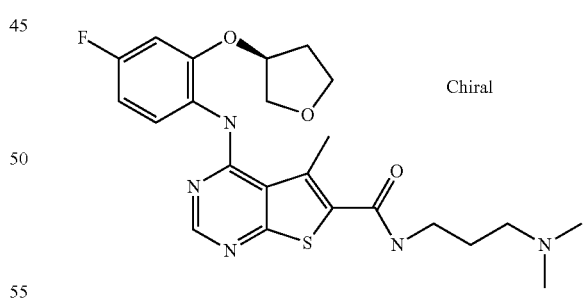

Prepared analogously to example 103.2. from compound 108.3 and N,N-dimethyl-1,3-propanediamine Yield: 120 mg ESI mass spectrum: m/z=474(M+H)$^+$ Retention time HPLC: 1.22 (method X)

The following compounds were prepared analogously to 108.4:

from compound 108.3 and the corresponding amine.

TABLE 8
| Example | Structure | Mass | Retention time | amines |
|---|---|---|---|---|
| 109 | 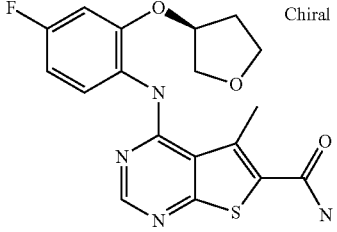 [SMILES: Cc1c(C(N)=O)sc2ncnc(Nc3ccc(F)cc3O[C@H]3CCOC3)c12] | 389 (M + H)⁺ | 1.28 (method X) | NH₃ |
| 110 | 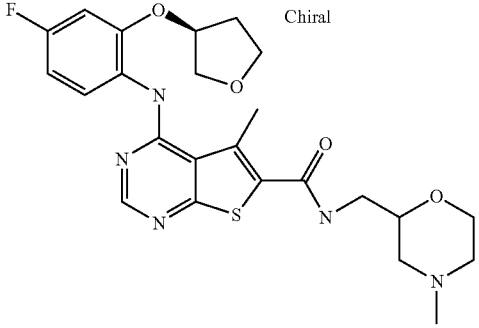 [SMILES: Cc1c(C(=O)NCC2CN(C)CCO2)sc2ncnc(Nc3ccc(F)cc3O[C@H]3CCOC3)c12] | 502 (M + H)⁺ | 1.22 (method X) | 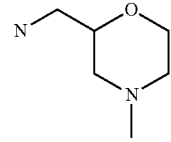 |
| 111 | 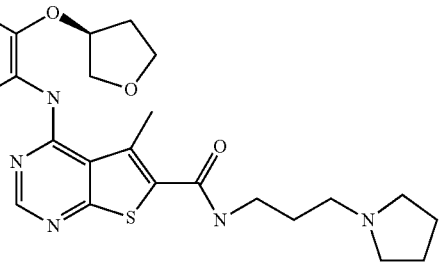 | 500 (M + H)⁺ | 1.23 (method X) | 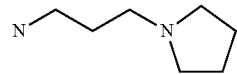 |
| 112 | 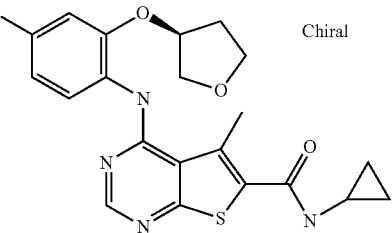 | 429 (M + H)⁺ | 1.35 (method X) |  |

Compound 113

4-[4-Fluoro-2-((3S,5S)-5-hydroxymethyl-1-methanesulfonyl-pyrrolidin-3-yloxy)-phenylamino]-5-methyl-thieno[2,3-d]pyrimidine-6-carboxylic acid amide

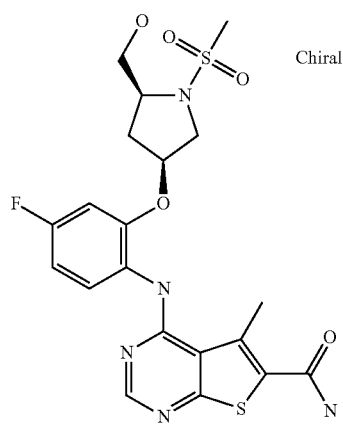 [SMILES: Cc1c(C(N)=O)sc2ncnc(Nc3ccc(F)cc3O[C@H]3C[C@@H](CO)N(S(C)(=O)=O)C3)c12]

113.1 4-[2-((3S,5S)-1-tert-Butoxycarbonyl-5-hydroxymethyl-pyrrolidin-3-yloxy)-4-fluoro-phenylamino]-5-methyl-thieno[2,3-d]pyrimidine-6-carboxylic acid methyl ester

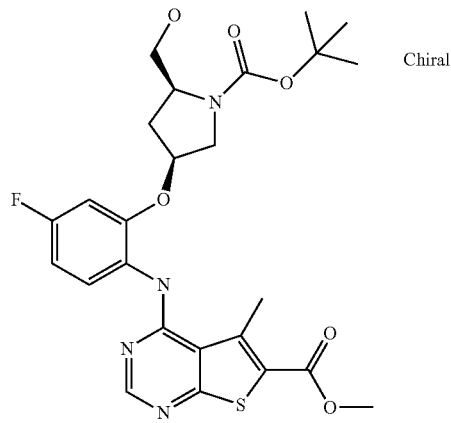 [SMILES: COC(=O)c1sc2ncnc(Nc3ccc(F)cc3O[C@H]3C[C@@H](CO)N(C(=O)OC(C)(C)C)C3)c2c1C]

Prepared analogously to example 1.1 from 4-chloro-5-methyl-thieno[2,3-d]pyrimidine-6-carboxylic acid methyl ester and (2S,4S)-tert-butyl 4-(2-amino-5-fluorophenoxy)-2-(hydroxymethyl)pyrrolidine-1-carboxylate.

Yield: 754 mg

113.2 4-[2-((3S,5S)-1-tert-Butoxycarbonyl-5-hydroxymethyl-pyrrolidin-3-yloxy)-4-fluoro-phenylamino]-5-methyl-thieno[2,3-d]pyrimidine-6-carboxylic acid

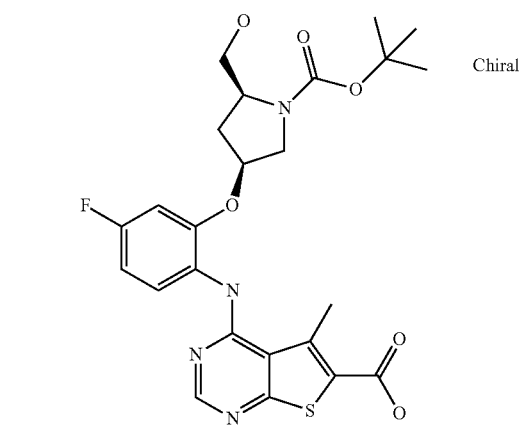 [SMILES: Cc1c(C(=O)O)sc2ncnc(Nc3ccc(F)cc3O[C@H]3C[C@@H](CO)N(C(=O)OC(C)(C)C)C3)c12]

Prepared analogously to example 65.2 from 4-[2-((3S,5S)-1-tert-butoxycarbonyl-5-hydroxymethyl-pyrrolidin-3-yloxy)-4-fluoro-phenylamino]-5-methyl-thieno[2,3-d]pyrimidine-6-carboxylic acid methyl ester.

Methanol was replaced by ethanol.

Yield: 1.49 g

113.3 4-[2-((3S,5S)-1-tert-Butoxycarbonyl-5-hydroxymethyl-pyrrolidin-3-yloxy)-4-fluoro-phenylamino]-5-methyl-thieno[2,3-d]pyrimidine-6-carboxylic acid amide Prepared analogously to example 1.4 from 4-[2-((3S,5S)-1-tert-butoxycarbonyl-5-hydroxymethyl-pyrrolidin-3-yloxy)-4-fluoro-phenylamino]-5-methyl-thieno[2,3-d]pyrimidine-6-carboxylic acid and ammonia in methanol.

Yield: 557 mg

113.4 (2S,4S)-2-Acetoxymethyl-4-[2-(6-carbamoyl-5-methyl-thieno[2,3-d]pyrimidin-4-ylamino)-5-fluoro-phenoxy]-pyrrolidine-1-carboxylic acid tert-butyl ester

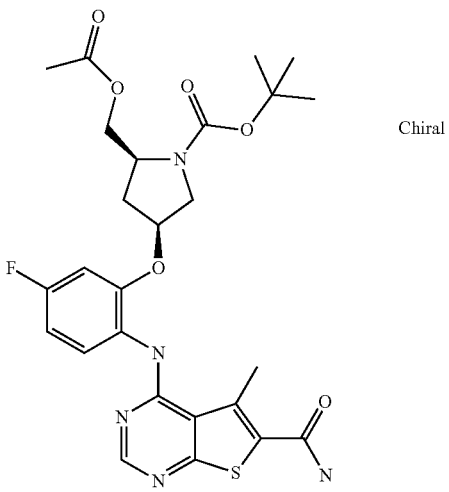 [SMILES: CC(=O)OC[C@@H]1C[C@H](Oc2cc(F)ccc2Nc2ncnc3sc(C(N)=O)c(C)c23)CN1C(=O)OC(C)(C)C]

Prepared analogously to example 96.4 from 4-[2-((3S,5S)-1-tert-butoxycarbonyl-5-hydroxymethyl-pyrrolidin-3-yloxy)-4-fluoro-phenylamino]-5-methyl-thieno[2,3-d]pyrimidine-6-carboxylic acid amide and acetic anhydride. The acetic anhydride was added at 0° C. and a catalytic amount of DMAP was used.

Yield: 533 mg

113.5 Acetic acid (2S,4S)-4-[2-(6-carbamoyl-5-methyl-thieno[2,3-d]pyrimidin-4-ylamino)-5-fluoro-phenoxy]-pyrrolidin-2-ylmethyl ester hydrochloride

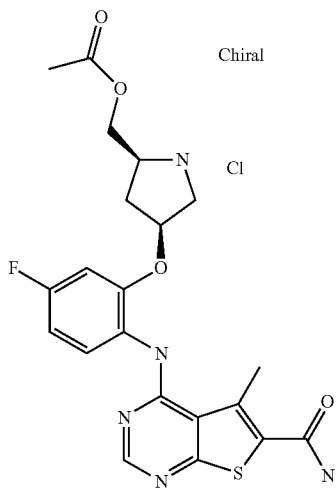 [SMILES: CC(=O)OC[C@@H]1C[C@H](Oc2cc(F)ccc2Nc2ncnc3sc(C(N)=O)c(C)c23)CN1 ; Cl]

Prepared analogously to example 10.1 from (2S,4S)-2-acetoxymethyl-4-[2-(6-carbamoyl-5-methyl-thieno[2,3-d]pyrimidin-4-ylamino)-5-fluoro-phenoxy]-pyrrolidine-1-carboxylic acid tert-butyl ester.

Yield: 453 mg

113.6 Acetic acid (2S,4S)-4-[2-(6-carbamoyl-5-methyl-thieno[2,3-d]pyrimidin-4-ylamino)-5-fluoro-phenoxy]-1-methanesulfonyl-pyrrolidin-2-ylmethyl ester

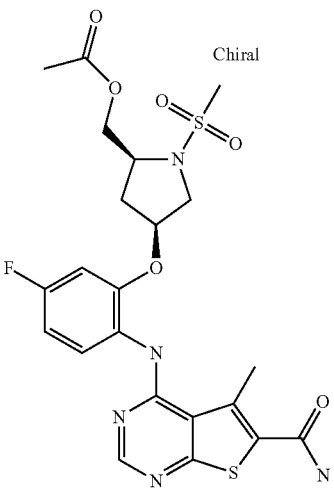 [SMILES: CC(=O)OC[C@@H]1C[C@H](Oc2cc(F)ccc2Nc2ncnc3sc(C(N)=O)c(C)c23)CN1S(C)(=O)=O]

Prepared analogously to example 10.2 from acetic acid (2S,4S)-4-[2-(6-carbamoyl-5-methyl-thieno[2,3-d]pyrimidin-4-ylamino)-5-fluoro-phenoxy]-pyrrolidin-2-ylmethyl ester hydrochloride and methanesulfonyl chloride. Methansulfonyl chloride was added at 0° C.

Yield: 367 mg

113.7 4-[4-Fluoro-2-((3S,5S)-5-hydroxymethyl-1-methanesulfonyl-pyrrolidin-3-yloxy)-phenylamino]-5-methyl-thieno[2,3-d]pyrimidine-6-carboxylic acid amide

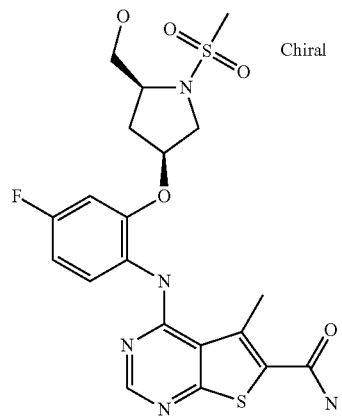 [SMILES: Cc1c(C(N)=O)sc2ncnc(Nc3ccc(F)cc3O[C@H]3C[C@@H](CO)N(S(C)(=O)=O)C3)c12]

Potassium carbonate (278 mg) was added to a solution of acetic acid (2S,4S)-4-[2-(6-carbamoyl-5-methyl-thieno[2,3-d]pyrimidin-4-ylamino)-5-fluoro-phenoxy]-1-methanesulfonyl-pyrrolidin-2-ylmethyl ester (360 mg) in MeOH (5 ml) and THF (2 ml). The reaction was stirred at room temperature for 90 h. 10% aq. KHSO4 was added and the resultant suspension was filtered. The filter cake was washed with dichloromethan and diethylether.

Yield: 157 mg
ESI mass spectrum: m/z=496(M+H)+
Retention time HPLC: 1.18 (method X)

Compound 114

4-[4-Fluoro-2-((6S,7aS)-3-oxo-tetrahydro-pyrrolo[1,2-d]oxazol-6-yloxy)-phenylamino]-5-methyl-thieno[2,3-d]pyrimidine-6-carboxylic acid methyl ester

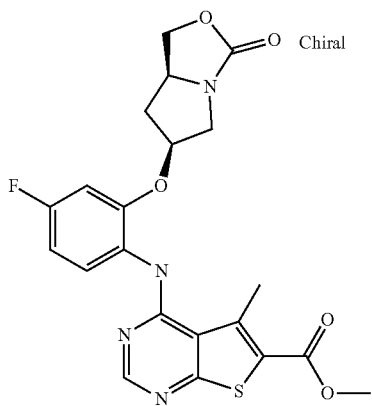 [SMILES: COC(=O)c1sc2ncnc(Nc3ccc(F)cc3O[C@H]3C[C@H]4COC(=O)N4C3)c2c1C]

114.1 4-[4-Fluoro-2-((3S,5S)-5-hydroxymethyl-pyrrolidin-3-yloxy)-phenylamino]-5-methyl-thieno[2,3-d]pyrimidine-6-carboxylic acid methyl ester

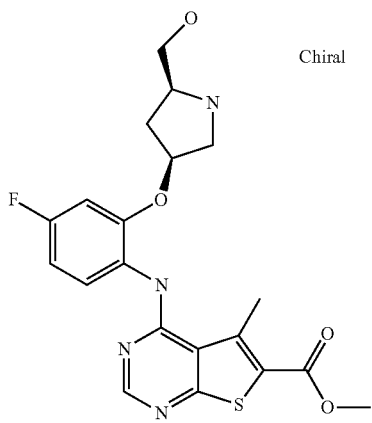 [SMILES: COC(=O)c1sc2ncnc(Nc3ccc(F)cc3O[C@@H]3CN[C@H](CO)C3)c2c1C]

Trifluoroacetic acid (1 ml) was added to a solution of 4-[2-((3S,5S)-1-tert-butoxycarbonyl-5-hydroxymethyl-pyrrolidin-3-yloxy)-4-fluoro-phenylamino]-5-methyl-thieno[2,3-d]pyrimidine-6-carboxylic acid amide (754 mg) in dichloromethane (10 ml). The reaction mixture was stirred for 4 h and a further aliqout of trifluoroacetic acid was added. The reaction mixture was stirred for 1 h again. The solvent was removed in vacuo. The mixture was diluted with dichloromethane and washed with 10% aq. K₂CO₃. The organic layer was concentrated and the residue was purified by flash column chromatography (silica gel, solvent: 100% dichloromethane→20:1:0,1 dichloromethane: MeOH: NH4OH)

Yield: 149 mg
ESI mass spectrum: m/z=433(M+H)+
Retention time HPLC: 1.22 (method X)

114.2 4-[4-Fluoro-2-((6S,7aS)-3-oxo-tetrahydro-pyrrolo[1,2-d]oxazol-6-yloxy)-phenylamino]-5-methyl-thieno[2,3-d]pyrimidine-6-carboxylic acid methyl ester

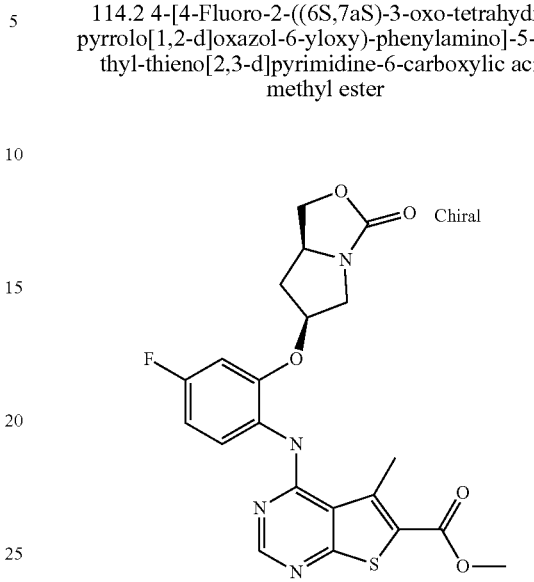

CDI (64 mg) was added to a suspension of 4-[4-fluoro-2-((3S,5S)-5-hydroxymethyl-pyrrolidin-3-yloxy)-phenylamino]-5-methyl-thieno[2,3-d]pyrimidine-6-carboxylic acid methyl ester (86 mg) in dichloromethane (2 ml). The reaction was stirred at room temperature for 3 h. The solvent was reduced in vacuo and the mixture treated with DMF. The mixture was warmed and stirred for 18 h. The mixture was diluted with EtOAc and water. The organic phase was washed with 10% aq. KHSO4 and 10% K2CO3. The resultant suspension was filtered and washed with ether. The filtrate was evaporated.

Yield: 26 mg
ESI mass spectrum: m/z=459(M+H)+
Retention time HPLC: 1.35 (method X)

Compound 115

4-[4-Fluoro-2-((3S,5S)-5-hydroxymethyl-pyrrolidin-3-yloxy)-phenylamino]-5-methyl-thieno[2,3-d]pyrimidine-6-carboxylic acid amide

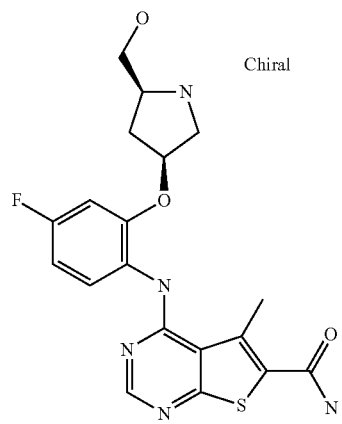 [SMILES: Cc1c(C(N)=O)sc2ncnc(Nc3ccc(F)cc3O[C@@H]3CN[C@H](CO)C3)c12]

Prepared analogously to example 65.4 from 4-[2-((3S,5S)-1-tert-butoxycarbonyl-5-hydroxymethyl-pyrrolidin-3-yloxy)-4-fluoro-phenylamino]-5-methyl-thieno[2,3-d]pyrimidine-6-carboxylic acid amide.

Yield: 32 mg
ESI mass spectrum: m/z=418(M+H)$^+$
Retention time HPLC: 1.1 (method X)

Compound 116

4-[4-Fluoro-2-(tetrahydro-pyran-4-yloxy)-phenylamino]-5-methyl-thieno[2,3-d]pyrimidine-6-carboxylic acid (4-methyl-morpholin-2-ylmethyl)-amide trifluoracetate

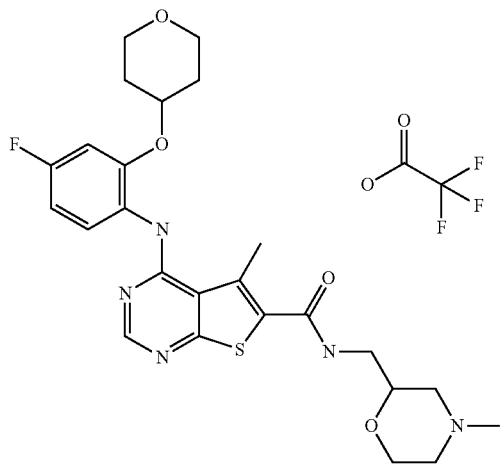 [SMILES: Cc1c(C(=O)NCC2CN(C)CCO2)sc2ncnc(Nc3ccc(F)cc3OC3CCOCC3)c12 ; O=C(O)C(F)(F)F]

116.1 4-[4-Fluoro-2-(tetrahydro-pyran-4-yloxy)-phenylamino]-5-methyl-thieno[2,3-d]pyrimidine-6-carboxylic acid methyl ester

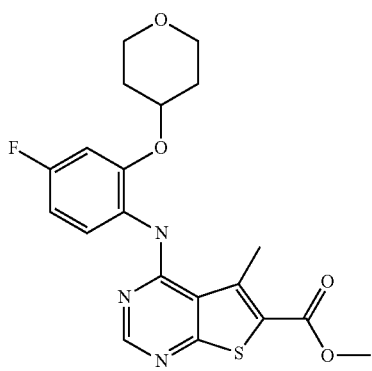 [SMILES: COC(=O)c1sc2ncnc(Nc3ccc(F)cc3OC3CCOCC3)c2c1C]

To a mixture of 4-chloro-5-methyl-thieno[2,3-d]pyrimidine-6-carboxylic acid methyl ester (8.5 g) and 4-fluoro-2-(tetrahydro-2H-pyran-4-yloxy)aniline (7.4 g) (intermediate XX) in dioxane (100 ml) was added HCl in dioxan (4M; 0.9 ml). The reaction was stirred at 100° C. overnight. The reaction mixture was allowed to warm to room temperature and water (50 ml) was added. The precipitate was isolated by filtration Yield: 13.45 mg
ESI mass spectrum: m/z=418(M+H)$^+$
Retention time HPLC: 2.47 (method F)

116.2 4-[4-Fluoro-2-(tetrahydro-pyran-4-yloxy)-phenylamino]-5-methyl-thieno[2,3-d]pyrimidine-6-carboxylic acid

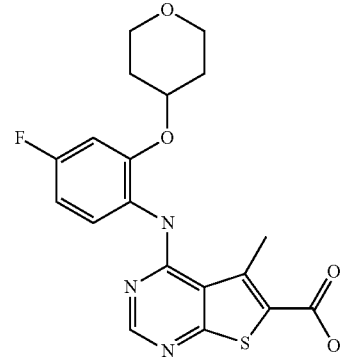 [SMILES: Cc1c(C(=O)O)sc2ncnc(Nc3ccc(F)cc3OC3CCOCC3)c12]

4-[4-Fluoro-2-(tetrahydro-pyran-4-yloxy)-phenylamino]-5-methyl-thieno[2,3-d]pyrimidine-6-carboxylic acid methylester (13.45 g) was dissolved in THF (100 ml) and lithium hydroxide (1M; 80.5 ml) was added. The reaction mixture was stirred at room temperature for 5 h. The mixture was acidified with HCl (1M) to pH 2, the resultant precipitate was filtered and washed with water.

Yield: 12.15 g
ESI mass spectrum: m/z=404 (M+H)$^+$
Retention time HPLC: 2.35 (method F)

116.3 4-[4-Fluoro-2-(tetrahydro-pyran-4-yloxy)-phenylamino]-5-methyl-thieno[2,3-d]pyrimidine-6-carboxylic acid (4-methyl-morpholin-2-ylmethyl)-amide trifluoracetate

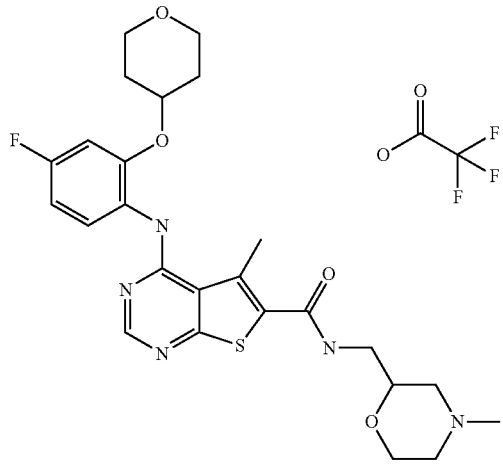 [SMILES: Cc1c(C(=O)NCC2CN(C)CCO2)sc2ncnc(Nc3ccc(F)cc3OC3CCOCC3)c12 ; O=C(O)C(F)(F)F]

4-[4-Fluoro-2-(tetrahydro-pyran-4-yloxy)-phenylamino]-5-methyl-thieno[2,3-d]pyrimidine-6-carboxylic acid (155 mg) was dissolved in DMF (10 ml) and diisopropylethylamin (65 µl) was added. To this mixture was added TBTU 126 mg) and the reaction was stirred at room temperature for a few minutes. After this time C-(4-Methyl-morpholin-2-yl)-methylamine (50 mg) was added and the mixture was stirred at room temperature overnight. K2CO3 (2M; 0.5 ml) was added and the mixture was concentrated in vacuo. The crude product was puffed by RP-chromatography (H2O+0.1% TFA/MeOH=35%→55%)

Yield: 2.6 mg

ESI mass spectrum: m/z=516 (M+H)+

Retention time HPLC: 1.89 (method F)

The following compounds were prepared analogously to 116.3:

| Example | NR1R2 | educt | Mass-spectrum | HPLC (retention time) |
|---|---|---|---|---|
| 117 | morpholine-N-CH3 | 116.2 | | |
| 118 | pyrrolidine-propyl | 116.2 | 514 (M+H)+ | 2.08 (method H) |
| 119 | N-methylpyrrolidine-ethyl | 116.2 | | |
| 120 | N-methylpiperazine-propyl | 116.2 | | |
| 121 | Chiral pyrrolidine-propyl-OCH3 | 116.2 | | |
| 122 | Chiral pyrrolidine-CH2OCH3-propyl | 116.2 | | |
| 123 | N-methylpiperidine-CH2 | 116.2 | | |
| 124 | 3,3-difluoropyrrolidine-propyl | 116.2 | | |
| 125 | 3,3-difluoroazetidine-propyl | 116.2 | | |
| 126 | (CH3)2N-CH2CH2-N(CH3)-propyl | 116.2 | | |
| 127 | morpholine-CH2 | 116.2 | 502 (M+H)+ | 1.8 (method H) |

159

-continued

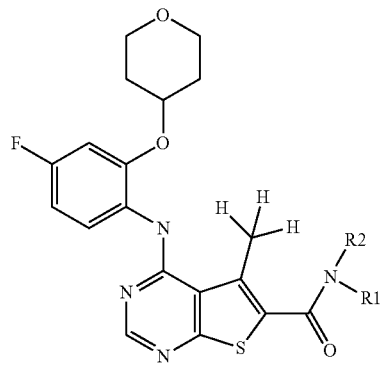

| Example | NR1R2 | educt | Mass-spectrum | HPLC (retention time) |
|---|---|---|---|---|
| 128 | N-CH2-C(=O)-NH2 | 116.2 | 460 (M + H)+ | 1.66 (method H) |
| 129 | N-cyclohexyl-CH2OH (trans) | 116.2 | 515 (M + H)+ | 1.83 (method H) |
| 130 | N-(CH2)3-NH-C(=O)CH3 | 116.2 | 502 (M + H)+ | 1.77 (method H) |
| 131 | N-(CH2)3-(2-oxopyrrolidin-1-yl) | 116.2 | 528 (M + H)+ | 1.81 (method H) |
| 132 | N-CH2CH2-COOH | 116.2 | 475 (M + H)+ | 1.19 (method H) |
| 133 | N-(piperidin-3-yl) | 116.2 | 486 (M + H)+ | 2.02 (method H) |
| 134 | N-CH2-C≡C-CH2-NH2 | 116.2 | 470 (M + H)+ | 1.77 (method H) |
| 135 | N-CH(CH3)2 | 116.2 | 445 (M + H)+ | 1.89 (method H) |
| 136 | N-(2-aminocyclopropyl) | 116.2 | 458 (M + H)+ | 1.81 (method H) |

160

-continued

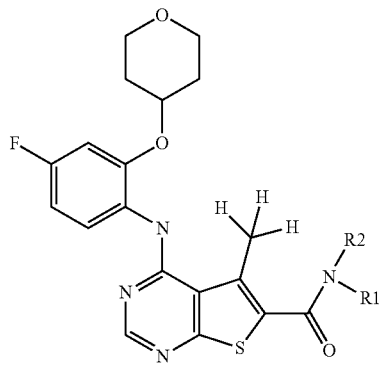

| Example | NR1R2 | educt | Mass-spectrum | HPLC (retention time) |
|---|---|---|---|---|
| 137 | N-(azetidin-3-yl) | 116.2 | 458 (M + H)+ | 1.93 (metod H) |
| 138 | N-(pyrrolidin-3-yl) | 116.2 | 472 (M + H)+ | 1.64 (method I) |
| 139 | N-CH2CH2-(pyrrolidin-2-yl) | 116.2 | 500 (M + H)+ | 2.35 (method H) |
| 140 | N-CH2-(1-aminocyclopentyl) | 116.2 | 500 (M + H)+ | 2.00 (method H) |
| 141 | N-CH2-(morpholin-3-yl) | 116.2 | 502 (M + H)+ | 1.87 (method H) |
| 142 | N-(3-aminocyclopentyl) | 116.2 | 486 (M + H)+ | 1.64 (method I) |
| 143 | N-(3-aminocyclobutyl) | 116.2 | 472 (M + H)+ | 1.84 (method H) |
| 144 | N-(2-aminocyclopropyl) | 116.2 | 458 (M + H)+ | 1.77 (method H) |
| 145 | N-CH2-(azetidin-3-yl) | 116.2 | 472 (M + H)+ | 1.84 (method H) |
| 146 | N-CH2CH2-NH-CH3 | 116.2 | 460 (M + H)+ | 1.90 (method H) |

-continued

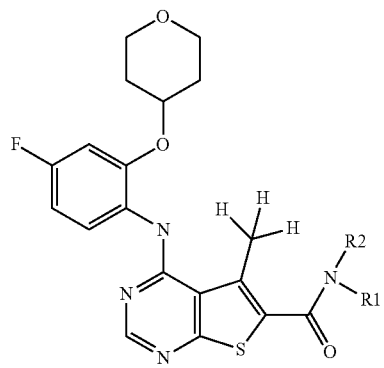

| Example | NR1R2 | educt | Mass-spectrum | HPLC (retention time) |
|---|---|---|---|---|
| 147 | N-CH(CH₃)-COOH (L-Ala) | 116.2 | 475 (M + H)⁺ | 1.19 (method H) |
| 148 | N-CH(CH₃)-COOH (D-Ala) | 116.2 | 475 (M + H)⁺ | 1.22 (method H) |
| 149 | N-CH₂-COOH | 116.2 | 461 (M + H)⁺ | 1.16 (method H) |
| 150 | N-CH₂-(5-oxopyrrolidin-2-yl) | 116.2 | 500 (M + H)⁺ | 1.79 (method H) |
| 151 | N-CH₂CH₂-imidazol-1-yl | 116.2 | 497 (M + H)⁺ | 1.79 (method H) |
| 152 | N-CH₂CH₂CH₂-OH | 116.2 | 461 (M + H)⁺ | 1.79 (method H) |
| 153 | N-CH(CH₂OH)₂ | 116.2 | 477 (M + H)⁺ | 1.70 (method H) |
| 154 | N-CH₂-C(CH₃)₂-CH₂-N(CH₃)₂ (with extra C(CH₃)) | 116.2 | 516 (M + H)⁺ | 2.15 (method H) |
| 155 | N-CH₂CH₂CH₂CH₂-OH | 116.2 | 475 (M + H)⁺ | 1.81 (method H) |

-continued

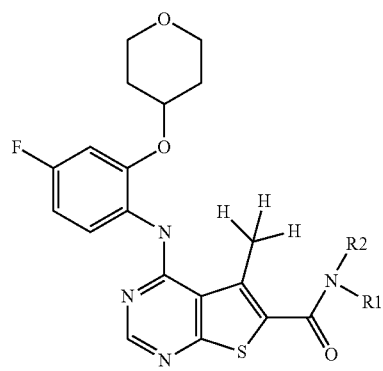

| Example | NR1R2 | educt | Mass-spectrum | HPLC (retention time) |
|---|---|---|---|---|
| 156 | N-CH(CH₃)-CH₂OH | 116.2 | 461 (M + H)⁺ | 1.80 (method H) |
| 157 | N-CH₂-C(O)-N(CH₃)₂ | 116.2 | 488 (M + H)⁺ | 1.81 (method H) |
| 158 | N-CH₂-CH(OH)-CH₃ | 116.2 | 461 (M + H)⁺ | 1.75 (method H) |
| 159 | N-CH₂-CF₃ | 116.2 | 485 (M + H)⁺ | 1.88 (method H) |
| 160 | N-CH₂CH₂-O-CH₃ | 116.2 | 475 (M + H)⁺ | 1.87 (method H) |
| 161 | N-CH₂CH₂-O-CH₂CH₂CH₃ | 116.2 | 489 (M + H)⁺ | 1.95 (method H) |
| 162 | N-CH₂CH₂-O-CH(CH₃)₂ | 116.2 | | |
| 163 | N-CH(CH₃)-CH₂-O-CH₃ | 116.2 | 475 (M + H)⁺ | 1.84 (method H) |
| 164 | N-CH₂-CN | 116.2 | 442 (M + H)⁺ | 1.75 (method H) |

163
-continued

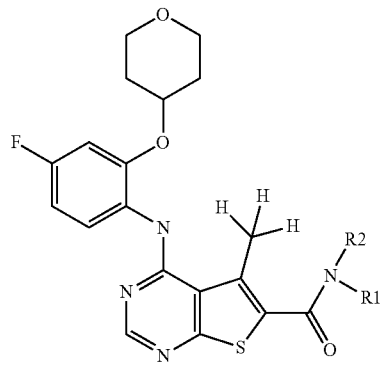

| Example | NR1R2 | educt | Mass-spectrum | HPLC (retention time) |
|---|---|---|---|---|
| 165 | 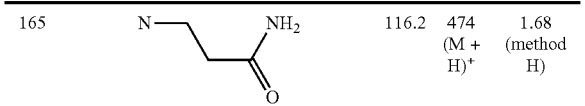 | 116.2 | 474 (M + H)+ | 1.68 (method H) |
| 166 | 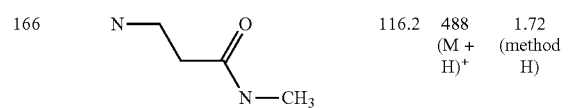 | 116.2 | 488 (M + H)+ | 1.72 (method H) |
| 167 | 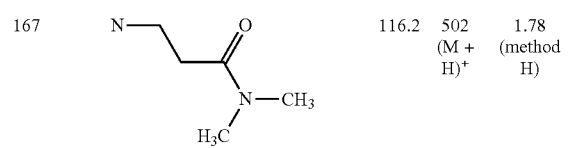 | 116.2 | 502 (M + H)+ | 1.78 (method H) |
| 168 | 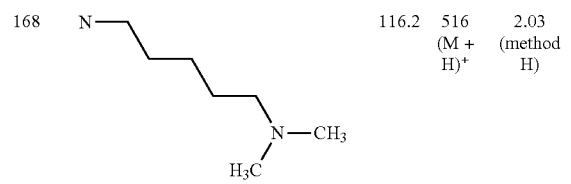 | 116.2 | 516 (M + H)+ | 2.03 (method H) |
| 169 | 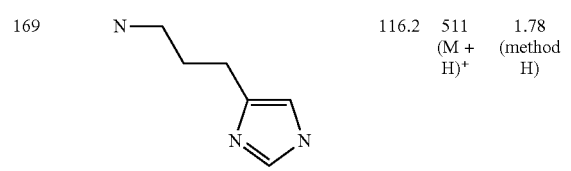 | 116.2 | 511 (M + H)+ | 1.78 (method H) |
| 170 | 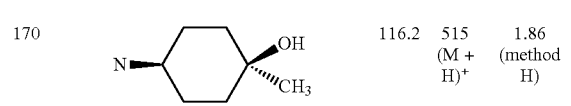 | 116.2 | 515 (M + H)+ | 1.86 (method H) |
| 171 | 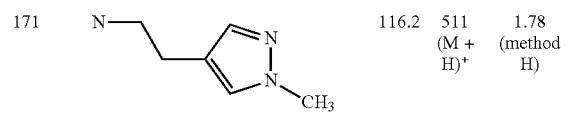 | 116.2 | 511 (M + H)+ | 1.78 (method H) |
| 172 | 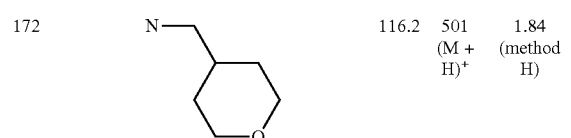 | 116.2 | 501 (M + H)+ | 1.84 (method H) |
| 173 | 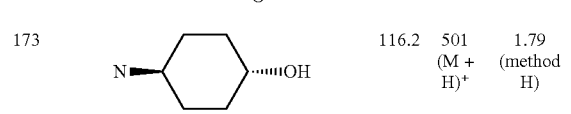 | 116.2 | 501 (M + H)+ | 1.79 (method H) |

164
-continued

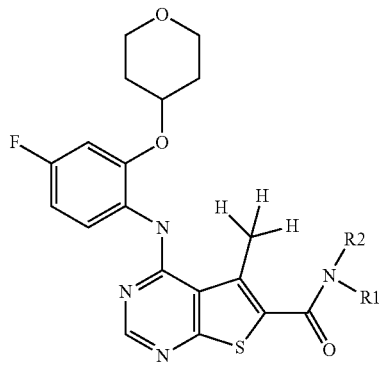

| Example | NR1R2 | educt | Mass-spectrum | HPLC (retention time) |
|---|---|---|---|---|
| 174 | 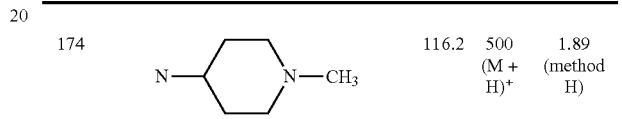 | 116.2 | 500 (M + H)+ | 1.89 (method H) |
| 175 | 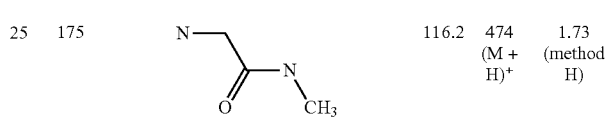 | 116.2 | 474 (M + H)+ | 1.73 (method H) |
| 176 | 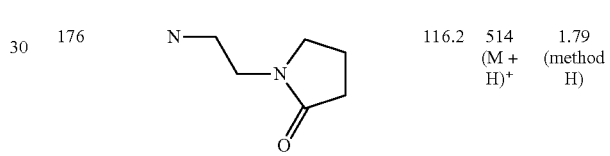 | 116.2 | 514 (M + H)+ | 1.79 (method H) |
| 177 | 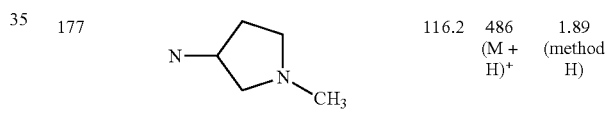 | 116.2 | 486 (M + H)+ | 1.89 (method H) |
| 178 | 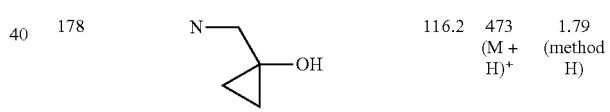 | 116.2 | 473 (M + H)+ | 1.79 (method H) |
| 179 | 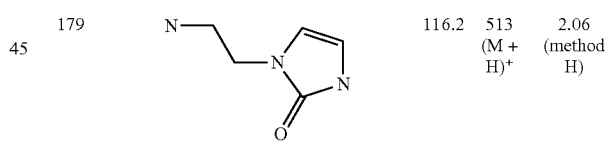 | 116.2 | 513 (M + H)+ | 2.06 (method H) |
| 180 | 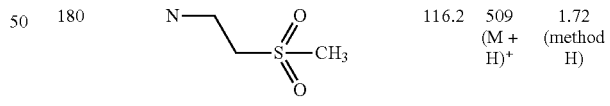 | 116.2 | 509 (M + H)+ | 1.72 (method H) |
| 181 | 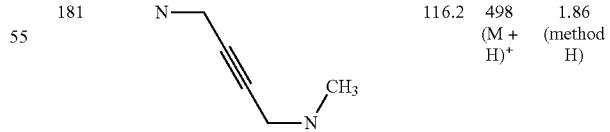 | 116.2 | 498 (M + H)+ | 1.86 (method H) |
| 182 | 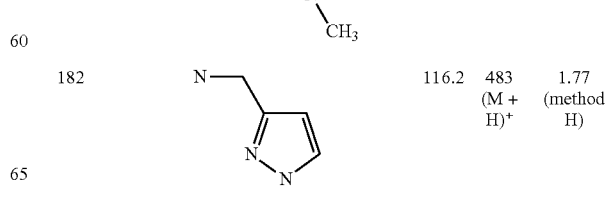 | 116.2 | 483 (M + H)+ | 1.77 (method H) |

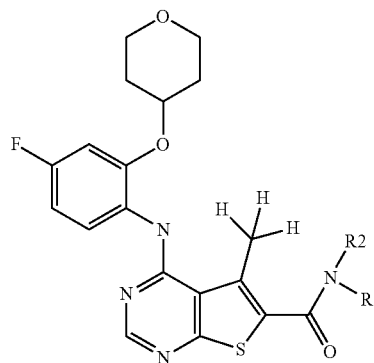

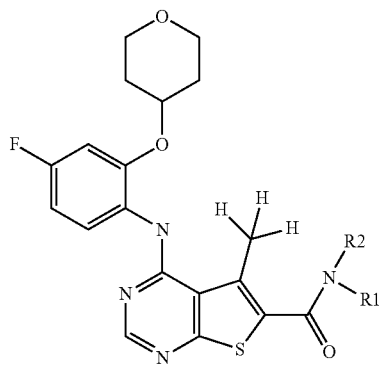

| Example | NR1R2 | educt | Mass-spectrum | HPLC (retention time) |
|---|---|---|---|---|
| 183 | N-CH2CH2-pyrazol-1-yl | 116.2 | 497 (M + H)+ | 2.29 (method H) |
| 184 | N-CH2-(1-methylimidazol-4-yl) | 116.2 | 497 (M + H)+ | 1.77 (method H) |
| 185 | N-CH2CH2-O-CH2CH2-N(CH3)2 | 116.2 | 518 (M + H)+ | 1.94 (method H) |
| 186 | N-CH2-oxazol-5-yl | 116.2 | 484 (M + H)+ | 1.78 (method H) |
| 187 | N-CH2-oxazol-2-yl | 116.2 | 484 (M + H)+ | 1.79 (method H) |
| 188 | N-CH2-(1-methyl-5-hydroxypyrazol-3-yl) | 116.2 | 513 (M + H)+ | 1.14 (method H) |
| 189 | N-CH2CH2-N(SO2CH3) | 116.2 | 524 (M + H)+ | 1.72 (method H) |
| 190 | N-CH2-C(CH3)2-OH | 116.2 | 475 (M + H)+ | 1.81 (method H) |
| 191 | N-(trans-4-hydroxycyclohexyl) | 116.2 | 501 (M + H)+ | 1.82 (method H) |
| 192 | N-(3-hydroxycyclohexyl) | 116.2 | 501 (M + H)+ | 1.83 (method H) |
| 193 | N-CH2CH2CH2-SO2CH3 | 116.2 | 523 (M + H)+ | 1.73 (method H) |
| 194 | N-(1-hydroxymethylcyclopropyl) | 116.2 | 473 (M + H)+ | 1.79 (method H) |
| 195 | N-CH2CH2-(3-hydroxypyrazol-4-yl) | 116.2 | 513 (M + H)+ | 1.74 (method H) |
| 196 | N-CH2CH2-SO2NH2 | 116.2 | 510 (M + H)+ | 1.67 (method H) |
| 197 | N-CH2-(tetrahydropyran-3-yl) | 116.2 | 501 (M + H)+ | 1.88 (method H) |
| 198 | N-CH2-oxazol-4-yl | 116.2 | 484 (M + H)+ | 1.78 (method H) |
| 199 | N-CH2-(2-oxopyrrolidin-4-yl) | 116.2 | 500 (M + H)+ | 1.71 (method H) |

-continued

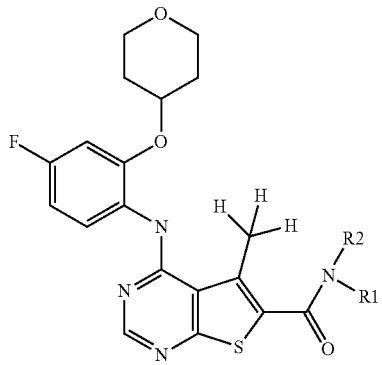

| Example | NR1R2 | educt | Mass-spectrum | HPLC (retention time) |
|---|---|---|---|---|
| 200 | N-azetidine-N-CH3 | 116.2 | 472 (M + H)+ | 1.84 (method H) |
| 201 | N-CH2-C(O)-pyrrolidine | 116.2 | 514 (M + H)+ | 1.81 (method H) |
| 202 | N-tetrahydrofuran-3-yl | 116.2 | 473 (M + H)+ | 1.80 (method H) |
| 203 | N-CH2-cyclopentyl-OH | 116.2 | 501 (M + H)+ | 1.90 (method H) |
| 204 | N-CH2-(3-CH3-1-CH3-pyrrolidine) | 116.2 | 514 (M + H)+ | 2.02 (method H) |
| 205 | N-CH2CH2-imidazole | 116.2 | | |
| 206 | N-CH2CH2-2-pyridyl | 116.2 | 508 (M + H)+ | 1.88 (method H) |
| 207 | N-CH2CH2-3-pyridyl | 116.2 | 508 (M + H)+ | 1.83 (method H) |
| 208 | N-CH2CH2-4-pyridyl | 116.2 | 508 (M + H)+ | 1.83 (method H) |
| 209 | N-CH2CH2-pyrrolidine | 116.2 | 500 (M + H)+ | 1.98 (method H) |

-continued

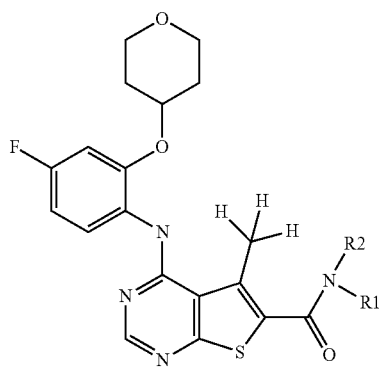

| Example | NR1R2 | educt | Mass-spectrum | HPLC (retention time) |
|---|---|---|---|---|
| 210 | N-CH2CH2-O-CH2CH2-OH | 116.2 | 491 (M + H)+ | 1.75 (method H) |
| 211 | N-CH2CH2-OH | 116.2 | 447 (M + H)+ | 1.72 (method H) |
| 212 | N-CH2CH2CH2-morpholine | 116.2 | 530 (M + H)+ | 1.85 (method H) |
| 213 | N-CH2-3-pyridyl | 116.2 | 494 (M + H)+ | 1.82 (method H) |
| 214 | N-CH2CH2-imidazolidinone | 116.2 | 515 (M + H)+ | 1.71 (method H) |
| 215 | N-CH2CH2CH2-O-CH3 | 116.2 | 475 (M + H)+ | 1.86 (method H) |
| 216 | N-CH2-C(CH3)2-CH2-OH | 116.2 | 489 (M + H)+ | 1.86 (method H) |
| 217 | N-CH2-tetrahydrofuran-2-yl | 116.2 | 487 (M + H)+ | 1.87 (method H) |

-continued

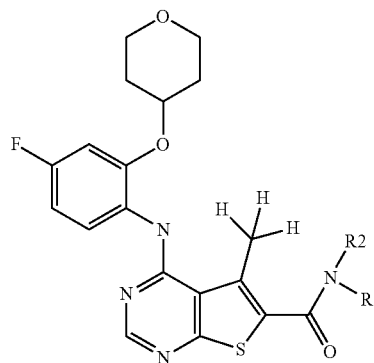

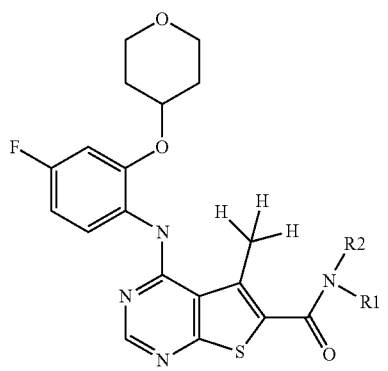

| Example | NR1R2 | educt | Mass-spectrum | HPLC (retention time) |
|---|---|---|---|---|
| 218 | N-propyl-O-ethyl | 116.2 | 489 (M + H)+ | 1.93 (method H) |
| 219 | N-CH2-(2-pyridyl) | 116.2 | 494 (M + H)+ | 1.89 (method H) |
| 220 | N-propyl-imidazolyl | 116.2 | 511 (M + H)+ | 1.79 (method H) |
| 221 | N-CH2-(4-pyridyl) | 116.2 | 494 (M + H)+ | 1.81 (method H) |
| 222 | N-ethyl-piperidinyl | 116.2 | 514 (M + H)+ | 2.03 (method H) |
| 223 | N-propyl-N(Et)2 | 116.2 | 516 (M + H)+ | 2.09 (method H) |
| 224 | H3C-CH(NH)-CH(OH) | 116.2 | 475 (M + H)+ | 1.82 (method H) |
| 225 | N-cyclopentyl-CH2OH | 116.2 | 501 (M + H)+ | 1.91 (method H) |
| 226 | H3C-C(CH3)(NH)-CH2OH | 116.2 | 475 (M + H)+ | 1.83 (method H) |
| 227 | N-ethyl | 116.2 | 431 (M + H)+ | 1.84 (method H) |
| 228 | N-CH2-CN | 116.2 | 456 (M + H)+ | 1.76 (method H) |
| 229 | N-CH2-C≡CH | 116.2 | 441 (M + H)+ | 1.80 (method H) |
| 230 | N-ethyl-NH-C(O)CH3 | 116.2 | 488 (M + H)+ | 1.74 (method H) |
| 231 | N-CH2-(2-imidazolyl) | 116.2 | 483 (M + H)+ | 1.77 (method H) |
| 232 | N-ethyl-O-CH(CH3)2 | 116.2 | 489 (M + H)+ | 1.93 (method H) |
| 233 | N-ethyl-imidazolyl | 116.2 | 497 (M + H)+ | 1.75 (method H) |
| 234 | N-ethyl-S-CH3 | 116.2 | 477 (M + H)+ | 1.77 (method E) |
| 235 | N-S(O)2-CH3 | 116.2 | 481 (M + H)+ | 1.88 (method E) |

| | 171 -continued | | | | | 172 -continued | | | |
|---|---|---|---|---|---|---|---|---|---|

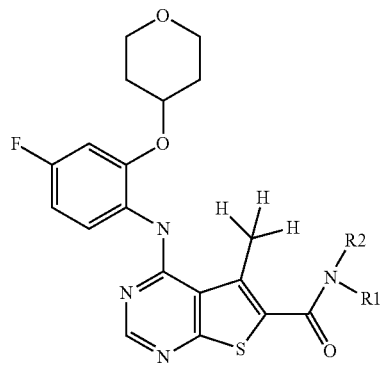

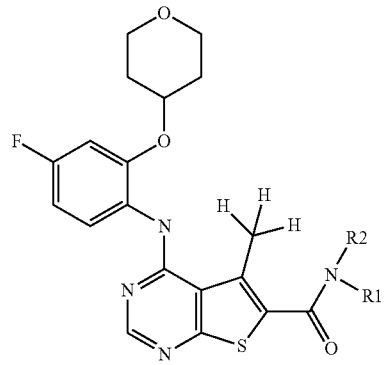

| Example | NR1R2 | educt | Mass-spectrum | HPLC (retention time) | Example | NR1R2 | educt | Mass-spectrum | HPLC (retention time) |
|---|---|---|---|---|---|---|---|---|---|
| 236 | N-CH2CH2CH2-S(O)-CH3 | 116.2 | 507 (M + H)+ | 1.43 (method E) | 245 | N-O-CH2CH2-O-CH3 | 116.2 | 477 (M + H)+ | 1.66 (method C) |
| 237 | N-CH2CH2CH2-S-CH3 | 116.2 | 491 (M + H)+ | 1.81 (method E) | 246 | 4-amino-3-hydroxy-piperidine | 116.2 | 502 (M + H)+ | 1.27 (method C) |
| 238 | N-CH2CH2-S(O)-CH3 | 116.2 | 493 (M + H)+ | 1.61 (method E) | 247 | N-(1-methyl-2-oxo-pyrimidin-4-yl) | 116.2 | 511 (M + H)+ | |
| 239 | N—O—CH3 | 116.2 | (M + H)+ | (method E) | 248 | N-CH2-CH(O)-CH2-N(Et)2 | 116.2 | 532 (M + H)+ | 1.74 (method L) |
| 240 | 2-hydroxy-cyclopentylamino | 116.2 | 433 (M + H)+ | 1.63 (method C) | 249 | N-CH2CH2CH2-(3-hydroxy-pyrrolidin-1-yl) | 116.2 | 530 (M + H)+ | 1.72 (method L) |
| 241 | 4-amino-3-hydroxy-1-Boc-piperidine | 116.2 | 602 (M + H)+ | 1.77 (method C) | 250 | N-CH2-C(O)-CH2-N | 116.2 | 476 (M + H)+ | 1.70 (method L) |
| 242 | cis-2-hydroxy-cyclopentylamino | 116.2 | 487 (M + H)+ | 1.64 (method C) | 251 | N-CH2CH2CH2-(3-hydroxy-pyrrolidin-1-yl) | 116.2 | 530 (M + H)+ | 1.72 (method L) |
| 243 | 2-hydroxy-cyclohexylamino | 116.2 | 501 (M + H)+ | 1.68 (method C) | 252 | morpholin-4-ylmethyl-piperidine | 116.2 | 570 (M + H)+ | 1.77 (method L) |
| 244 | N—OH | 116.2 | 419 (M + H)+ | 1.62 (method C) | | | | | |

-continued

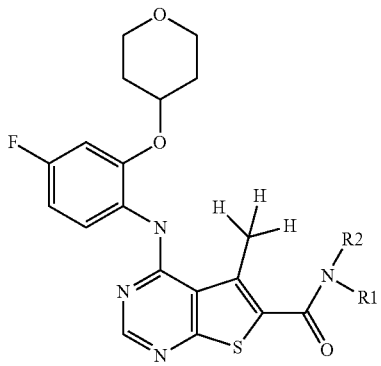

| Example | NR1R2 | educt | Mass-spectrum | HPLC (retention time) |
|---|---|---|---|---|
| 253 | N-propyl-(4-hydroxy-piperidin-1-yl) | 116.2 | 544 (M + H)+ | 1.73 (method L) |
| 254 | N-(2-hydroxy-cyclopentyl) | 116.2 | 487 (M + H)+ | 2.72 (method D) |
| 255 | N-(2-hydroxy-cyclopentyl) | 116.2 | 487 (M + H)+ | 2.70 (method D) |

Compound 256

4-[4-Fluoro-2-(tetrahydro-pyran-4-yloxy)-phenylamino]-5-methyl-thieno[2,3-d]pyrimidine-6-carboxylic acid (3-dimethylamino-2-hydroxy-propyl)-amide-hydrochloride

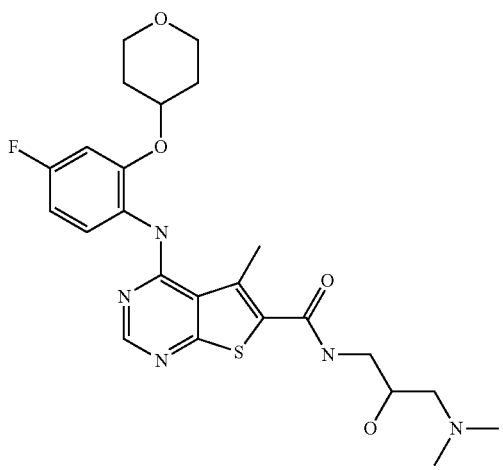 [SMILES: Cc1c(C(=O)NCC(O)CN(C)C)sc2ncnc(Nc3ccc(F)cc3OC3CCOCC3)c12]

To a mixture of 4-[4-fluoro-2-(tetrahydro-pyran-4-yloxy)-phenylamino]-5-methyl-thieno[2,3-d]pyrimidine-6-carboxylic acid (3-amino-2-hydroxy-propyl)-amide (11 mg, 0.02 mmol), formaldehyde solution (10 μl, 37% sol., 0.13 mmol) and 2 ml methanol was added sodium cyanoborohydride (10 mg, 95%, 0.15 mmol). The mixture was stirred at room temperature for two hours. Purification was achieved via chromatography.
Yield: 3 mg (30%)
ESI mass spectrum: m/z=504 (M+H)+
Retention time HPLC: 1.70 (method L)

Compound 257

4-[4-Fluoro-2-(tetrahydro-pyran-4-yloxy)-phenylamino]-5-methyl-thieno[2,3-d]pyrimidine-6-carboxylic acid ((S)-3-hydroxy-1-methyl-piperidin-4-yl)-amide-hydrochloride

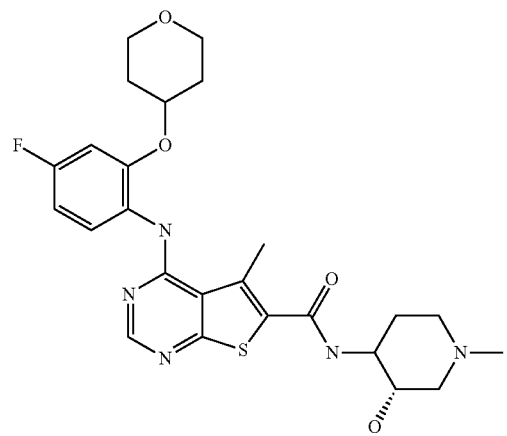 [SMILES: Cc1c(C(=O)NC2CCN(C)C[C@@H]2O)sc2ncnc(Nc3ccc(F)cc3OC3CCOCC3)c12]

Prepared analogously to compound 251 from 4-[4-fluoro-2-(tetrahydro-pyran-4-yloxy)-phenylamino]-5-methyl-thieno[2,3-d]pyrimidine-6-carboxylic acid ((S)-3-hydroxy-piperidin-4-yl)-amide.
Yield: 22 mg (53%)
ESI mass spectrum: m/z=516 (M+H)+
Retention time HPLC: 1.70 (method L)

Compound 258

4-{4-Fluoro-2-[(R)-(tetrahydro-pyran-3-yl)oxy]-phenylamino}-5-methyl-thieno[2,3-d]pyrimidine-6-carboxylic acid (3-pyrrolidin-1-yl-propyl)-amide

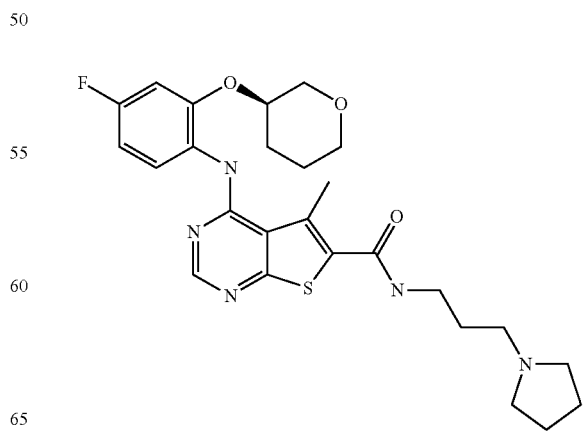

Prepared analogously to example 10.4 from 4-{4-fluoro-2-[(R)-(tetrahydro-pyran-3-yl)oxy]-phenylamino}-5-methyl-thieno[2,3-d]pyrimidine-6-carboxylic acid and 3-pyrrolidin-1-yl-propylamine.

Yield: 36 mg (47%)
ESI mass spectrum: m/z=514 (M+H)⁺
Retention time HPLC: 1.23 (method E)

Compound 259

4-{4-Fluoro-2-[(R)-(tetrahydro-pyran-3-yl)oxy]-phenylamino}-5-methyl-thieno[2,3-d]pyrimidine-6-carboxylic acid (1-methyl-piperidin-4-yl)-amide

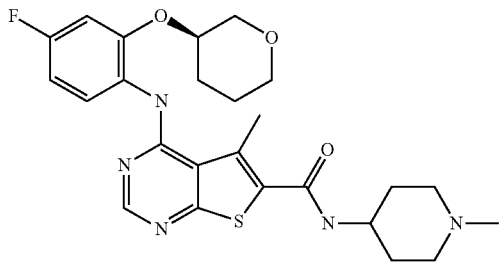 [SMILES: Cc1c(C(=O)NC2CCN(C)CC2)sc2ncnc(Nc3ccc(F)cc3O[C@@H]3CCCOC3)c12]

Prepared analogously to example 10.4 from 4-{4-fluoro-2-[(R)-(tetrahydro-pyran-3-yl)oxy]-phenylamino}-5-methyl-thieno[2,3-d]pyrimidine-6-carboxylic acid and 1-methyl-piperidin-4-ylamine.

Yield: 51 mg (69%)
ESI mass spectrum: m/z=500 (M+H)⁺
Retention time HPLC: 1.21 (method E)

Compound 260

5-Methyl-4-{2-[(R)-(tetrahydro-pyran-3-yl)oxy]-pyridin-3-ylamino}-thieno[2,3-d]pyrimidine-6-carboxylic acid (2-hydroxy-ethyl)-amide

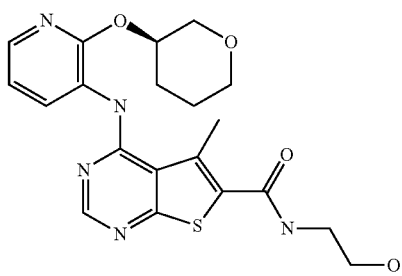 [SMILES: Cc1c(C(=O)NCCO)sc2ncnc(Nc3cccnc3O[C@@H]3CCCOC3)c12]

260.1 5-Methyl-4-{2-[(R)-(tetrahydro-pyran-3-yl)oxy]-Pyridin-3-ylamino}-thieno[2,3-d]pyrimidine-6-carboxylic acid methyl ester

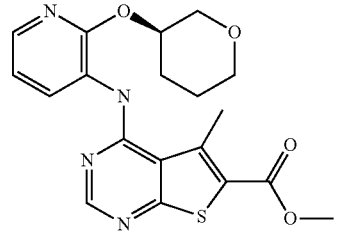 [SMILES: COC(=O)c1sc2ncnc(Nc3cccnc3O[C@@H]3CCCOC3)c2c1C]

Prepared analogously to example 1.1 from 4-Chloro-5-methyl-thieno[2,3-d]pyrimidine-6-carboxylic acid methyl ester and 2-[(R)-(Tetrahydro-pyran-3-yl)oxy]-pyridin-3-ylamine Yield: 1.4 g (76%)
ESI mass spectrum: m/z=401 (M+H)⁺

260.2 5-Methyl-4-{2-[(R)-(tetrahydro-pyran-3-yl)oxy]-pyridin-3-ylamino}-thieno[2,3-d]pyrimidine-6-carboxylic acid

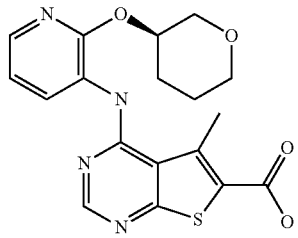 [SMILES: Cc1c(C(=O)O)sc2ncnc(Nc3cccnc3O[C@@H]3CCCOC3)c12]

A mixture of 1.4 g (3.14 mmol) 5-methyl-4-{2-[(R)-(tetrahydro-pyran-3-yl)oxy]-pyridin-3-ylamino}-thieno[2,3-d]pyrimidine-6-carboxylic acid methyl ester, 20 ml methanol, 7 ml THF and 6.29 ml sodium hydroxid solution (1 M) was stirred at room temperature for 48 hours. Then 6.3 ml hydrochloric acid solution (1M) were added followed by addition of water. The mixture was filtered. The solid was washed with water and diisopropylether and dried in an oven (vacuo).

Yield: 1.3 g (96%)
ESI mass spectrum: m/z=387 (M+H)⁺

260.3 5-Methyl-4-{2-[(R)-(tetrahydro-pyran-3-yl)oxy]-pyridin-3-ylamino}-thieno[2,3-d]pyrimidine-6-carboxylic acid (2-hydroxy-ethyl)-amide

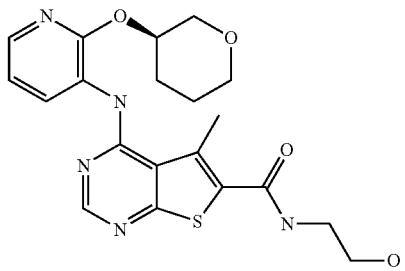 [SMILES: Cc1c(C(=O)NCCO)sc2ncnc(Nc3cccnc3O[C@@H]3CCCOC3)c12]

Prepared analogously to example 10.4 from 5-methyl-4-{2-[(R)-(tetrahydro-pyran-3-yloxy]-pyridin-3-ylamino}-thieno[2,3-d]pyrimidine-6-carboxylic acid and ethanolamine.

Yield: 45 mg (41%)

ESI mass spectrum: m/z=430 (M+H)$^+$

Retention time HPLC: 1.54 (method E)

The following compounds were prepared analogously to 260.3:

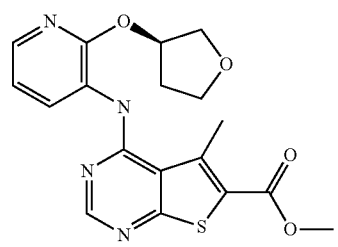

| Example | NR1R2 | educt | mass-spectrum | HPLC (retention time) |
|---|---|---|---|---|
| 261 | N—O\ | 260.2 | 416 (M + H)$^+$ | 1.65 (method E) |
| 262 | (N-propyl-pyrrolidine) | 260.2 | 497 (M + H)$^+$ | 1.3 (method E) |
| 263 | (N-methyl-piperidin-4-yl-amino) | 260.2 | 483 (M + H)$^+$ | 1.28 (method E) |
| 264 | (butynyl-dimethylamino) | 260.2 | 481 (M + H)$^+$ | 1.29 (method E) |
| 265 | (propyl-N-methyl) | 260.2 | 471 (M + H)$^+$ | 1.41 (method E) |
| 266 | (cyanomethyl) | 260.2 | 425 (M + H)$^+$ | 1.68 (method E) |

Compound 267

5-Methyl-4-{2-[(R)-(tetrahydro-furan-3-yl)oxy]-pyridin-3-ylamino}-thieno[2,3-d]pyrimidine-6-carboxylic acid amide

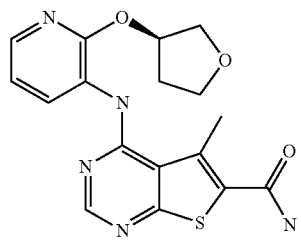 [SMILES: Cc1c(C(N)=O)sc2ncnc(Nc3cccnc3O[C@@H]3CCOC3)c12]

267.1 5-Methyl-4-{2-[(R)-(tetrahydro-furan-3-yl)oxy]-pyridin-3-ylamino}-thieno[2,3-d]pyrimidine-6-carboxylic acid methylester A mixture of 166 mg (0.92 mmol) 2-[(R)-(tetrahydro-furan-3-yl)oxy]-pyridin-3-ylamine, 364 mg (1.5 mmol) 4-chloro-5-methyl-thieno[2,3-d]pyrimidine-6-carboxylic acid methyl ester and 39 µl hydrochloric acid (4M in dioxane) and 30 ml dioxane was stirred at 100° C. for 1.5 days. The reaction mixture was concentrated and used for the next synthesis step without further purification.

Yield: 569 m g

267.2 5-Methyl-4-{2-[(R)-(tetrahydro-furan-3-yl)oxy]-pyridin-3-ylamino}-thieno[2,3-d]pyrimidine-6-carboxylic acid

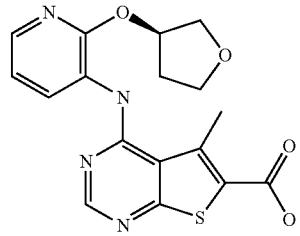 [SMILES: Cc1c(C(=O)O)sc2ncnc(Nc3cccnc3O[C@@H]3CCOC3)c12]

Prepared analogously to example 1.2 from 5-methyl-4-{2-[(R)-(tetrahydro-furan-3-yl)oxy]-pyridin-3-ylamino}-thieno[2,3-d]pyrimidine-6-carboxylic acid methylester Yield: 823 mg (97%)

Retention time HPLC: 2.3 (method K)

267.3 5-Methyl-4-{2-[(R)-(tetrahydro-furan-3-yl)oxy]-pyridin-3-ylamino}-thieno[2,3-d]pyrimidine-6-carboxylic acid amide

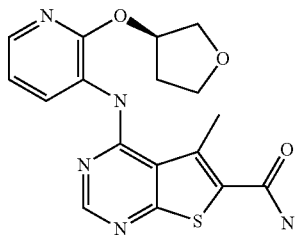 [SMILES: Cc1c(C(N)=O)sc2ncnc(Nc3cccnc3O[C@@H]3CCOC3)c12]

Prepared analogously to example 10.4 from 5-methyl-4-{2-[(R)-(tetrahydro-furan-3-yl)oxy]-pyridin-3-ylamino}-thieno[2,3-d]pyrimidine-6-carboxylic acid and ammonia.

Yield: 72 mg (44%)

ESI mass spectrum: m/z=372 (M+H)$^+$

Retention time HPLC: 2.12 (method K)

Compound 268

5-Methyl-4-{2-[(R)-(tetrahydro-furan-3-yloxy]-pyridin-3-ylamino}-thieno[2,3-d]pyrimidine-6-carboxylic acid (3-dimethylamino-propyl)-amide trifluoroacetae

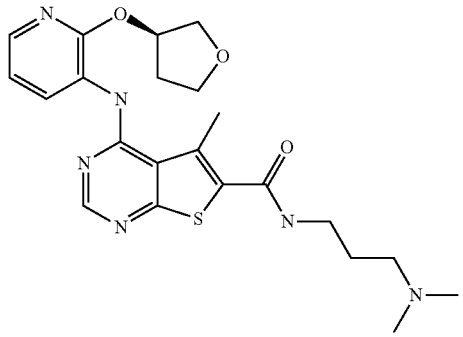 [SMILES: Cc1c(C(=O)NCCCN(C)C)sc2ncnc(Nc3cccnc3O[C@@H]3CCOC3)c12]

Prepared analogously to example 10.4 from 5-methyl-4-{2-[(R)-(tetrahydro-furan-3-yloxy]-pyridin-3-ylamino}-thieno[2,3-d]pyrimidine-6-carboxylic acid and N$^1$,N$^1$-dimethyl-propane-1,3-diamine.

Yield: 211 mg (84%)

ESI mass spectrum: m/z=457 (M+H)$^+$

Retention time HPLC: 1.79 (method K)

Compound 269

5-Methyl-4-{2-[(S)-(tetrahydro-furan-3-yl)oxy]-pyridin-3-ylamino}-thieno[2,3-d]pyrimidine-6-carboxylic acid amide

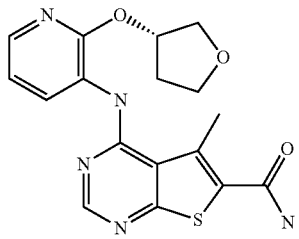 [SMILES: Cc1c(C(N)=O)sc2ncnc(Nc3cccnc3O[C@H]3CCOC3)c12]

269.1 5-Methyl-4-{2-[(S)-(tetrahydro-furan-3-yl)oxy]-pyridin-3-ylamino}-thieno[2,3-d]pyrimidine-6-carboxylic acid methylester

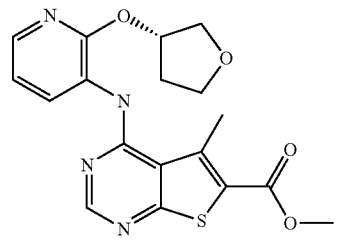 [SMILES: COC(=O)c1sc2ncnc(Nc3cccnc3O[C@H]3CCOC3)c2c1C]

Prepared analogously from 2-[(S)-(tetrahydro-furan-3-yl)oxy]-pyridin-3-ylamine and 4-chloro-5-methyl-thieno[2,3-d]pyrimidine-6-carboxylic acid methyl ester.

Yield: 70 mg (69%)

269.2 5-Methyl-4-{2-[(S)-(tetrahydro-furan-3-yl)oxy]-pyridin-3-ylamino}-thieno[2,3-d]pyrimidine-6-carboxylic acid

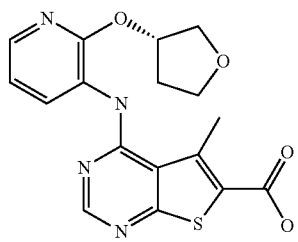 [SMILES: Cc1c(C(=O)O)sc2ncnc(Nc3cccnc3O[C@H]3CCOC3)c12]

Prepared analogously to example 1.2 from 5-methyl-4-{2-[(S)-(tetrahydro-furan-3-yl)oxy]-pyridin-3-ylamino}-thieno[2,3-d]pyrimidine-6-carboxylic acid methylester Yield: 301 mg Retention time HPLC: 2.33 (method K)

269.3 5-Methyl-4-{2-[(R)-(tetrahydro-furan-3-yl)oxy]-pyridin-3-ylamino}-thieno[2,3-d]pyrimidine-6-carboxylic acid amide

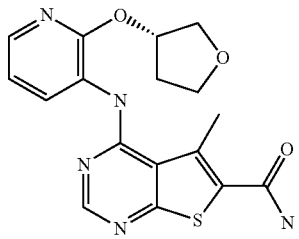 [SMILES: Cc1c(C(N)=O)sc2ncnc(Nc3cccnc3O[C@H]3CCOC3)c12]

Prepared analogously to example 10.4 from 5-methyl-4-{2-[(S)-(tetrahydro-furan-3-yl)oxy]-pyridin-3-ylamino}-thieno[2,3-d]pyrimidine-6-carboxylic acid and ammonia.

Yield: 7 mg (31%)

ESI mass spectrum: m/z=372 (M+H)$^+$

Retention time HPLC: 2.03 (method K)

Compound 270

5-Methyl-4-{2-[(S)-(tetrahydro-furan-3-yl)oxy]-pyridin-3-ylamino}-thieno[2,3-d]pyrimidine-6-carboxylic acid (3-dimethylamino-propyl)-amide

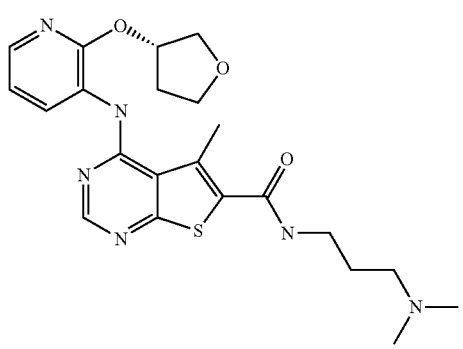 [SMILES: Cc1c(C(=O)NCCCN(C)C)sc2ncnc(Nc3cccnc3O[C@H]3CCOC3)c12]

Prepared analogously to example 10.4 from 5-methyl-4-{2-[(S)-(tetrahydro-furan-3-yl)oxy]-pyridin-3-ylamino}-thieno[2,3-d]pyrimidine-6-carboxylic acid and N$^1$,N$^1$-dimethyl-propane-1,3-diamine.

Yield: 26 mg (94%)

ESI mass spectrum: m/z=456 (M)$^+$

Retention time HPLC: 1.57 (method M)

Compound 271

4-{4-Fluoro-2-[(S)-(tetrahydro-furan-3-yl)oxy]-phenylamino}-5-methyl-thieno[2,3-d]pyrimidine-6-carboxylic acid (1-methyl-piperidin-4-yl)-amide

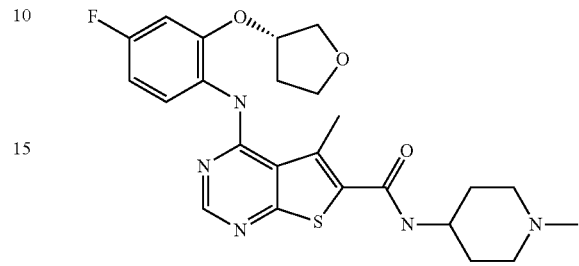

Prepared analogously to example 1.4 from 4-{4-fluoro-2-[(S)-(tetrahydro-furan-3-yl)oxy]-phenylamino}-5-methyl-thieno[2,3-d]pyrimidine-6-carboxylic acid and 1-methyl-piperidin-4-ylamine.

Yield: 222 mg (89%)

ESI mass spectrum: m/z=486 (M+H)$^+$

Retention time HPLC: 1.28 (method C)

Compound 272

4-[(4-{4-Fluoro-2-[(S)-(tetrahydro-furan-3-yl)oxy]-phenylamino}-5-methyl-thieno[2,3-d]pyrimidine-6-carbonyl)-amino]-azepane-1-carboxylic acid tert-butyl ester

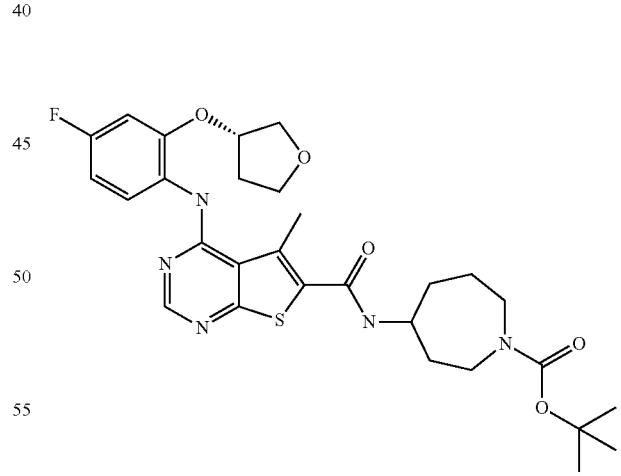

Prepared analogously to example 1.4 from 4-{4-fluoro-2-[(S)-(tetrahydro-furan-3-yl)oxy]-phenylamino}-5-methyl-thieno[2,3-d]pyrimidine-6-carboxylic acid and 4-amino-azepane-1-carboxylic acid tert-butyl ester.

Yield: 457 mg (100%)

ESI mass spectrum: m/z=586 (M+H)$^+$

Retention time HPLC: 1.95 (method C)

Compound 273

4-{4-Fluoro-2-[(S)-(tetrahydro-furan-3-yl)oxy]-phenylamino}-5-methyl-thieno[2,3-d]pyrimidine-6-carboxylic acid azepan-4-ylamide trifluoroacetate

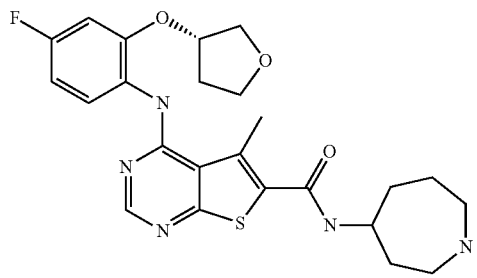 [SMILES: Cc1c(C(=O)NC2CCCNCC2)sc2ncnc(Nc3ccc(F)cc3O[C@H]3CCOC3)c12]

A mixture of 380 mg (0.65 mmol) 4-[(4-{4-fluoro-2-[(S)-(tetrahydro-furan-3-yl)oxy]-phenylamino}-5-methyl-thieno[2,3-d]pyrimidine-6-carbonyl)-amino]-azepane-1-carboxylic acid tert-butyl ester and 0.15 ml trifluoroacetic acid and 10 ml dichloromethane was stirred at room temperature overnight. The reaction mixture was concentrated in vacuo.

Yield: 382 mg (98%)

ESI mass spectrum: m/z=486 (M+H)$^+$

Retention time HPLC: 1.29 (method D)

The following compounds were prepared analogously to 1.4:

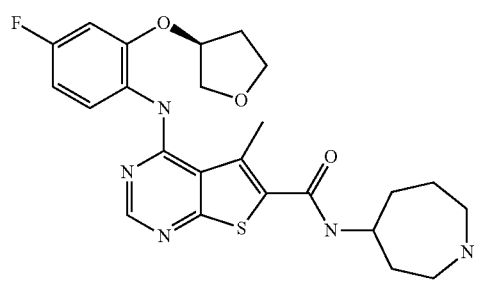 [SMILES: Cc1c(C(=O)NC2CCCNCC2)sc2ncnc(Nc3ccc(F)cc3O[C@H]3CCOC3)c12]

| Example | NR1R2 | educt | mass-spectrum | HPLC (retention time) |
|---|---|---|---|---|
| 274 | 2) | 100.2 | 484 (M + H)$^+$ | 2.17 (method D) |
| 275 | | 100.2 | 586 (M + H)$^+$ | 1.95 (method D) |
| 276 | | 100.2 | 486 (M + H)$^+$ | 1.28 (method D) |

Compound 277

4-{4-Fluoro-2-[(R)-(tetrahydro-furan-3-yl)oxy]-phenylamino}-5-methyl-thieno[2,3-d]pyrimidine-6-carboxylic acid azepan-4-ylamide trifluoroacetate Prepared analogously to 273 from 4-[(4-{4-fluoro-2-[(R)-(tetrahydro-furan-3-yl)oxy]-phenylamino}-5-methyl-thieno[2,3-d]pyrimidine-6-carbonyl)-amino]-azepane-1-carboxylic acid tert-butyl ester.

Yield: 435 mg (100%)

ESI mass spectrum: m/z=486 (M+H)$^+$

Retention time HPLC: 1.88 (method D)

Compound 278

5-Methyl-4-[2-(tetrahydro-pyran-4-yloxy)-pyridin-3-ylamino]-thieno[2,3-d]pyrimidine-6-carboxylic acid ((1S,2S)-2-hydroxy-cyclopentyl)-amide

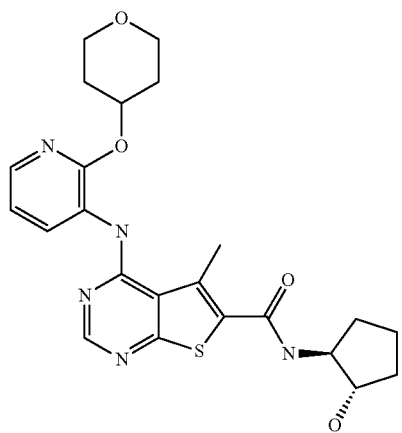 [SMILES: Cc1c(C(=O)N[C@H]2CCC[C@@H]2O)sc2ncnc(Nc3cccnc3OC3CCOCC3)c12]

278.1 5-Methyl-4-[2-(tetrahydro-pyran-4-yloxy)-pyridin-3-ylamino]-thieno[2,3-d]pyrimidine-6-carboxylic acid methyl ester

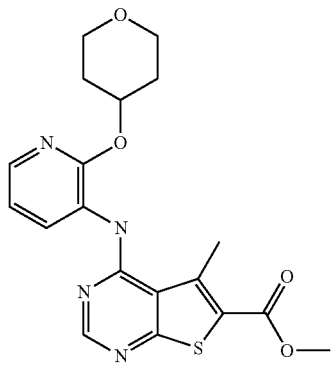 [SMILES: COC(=O)c1sc2ncnc(Nc3cccnc3OC3CCOCC3)c2c1C]

Prepared analogously to 1.1 from 4-chloro-5-methyl-thieno[2,3-d]pyrimidine-6-carboxylic acid methyl ester and 2-(tetrahydro-pyran-4-yloxy)-pyridin-3-ylamine.

Yield: 635 mg (77%)

ESI mass spectrum: m/z=401 (M+H)$^+$

278.2 5-Methyl-4-[2-(tetrahydro-pyran-4-yloxy)-pyridin-3-ylamino]-thieno[2,3-d]pyrimidine-6-carboxylic acid

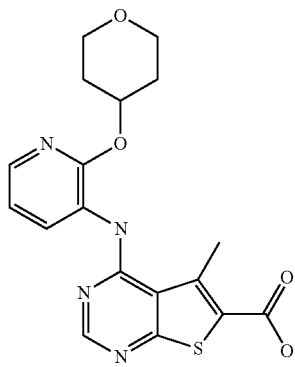 [SMILES: Cc1c(C(=O)O)sc2ncnc(Nc3cccnc3OC3CCOCC3)c12]

Prepared analogously to 1.2. from 5-methyl-4-[2-(tetrahydro-pyran-4-yloxy)-pyridin-3-ylamino]-thieno[2,3-d]pyrimidine-6-carboxylic acid methyl ester. Lithium hydroxide was replaced by sodium hydroxide (2M).

Yield: 571 mg (93%)

ESI mass spectrum: m/z=387 (M+H)$^+$

Retention time HPLC: 2.87 (method D)

278.3 5-Methyl-4-[2-(tetrahydro-pyran-4-yloxy)-3-pyridin-3-ylamino]-thieno[2,3-d]pyrimidine-6-carboxylic acid ((1S,2S)-2-hydroxy-cyclopentyl)-amide

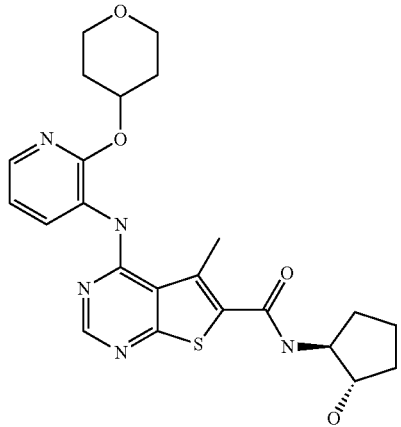 [SMILES: Cc1c(C(=O)N[C@H]2CCC[C@@H]2O)sc2ncnc(Nc3cccnc3OC3CCOCC3)c12]

Prepared analogously to 1.4. from 5-methyl-4-[2-(tetrahydro-pyran-4-yloxy)-pyridin-3-ylamino]-thieno[2,3-d]pyrimidine-6-carboxylic acid and trans-(1S,2S)-2-aminocyclopentanol hydrochloride.

Yield: 100 mg (82%)

ESI mass spectrum: m/z=470 (M+H)$^+$

Retention time HPLC: 2.62 (method D)

The following compounds were prepared analogously to 1.4:

| Example | NR1R2 | educt | mass-spectrum | HPLC (retention time) |
|---|---|---|---|---|
| 279 | N⁀⁀S⁀ | 278.2 | 474 (M + H)$^+$ | 3.00 (method D) |
| 280 | N⁀⁀S(O)⁀ | 278.2 | 476 (M + H)$^+$ | 2.33 (method D) |
| 281 | N-methylpiperidin-4-ylamino | 278.2 | 483 (M + H)$^+$ | 1.95 (method D) |

Compound 282

5-Methyl-4-[2-(tetrahydro-pyran-4-yloxy)-pyridin-3-ylamino]-thieno[2,3-d]pyrimidine-6-carboxylic acid (3-methanesulfinyl-propyl)-amide

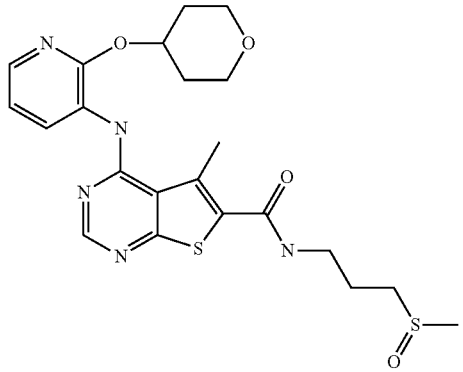 [SMILES: Cc1c(C(=O)NCCCS(C)=O)sc2ncnc(Nc3cccnc3OC3CCOCC3)c12]

A mixture of 100 mg (0.21 mmol) 5-methyl-4-[2-(tetrahydro-pyran-4-yloxy)-pyridin-3-ylamino]-thieno[2,3-d]pyrimidine-6-carboxylic acid (3-methylsulfanyl-propyl)-amide, 52 mg (0.21 mmol) 3-chloro-perbenzoic acid and 5 ml dichloromethane was stirred at room temperature over night. Then the mixture was extracted with water. The organic phase was dried over magnesium sulfate. After filtration the filtrate was evaporated. DMF was added to the residue. The precipitate was isolated by filtration.

Yield: 37 mg (36%)

ESI mass spectrum: m/z=490 (M+H)$^+$

Retention time HPLC: 2.33 (method D)

The invention claimed is:

1. A compound of Formula (I)

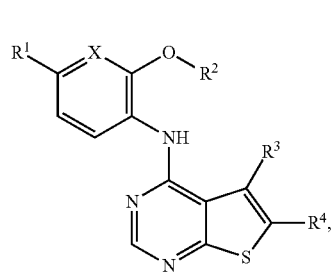

wherein

X is CH or N, $R^1$ is H, halogen, CN, $CH_3$ or $CF_3$, $R^2$ is a group selected from

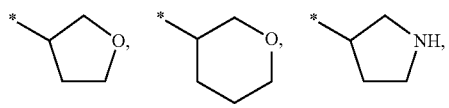

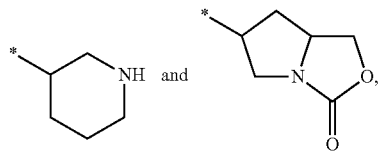

wherein the

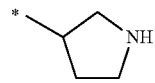

group may be substituted at the nitrogen atom by —$SO_2$—($C_{1-3}$ alkyl), —CO—($C_{1-3}$ alkyl), —CO—$(CH_2)_n$—O—($C_{1-3}$ alkyl), —CO—$(CH_2)_n$—N($C_{1-3}$ alkyl)$_2$, $C_{1-4}$ alkyl, —$(CH_2)_n$—$CF_3$, —$(CH_2)_n$—$CHF_2$, —$(CH_2)_n$—OH, —$(CH_2)_n$—O—($C_{1-3}$ alkyl), —$(CH_2)_n$—CN,

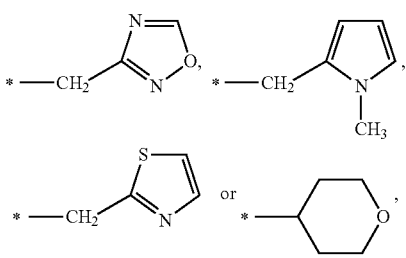

and wherein it may be substituted on a carbon atom by a —CH₂OH group,
wherein n is 1 or 2,
and wherein the

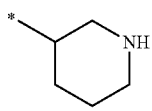

group may be substituted at the nitrogen atom by linear or branched $C_{1-4}$ alkyl, —$(CH_2)_n$—$CF_3$, —$(CH_2)_n$—$CHF_2$, —$(CH_2)_n$—OH, —$(CH_2)_n$—O—($C_{1-3}$ alkyl), —$(CH_2)_n$—CN, —$(CH_2)_n$—CO—N($C_{1-3}$ alkyl)₂, —$SO_2$—($C_{1-3}$ alkyl), —CO—($C_{1-3}$ alkyl), —$CO_2$($C_{1-4}$ alkyl), —$CO_2$—$(CH_2)_p$—$CF_3$, —$CO_2$—$(CH_2)_n$—O—($C_{1-3}$ alkyl), —$CO_2$—$(CH_2)_n$—CO—N($C_{1-3}$ alkyl)₂,

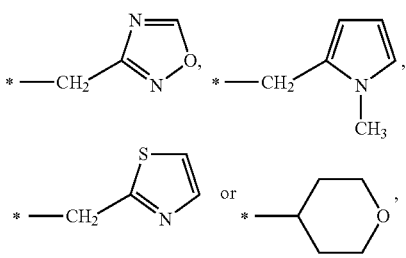

wherein n is 1 or 2,
$R^3$ is a $C_{1-2}$ alkyl group, and
$R^4$ is —COOH, —$CO_2$—($C_{1-3}$ alkyl), —$CO_2$—$(CH_2)_n$—N($C_{1-3}$ alkyl)₂, —$CONH_2$, —CO—$NHR^5$, —CO—NH—$(CH_2)_p$—$R^6$, —CO—NH—$(CH_2)_m$—$R^7$, —CO—N($CH_3$)—$(CH_2)_m$—$R^7$, CO—N($CH_3$)—($CH_2$)-cyclohexyl,

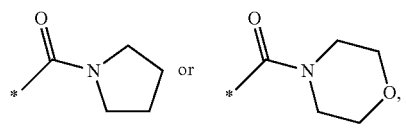

$R^5$ is —CN, —OH, linear or branched $C_{1-6}$ alkyl, —O($C_{1-3}$ alkyl), $C_{3-6}$ cycloalkyl, —$SO_2$—($C_{1-3}$ alkyl); pyrazolyl optionally substituted by methyl; or piperidinyl optionally substituted by methyl,
wherein the $C_{3-6}$ cycloalkyl group may be substituted by —$NH_2$, —OH or —$OCH_3$;
$R^6$ is —C($CH_3$)₂Cl; —C($CH_3$)₂OH; —$CHC_{3-6}$ cycloalkyl, which is optionally substituted by OH;

imidazolyl, which is optionally substituted by methyl; pyrrolidinyl, which is optionally substituted by $C_{1-3}$ alkyl or by an oxo group; tetrahydrofuranyl; tetrahydropyranyl; phenyl, which is optionally substituted by one or two —F, —Cl, —CN, —OH, $C_{1-3}$ alkyl or —O($C_{1-3}$ alkyl); naphthyl; pyridinyl; furanyl; thiophenyl; oxazolyl; thiazolyl; pyrazolyl; morpholinyl, which is optionally substituted by methyl; benzothiophenyl; —CO-phenyl; or —$SO_2$—N($C_{1-3}$ alkyl)₂, and
$R^7$ is F, —OH, —$OCF_3$, —O—($C_{1-3}$ alkyl), —O-phenyl, —O—$(CH_2)_m$—OH, —N($C_{1-3}$ alkyl)₂, —NH-phenyl, piperidinyl, pyrrolidinyl, azetedinyl or aziridinyl,
wherein said NH-phenyl, piperidinyl, pyrrolidinyl, azetedinyl and aziridinyl groups at $R^7$ may each be substituted at the nitrogen atom by $C_{1-3}$ alkyl,
wherein p is 1, 2 or 3,
m is 2 or 3, and
* indicates the point of attachment of the R group to the rest of the molecule,
or a tautomer, enantionmer, diastereomer or a salt thereof.

2. A compound of Formula (I) according to claim 1, wherein
$R^3$ is methyl,
or a tautomer or a pharmaceutically acceptable salt thereof.

3. A compound of Formula (I) according to claim 1, wherein
X is CH and
$R^1$ is F, Cl, CN, $CH_3$ or $CF_3$,
or a tautomer or a pharmaceutically acceptable salt thereof.

4. A compound of Formula (I) according to claim 1, wherein
X is N and
$R^1$ is H,
or a tautomer or a pharmaceutically acceptable salt thereof.

5. A compound of Formula (I) according to claim 1, wherein
$R^2$ is

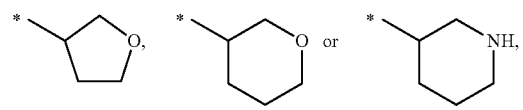

wherein the

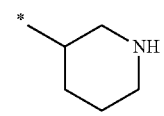

group may be substituted at the nitrogen atom by linear or branched $C_{1-4}$ alkyl, —$(CH_2)_n$—$CF_3$, —$(CH_2)_n$—$CHF_2$, —$(CH_2)_n$—OH, —$(CH_2)_n$—O—($C_{1-3}$ alkyl), —$(CH_2)_n$—CN, —$(CH_2)_n$—CO—N($C_{1-3}$ alkyl)₂ or —$SO_2$—($C_{1-3}$ alkyl),
wherein n is 1 or 2,
or a tautomer or a pharmaceutically acceptable salt thereof.

6. A compound of Formula (I) according to claim 1, wherein

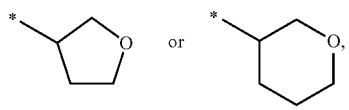

R² is or a tautomer or a pharmaceutically acceptable salt thereof.

7. A compound of Formula (I) according to claim 1, wherein

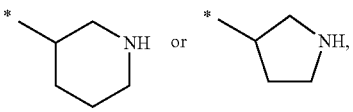

R² is
wherein the

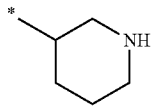

group may be substituted at the nitrogen atom by linear or branched $C_{1-4}$ alkyl, —$(CH_2)_n$—$CF_3$, —$(CH_2)_n$—$CHF_2$, —$(CH_2)_n$—OH, —$(CH_2)_n$—O—$(C_{1-3}$ alkyl), —$(CH_2)_n$—CN, —$(CH_2)_n$—CO—N$(C_{1-3}$ alkyl)$_2$ or —$SO_2$—$(C_{1-3}$ alkyl),
wherein n is 1 or 2,
and wherein the

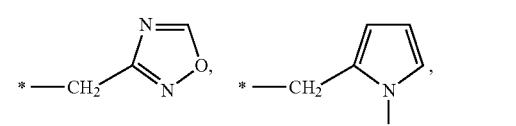

group may be substituted at the nitrogen atom by —$SO_2$—$(C_{1-3}$ alkyl), $C_{1-4}$ alkyl, —$(CH_2)_n$—$CF_3$, —$(CH_2)_n$—$CHF_2$, —$(CH_2)_n$—OH, —$(CH_2)_n$—O—$(C_{1-3}$ alkyl), —$(CH_2)_n$—CN,

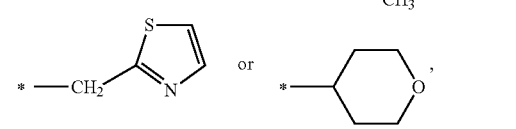

or a tautomer or a pharmaceutically acceptable salt thereof.

8. A compound of Formula (I) according to claim 1, wherein
R⁴ is —$CONH_2$, —CO—$NHR^5$, —CO—NH—$(CH_2)_p$—R⁶, —CO—NH—$(CH_2)_m$—R⁷,
R⁵ is —CN, —OH, linear or branched $C_{1-6}$ alkyl, —O($C_{1-3}$ alkyl), $C_{3-6}$ cycloalkyl, —$SO_2$—$(C_{1-3}$ alkyl); pyrazolyl optionally substituted by methyl; or piperidinyl optionally substituted by methyl, wherein the $C_{3-6}$ cycloalkyl group may be substituted by —$NH_2$, —OH or OMe;
R⁶ is —$C(CH_3)_2Cl$; —$C(CH_3)_2OH$; —$CHC_{3-6}$ cycloalkyl, which is optionally substituted by OH; imidazolyl, which is optionally substituted by methyl; pyrrolidinyl, which is optionally substituted by $C_{1-3}$ alkyl or by an oxo group; tetrahydrofuranyl; tetrahydropyranyl; phenyl, which is optionally substituted by one or two —F, —Cl, —CN, —OH, $C_{1-3}$ alkyl or —O($C_{1-3}$ alkyl); naphthyl; pyridinyl; furanyl; thiophenyl; oxazolyl; thiazolyl; pyrazolyl; morpholinyl, which is optionally substituted by methyl; benzothiophenyl; —CO-phenyl; or —$SO_2$—$N(C_{1-3}$ alkyl)$_2$, and
R⁷ is F, —OH, —$OCF_3$, —O—($C_{1-3}$ alkyl), —O-phenyl, —O—$(CH_2)_m$—OH, —$N(C_{1-3}$ alkyl)$_2$, —NH-phenyl, pyrrolidinyl, azetedinyl or aziridinyl,
wherein said NH-phenyl, pyrrolidinyl, azetedinyl and aziridinyl groups at R⁷ may each be substituted at the nitrogen atom by $C_{1-3}$ alkyl,
wherein p is 1, 2 or 3, and
m is 2 or 3,
or a tautomer, enantionmer, diastereomer or a pharmaceutically acceptable salt thereof.

9. A compound of Formula (I) according to claim 1, wherein
R⁴ is —$CONH_2$, —CO—$NHR^5$, —CO—NH—$(CH_2)_p$—R⁶, —CO—NH—$(CH_2)_m$—R⁷,
R⁵ is —CN, linear or branched $C_{1-6}$ alkyl, —O($C_{1-3}$ alkyl), $C_{3-6}$ cycloalkyl, piperidinyl optionally substituted by methyl,
wherein the $C_{3-6}$ cycloalkyl group may be substituted by —$NH_2$, —OH or OMe;
R⁶ is imidazolyl, which is optionally substituted by methyl; pyrrolidinyl, which is optionally substituted by $C_{1-3}$ alkyl or by an oxo group; tetrahydrofuranyl; tetrahydropyranyl; pyridinyl; oxazolyl; thiazolyl; pyrazolyl; morpholinyl, which is optionally substituted by methyl and
R⁷ is F, —OH, —$OCF_3$, —O—($C_{1-3}$ alkyl), —O-phenyl, —O—$(CH_2)_m$—OH, —$N(C_{1-3}$ alkyl)$_2$, piperidinyl, pyrrolidinyl, azetedinyl or aziridinyl,
wherein said piperidinyl, pyrrolidinyl, azetedinyl and aziridinyl groups at R⁷ may each be substituted at the nitrogen atom by $C_{1-3}$ alkyl,
wherein p is 1, 2 or 3, and
m is 2 or 3,
or a tautomer, enantionmer, diastereomer or a pharmaceutically acceptable salt thereof.

10. A compound of Formula (I) according to claim 1 selected from a group consisting of:

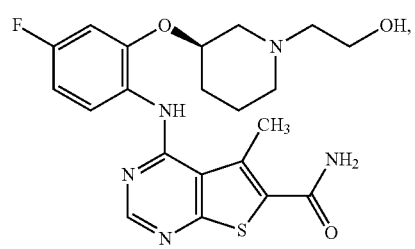

-continued

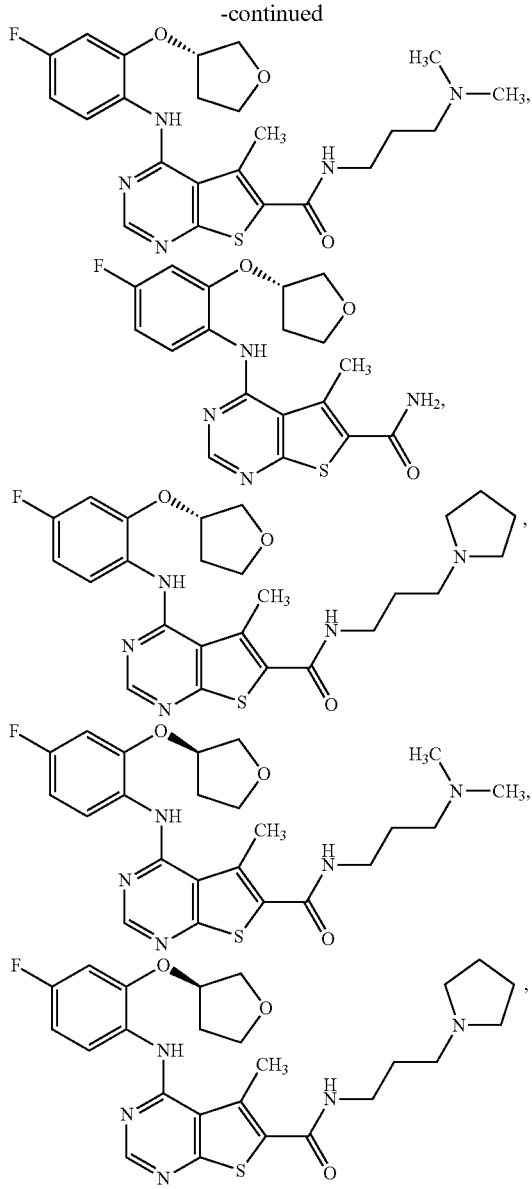

-continued

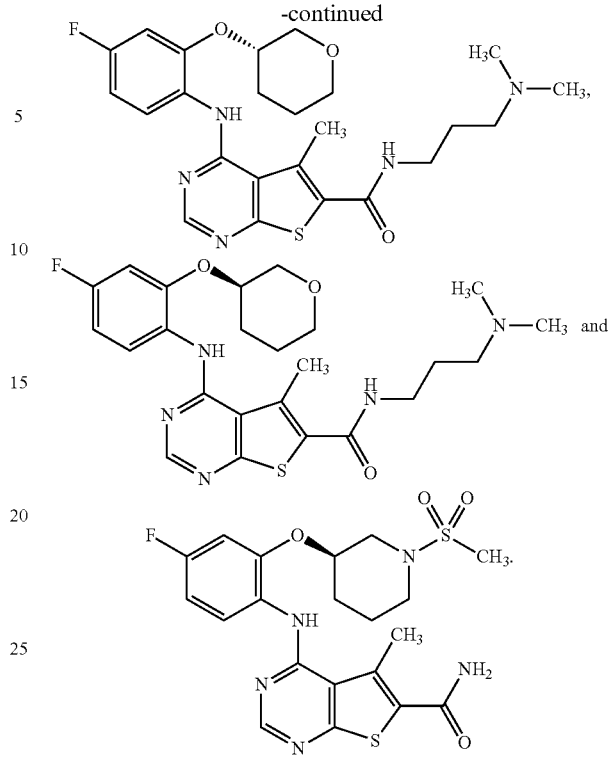

11. A pharmaceutically acceptable salt of a compound according to claim 1.

12. A pharmaceutical composition comprising a compound according to claim 1 or a pharmaceutically acceptable salt thereof and optionally a pharmaceutically acceptable carrier.

13. The pharmaceutical composition according to claim 12 further comprising an additional therapeutic agent.

14. The pharmaceutical composition according to claim 13 wherein the additional therapeutic agent is selected from an antidiabetic agent, a lipid lowering agent, a cardiovascular agent, an antihypertensive agent, a diuretic agent, a thrombocyte aggregation inhibitor, an antineoplastic agent and an anti-obesity agent.

* * * * *